US011230572B2

(12) United States Patent
Barouch et al.

(10) Patent No.: US 11,230,572 B2
(45) Date of Patent: Jan. 25, 2022

(54) SIGNATURE-BASED HUMAN IMMUNODEFICIENCY VIRUS (HIV) ENVELOPE (ENV) TRIMER VACCINES AND METHODS OF USING THE SAME

(71) Applicants: Beth Israel Deaconess Medical Center, Inc., Boston, MA (US); Triad National Security, LLC, Los Alamos, NM (US)

(72) Inventors: Dan H. Barouch, Brookline, MA (US); Christine Bricault, Boston, MA (US); Bette T. Korber, Los Alamos, NM (US); Karina Yusim, Los Alamos, NM (US)

(73) Assignees: Beth Israel Deaconess Medical Center, Inc., Boston, MA (US); Triad National Security, LLC, Los Alamos, NM (US)

( * ) Notice: Subject to any disclaimer, the term of this patent is extended or adjusted under 35 U.S.C. 154(b) by 91 days.

(21) Appl. No.: 16/342,866

(22) PCT Filed: Oct. 17, 2017

(86) PCT No.: PCT/US2017/057045

§ 371 (c)(1),
(2) Date: Apr. 17, 2019

(87) PCT Pub. No.: WO2018/075559

PCT Pub. Date: Apr. 26, 2018

(65) Prior Publication Data

US 2020/0055901 A1 Feb. 20, 2020

Related U.S. Application Data

(60) Provisional application No. 62/409,363, filed on Oct. 17, 2016.

(51) Int. Cl.

| | |
|---|---|
| *A61K 39/21* | (2006.01) |
| *A61K 39/00* | (2006.01) |
| *C07K 16/10* | (2006.01) |
| *A61K 39/12* | (2006.01) |
| *C07K 14/005* | (2006.01) |
| *A61K 47/68* | (2017.01) |
| *A61P 31/18* | (2006.01) |

(52) U.S. Cl.

CPC ............ *C07K 14/005* (2013.01); *A61K 39/21* (2013.01); *A61K 47/6803* (2017.08); *A61K 47/6841* (2017.08); *A61P 31/18* (2018.01); *C07K 16/1045* (2013.01); *A61K 2039/545* (2013.01); *C07K 2317/24* (2013.01); *C12N 2740/16122* (2013.01); *C12N 2740/16134* (2013.01)

(58) Field of Classification Search

CPC .. A61K 39/21; C07K 14/005; C07K 16/1063; C12N 2740/16122; A61P 31/18

See application file for complete search history.

(56) References Cited

U.S. PATENT DOCUMENTS

| | | | |
|---|---|---|---|
| 4,603,112 | A | 7/1986 | Paoletti et al. |
| 5,639,649 | A | 6/1997 | Almond et al. |
| 5,643,576 | A | 7/1997 | Johnston et al. |
| 5,762,938 | A | 6/1998 | Paoletti et al. |
| 6,913,922 | B1 | 7/2005 | Bout et al. |
| 7,153,509 | B2 | 12/2006 | Haynes et al. |
| 7,172,761 | B2 | 2/2007 | Haynes et al. |
| 7,195,768 | B2 | 3/2007 | Haynes et al. |
| 7,270,811 | B2 | 9/2007 | Bout et al. |
| 7,592,014 | B2 | 9/2009 | Binley et al. |
| 7,598,078 | B2 | 10/2009 | Havenga et al. |
| 7,741,099 | B2 | 6/2010 | Havenga et al. |
| 7,906,113 | B2 | 3/2011 | Bout et al. |
| 7,939,083 | B2 | 5/2011 | Dey et al. |
| 7,951,377 | B2 | 5/2011 | Korber et al. |
| 7,968,286 | B2 | 6/2011 | Havenga et al. |
| 8,012,467 | B2 | 9/2011 | Havenga et al. |
| 8,052,967 | B2 | 11/2011 | Vogels et al. |
| 8,071,107 | B2 | 12/2011 | Haynes et al. |
| 8,076,131 | B2 | 12/2011 | Vogels et al. |
| 9,017,691 | B2 | 4/2015 | Barouch et al. |

(Continued)

FOREIGN PATENT DOCUMENTS

| | | | |
|---|---|---|---|
| AU | 2013204885 | A1 | 5/2013 |
| WO | WO-2004/0044155 | A2 | 5/2004 |

(Continued)

OTHER PUBLICATIONS

Diaz-Aguilar et al., "Significant differences in cell-cell fusion and viral entry between strains revealed by scanning mutagenesis of the C-heptad repeat of HIV gp41," Biochemistry. 52(20):3552-63 (2013).

(Continued)

*Primary Examiner* — Barry A Chestnut
(74) *Attorney, Agent, or Firm* — Clark & Elbing LLP

(57) ABSTRACT

The invention features immunogenic compositions and vaccines containing an optimized human immunodeficiency virus (HIV) envelope (Env) polypeptide (e.g., a stabilized trimer of optimized HIV Env polypeptides) or a polynucleotide encoding an optimized HIV Env polypeptide and uses thereof. The invention also features methods of treating and/or preventing a HIV infection by administering an immunogenic composition or vaccine of the invention to a subject (e.g., a human).

30 Claims, 43 Drawing Sheets
(35 of 43 Drawing Sheet(s) Filed in Color)
Specification includes a Sequence Listing.

(56) References Cited

U.S. PATENT DOCUMENTS

| | | | |
|---|---|---|---|
| 2003/0147888 | A1 | 8/2003 | Haynes et al. |
| 2003/0207287 | A1 | 11/2003 | Short |
| 2003/0219452 | A1 | 11/2003 | Haynes et al. |
| 2004/0001851 | A1 | 1/2004 | Haynes et al. |
| 2004/0086506 | A1 | 5/2004 | Haynes et al. |
| 2005/0196384 | A1 | 9/2005 | Vogels et al. |
| 2005/0221493 | A1 | 10/2005 | Vogels et al. |
| 2005/0232900 | A1 | 10/2005 | Vogels et al. |
| 2007/0054262 | A1 | 3/2007 | Baker et al. |
| 2007/0178562 | A1 | 8/2007 | Haynes et al. |
| 2007/0298051 | A1 | 12/2007 | Barouch et al. |
| 2008/0153083 | A1 | 6/2008 | Vogels et al. |
| 2008/0171018 | A1 | 7/2008 | Bout et al. |
| 2008/0199939 | A1 | 8/2008 | Havenga et al. |
| 2008/0279879 | A1 | 11/2008 | Zolla-Pazner |
| 2009/0162384 | A1 | 6/2009 | Haynes |
| 2009/0198042 | A1 | 8/2009 | Korber et al. |
| 2009/0324631 | A1 | 12/2009 | Korber et al. |
| 2010/0015176 | A1 | 1/2010 | Vogels et al. |
| 2010/0034774 | A1 | 2/2010 | Vogels et al. |
| 2010/0104596 | A1 | 4/2010 | Haynes et al. |
| 2010/0143302 | A1 | 6/2010 | Havenga et al. |
| 2011/0150915 | A1 | 6/2011 | Korber et al. |
| 2011/0250220 | A1 | 10/2011 | Dey et al. |
| 2011/0301328 | A1 | 12/2011 | Korber et al. |
| 2011/0305749 | A1 | 12/2011 | Duch et al. |
| 2012/0045472 | A1 | 2/2012 | Harrison et al. |
| 2013/0189754 | A1 | 7/2013 | Parks et al. |
| 2014/0302080 | A1 | 10/2014 | Barouch et al. |
| 2014/0335126 | A1 | 11/2014 | Haynes et al. |
| 2014/0348791 | A1 | 11/2014 | Barouch et al. |
| 2015/0291935 | A1 | 10/2015 | Barouch et al. |

FOREIGN PATENT DOCUMENTS

| | | | |
|---|---|---|---|
| WO | WO-2006/040330 | A2 | 4/2006 |
| WO | WO-2007/024941 | A2 | 3/2007 |
| WO | WO-2007/104792 | A2 | 9/2007 |
| WO | WO-2007/149491 | A2 | 12/2007 |
| WO | WO-2010/019262 | A2 | 2/2010 |
| WO | WO-2010/042817 | A1 | 4/2010 |
| WO | WO-2010/042942 | A2 | 4/2010 |
| WO | WO-2010/059732 | A1 | 5/2010 |
| WO | WO-2010/096561 | A1 | 8/2010 |
| WO | WO-2011/139385 | A2 | 11/2011 |
| WO | WO-2012/030904 | A2 | 3/2012 |
| WO | WO-2013/055908 | A1 | 4/2013 |
| WO | WO-2014/047261 | A1 | 3/2014 |
| WO | WO-2015/048770 | A2 | 4/2015 |
| WO | WO-2015/051270 | A1 | 4/2015 |
| WO | WO-2015/095499 | A1 | 6/2015 |
| WO | WO2016/037154 | * | 3/2016 |
| WO | WO-2016/037154 | A1 | 3/2016 |

OTHER PUBLICATIONS

Mayr et al., "Epitope mapping of conformational V2-specific anti-HIV human monoclonal antibodies reveals an immunodominant site in V2," PLoS One. 8(7):e70859 (2013) (9 pages).

Weng et al., "Mutational analysis of residues in the coiled-coil domain of human immunodeficiency virus type 1 transmembrane protein gp41," J Virol. 72(12):9676-82 (1998).

Bricault et al., "Antibody Signature-based Design of HIV-1 ENV gp140 Expands Tier 2 Neutralizing Antibody Breadth in Guinea Pigs," AIDS Res Hum Retrovir. 32:77 (2016).

Bricault et al., "HIV-1 Neutralizing Antibody Signatures and Application to Epitope-Targeted Vaccine Design," Cell Host Microbe. 25(1):59-72 (2019) (23 pages).

EMBL Database Accession No. EMBL:AAC32935, "Human immunodeficiency virus 1 partial envelope glycoprotein," Sep. 4, 1998, available <www.ebi.ac.uk/ena/data/view/AAC32935>, retrieved Apr. 27, 2020 (1 page).

Extended European Search Report for European Patent Application No. 17861431.9, dated May 8, 2020 (16 pages).

Rademeyer et al., "Features of Recently Transmitted HIV-1 Clade C Viruses That Impact Antibody Recognition: Implications for Active and Passive Immunization," PLoS Pathog. 12(7):e1005742 (2016) (29 pages).

UniProtKB Accession No. G9IPE1_9HIV1, Feb. 22, 2012, available <www.uniprot.org/uniprot/G9IPE1> (6 pages).

UniProtKB Accession No. C6FXK1_9HIV1, Sep. 1, 2009, available <www.uniprot.org/uniprot/C6FXK1> (6 pages).

UniProtKB Accession No. E1B4A5_9HIV1, Nov. 2, 2010, available <www.uniprot.org/uniprot/E1B4A5> (1 page).

UniProtKB Accession No. S4SWB9_9HIV1, Oct. 16, 2013, available <www.uniprot.org/uniprot/S4SWB9> (6 pages).

UniProtKB Database Accession No. A1XI08_9HIV1, Feb. 6, 2007, available <www.uniprot.org/uniprot/A1XI08> (2 pages).

International Search Report and Written Opinion for International Application No. PCT/US17/57045, dated Feb. 28, 2018 (17 pages).

Blondelle et al., "Immunogenically optimized peptides derived from natural mutants of HIV CTL epitopes and peptide combinatorial libraries," Biopolymers. 90(5):683-694 (2008).

Fischer et al., "Coping with viral diversity in HIV vaccine design: A response to Nickle et al.," PLoS Comput Biol. 4(1):e15 (2008) (5 pages).

Fischer et al., "Polyvalent vaccines for optimal coverage of potential T-cell epitopes in global HIV-1 variants," Nat Med. 13(1):100-106 (2007).

Kong et al., "Expanded breadth of the T-cell response to mosaic human immunodeficiency virus type 1 envelope DNA vaccination," J Virol. 83(5):2201-2215 (2009).

Korber et al., "T-Cell vaccine strategies for human immunodeficiency virus, the virus with a thousand faces," J Virol. 83(17):8300-8314 (2009).

NCBI Blast for Accession No. AAY23526. Retrieved on Feb. 13, 2010 (2 pages).

Thurmond et al., "Web-based design and evaluation of T-cell vaccine candidates," Bioinformatics. 24(14):1639-1640 (2008).

English Translation of the Office Action in Chinese Patent Application No. 200980154787.4 dated Feb. 7, 2014 (5 pages).

Communication Pursuant to Rules 161 (2) and 162 EPC for European Patent Application No. 09828172.8, dated Jul. 4, 2011 (2 pages).

Extended European Search Report for European Patent Application No. 09828172.8, dated Jul. 1, 2013 (16 pages).

First Examination Report for New Zealand Patent Application No. 593598, dated Jul. 7, 2011 (3 pages).

First Examination Report for New Zealand Patent Application No. 602504, dated Sep. 24, 2012 (4 pages).

Second Examination Report for New Zealand Patent Application No. 593598, dated Oct. 9, 2012 (3 pages).

Third Examination Report for New Zealand Patent Application No. 593598, dated Dec. 21, 2012 (1 page).

English Translation of the Notification of the First Office Action for Chinese Patent Application No. 200980154787.4, dated Mar. 7, 2013 (4 pages).

International Search Report for International Application No. PCT/US2009/064999, dated Mar. 5, 2010 (4 pages).

International Preliminary Report on Patentability and Written Opinion of the International Searching Authority for International Application No. PCT/US2009/064999, dated May 24, 2011 (9 pages).

Barouch, "Challenges in the development of an HIV-1 vaccine" Nature. 455(7213):613-9 (2008).

Cohen, J. "AIDS research. Did Merck's failed HIV vaccine cause harm?" Science. 318(5853):1048-9 (2007).

Girard, et al. "A review of vaccine research and development: the human immunodeficiency virus (HIV)" Vaccine. 24(19):4062-81 (2006).

Gotch, et al. "Candidate vaccines for immunotherapy in HIV" HIV Med. 2(4):260-5 (2001).

Office Action in Japanese Patent Application No. 2011-537586 dated May 27, 2014 (with English Translation) (4 pages).

Examination Report for Singapore Patent Application No. 201103573-0, dated Sep. 8, 2014 (13 pages).

(56) References Cited

OTHER PUBLICATIONS

Examination and Search Report for African Regional Intellectual Property Organization Patent Application No. AP/P/2011/005767, dated Mar. 19, 2015 (8 pages).
Examination Report for African Regional Intellectual Property Organization Patent Application No. AP/P/2011/005767, dated Oct. 8, 2015 (5 pages).
Examination Report for Australian Patent Application No. 2009316629, dated Dec. 17, 2014 (4 pages).
Fourth Office Action for Chinese Patent Application No. 200980154787.4, dated Apr. 3, 2015 (7 pages).
Communication pursuant to Rules 70(2) and 70a(2) EPC for European Application No. 09828172.8, dated Jul. 18, 2013 (1 page).
Office Action for Israeli Patent Application No. 212984, dated Oct. 14, 2014 (6 pages).
Office Action for Israeli Patent Application No. 212984, dated Oct. 14, 2015 (6 pages).
Office Action for Israeli Patent Application No. 212984, dated Aug. 26, 2013 (4 pages).
Office Action for Japanese Patent Application No. 2015-021128, dated Dec. 15, 2015 (7 pages).
Abbink et al., "Comparative seroprevalence and immunogenicity of six rare serotype recombinant adenovirus vaccine vectors from subgroups B and D," J Virol. 81(9):4654-63 (2007).
Abrahams et al., "Quantitating the multiplicity of infection with human immunodeficiency virus type 1 subtype C reveals a non-poisson distribution of transmitted variants," J Virol. 83(8):3556-67 (2009).
Barouch et al., "Dynamic immune responses maintain cytotoxic T lymphocyte epitope mutations in transmitted simian immunodeficiency virus variants," Nat Immunol. 6(3):247-52 (2005).
Barouch, "Novel adenovirus vector-based vaccines for HIV-1," available in PMC Sep. 1, 2011, published in final edited form as: Curr Opin HIV AIDS. 5(5):386-90 (2010) (8 pages).
Barouch et al., "Mosaic HIV-1 vaccines expand the breadth and depth of cellular immune responses in rhesus monkeys," available in PMC Sep. 1, 2010, published in final edited form as: Nat Med. 16(3):319-23 (2010) (14 pages).
Barouch et al., "International seroepidemiology of adenovirus serotypes 5, 26, 35, and 48 in pediatric and adult populations," Vaccine. 29(32):5203-9 (2011) (14 pages).
Barouch et al.,"HIV-1 vaccine development after STEP," available in PMC Jan. 1, 2011, published in final edited form as: Annu Rev Med. 61:153-67 (2010) (19 pages).
Barouch et al., "Adenovirus vector-based vaccines for human immunodeficiency virus type 1," Hum Gene Ther. 16(2):149-56 (2005).
Barouch et al., "Immunogenicity of recombinant adenovirus serotype 35 vaccine in the presence of pre-existing anti-Ad5 immunity," J Immunol. 172(10):6290-7 (2004) (9 pages).
Barouch et al., "Vaccine protection against acquisition of neutralization-resistant SIV challenges in rhesus monkeys," Nature. 482(7383):89-93 (2012) (6 pages).
Beerenwinkel et al., "Computational methods for the design of effective therapies against drug resistant HIV strains," Bioinformatics. 21(21):3943-50 (2005).
Burgers et al., "Measurements of immune responses for establishing correlates of vaccine protection against HIV," AIDS Res Hum Retroviruses. 27(00):1-8 (2011).
Cao et al., "Cytotoxic T-lymphocyte cross-reactivity among different human immunodeficiency virus type 1 clades: implications for vaccine development," J Virol. 71(11):8615-23 (1997).
Engelhardt et al., "Ablation of E2A in recombinant adenoviruses improves transgene persistence and decreases inflammatory response in mouse liver," Proc Natl Acad Sci USA. 91(13):6196-200 (1994).
Frahm et al., "Increased detection of HIV-specific T cell responses by combination of central sequences with comparable immunogenicity," AIDS. 22(4):447-56 (2008).
Frahm et al., "Consistent cytotoxic-T-lymphocyte targeting of immunodominant regions in human immunodeficiency virus across multiple ethnicities," J Virol. 78(5):2187-200 (2004).
Frahm et al., "Control of human immunodeficiency virus replication by cytotoxic T lymphocytes targeting subdominant epitopes," Nat Immunol. 7:173-8 (2006).
Gao et al., "Broadly reactive monoclonal antibodies to multiple HIV-1 subtype and SIVcpz envelope glycoproteins," available in PMC Nov. 10, 2010, published in final edited form as: Virology. 394(1):91-8 (2009) (16 pages).
Gao et al., "Centralized HIV-1 envelope immunogens and neutralizing antibodies," Curr HIV Res. 5(6):572-7 (2007).
Gao et al., "Antigenicity and immunogenicity of a synthetic human immunodeficiency virus type 1 group m consensus envelope glycoprotein," J Virol. 79(2):1154-63 (2005).
Genbank Accession No. AAY23526. Retrieved on Feb. 13, 2010<http://www.ncbi.nlm.nih.gov/protein/62956393> (2 pages).
Gnanakaran et al., "Genetic signatures in the envelope glycoproteins of HIV-1 that associate with broadly neutralizing antibodies," PLoS Comput Biol. 6(10):e1000955 (2010) (26 pages).
Hudgens et al., "Power to detect HIV vaccine effects in repeated low-dose challenge experiments," available in PMC Aug. 15, 2010, published in final edited form as: J Infect Dis. 200(4):609-13 (2009) (8 pages).
Haynes et al., "Analysis of HIV-1 subtype B third variable region peptide motifs for induction of neutralizing antibodies against HIV-1 primary isolates," Virology. 345(1):44-55 (2006).
Hulot et al., "Vaccine-induced CD8+ T lymphocytes of rhesus monkeys recognize variant forms of an HIV epitope but do not mediate optimal functional activity," J Immunol. 186(10):5663-74 (2011).
Kaufman et al., "Route of adenovirus-based HIV-1 vaccine delivery impacts the phenotype and trafficking of vaccine-elicited CD8+ T lymphocytes," J Virol. 84(12):5986-96 (2010).
Kaufman et al., "Focus and breadth of cellular immune responses elicited by a heterologous insert prime-boost vaccine regimen in rhesus monkeys," Vaccine. 30(3):506-9 (2012).
Kaufman et al., "Translational Mini-Review Series on Vaccines for HIV: T lymphocyte trafficking and vaccine-elicited mucosal immunity," Clin Exp Immunol. 157(2):165-73 (2009).
Korber et al., "The implications of patterns in HIV diversity for neutralizing antibody induction and susceptibility," Curr Opin HIV AIDS. 4(5):408-17 (2009).
Kothe et al., "Antigenicity and immunogenicity of HIV-1 consensus subtype B envelope glycoproteins," available in PMC Mar. 30, 2008, published in final edited form as: Virology. 360(1):218-34 (2007) (29 pages).
Kothe et al., "Ancestral and consensus envelope immunogens for HIV-1 subtype C," Virology. 352(2):438-49 (2006).
Koup et al., "Priming immunization with DNA augments immunogenicity of recombinant adenoviral vectors for both HIV-1 specific antibody and T-cell responses," PLoS One. 5(2):e9015 (2010) (15 pages).
Kulkarni et al., "Highly complex neutralization determinants on a monophyletic lineage of newly transmitted subtype C HIV-1 Env clones from India," available in PMC Mar. 15, 2010, published in final edited form as: Virology. 385(2):505-20 (2009) (33 pages).
Launay et al., "Immunological efficacy of a three-dose schedule of hepatitis A vaccine in HIV-infected adults: HEPAVAC study," J Acquir Immune Defic Syndr. 49(3):272-5 (2008).
Létourneau et al., "Design and pre-clinical evaluation of a universal HIV-1 vaccine," PLoS One. 2(10):e984 (2007) (11 pages).
Li et al., "Mapping HIV-1 vaccine induced T-cell responses: bias towards less-conserved regions and potential impact on vaccine efficacy in the Step study," PLoS One. 6(6):e20479 (2011) (9 pages).
Li et al., "Genetic and neutralization properties of subtype C human immunodeficiency virus type 1 molecular env clones from acute and early heterosexually acquired infections in Southern Africa," J Virol. 80(23):11776-90 (2006).
Liao et al., "A group M consensus envelope glycoprotein induces antibodies that neutralize subsets of subtype B and C HIV-1 primary

(56) References Cited

OTHER PUBLICATIONS viruses," available in PMC Sep. 30, 2007, published in final edited form as: Virology. 353(2):268-82 (2006) (30 pages).
Liu et al., "Immune control of an SIV challenge by a T-cell-based vaccine in rhesus monkeys," available in PMC Jul. 1, 2009, published in final edited form as: Nature. 457(7225):87-91 (2009) (13 pages).
Liu et al., "Magnitude and phenotype of cellular immune responses elicited by recombinant adenovirus vectors and heterologous prime-boost regimens in rhesus monkeys," J Virol. (82)10:4844-52 (2008).
Liu et al., "Modulation of DNA vaccine-elicited CD8+ T-lymphocyte epitope immunodominance hierarchies," J Virol. 80(24):11991-7 (2006).
Masek-Hammerman et al., "Mucosal trafficking of vector-specific CD4+ T lymphocytes following vaccination of rhesus monkeys with adenovirus serotype 5," J Virol. 84(19):9810-6 (2010).
Moore et al., "Inter- and intraclade neutralization of human immunodeficiency virus type 1: genetic clades do not correspond to neutralization serotypes but partially correspond to gp120 antigenic serotypes," J Virol. 70(1):427-44 (1996).
Mothe et al., "Definition of the viral targets of protective HIV-1-specific T cell responses," J Transl Med. 9:208 (2011) (20 pages).
Nanda et al., "Immunogenicity of recombinant fiber-chimeric adenovirus serotype 35 vector-based vaccines in mice and rhesus monkeys," J Virol. 79(22):14161-8 (2005).
Ndhlovu et al., "Mosaic HIV-1 Gag antigens can be processed and presented to human HIV-specific CD8+ T cells," available in PMC Dec. 15, 2011, published in final edited form as: J Immunol. 186(12):6914-24 (2011) (24 pages).
Nkolola et al., "Breadth of neutralizing antibodies elicited by stable, homogeneous clade A and clade C HIV-1 gp140 envelope trimers in guinea pigs," J Virol. 84(7):3270-9 (2010).
O'Brien et al., "Adenovirus-specific immunity following immunization with an Ad5 HIV-1 vaccine candidate in humans," available in PMC Feb. 1, 2010, published in final edited form as: Nat Med. 15(8):873-5 (2009) (8 pages).
Priddy et al., "Safety and immunogenicity of a replication-incompetent adenovirus type 5 HIV-1 clade B gag/pol/nef vaccine in healthy adults," Clin Infect Dis. 46(11):1769-81 (2008).
Rhee et al., "Translational Mini-Review Series on Vaccines for HIV: Harnessing innate immunity for HIV vaccine development," Clin Exp Immunol. 157(2):174-80 (2009).
Roberts et al., "Hexon-chimaeric adenovirus serotype 5 vectors circumvent pre-existing anti-vector immunity," Nature. 441 (7090):239-43 (2006).
Salazar-Gonzalez et al., "Deciphering human immunodeficiency virus type 1 transmission and early envelope diversification by single-genome amplification and sequencing," J Virol. 82(8):3952-70 (2008).
Santra et al., "Mosaic vaccines elicit CD8+ T lymphocyte responses in monkeys that confer enhanced immune coverage of diverse HIV strains," available in PMC Sep. 1, 2010, published in final edited form as: Nat Med. 16(3):324-8 (2010) (12 pages).
Santra et al., "A centralized gene-based HIV-1 vaccine elicits broad cross-clade cellular immune responses in rhesus monkeys," Proc Natl Acad Sci U S A. 105(30):10489-94 (2008).
Santra et al., "Replication-defective adenovirus serotype 5 vectors elicit durable cellular and humoral immune responses in nonhuman primates," J Virol. 79(10):6516-22 (2005).
Seaman et al., "Tiered categorization of a diverse panel of HIV-1 Env pseudoviruses for assessment of neutralizing antibodies," J Virol. 84(3):1439-52 (2010).
Sumida et al., "Neutralizing antibodies and CD8+ T lymphocytes both contribute to immunity to adenovirus serotype 5 vaccine vectors," J Virol. 78(6):2666-73 (2004).
Sumida et al., "Neutralizing antibodies to adenovirus serotype 5 vaccine vectors are directed primarily against the adenovirus hexon protein," J Immunol. 174(11):7179-85 (2005).

Tang et al., "Epitopes immediately below the base of the V3 loop of gp120 as targets for the initial autologous neutralizing antibody response in two HIV-1 subtype B-infected individuals," J Virol. 85(18):9286-99 (2011).
Weaver et al., "Cross-subtype T-cell immune responses induced by a human immunodeficiency virus type 1 group m consensus env immunogen," J Virol. 80(14):6745-56 (2006).
Yusim et al., "Genotype 1 and global hepatitis C T-cell vaccines designed to optimize coverage of genetic diversity," J Gen Virol. 91( Pt 5):1194-206 (2010).
Doria-Rose et al., "Breadth of human immunodeficiency virus-specific neutralizing activity in sera: clustering analysis and association with clinical variables," J. Virol. 84(3):1631-6 (2010).
Kochanek et al., "A new adenoviral vector: Replacement of all viral coding sequences with 28 kb of DNA independently expressing both full-length dystrophin and beta-galactosidase," Proc Natl Acad Sci U.S.A. 93(12):5731-6 (1996).
Fynan et al., "DNA vaccines: protective immunizations by parenteral, mucosal, and gene-gun inoculations," Proc Natl Acad Sci U.S.A. 90(24):11478-82 (1993).
Mangeat et al., "Lentiviral vectors and antiretroviral intrinsic immunity," Hum Gene Ther. 16(8):913-20 (2005).
Wiznerowicz et al., "Harnessing HIV for therapy, basic research and biotechnology," Trends Biotechnol. 23(1):42-7 (2005).
Wattanapitayakul et al., "Recent developments in gene therapy for cardiac disease," Biomed Pharmacother. 54(10):487-504 (2000).
Cohen, J. "Naked DNA points way to vaccines," Science. 259(5102):1691-2 (1993).
Stemmer et al., "Single-step assembly of a gene and entire plasmid from large numbers of oligodeoxyribonucleotides," Gene. 164(1):49-53 (1995).
Matthews et al., "Prospects for development of a vaccine against HTLV-III-related disorders," Aids Res Hum Retroviruses. 3(1):197-206. (1987).
International Search Report for International Application No. PCT/US2014/010543 dated Mar. 21, 2014 (5 pages).
Written Opinion of the International Searching Authority for International Application No. PCT/US2014/010543 dated Mar. 21, 2014 (6 pages).
International Preliminary Report on Patentability for International Application No. PCT/US2014/010543, dated Mar. 21, 2014 (7 pages).
Lee et al., "A single point mutation in HIV-1 V3 loop alters the immunogenic properties of rgp120," Arch Virol. 145(10):2087-103 (2000).
Watkins et al., "Immune escape by human immunodeficiency virus type 1 from neutralizing antibodies: evidence for multiple pathways," J Virol. 67(12):7493-500 (1993).
Walker et al., "Toward an AIDS vaccine," Science 320(5877)760-4 (2008).
McElrath et al., "Induction of immunity to human immunodeficiency virus type-1 by vaccination," Immunity 33(4):542-54 (2010).
Jeffs et al., "Expression and characterisation of recombinant oligomeric envelope glycoproteins derived from primary isolates of HIV-1," Vaccine. 22(8):1032-46 (2004).
Chen et al., "Expression, purification, and characterization of gp160e, the soluble, trimeric ectodomain of the simian immunodeficiency virus envelope glycoprotein, gp160," J Biol Chem. 275(45):34946-53 (2000).
Search Report and Written Opinion for Singaporean Patent Application No. 11201505229X, dated May 5, 2016 (9 pages).
International Search Report and Written Opinion for International Patent Application No. PCT/US2014/059093, dated Jan. 22, 2015 (12 pages).
McGuire et al., "Engineering HIV envelope protein to activate germline B cell receptors of broadly neutralizing anti-CD4 binding site antibodies," J Exp Med. 210(4):655-63 (2013).
GenBank Accession No. KC769514. Retrieved on Dec. 30, 2014 (2 pages).
International Preliminary Report on Patentability for International Patent Application No. PCT/US2014/059093, dated Apr. 5, 2016 (7 pages).

(56) References Cited

OTHER PUBLICATIONS

Yang et al., "Highly stable trimers formed by human immunodeficiency virus type 1 envelope glycoproteins fused with the trimeric motif of t4 bacteriophage fibritin," J Virol. 76(9):4634-42 (2002).
Chen et al., "A chimeric protein of simian immunodeficiency virus envelope glycoprotein gp140 and *Escherichia coli* aspartate transcarbamoylase," J Virol. 78(9):4508-16 (2004).
Fischer et al., "Polyvalent vaccines for optimal coverage of potential T-cell epitopes in global HIV-1 variants," Nat Med. 13(1):100-6 (2007).
Cohen, "Naked DNA pointsway to vaccines," Science. 259(5102):1691-2 (1993).
Mascola et al., "Protection of Macaques against pathogenic simian/human immunodeficiency virus 89.6PD by passive transfer of neutralizing antibodies," J Virol. 73(5):4009-18 (1999).
Frey et al., "A fusion-intermediate state of HIV-1 gp41 targeted by broadly neutralizing antibodies," Proc Natl Acad Sci USA. 105(10):3739-44 (2008).
Nkolola et al., "Characterization and immunogenicity of a novel mosaic M HIV-1 gp140 trimer," J Virol. 88(17):9538-52 (2014).
Freeman et al., "Crystal structure of HIV-1 primary receptor CD4 in complex with a potent antiviral antibody," Structure. 18(12):1632-41 (2010).
Kovacs et al., "HIV-1 envelope trimer elicits more potent neutralizing antibody responses than monomeric gp120," Proc Natl Acad Sci USA. 109(30):12111-6 (2012).
Walker et al., "Broad and potent neutralizing antibodies from an African donor reveal a new HIV-1 vaccine target," Science. 326(5950):285-9 (2009).
Davenport et al., "Binding interactions between soluble HIV envelope glycoproteins and quaternary-structure-specific monoclonal antibodies PG9 and PG16," J Virol. 85(14):7095-107 (2011).
Julien et al., "Asymmetric recognition of the HIV-1 trimer by broadly neutralizing antibody PG9," Proc Natl Acad Sci USA. 110(11):4351-6 (2013).
Mouquet et al., "Complex-type N-glycan recognition by potent broadly neutralizing HIV antibodies," Proc Natl Acad Sci U.S.A. 109(47):E3268-77 (2012).
Julien et al., "Broadly neutralizing antibody PGT121 allosterically modulates CD4 binding via recognition of the HIV-1 gp120 V3 base and multiple surrounding glycans," PLoS Pathog. 9(5):e1003342 (2013) (15 pages).
Scheid et al., "Sequence and structural convergence of broad and potent HIV antibodies that mimic CD4 binding," Science. 333(6049):1633-7 (2011).
Cardoso et al., "Broadly neutralizing anti-HIV antibody 4E10 recognizes a helical conformation of a highly conserved fusion-associated motif in gp41," Immunity. 22(2):163-73 (2005).
Wu et al., "Rational design of envelope identifies broadly neutralizing human monoclonal antibodies to HIV-1," Science. 329(5993):856-61 (2010).
Huang et al., "Broad and potent neutralization of HIV-1 by a gp41-specific human antibody," Nature. 491(7424):406-12 (2012).
Plotkin et al., "Postscript relating to new allegations made by Edward Hooper at The Royal Society Discussion Meeting on Sep. 11, 2000," Philos Trans R Soc Lond B Biol Sci. 356(1410):825-9(2001).
Mascola et al., "Protection of macaques against vaginal transmission of a pathogenic HIV-1/SIV chimeric virus by passive infusion of neutralizing antibodies," Nat Med. 6(2):207-10 (2000).
Ofek et al., "Structure and mechanistic analysis of the anti-human immunodeficiency virus type 1 antibody 2F5 in complex with its gp41 epitope," J Virol. 78(19):10724-37 (2004).
Falkowska et al., "PGV04, an HIV-1 gp120 CD4 binding site antibody, is broad and potent in neutralization but does not induce conformational changes characteristic of CD4," J Virol. 86(8):4394-403 (2012).

Doores et al., "Antibody 2G12 recognizes di-mannose equivalently in domain- and nondomain-exchanged forms but only binds the HIV-1 glycan shield if domain exchanged," J Virol. 84(20):10690-9 (2010).
Pancera et al., "Structure of HIV-1 gp120 with gp41-interactive region reveals layered envelope architecture and basis of conformational mobility," Proc Natl Acad Sci USA. 107(3):1166-71 (2010).
Yang et al., "Improved elicitation of neutralizing antibodies against primary human immunodeficiency viruses by soluble stabilized envelope glycoprotein trimers," J Virol. 75(3): 1165-71 (2001).
Grundner et al., "Analysis of the neutralizing antibody response elicited in rabbits by repeated inoculation with trimeric HIV-1 envelope glycoproteins," Virology. 331(1):33-46 (2005).
Cho et al., "Polyvalent envelope glycoprotein vaccine elicits a broader neutralizing antibody response but is unable to provide sterilizing protection against heterologous Simian/human immunodeficiency virus infection in pigtailed macaques," J Virol. 75(5):2224-34 (2001).
Seaman et al., "Multiclade human immunodeficiency virus type 1 envelope immunogens elicit broad cellular and humoral immunity in rhesus monkeys," J Virol. 79(5):2956-63 (2005).
Wang et al., "Polyvalent HIV-1 Env vaccine formulations delivered by the DNA priming plus protein boosting approach are effective in generating neutralizing antibodies against primary human immunodeficiency virus type 1 isolates from subtypes A, B, C, D and E," Virology. 350(1):34-47 (2006).
Vaine et al., "Profiles of human serum antibody responses elicited by three leading HIV vaccines focusing on the induction of Env-specific antibodies," PLoS One. 5(11):e13916 (2010) (8 pages).
Malherbe et al., "Sequential immunization with a subtype B HIV-1 envelope quasispecies partially mimics the in vivo development of neutralizing antibodies," J Virol. 85(11):5262-74 (2011).
McCoy et al., "Potent and broad neutralization of HIV-1 by a llama antibody elicited by immunization," J Exp Med. 209(6):1091-103 (2012).
McBurney et al., "Evaluation of heterologous vaginal SHIV SF162p4 infection following vaccination with a polyvalent Clade B virus-like particle vaccine," AIDS Res Hum Retroviruses. 28(9):863-72 (2012).
Gray et al., "Isolation of a monoclonal antibody that targets the alpha-2 helix of gp120 and represents the initial autologous neutralizing-antibody response in an HIV-1 subtype C-infected individual," J Virol. 85(15):7719-29 (2011).
Li et al., "Evidence for potent autologous neutralizing antibody titers and compact envelopes in early infection with subtype C human immunodeficiency virus type 1," J Virol. 80(11):5211-8 (2006).
Pejchal et al., "Structure and function of broadly reactive antibody PG16 reveal an H3 subdomain that mediates potent neutralization of HIV-1," Proc Natl Acad Sci USA. 107(25):11483-8 (2010).
Pancera et al., "Crystal structure of PG16 and chimeric dissection with somatically related PG9: structure-function analysis of two quaternary-specific antibodies that effectively neutralize HIV-1," J Virol. 84(16):8098-110 (2010).
Li et al., "Removal of a single N-linked glycan in human immunodeficiency virus type 1 gp120 results in an enhanced ability to induce neutralizing antibody responses," J Virol. 82(2):638-51 (2008).
Lynch et al., "The development of CD4 binding site antibodies during HIV-1 infection," J Virol. 86(14):7588-95 (2012).
Gao et al., "Molecular cloning and analysis of functional envelope genes from human immunodeficiency virus type 1 sequence subtypes A through G," J Virol. 70(3):1651-67 (1996).
Li et al., "Human immunodeficiency virus type 1 env clones from acute and early subtype B infections for standardized assessments of vaccine-elicited neutralizing antibodies," J Virol. 79(16):10108-25 (2005).
Fiebig et al., "Neutralizing antibodies against conserved domains of p15E of porcine endogenous retroviruses: basis for a vaccine for xenotransplantation?" Virology. 307(2):406-13 (2003).
Plotkin, "Correlates of Protection Induced by Vaccination," Clin Vaccine Immunol. 17(7):1055-65 (2010).

(56) References Cited

OTHER PUBLICATIONS

Amanna et al., "Contributions of humoral and cellular immunity to vaccine-induced protection in humans," Virology. 411(2):206-15 (2011).
Rerks-Ngarm et al., "Vaccination with ALVAC and AIDSVAX to prevent HIV-1 infection in Thailand," N Engl J Med. 361(23):2209-20 (2009).
Haynes et al., "Immune-correlates analysis of an HIV-1 vaccine efficacy trial," N Engl J Med. 366(14):1275-86 (2012).
Hammer et al., "Efficacy trial of a DNA/rAd5 HIV-1 preventive vaccine," N Engl J Med. 369(22):2083-92 (2013).
Stamatatos et al., "Neutralizing antibodies generated during natural HIV-1 infection: good news for an HIV-1 vaccine?," Nat Med. 15(8):866-70 (2009).
Doria-Rose et al., "Frequency and phenotype of human immunodeficiency virus envelope-specific B cells from patients with broadly cross-neutralizing antibodies," J Virol. 83(1):188-99 (2009).
Simek et al., "Human immunodeficiency virus type 1 elite neutralizers: individuals with broad and potent neutralizing activity identified by using a high-throughput neutralization assay together with an analytical selection algorithm," J Virol. 83(14):7337-48 (2009).
Walker et al., "Broad neutralization coverage of HIV by multiple highly potent antibodies," available in PMC Jul. 10, 2012, published in final edited form as: Nature. 477(7365):466-70 (2011) (14 pages).
Li et al., "Characterization of antibody responses elicited by human immunodeficiency virus type 1 primary isolate trimeric and monomeric envelope glycoproteins in selected adjuvants," J Virol. 80(3):1414-26 (2006).
Yasmeen et al., "Differential binding of neutralizing and non-neutralizing antibodies to native-like soluble HIV-1 Env trimers, uncleaved Env proteins, and monomeric subunits," Retrovirology. 11:41 (2014) (17 pages).
Liao et al., "Antigenicity and immunogenicity of transmitted/founder, consensus, and chronic envelope glycoproteins of human immunodeficiency virus type 1," J Virol. 87(8):4185-201 (2013).
Baba et al., "Human neutralizing monoclonal antibodies of the IgG1 subtype protect against mucosal simian-human immunodeficiency virus infection," Nat Med. 6(2):200-6 (2000).
Graham et al., "Phase 1 safety and immunogenicity evaluation of a multiclade HIV-1 DNA candidate vaccine," J Infect Dis. 194(12):1650-60 (2006).
Calarese et al., "Antibody domain exchange is an immunological solution to carbohydrate cluster recognition," Science. 300(5628):2065-71 (2003).
Burke et al., "Neutralizing antibody responses to subtype B and C adjuvanted HIV envelope protein vaccination in rabbits," Virology. 387(1):147-56 (2009).
Wang et al., "Enhanced immunogenicity of gp120 protein when combined with recombinant DNA priming to generate antibodies that neutralize the JR-FL primary isolate of human immunodeficiency virus type 1," J Virol. 79(12):7933-7 (2005).
Gaschen et al., "Diversity consideration in HIV-1 vaccine selection," Science. 296(5577):2354-60 (2002).
Kwong et al., "Structure of an HIV gp120 envelope glycoprotein in complex with the CD4 receptor and a neutralizing human antibody," Nature. 393(6686):648-59 (1998).
Pejchal et al., "A potent and broad neutralizing antibody recognizes and penetrates the HIV glycan shield," Science. 334(6059):1097-103 (2011).
Plotkin, "The RV144 Thai HIV vaccine trial," Hum Vaccin. 6(2):159 (2010).
Seaman et al., "Standardized assessment of NAb responses elicited in rhesus monkeys immunized with single- or multi-clade HIV-1 envelope immunogens," Virology. 367(1):175-86 (2007).
Sok et al., "Promiscuous glycan site recognition by antibodies to the high-mannose patch of gp120 broadens neutralization of HIV," Sci Transl Med. 6(236):236ra63 (2014) (13 pages).
Buchbinder et al., "Efficacy assessment of a cell-mediated immunity HIV-1 vaccine (the Step Study): a double-blind, randomised, placebo-controlled, test-of-concept trial," available in PMC Nov. 29, 2009, published in final edited form as: Lancet. 372(9653):1881-93 (2008) (25 pages).
Catanzaro et al., "Phase I clinical evaluation of a six-plasmid multiclade HIV-1 DNA candidate vaccine," Vaccine. 25(20):4085-92 (2007).
Cardoso et al., "Structural basis of enhanced binding of extended and helically constrained peptide epitopes of the broadly neutralizing HIV-1 antibody 4E10," J Mol Biol. 365(5):1533-44 (2007).
Checkley et al., "HIV-1 Envelope Glycoprotein Biosynthesis, Trafficking, and Incorporation," available in PMC Jul. 22, 2012, published in final edited form as: J Mol Biol. 410(4):582-608 (2011) (40 pages).
Fischer et al., "Identification of a peptide mimicking the binding pattern of an antiphospholipid antibody," Immunobiology. 211(9):695-99 (2006).
Georgiev et al., "Delineating antibody recognition in polyclonal sera from patterns of HIV-1 isolate neutralization," Science. 340(6133)751-6 (2013).
Gray et al., "Safety and efficacy of the HVTN 503/Phambili study: a double-blind randomized placebo-controlled test-of-concept study of a clade b-based HIV-1 vaccine in south africa," available in PMC Aug. 13, 2012, published in final edited form as: Lancet Infect Dis. 11 (7):507-15 (2011) (19 pages).
Kim et al., "Comparison of HIV Type 1 ADA gp120 monomers versus gp140 trimers as immunogens for the induction of neutralizing antibodies," Aids Res Hum Retroviruses. 21(1):58-67 (2005).
Li et al., "Broad HIV-1 neutralization mediated by CD4-binding site antibodies," available in PMC Nov. 19, 2008, published in final edited form as: Nat Med. 13(9):1032-4 (2007) (7 pages).
Liao et al., "Co-evolution of a broadly neutralizing HIV-1 antibody and founder virus," available in PMC Oct. 25, 2013, published in final edited form as: Nature. 496(7446):469-76 (2013) (25 pages).
Lin et al., "Designing immunogens to elicit broadly neutralizing antibodies to the HIV-1 envelope glycoprotein," Curr HIV Res. 5(6):514-41 (2007).
McBurney et al., "Human immunodeficiency virus-like particles with consensus envelopes elicited broader cell-mediated peripheral and mucosal immune responses than polyvalent and monovalent Env vaccines," Vaccine. 27(32):4337-49 (2009).
McLellan et al., "Structure of HIV-1 gp120 V1/V2 domain with broadly neutralizing antibody PG9," available in PMC Dec. 15, 2012, published in final edited form as: Nature. 480(7377):336-43 (2011) (17 pages).
Montefiori, "Evaluating neutralizing antibodies against HIV, SIV, and SHIV in luciferase reporter gene assays," Curr Protoc Immunol. 12:Unit 12.11 (2005) (17 pages).
Pinter, "Roles of HIV-1 Env variable regions in viral neutralization and vaccine development," Curr HIV Res. 5(6):542-53 (2007).
Plotkin, "Immunologic correlates of protection induced by vaccination," Pediatr Infect Dis J. 20(1):63-75 (2001).
Rodenburg et al., "Near full-length clones and reference sequences for subtype C isolates of HIV type 1 from three different continents," AIDS Res Hum Retrovirsuses. 17(2):161-8 (2001).
Saphire et al., "Crystal structure of a neutralizing human IgG against HIV-1: a template for vaccine design," Science. 293(5532):1155-9 (2001).
Wang et al., "Cross-subtype antibody and cellular immune responses induced by a polyvalent DNA prime-protein boost HIV-1 vaccine in healthy human volunteers," available in PMC Aug. 14, 2013, published in final edited form as: Vaccine. 26(31):3947-57 (2008) (22 pages).
Vaine et al., "Antibody responses elicited through homologous or heterologous prime-boost DNA and protein vaccinations differ in functional activity and avidity," available in PMC Apr. 9. 2011, published in final edited form as: Vaccine. 28(17):2999-3007 (2010) (21 pages).
Zhou et al., "Structural basis for broad and potent neutralization of HIV-1 by antibody VRC01," available in PMC Aug. 13, 2011, published in final edited format as: Science. 329(5993):811-7 (2010) (19 pages).
Extended European Search Report for European Patent Application No. 14735323.9, dated Aug. 16, 2016 (9 pages).

(56) References Cited

OTHER PUBLICATIONS

Bricault et al., "A multivalent clade C HIV-1 Env trimer cocktail elicits a higher magnitude of neutralizing antibodies than any individual component," J Virol. 89(5):2507-19 (2015).

Extended European Search Report for European Patent Application No. 14851250.2, dated Apr. 11, 2017 (5 pages).

Lynch et al., "The B cell response is redundant and highly focused on V1V2 during early subtype C infection in a Zambian seroconverter," J Virol. 85(2):905-15 (2011).

Huang et al., "Coreceptor tropism can be influenced by amino acid substitutions in the gp41 transmembrane subunit of human immunodeficiency virus type 1 envelope protein," J Virol. 82(11):5584-93 (2008).

Kwong et al., "Rational design of vaccines to elicit broadly neutralizing antibodies to HIV-1," Cold Spring Harb Perspect Med. 1(1):a007278 (2011) (16 pages).

Lewis et al., "Antibody persistence and T-cell balance: two key factors confronting HIV vaccine development," Proc Natl Acad Sci U.S.A. 111(44):15614-21 (2014).

West et al., "Structural insights on the role of antibodies in HIV-1 vaccine and therapy," Cell 156(4):633-48 (2014).

Zolla-Pazner, "A critical question for HIV vaccine development: which antibodies to induce?," Science 345(6193):167-8 (2014) (3 pages).

Du et al., "Effect of trimerization motifs on quaternary structure, antigenicity, and immunogenicity on a noncleavable HIV-1 gp140 envelope glycoprotein," Virol. 395(1):33-44 (2009).

Communication pursuant to Article 94(3) EPC for European Patent Application No. 14851250.2, dated Dec. 4, 2017 (5 pages).

Merk et al., "HIV-1 envelope glycoprotein structure," available in PMC Apr. 18, 2014, published in final edited form as: Curr Opin Struct Biol. 23(2):268-76 (2013) (16 pages).

Ex parte Alessandro D. Santin and Fabrizio Comper, decision of the Board of Patent Appeals and Interferences, U.S. Appl. No. 11/248,702, Appeal No. 2010-012332, 10 pages.

Wang et al., "Improved expression of secretory and trimeric proteins in mammalian cells via the introduction of a new trimer motif and a mutant of the tPA signal sequence," Appl Microbiol Biotechnol. 91(3):731-40 (2011).

Communication pursuant to Article 94(3) EPC for European Patent Application No. 14851250.2, dated Aug. 29, 2018 (4 pages).

Pancera et al., "Structure and immune recognition of trimeric prefusion HIV-1 Env," available in PMC Apr. 23, 2015, published in final edited form as: Nature. 514(7523):455-61 (2014).

Kwon et al., "Crystal structure, conformational fixation, and entry-related interactions of mature ligand-free HIV-1 Env," available in PMC Jan. 8, 2016, published in final edited form as: Nat Struc Mol Biol. 22(7):522-31 (2015).

* cited by examiner

Fig. 1A

Variable Loop 2/Glycan Modified

|          |      |                    |            |
|----------|------|--------------------|------------|
| 459C WT  | NKNT | NSNATTEIRDRKKEMY   | YFTSDENRN  |
| 459C V2 Opt | NKET | NSNMTTELRDKKKVS | YYISDKSRN  |
| 459C V2 Alt | NEDK | NTNITTSVKGKRQQEH | YYVSEKSRN  |

― Associated with sensitivity
⋯ Associated with resistance
▬ Conflicting associations

Fig. 1B

Variable Loop 3/Glycan Modified

|          |          |                        |            |
|----------|----------|------------------------|------------|
| 459C WT  | DVNTLNNT | VTNNTRIIGDIRQHNS      | ENTRWNTS   |
| 459C V3 Opt | DVKTITNT | NTGNTRIIGDIRQHNS    | ANTQANTS   |
| 459C V3 Alt | DVNTITNS | TISNTRVIGNIRKYEN    | TNTNSNSS   |

― Associated with sensitivity
⋯ Associated with resistance
▬ Conflicting associations

Fig. 3A

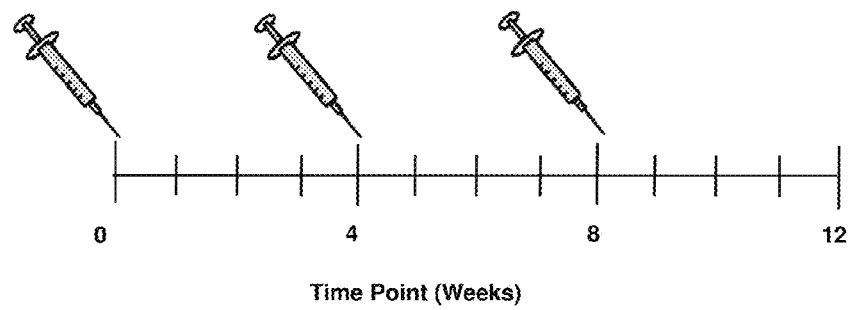

| Name | Prime | Boost 1 | Boost 2 | n |
|---|---|---|---|---|
| 459C WT | 459C WT | 459C WT | 459C WT | 15 |
| V2 Opt | V2 Opt | V2 Opt | V2 Opt | 5 |
| V2 Alt | V2 Alt | V2 Alt | V2 Alt | 5 |
| V3 Opt | V3 Opt | V3 Opt | V3 Opt | 10 |
| V3 Alt | V3 Alt | V3 Alt | V3 Alt | 10 |
| V2 Opt+V2 Alt | V2 Opt+V2 Alt | V2 Opt+V2 Alt | V2 Opt+V2 Alt | 5 |
| V3 Opt+V3 Alt | V3 Opt+V3 Alt | V3 Opt+V3 Alt | V3 Opt+V3 Alt | 5 |
| V2 Mixture | WT+V2 Opt+V2 Alt | WT+V2 Opt+V2 Alt | WT+V2 Opt+V2 Alt | 5 |
| V3 Mixture | WT+V3 Opt+V3 Alt | WT+V3 Opt+V3 Alt | WT+V3 Opt+V3 Alt | 5 |
| V2 Prime/Boost | V2 Opt | WT+V2 Alt | WT+V2 Alt | 5 |
| V3 Prime/Boost | V3 Opt | WT+V3 Alt | WT+V3 Alt | 5 |

Fig. 3B

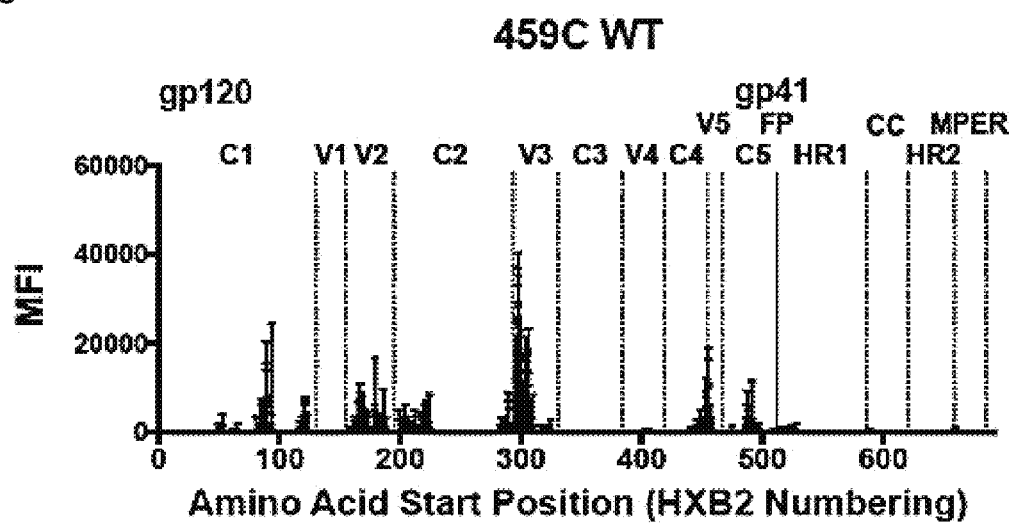

Fig. 4A

V2 Modified Immunogens

WT

V2 Mixture

V2 Prime/Boost

V2 Opt

V2 Alt

V2 Opt + V2 Alt

Global Panel: CRF07_BC.CH119, G.X1632, B.X2278, A.398-F1, C.25710, B.TRO.11, CRF07_BC.BJOX2000, CRF01_AE.CNE55, C.Ce1176, AC.246_F3, CRF01_AE.CNE8, C.Ce0217

Rationally Selected: C.CT349_39_16, CRF02_AG.T250-4, C.Du156.12, CRF07_BC.CNE20, C.234-F1_16_57, C.CNE58, C.CA240_A5.5, CRF01_AE.C3347_C11

Positive Geomean, Geomean

Color Key/Histogram

Fig. 4B

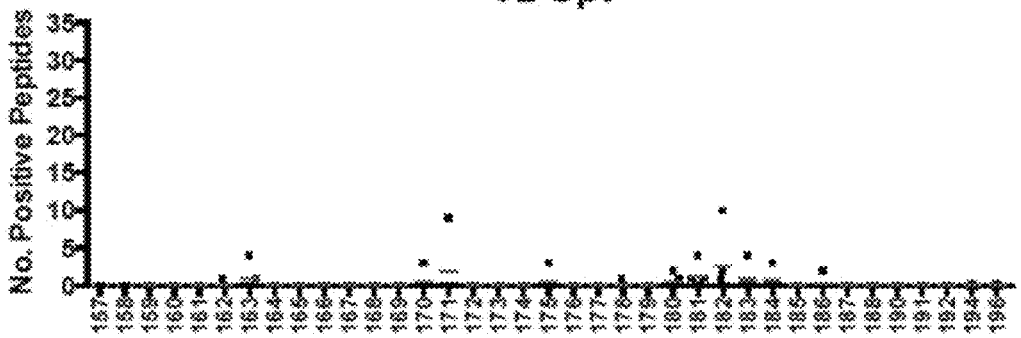
Fig. 9D V2 Opt
Fig. 9E V2 Alt
Fig. 9F V3 Opt
Fig. 9G V3 Alt

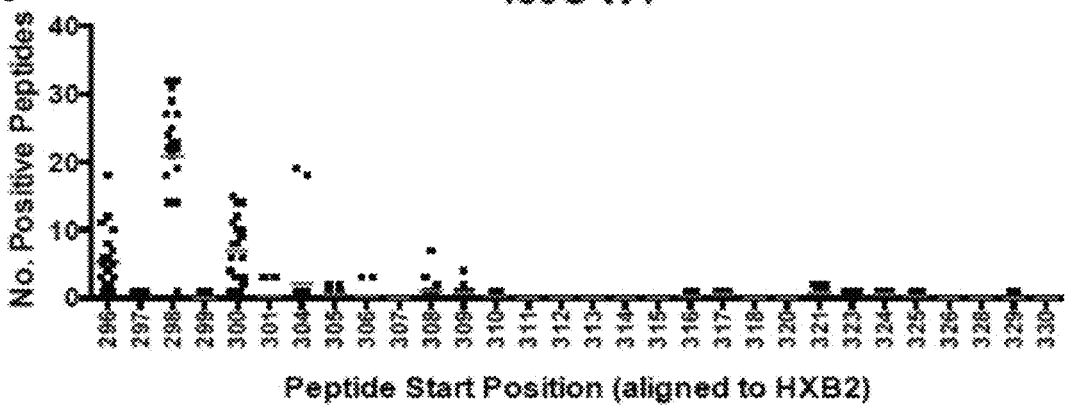
Fig. 9K 459C WT
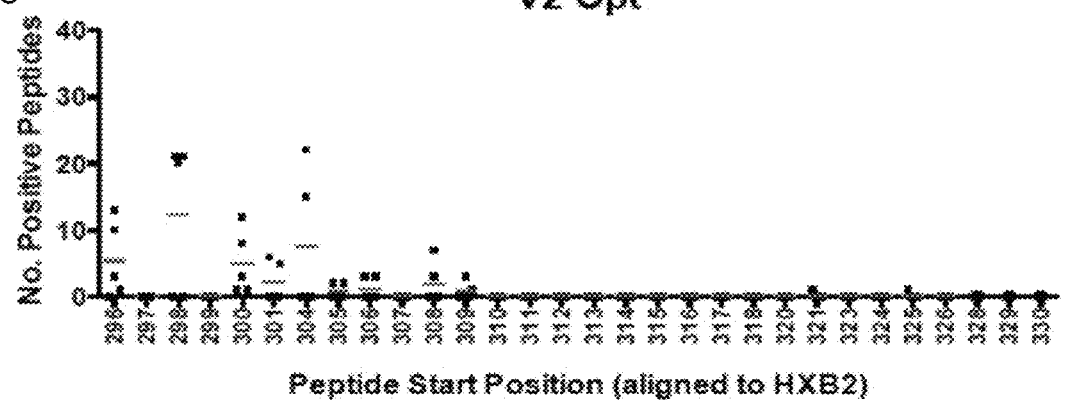
Fig. 9L V2 Opt
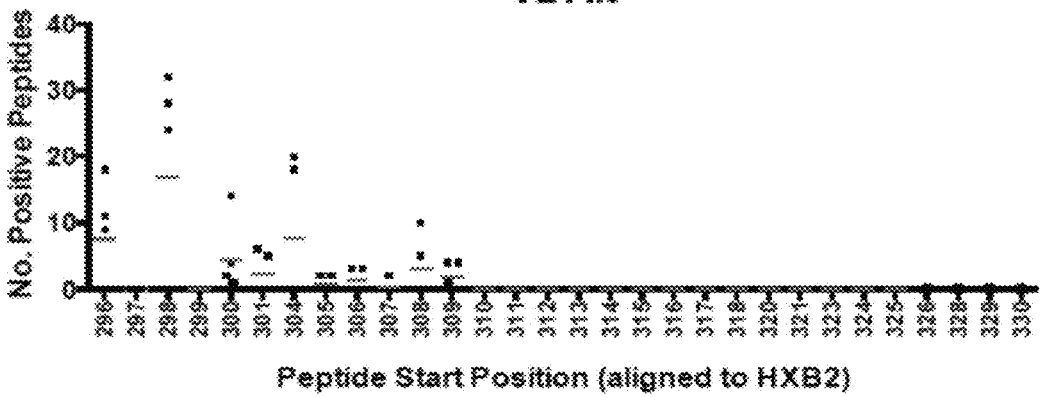
Fig. 9M V2 Alt
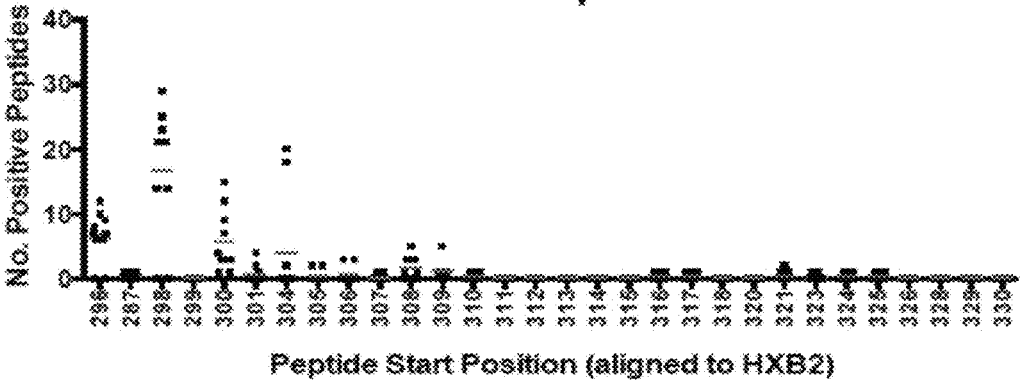
Fig. 9N V3 Opt

Fig. 11A

MW965.26 (Clade C Tier 1A)

Fig. 11B

SF162.LS (Clade B Tier 1A)

Fig. 11C

SS1196.1 (Clade B Tier 1B)

Fig. 11D

ZM109F.PB4 (Clade C Tier 1B)

Fig. 11E

DJ263.8 (Clade A Tier 1B)

Fig. 11F

TV1.21 (Clade C Tier 1B)

Fig. 11G

6535.3 (Clade B Tier 1B)

Fig. 11H

BaL.26 (Clade B Tier 1B)

Fig. 11I

V2 Modified Immunogens

459C WT
V2 Mixture
V2 Opt+V2 Alt
V2 Prime/Boost
V2 Opt
V2 Alt

Pseudovirion: C.MW965.26, B.SF162.LS, A.DJ263.8, C.TV1.21, C.ZM109F.PB4, B.BaL.26, B.SS1196.1, B.6535.3

Color Key/Histogram

Fig. 11J

V3 Modified Immunogens

459C WT
V3 Mixture
V3 Opt+V3 Alt
V3 Prime/Boost
V3 Opt
V3 Alt

Pseudovirion: C.MW965.26, B.SF162.LS, A.DJ263.8, C.TV1.21, C.ZM109F.PB4, B.BaL.26, B.SS1196.1, B.6535.3

Color Key/Histogram

Fig. 15A
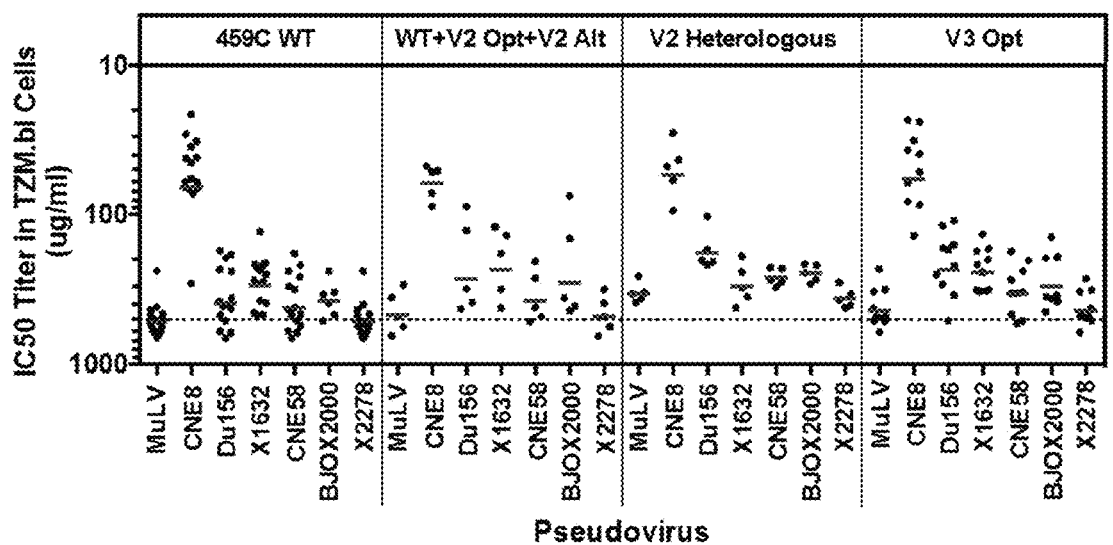
Fig. 15B
Purified IgG
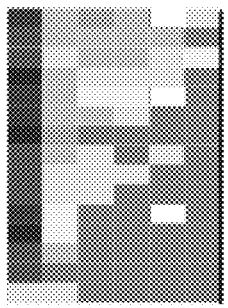
WT
V2 Mixture
V2 Prime/Boost
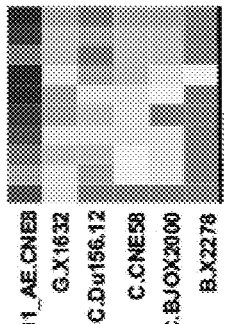
V3 Opt
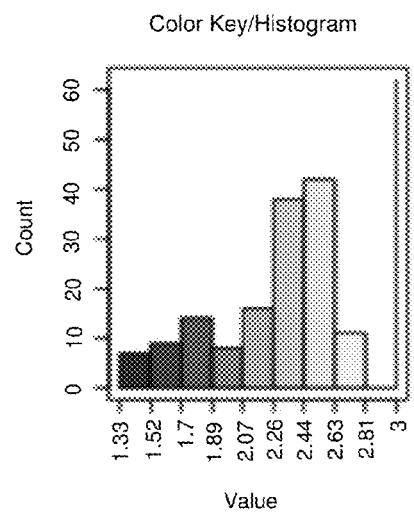

Fig. 16B

V2 Mixture vs WT in MPLA

Fig. 16C

● WT   ● V2 Mixture

Fig. 17A
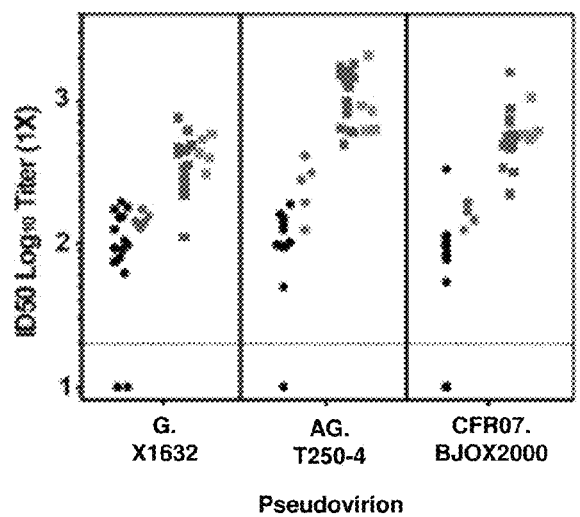
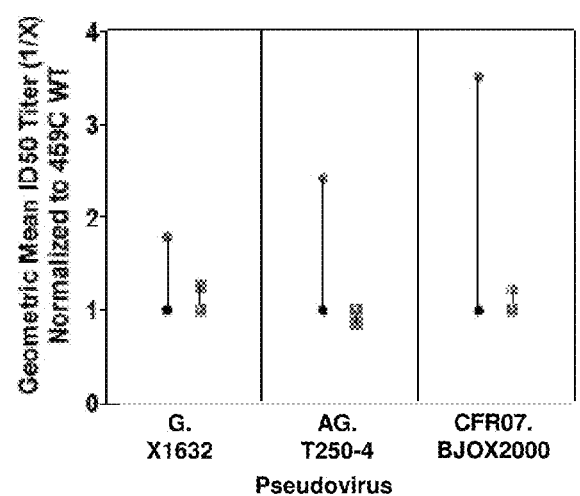
Fig. 17B
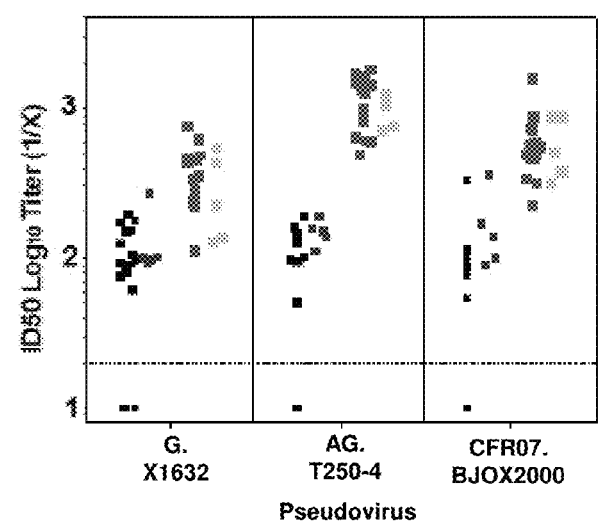
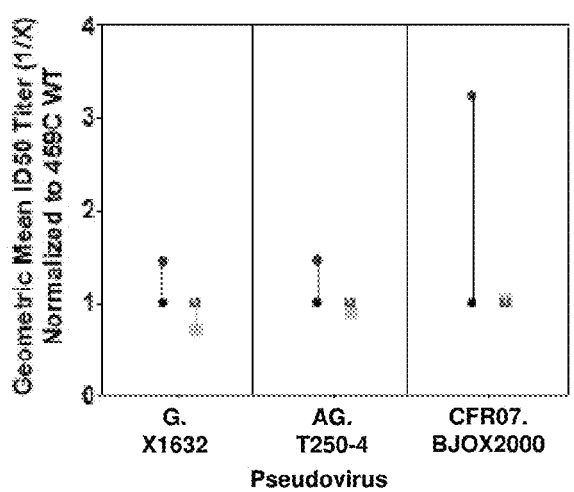

Fig. 17C
Fig. 17D
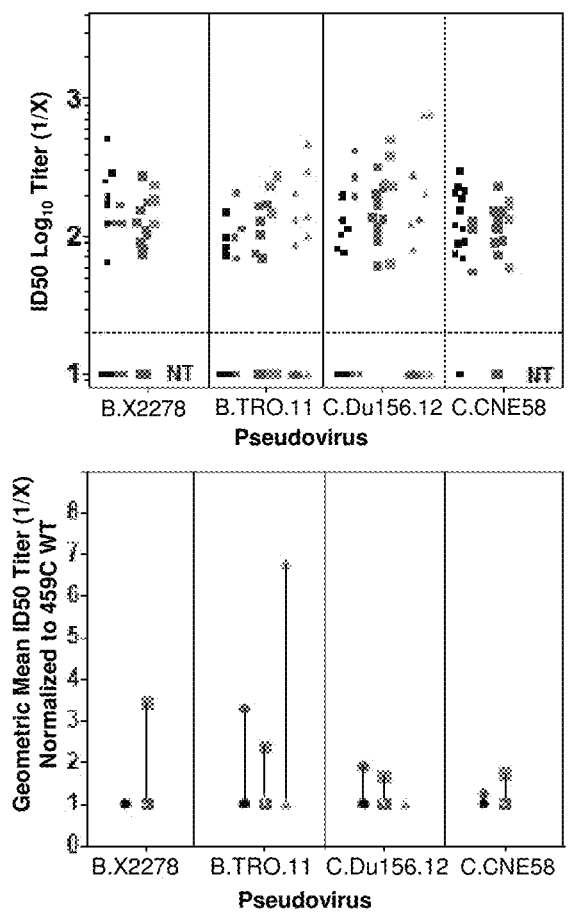
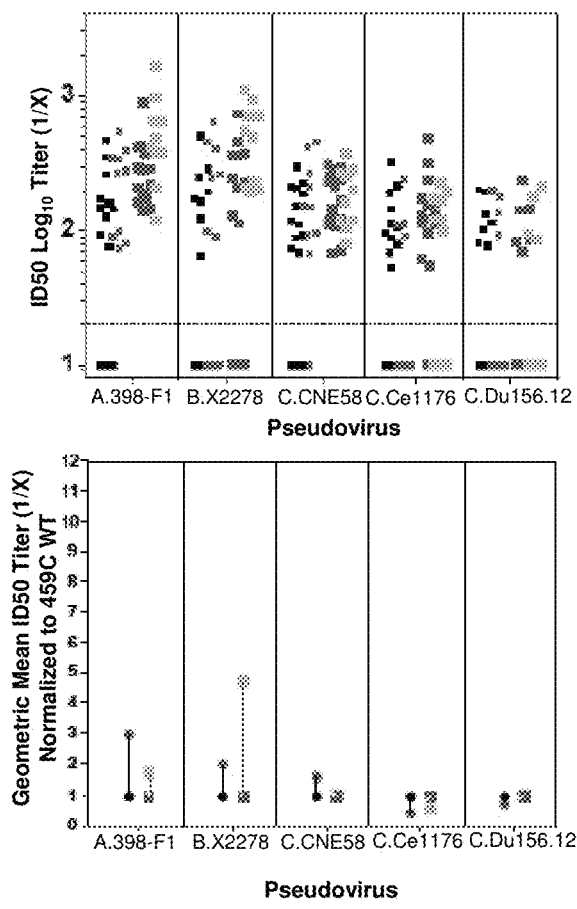

US 11,230,572 B2

SIGNATURE-BASED HUMAN IMMUNODEFICIENCY VIRUS (HIV) ENVELOPE (ENV) TRIMER VACCINES AND METHODS OF USING THE SAME

FIELD OF THE INVENTION

The invention generally relates to the treatment or prevention of human immunodeficiency virus (HIV) infections.

BACKGROUND OF THE INVENTION

Vaccines that elicit cellular immune responses against viruses seek to reflect global viral diversity in order to effectively treat or prevent viral infection. For HIV vaccines, the initiation of robust and diverse human immunodeficiency virus (HIV)-specific B cell responses is desirable for an effective HIV vaccine. The highly variable Envelope protein (Env) is the primary target for neutralizing antibodies against HIV, and vaccine antigens may be tailored accordingly to elicit these antibody responses. To this end, immunogens mimicking the trimeric structure of Env on the native HIV virion are actively being pursued as antibody-based HIV vaccines. However, it has proven difficult to produce biochemically stable trimeric Env immunogens that elicit diverse neutralizing antibody responses.

Thus, there is an unmet need in the field for the development of vaccines that can elicit a broad immune response (e.g., a broadly neutralizing antibody response) against diverse HIV Env polypeptides in order to promote robust HIV vaccination outcomes.

SUMMARY OF THE INVENTION

In a first aspect, the invention features an isolated polypeptide that is:
- (a) a human immunodeficiency virus (HIV) envelope (Env) glycoprotein comprising amino an asparagine residue at position 33, a lysine residue at position 49, a glutamic acid residue at position 130, and a threonine residue at position 132 relative to the sequence of HXB2 (GenBank Accession No. AF033819.3); and/or
- (b) a HIV Env glycoprotein comprising an asparagine residue at position 156, a serine residue at position 158, an asparagine residue at position 160, a methionine residue at position 161, a threonine residue at position 162, a threonine residue at position 163, a glutamic acid residue at position 164, a lysine residue at position 165, an arginine residue at position 166, an aspartic acid residue at position 167, a lysine residue at position 168, a lysine residue at position 169, a lysine residue at position 170, a lysine residue at position 171, a valine residue at position 172, and a serine residue at position 173 relative to the sequence of HXB2 (GenBank Accession No. AF033819.3); and/or
- (c) a HIV Env glycoprotein comprising a tyrosine residue at position 177, a tyrosine residue at position 223, an isoleucine residue at position 297, a serine residue at position 306, an aspartic acid residue at position 322, a lysine residue at position 335, a serine residue at position 636, an arginine residue at position 644, and an asparagine residue at position 677 relative to the sequence of HXB2 (GenBank Accession No. AF033819.3).

In a second aspect, the invention features an isolated polypeptide that is:
- (a) a HIV Env glycoprotein comprising an asparagine residue at position 33, a glutamic acid residue at position 49, an aspartic acid residue at position 130, and a lysine residue at position 132 relative to the sequence of HXB2 (GenBank Accession No. AF033819.3); and/or
- (b) a HIV Env glycoprotein comprising an asparagine residue at position 156, a threonine residue at position 158, an asparagine residue at position 160, an isoleucine residue at position 161, a threonine residue at position 162, a threonine residue at position 163, a serine residue at position 164, a valine residue at position 165, a lysine residue at position 166, a glycine residue at position 167, a lysine residue at position 168, an arginine residue at position 169, a glutamine residue at position 170, a glutamine residue at position 171, a glutamic acid residue at position 172, and a histidine residue at position 173 relative to the sequence of HXB2 (GenBank Accession No. AF033819.3); and/or
- (c) a HIV Env glycoprotein comprising a tyrosine residue at position 177, a tyrosine residue at position 223, a valine residue at position 297, a serine residue at position 306, a glutamic acid residue at position 322, a lysine residue at position 335, a serine residue at position 636, an arginine residue at position 644, and an asparagine residue at position 677 relative to the sequence of HXB2 (GenBank Accession No. AF033819.3).

In a third aspect, the invention features an isolated polypeptide that is:
- (a) a HIV Env glycoprotein comprising an aspartic acid residue at position 62, a valine residue at position 85, a lysine residue at position 160, a threonine residue at position 162, an isoleucine residue at position 184, a threonine residue at position 240, an asparagine residue at position 276, and a threonine residue at position 278 relative to the sequence of HXB2 (GenBank Accession No. AF033819.3); and/or
- (b) a HIV Env glycoprotein comprising an asparagine residue at position 295, a threonine residue at position 297, a glycine residue at position 300, an asparagine residue at position 301, a threonine residue at position 303, an arginine residue at position 304, an isoleucine residue at position 307, an isoleucine residue at position 323, a glycine residue at position 324, an aspartic acid residue at position 325, an isoleucine residue at position 326, an arginine residue at position 327, a glutamine residue at position 328, a histidine residue at position 330, an asparagine residue at position 332, and a serine residue at position 334 relative to the sequence of HXB2 (GenBank Accession No. AF033819.3); and/or
- (c) a HIV Env glycoprotein comprising an alanine residue at position 336, an asparagine residue at position 339, a threonine residue at position 341, a glutamine residue at position 344, an alanine residue at position 346, an asparagine residue at position 392, a threonine residue at position 394, and a serine residue at position 668 relative to the sequence of HXB2 (GenBank Accession No. AF033819.3).

In a fourth aspect, the invention features an isolated polypeptide that is:
- (a) a HIV Env glycoprotein comprising an aspartic acid residue at position 62, a valine residue at position 85, an asparagine residue at position 160, a threonine residue at position 162, an isoleucine residue at position 184, a threonine residue at position 240, an asparagine residue at position 276, and a serine residue at position 278 relative to the sequence of HXB2 (GenBank Accession No. AF033819.3); and/or (b) a HIV Env glycoprotein comprising a threonine residue at position 295, an isoleucine residue at position 297, a serine residue at position 300, an asparagine residue at position 301, a threonine residue at position 303, an arginine residue at position 304, a valine residue at position 307, an isoleucine residue at position 323, a glycine residue at position 324, an asparagine residue at position 325, an isoleucine residue at position 326, an arginine residue at position 327, a lysine residue at position 328, a tyrosine residue at position 330, a glutamic acid residue at position 332, and an asparagine residue at position 334 relative to the sequence of HXB2 (GenBank Accession No. AF033819.3); and/or (c) a HIV Env glycoprotein comprising a threonine residue at position 336, an asparagine residue at position 339, a threonine residue at position 341, an asparagine residue at position 344, a serine residue at position 346, an asparagine residue at position 392, a serine residue at position 394, and a serine residue at position 668 relative to the sequence of HXB2 (GenBank Accession No. AF033819.3).

In any of the first, second, third, and fourth aspects, the isolated polypeptide has the sequence of any one or more of SEQ ID NOs: 1-4, 11-14, 19-22, and 33-36, or an amino acid sequence having at least 85%, 86%, 87%, 88%, 89%, 90%, 91%, 92%, 93%, 94%, 95%, 96%, 97%, 98%, 99%, or 100% sequence identity to the amino acid sequence of SEQ ID NOs: 1-4, 11-14, 19-22, and 33-36. In other embodiments, the polypeptide further comprises a sequence having at least 50, 100, 150, 200, 250, 300, 350, 400, 450, 500, 550, 600, 650, 700, or more consecutive amino acids of the sequence of any one of SEQ ID NOs: 1-4, 11-14, 19-22, or a variant thereof having a sequence with at least 92% sequence identity (e.g., 93%, 94%, 95%, 96%, 97%, 98%, 99%, or 100% sequence identity) to a sequence comprising at least 50, 100, 150, 200, 250, 300, 350, 400, 450, 500, 550, 600, 650, 700, or more consecutive amino acids of the sequence of SEQ ID NOs: 1-4, 11-14, 19-22.

In other embodiments, the isolated polypeptide of any one of the first, second, third, and fourth aspects further comprises a trimerization domain (e.g., a trimerization domain having at least 90% sequence identity (e.g., 91%, 92%, 93%, 94%, 95%, 96%, 97%, 98%, 99%, or 100% sequence identity)) to the amino acid sequence of SEQ ID NO: 5. The trimerization domain is at the carboxy-terminus of the polypeptide. The polypeptide may also have a histidine tag (e.g., at the carboxy-terminus of the trimerization domain). The histidine tag may be one to twenty contiguous histidine residues (e.g., six contiguous histidine residues). The polypeptide may also have a leader signal sequence at the amino terminus of the polypeptide (e.g., a leader signal sequence having at least 90% sequence identity (e.g., 91%, 92%, 93%, 94%, 95%, 96%, 97%, 98%, 99%, or 100% sequence identity) to the amino acid sequence of SEQ ID NO: 17).

In other embodiments, the isolated polypeptide of any one of the first, second, third, and fourth aspects is a human immunodeficiency virus (HIV) envelope glycoprotein (e.g., an HIV gp140 polypeptide, such as a clade C HIV envelope glycoprotein).

A fifth aspect of the invention features a stabilized trimer that includes three polypeptides of any one of the first, second, third, and fourth aspects of the invention (e.g., gp140 polypeptides). In particular, two or each of the polypeptides of the trimer is the polypeptide of any one of the first, second, third, and fourth aspects of the invention (e.g., preferably each of the polypeptides of the trimer is the polypeptide of any one of the first, second, third, and fourth aspects of the invention). In an embodiment, each of the polypeptides of the trimer has an amino acid sequence having at least 92% sequence identity (e.g., 93%, 94%, 95%, 96%, 97%, 98%, 99%, or 100% sequence identity) to the amino acid sequence of any one of SEQ ID NO: 11 to 14. In other embodiments, two or each polypeptide of the trimer is the same or is different. In an embodiment, each polypeptide of the stabilized trimer has the amino acid sequence of SEQ ID NO: 11, 12, 13, or 14.

A sixth aspect of the invention features an isolated nucleic acid molecule that includes a nucleotide sequence that encodes the polypeptide of any one of the first, second, third, and fourth aspects of the invention. The isolated nucleic acid molecule has a nucleic acid sequence with at least 92% sequence identity (e.g., 93%, 94%, 95%, 96%, 97%, 98%, 99%, or 100% sequence identity) to the nucleic acid sequence of any one of SEQ ID NOs: 7 to 10, 15, 24 to 28, or 37 to 40.

A seventh aspect of the invention features a recombinant vector containing the nucleic acid molecule of any one of the sixth aspect of the invention. In an embodiment, the recombinant vector includes two or more of the polypeptides of the first, second, third, and fourth aspects of the invention. In other embodiments, the vector is a viral vector (e.g., an adenovirus vector or a poxvirus vector). In other embodiments, the adenovirus is an adenovirus serotype 11 (Ad11), adenovirus serotype 15 (Ad15), adenovirus serotype 24 (Ad24), adenovirus serotype 26 (Ad26), adenovirus serotype 34 (Ad34), adenovirus serotype 35 (Ad35), adenovirus serotype 48 (Ad48), adenovirus serotype 49 (Ad49), adenovirus serotype 50 (Ad50), Pan9 (AdC68), or a chimeric variant thereof. In still other embodiments, the poxvirus is a modified vaccinia virus Ankara (MVA).

An eighth aspect of the invention features an isolated host cell (e.g., a mammalian cell, such as a human cell, a 293T cell, a CHO cell, a Vero cell, a BHK-21 cell, a MDCK cell, a HeLa cell, a CAP cell, an AGE1-CR cell, or an EB66 cell), that contains the polypeptide of any one of the first, second, third, and fourth aspects of the invention, the stabilized trimer of the fifth aspect of the invention, the nucleic acid molecule of the sixth aspect of the invention, or the recombinant vector of any one of seventh aspect of the invention.

A ninth aspect of the invention features a composition comprising the polypeptide of any one of the first, second, third, and fourth aspects of the invention, the stabilized trimer of the fifth aspect of the invention, the nucleic acid molecule of the sixth aspect of the invention, the recombinant vector of any one of seventh aspect of the invention, or the host cell of the eight aspect of the invention. In an embodiment, the composition comprises a homogenous or heterogeneous population of stabilized trimers (e.g., at least two or three different stabilized trimers). In particular, each of the one or more stabilized trimers has three polypeptides with at least 90% sequence identity (e.g., 91%, 92%, 93%, 94%, 95%, 96%, 97%, 98%, 99%, or 100% sequence identity) to the amino acid sequence of SEQ ID NO: 11, 12, 13, 14, or 16. In particular, the composition comprises one or more of three different stabilized trimers, wherein a first said stabilized trimer comprises three polypeptides each of which has at least 92% sequence identity (e.g., 93%, 94%, 95%, 96%, 97%, 98%, 99%, or 100% sequence identity) to the amino acid sequence of SEQ ID NO: 30, a second said stabilized trimer comprises three polypeptides each of which has at least 92% sequence identity (e.g., 93%, 94%, 95%, 96%, 97%, 98%, 99%, or 100% sequence identity) to the amino acid sequence of SEQ ID NO: 31, and a third said stabilized trimer comprises three polypeptides each of which has at least 92% sequence identity (e.g., 93%, 94%, 95%, 96%, 97%, 98%, 99%, or 100% sequence identity) to the amino acid sequence of SEQ ID NO: 32.

In another embodiment, the composition has more than one said nucleic acid molecule (e.g., a nucleic acid molecule that encodes a plurality of the polypeptides of any one the first, second, third, and fourth aspects of the invention, such as a polypeptide having at least 90% sequence identity (e.g., 91%, 92%, 93%, 94%, 95%, 96%, 97%, 98%, 99%, or 100% sequence identity) to the amino acid sequence of SEQ ID NO: 11, 12, 13, 14, or 16. In other embodiments, the composition has a pharmaceutically acceptable carrier, excipient, or diluent or an adjuvant.

A tenth aspect of the invention features a method of optimizing the variable loop 2 (V2) region or the variable loop 3 (V3) region of a HIV envelope polypeptide to produce first and/or second optimized antigenic polypeptides, comprising:
a) i) mapping epitopes surrounding and/or within the V2 and/or V3 regions of HIV envelope glycoproteins specifically bound by known V2 and/or V3 neutralizing antibodies to identify one or more amino acid residues at one or more positions surrounding and/or within the V2 and/or V3 regions that are characterized by resistance to neutralization by the known V2 and/or V3 neutralizing antibodies; and
 ii) substituting one or more amino acid residues surrounding and/or within the V2 and/or V3 regions of a target HIV envelope glycoprotein with an amino acid residue identified in step a) i) as being characterized by resistance to neutralization, thereby producing the first optimized antigenic polypeptide; and/or
b) i) mapping epitopes surrounding and/or within the V2 and/or V3 regions of HIV envelope glycoproteins specifically bound by known V2 and/or V3 neutralizing antibodies to identify one or more amino acid residues at one or more positions surrounding and/or within the V2 and/or V3 regions that are characterized by sensitivity to neutralization by the known V2 and/or V3 neutralizing antibodies; and
 ii) substituting one or more amino acid residues surrounding and/or within the V2 and/or V3 regions of a target HIV envelope glycoprotein with an amino acid residue identified in step a) i) as being characterized by sensitivity to neutralization, thereby producing the first optimized antigenic polypeptide.

The method comprises performing steps a) and b) to produce the first and second optimized antigenic polypeptides and/or substituting a plurality of amino acid residues surrounding and/or within the V2 and/or V3 regions of the target HIV envelope glycoprotein in steps a) and/or b). The amino acids residues identified in step a) i) may also be within an epitope that is specifically bound by the known V2 and/or V3 neutralizing antibodies. Also, the V2 region of the target HIV envelope glycoprotein comprises amino acid residues 157 to 196 of wild-type 459C (SEQ ID NO: 16; residue numbering corresponding to HXB2 reference numbering) or the V3 region of the target HIV envelope glycoprotein comprises amino acids 296 to 331 of wild-type 459C (SEQ ID NO: 16; residue numbering corresponding to HXB2 reference numbering). The V2 region of the target HIV envelope glycoprotein may further comprise an amino acid sequence having at least 50, 100, 150, 200, 250, 300, 350, 400, 450, 500, 550, 600, 650, 700, or more consecutive amino acids of SEQ ID NO: 19 or 20, or a variant thereof having an amino acid sequence with at least 92% sequence identity (e.g., 93%, 94%, 95%, 96%, 97%, 98%, 99%, or 100% sequence identity) to an amino acid sequence with at least 50, 100, 150, 200, 250, 300, 350, 400, 450, 500, 550, 600, 650, 700, or more consecutive amino acids of SEQ ID NOs: 19 or 20. The V3 region of the target HIV envelope glycoprotein may further comprise an amino acid sequence having at least 50, 100, 150, 200, 250, 300, 350, 400, 450, 500, 550, 600, 650, 700, or more consecutive amino acids of SEQ ID NOs: 21 or 22, or a variant thereof having an amino acid sequence with at least 92% sequence identity (e.g., 93%, 94%, 95%, 96%, 97%, 98%, 99%, or 100% sequence identity) to an amino acid sequence with at least 50, 100, 150, 200, 250, 300, 350, 400, 450, 500, 550, 600, 650, 700, or more consecutive amino acids of SEQ ID NOs: 21 or 22.

An eleventh aspect of the invention features a composition comprising the first and/or second optimized antigenic polypeptides of the tenth aspect of the invention.

A twelfth aspect of the invention features a vaccine comprising the composition of any one of the eleventh aspect of the invention. The vaccine is capable of treating or reducing the risk of a human immunodeficiency virus (HIV) infection in a subject in need thereof or of eliciting production of neutralizing anti-HIV antisera after administration to said subject (e.g., a human). In particular, the anti-HIV antisera is capable of neutralizing HIV selected from any one or more of clade A, clade B, and clade C. In particular, the HIV strain is a heterologous, tier 2 neutralization resistant strain of HIV-1.

The composition or vaccine of the invention can be used for treating or reducing the risk of a human immunodeficiency virus (HIV) infection in a subject (e.g., a human) in need thereof. The composition is capable of treating or reducing the risk of a human immunodeficiency virus (HIV) infection in the subject in need thereof or of eliciting production of neutralizing anti-HIV antisera after administration to said subject. The anti-HIV antisera is capable of neutralizing HIV selected from any one or more of clade A, clade B, and clade C or the HIV strain is a heterologous, tier 2 neutralization resistant strain of HIV-1.

A thirteenth aspect of the invention features a composition comprising a plurality of polyclonal antibodies, wherein the plurality of polyclonal antibodies specifically binds the V2 region of SEQ ID NO: 33 or 34 or the V3 region of SEQ ID NO: 35 or 36. The plurality of polyclonal antibodies specifically bind to the V2 and/or V3 region with a $K_D$ of less than about 100 nM and/or wherein the plurality of polyclonal antibodies comprise a non-native constant region. The plurality of polyclonal antibodies were generated by administering to a mammal (e.g., a human) the compositions of the first to eleventh aspects of the invention. The plurality of antibodies are humanized, have an isotype selected from the group consisting of IgG, IgA, IgM, IgD, and IgE, or are conjugated to a therapeutic agent (e.g., a cytotoxic agent).

A fourteenth aspect of the invention features a method of producing a plurality of polyclonal antibodies comprising administering any one of the compositions of the first to eleventh aspects of the invention to a subject to elicit the production of neutralizing anti-HIV antisera in the subject (e.g., a human). The method may further comprise collecting the plurality of polyclonal antibodies from the antisera. The method may further comprises screening the plurality of polyclonal antibodies for binding to the V2 and/or V3 regions of a HIV envelope glycoprotein. The HIV envelope glycoprotein is a HIV gp140 polypeptide having the amino acid sequence of any one of SEQ ID NOs: 1 to 4, or 11 to 18. The method comprises eliciting a plurality of polyclonal antibodies that specifically bind to an epitope within any one of SEQ ID NOs: 33 to 36. The method further comprises producing one or more recombinant constructs that express the plurality of polyclonal antibodies. The method further comprises modification of the one of more recombinant constructs to introduce targeting moieties, epitopes, or antibody fragments.

A fifteenth aspect of the invention features a method of treating or reducing the risk of an HIV infection in a subject (e.g., a human) in need thereof by administering a therapeutically effective amount of the composition of any one of first to eleventh aspects of the invention to the subject or a method of reducing an HIV-mediated activity in a subject infected with HIV comprising administering a therapeutically effective amount of any one of first to eleventh aspects of the invention to the subject. HIV-mediated activity is viral spread, infection, or cell fusion (e.g., target cell entry or syncytial formation). HIV titer in the subject infected with HIV is decreased after administration of the composition or the vaccine to the subject. The composition or vaccine is administered intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in creams, or in lipid compositions. The subject is administered at least one (e.g., two or more) dose of the composition or vaccine. The composition or vaccine is administered to the subject as a prime, a boost, or as a prime-boost (e.g., as a boost). The boost is administered to the subject 1, 2, 3, or 4 weeks after administration of the previous dose. The composition or vaccine generates neutralizing antibodies (NAbs) to HIV (e.g., the HIV is a heterologous, tier 2 neutralization resistant strain of HIV-1 or is a clade A, B, or C HIV).

A sixteenth aspect of the invention features a method of manufacturing a vaccine for treating or reducing the risk of an HIV infection in a subject in need thereof by the steps of:
  (a) contacting the recombinant vector of the invention with a cell; and
  (b) expressing the polypeptide in the cell.
The method is performed in vitro or ex vivo. The cell is a bacterial, plant, or mammalian cell (e.g., a 293T cell or a CHO cell).

A seventeenth aspect of the invention features a kit comprising (a) a composition of any one of the first to eleventh aspects of the invention and (b) instructions for use thereof; the kit optionally includes an adjuvant.

Definitions

As used herein, the term "about" means+/−10% of the recited value.

By "adenovirus" is meant a medium-sized (90-100 nm), non-enveloped icosahedral virus that includes a capsid and a double-stranded linear DNA genome. The adenovirus can be a naturally occurring, but isolated, adenovirus (e.g., sAd4287, sAd4310A, or sAd4312) or a recombinant adenovirus (e.g., replication-defective or replication competent sAd4287, sAd4310A, or sAd4312, or a chimeric variant thereof).

The terms "adenovirus vector" and "adenoviral vector" are used interchangeably and refer to a genetically-engineered adenovirus that is designed to insert a polynucleotide of interest (e.g., a polynucleotide encoding a HIV immunogen of the invention) into a eukaryotic cell, such that the polynucleotide is subsequently expressed. Examples of adenoviruses that can be used as a viral vector of the invention include those having, or derived from, the serotypes Ad2, Ad5, Ad11, Ad12, Ad24, Ad26, Ad34, Ad35, Ad40, Ad48, Ad49, Ad50, and Pan9 (also known as AdC68).

The term "adjuvant" refers to a pharmacological or immunological agent that modifies the effect of other agents (e.g., an antigen) while having few if any direct effects when given by itself. They are often included in vaccines to enhance the recipient's immune response to a supplied antigen.

As used herein, "administering" is meant a method of giving a dosage of a pharmaceutical composition (e.g., a composition of the invention, such as a polypeptide, stabilized trimer, nucleic acid molecule, vector, host cells, and/or vaccine of the invention) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in creams, or in lipid compositions. The preferred method of administration can vary depending on various factors (e.g., the components of the composition being administered and the severity of the condition being treated).

As used herein, the terms "antibody" and "immunoglobulin (Ig)" are used interchangeably in the broadest sense and refer to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bi- tri- and quad-specific antibodies, diabodies, triabodies, and tetrabodies), and antigen-binding fragments of antibodies, including e.g., Fab', F(ab')$_2$, Fab, Fv, rIgG, and scFv fragments. An antibody typically comprises both "light chains" and "heavy chains." The light chains of antibodies (immunoglobulins) from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known. Moreover, unless otherwise indicated, the term "monoclonal antibody" (mAb) is meant to include both intact molecules, as well as, antibody fragments (such as, for example, Fab and F(ab')₂ fragments) that are capable of specifically binding to a target protein. Fab and F(ab')₂ fragments lack the Fc fragment of an intact antibody, clear more rapidly from the circulation of the animal, and may have less non-specific tissue binding than an intact antibody (see Wahl et al., J. Nucl. Med. 24:316, 1983; incorporated herein by reference).

The term "antigen-binding fragment," as used herein, refers to one or more fragments of an antibody that retain the ability to specifically bind to a target antigen. The antigen-binding function of an antibody can be performed by fragments of a full-length antibody. The antibody fragments can be a Fab, F(ab')2, scFv, SMIP, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the $V_L$, $V_H$, $C_L$, and $C_H1$ domains; (ii) a F(ab')₂ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment (Ward et al., Nature 341:544-546, 1989), which consists of a $V_H$ domain; (vii) a dAb which consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single-chain Fv (scFv); see, e.g., Bird et al., Science 242: 423-426, 1988, and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in some embodiments, by chemical peptide synthesis procedures known in the art.

As used herein, the term "clade" refers to related human immunodeficiency viruses (HIVs) classified according to their degree of genetic similarity. A clade generally refers to a distinctive branch in a phylogenetic tree. There are currently three groups of HIV-1 isolates: M, N and O. Group M (the Main group) consists of at least ten clades, A through J, and many inter-clade recombinants and circulating forms. Group O (Other) is both rare and very distinctive for M, and also has some sub-clades. Group N is a newer HIV-1 isolate that is extremely rare. O and N groups are likely the result of separate introductions into the human population from non-human primates. In certain exemplary embodiments, a composition of the invention (e.g., a polypeptide, stabilized trimer, nucleic acid molecule, vector, host cells, and/or vaccine of the invention) as described herein can be used to elicit an immune response (e.g., neutralizing anti-HIV antisera) against two, three, four, five, six, seven, eight, nine, ten or more clades.

As used herein, the term "characterized by resistance to neutralization" refers to amino acid residues that are not bound or are bound at low frequency by the CDRs of known neutralizing antibodies or are characterized by binding to known neutralizing antibodies but with low potency (e.g., known neutralizing antibodies such as PGT121, PGT122, PGT123, PGT124, PGT125, PGT126, PGT127, PGT128, PGT130, PGT131, PGT132, PGT133, PGT134, PGT135, PGT136, PGT137, PGT138, PGT139, PGT141, PGT142, PGT143, PGT144, PGT145, PGT151, PGT152, PGT153, PGT154, PGT155, PGT156, PGT157, PGT158, 10-1074, PG9, PG16, CAP256, or CH01) against HIV Env. Amino acid residues that are resistant to neutralizing antibodies can also be characterized as amino acid residues that can be substituted without substantial or any loss of specific binding by known neutralizing HIV antibodies (e.g., there is no substantial change in the $K_D$ of the antibody binding reaction).

As used herein, the term "characterized by sensitivity to neutralization" refers to amino acid residues that are bound or present in epitopes bound by the CDRs of known neutralizing antibodies (e.g., PGT121, PGT122, PGT123, PGT124, PGT125, PGT126, PGT127, PGT128, PGT130, PGT131, PGT132, PGT133, PGT134, PGT135, PGT136, PGT137, PGT138, PGT139, PGT141, PGT142, PGT143, PGT144, PGT145, PGT151, PGT152, PGT153, PGT154, PGT155, PGT156, PGT157, PGT158, 10-1074, PG9, PG16, CAP256, or CH01) against HIV Env. Amino acid residues that are sensitive to neutralization can also be characterized as amino acid residues bound or present in epitopes bound by the CDRs of known neutralizing antibodies that, when replaced with a different amino acid residue (e.g., one that alters the length of the antibody-binding region or its charge), reduce or eliminate specific binding by known neutralizing HIV antibodies (e.g., the amino acid substitution results in an increase in the $K_D$ of the antibody binding reaction).

The term "codon" as used herein refers to any group of three consecutive nucleotide bases in a given messenger RNA molecule, or coding strand of DNA, that specifies a particular amino acid or a starting or stopping signal for translation. The term codon also refers to base triplets in a DNA strand.

As used herein, the term "complementarity determining region" (CDR) refers to a hypervariable region found both in the light chain and the heavy chain variable domains. The more highly conserved portions of variable domains are called the framework regions (FRs). As is appreciated in the art, the amino acid positions that delineate a hypervariable region of an antibody can vary, depending on the context and the various definitions known in the art. The variable domains of native heavy and light chains each comprise four framework regions that primarily adopt a β-sheet configuration, connected by three CDRs, which form loops that connect, and in some cases form part of, the β-sheet structure. The CDRs in each chain are held together in close proximity by the FR regions in the order FR1-CDR1-FR2-CDR2-FR3-CDR3-FR4 and, with the CDRs from the other antibody chains, contribute to the formation of the target binding site of antibodies (see Kabat et al, Sequences of Proteins of Immunological Interest (National Institute of Health, Bethesda, Md. 1987; incorporated herein by reference). As used herein, numbering of immunoglobulin amino acid residues is done according to the immunoglobulin amino acid residue numbering system of Kabat et al, unless otherwise indicated.

Throughout this specification and claims, the word "comprise," or variations such as "comprises" or "comprising," will be understood to imply the inclusion of a stated integer or group of integers but not the exclusion of any other integer or group of integers.

By "isolated" is meant separated, recovered, or purified from a component of its natural environment. For example, a nucleic acid molecule or polypeptide of the invention may be isolated from a component of its natural environment by 1% (2%, 3%, 4%, 5%, 6%, 7%, 8% 9% 10%, 20%, 30%, 40%, 50%, 60% 70%, 80%, or 90%) or more by weight.

As used herein, the term "envelope glycoprotein" refers, but is not limited to, the glycoprotein that is expressed on the surface of the envelope of HIV virions and the surface of the plasma membrane of HIV infected cells. The env gene encodes gp160, which is proteolytically cleaved into the gp120 and gp41 Envelope (Env) proteins. Gp120 binds to the CD4 receptor on a target cell that has such a receptor, such as, e.g., a T-helper cell. Gp41 is non-covalently bound to gp120, and provides the second step by which HIV enters the cell. It is originally buried within the viral envelope, but when gp120 binds to a CD4 receptor, gp120 changes its conformation causing gp41 to become exposed, where it can assist in fusion with the host cell. Gp140 is a soluble form of gp160 that lacks the transmembrane and C-terminal regions. The numbering of the HIV Env glycoproteins described herein is consistent with the HXB2 numbering system (Korber et al., Numbering Positions in HIV Relative to HXB2CG, in the database compendium, *Human Retroviruses and AIDS*, 1998).

A "gene delivery vehicle" is defined as any molecule, composition, or construct that can carry inserted polynucleotides into a host cell. Examples of gene delivery vehicles are liposomes; biocompatible polymers, including natural polymers and synthetic polymers; lipoproteins; polypeptides; polysaccharides; lipopolysaccharides; artificial viral envelopes; metal particles; bacteria and viruses, such as baculovirus, adenovirus, and retrovirus; bacteriophage; cosmid; plasmid; fungal vectors; and other recombination vehicles typically used in the art that have been described for expression in a variety of eukaryotic and prokaryotic hosts, and may be used for gene therapy as well as for simple protein expression.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of techniques such as, for example, vector-mediated gene transfer (e.g., viral infection/transfection, or various other protein-based or lipid-based gene delivery complexes) as well as techniques facilitating the delivery of "naked" polynucleotides (such as electroporation, "gene gun" delivery, and various other techniques used for the introduction of polynucleotides).

By "gene product" is meant to include mRNAs transcribed from a gene (and any corresponding complementary DNAs (cDNAs)), as well as polypeptides translated from those mRNAs. The gene product is from a virus (e.g., a HIV) and may include, for example, any one or more of the viral proteins, or fragments thereof, described herein.

By "heterologous nucleic acid molecule" or "heterologous gene" is meant any exogenous nucleic acid molecule (e.g., a nucleic acid molecule encoding an optimized gp140 Env polypeptide of the invention) that can be inserted into a vector of the invention (e.g., an adenovirus or poxvirus vector) for transfer into a cell, tissue, or organism, for subsequent expression of a gene product of interest or fragment thereof encoded by the heterologous nucleic acid molecule or gene. The heterologous nucleic acid molecule, which can be administered to a cell or subject as part of the invention, can include, but is not limited to, a nucleic acid molecule encoding at least one optimized clade C Env polypeptide (e.g., an optimized 459C gp140 polypeptide).

The term "host cell," refers to cells into which a heterologous nucleic acid molecule has been introduced, including the progeny of such cells. Host cells include "transformants" and "transformed cells," which include the primary transformed cell and progeny derived therefrom without regard to the number of passages. Host cells include cells within the body of a subject (e.g., a mammalian subject (e.g., a human)) into which the heterologous nucleic acid molecule has been introduced.

By "human immunodeficiency virus" or "HIV" is meant a virus of the genus *Lentivirus*, part of the family of Retroviridae, and includes, but is not limited to, HIV type 1 (HIV-1) and HIV type 2 (HIV-2), two species of HIV that infect humans. Additionally, HIV isolates may be categorized by sensitivity to neutralizing antibodies, and includes, but is not limited to, those having very high (tier 1A), above-average (tier 1B), moderate (tier 2), or low (tier 3) sensitivity to antibody-mediated neutralization (see, e.g., Seaman et al., *J. Virol.* 84(3):1439-1452, 2010).

By "immune response" is meant a response by the immune system of a subject (e.g., a human) against an antigen or antigenic determinant introduced into the body of the subject or to immune cells of the subject. Exemplary immune responses include humoral immune responses (e.g., production of antigen-specific antibodies, e.g., neutralizing antibodies (NAbs)) and cell-mediated immune responses (e.g., lymphocyte proliferation).

By "neutralizing antibody" or "NAb" is meant an antibody that recognizes a specific antigen (e.g., HIV Env glycoprotein, such as a gp140 polypeptide or a gp120 polypeptide) and inhibits the ability of the antigen to mediate infection of a target cell; NAbs have been shown by passive transfer in non-human primate models to block infection. Thus, elicitation of NAbs by a vaccine is considered highly desirable. As used herein, the antibody can be a single antibody or a plurality of antibodies. The NAb may be purified from, or present in, serum.

As used herein, the term "non-native constant region" refers to an antibody constant region that is derived from a source that is different from the antibody variable region or that is a human-generated synthetic polypeptide having an amino sequence that is different from the native antibody constant region sequence. For instance, an antibody containing a non-native constant region may have a variable region derived from a non-human source (e.g., a mouse, rat, or rabbit) and a constant region derived from a human source (e.g., a human antibody constant region).

The terms "nucleic acid molecule" and "polynucleotide," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or C$_H$2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

By "optimized" is meant an immunogenic polypeptide that is not a naturally-occurring peptide, polypeptide, or protein, such as a non-naturally occurring viral polypeptide (e.g., a clade C gp140 polypeptide of the invention). An optimized viral polypeptide (e.g., a gp140 polypeptide) sequence is initially generated by modifying the amino acid residues relative to one or more naturally-occurring viral gene products (e.g., HIV Env peptides, polypeptides, and proteins) to increase the breadth, intensity, depth, or longevity of the antiviral immune response (e.g., cellular or humoral immune responses) generated upon immunization (e.g., when incorporated into a composition of the invention, e.g., vaccine of the invention) of a subject (e.g., a human). Thus, the optimized viral polypeptide may be derived from a "parent" viral gene sequence (e.g., a HIV sequence); alternatively, the optimized viral polypeptide may not correspond to a specific "parent" viral gene sequence but may correspond to analogous sequences from various strains or quasi-species of a virus. Modifications to the viral gene sequence that can be included in an optimized viral polypeptide include amino acid additions, substitutions, and deletions. For example, the optimized polypeptide may be derived from a "parent" 459C gp140 polypeptide that has been altered to include one or more of modifications intended to enhance access to an epitope of interest or to reflect the common diversity of that epitope. The optimized viral polypeptide may further include a leader/signal sequence for maximal protein expression (see, e.g., SEQ ID NO: 17), a factor Xa cleavage site, and/or a foldon trimerization domain (see, e.g., SEQ ID NO: 5). An optimized polypeptide of the invention may, but need not, also include a cleavage site mutation(s) (a description of these modifications can be found in, e.g., Fisher et al., *Nat. Med.* 13(1):100-106, 2007 and International Patent Application Publication WO 2007/024941, herein incorporated by reference). Once the optimized viral polypeptide sequence is generated, the corresponding polypeptide can be produced or administered by standard techniques (e.g., recombinant viral vectors, such as the adenoviral vectors disclosed in International Patent Application Publications WO 2006/040330 and WO 2007/104792, herein incorporated by reference) and optionally assembled to form a stabilized polypeptide trimer of the invention.

By "pharmaceutical composition" is meant any composition that contains a therapeutically or biologically active agent, such as an immunogenic composition or vaccine of the invention (e.g., an optimized HIV Env gp140 nucleic acid molecule, vector, and/or polypeptide (e.g., a stabilized polypeptide trimer), or a host cell containing the same, of the invention) that is suitable for administration to a subject and that treats or prevents a disease (e.g., HIV infection) or reduces or ameliorates one or more symptoms of the disease (e.g., HIV viral titer, viral spread, infection, and/or cell fusion)). For the purposes of this invention, pharmaceutical compositions include, but are not limited to, vaccines, and pharmaceutical compositions suitable for delivering a therapeutic or biologically active agent can include, for example, tablets, gelcaps, capsules, pills, powders, granulates, suspensions, emulsions, solutions, gels, hydrogels, oral gels, pastes, eye drops, ointments, creams, plasters, drenches, delivery devices, suppositories, enemas, solutions, injectables, implants, sprays, or aerosols. Any of these formulations can be prepared by well-known and accepted methods of art. See, for example, *Remington: The Science and Practice of Pharmacy* (21$^{st}$ ed.), ed. A. R. Gennaro, Lippincott Williams & Wilkins, 2005, and *Encyclopedia of Pharmaceutical Technology*, ed. J. Swarbrick, Informa Healthcare, 2006, each of which is hereby incorporated by reference.

By "pharmaceutically acceptable diluent, excipient, carrier, or adjuvant" is meant a diluent, excipient, carrier, or adjuvant, respectively, which is physiologically acceptable to the subject while retaining the therapeutic properties of the pharmaceutical composition with which it is administered. One exemplary pharmaceutically acceptable carrier is physiological saline. Other physiologically acceptable diluents, excipients, carriers, or adjuvants and their formulations are known to one skilled in the art (see, e.g., U.S. Pub. No. 2012/0076812).

By "promotes an immune response" is meant eliciting a humoral response (e.g., the production of antibodies) or a cellular response (e.g., the activation of T cells, macrophages, neutrophils, and/or natural killer cells) directed against, for example, one or more infective agents (e.g., a virus (e.g., a HIV)) or protein targets in a subject to which the pharmaceutical composition (e.g., an immunogenic composition or vaccine) has been administered. The compositions of the invention can be used, in particular, to promote a humoral immune response against HIV (e.g., a neutralizing antibody response against the HIV envelope glycoprotein, e.g., of Tier 1 and/or Tier 2 HIV).

By "recombinant," with respect to a composition of the invention (e.g., a vector of the invention, such as an adenovirus or poxvirus vector), is meant a composition that has been manipulated, e.g., in vitro (e.g., using standard cloning techniques) to introduce changes (e.g., changes to the composition, e.g., adenovirus or poxvirus genome of an adenovirus or poxvirus vector, respectively) that promote the introduction of a therapeutic agent into a subject (e.g., a human) or a host cell. The recombinant composition of the invention may therefore be an adenoviral or poxviral gene delivery vehicle (e.g., a replication-defective adenoviral or poxviral vector) for delivery of one or more of the stabilized clade C gp140 polypeptide trimers of the invention.

As used herein, the term "reducing" with respect to HIV refers to a reduction or decrease of an HIV-mediated activity (e.g., infection, fusion (e.g., target cell entry and/or syncytia formation), viral spread, etc.) and/or a decrease in viral titer. HIV-mediated activity and/or HIV titer may be decreased by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more compared to that of a control subject (e.g., an untreated subject or a subject treated with a placebo).

By "sequence identity" or "sequence similarity" is meant that the identity or similarity between two or more amino acid sequences, or two or more nucleotide sequences, is expressed in terms of the identity or similarity between the sequences. Sequence identity can be measured in terms of "percentage (%) identity," in which the higher the percentage, the more identity shared between the sequences. Sequence similarity can be measured in terms of percentage similarity (which takes into account conservative amino acid substitutions); the higher the percentage, the more similarity shared between the sequences. Homologs or orthologs of nucleic acid or amino acid sequences possess a relatively high degree of sequence identity/similarity when aligned using standard methods. Sequence identity may be measured using sequence analysis software on the default setting (e.g., Basic Local Alignment Search Tool (BLAST), Altschul et al., 1990). Such software may match similar sequences by assigning degrees of homology to various substitutions, deletions, and other modifications.

As used herein, the phrase "specifically binds" refers to a binding reaction which is determinative of the presence of an antigen in a heterogeneous population of proteins and other biological molecules that is recognized, e.g., by an antibody or antigen-binding fragment thereof, with particularity. An antibody or antigen-binding fragment thereof that specifically binds to an antigen will bind to the antigen with a $K_D$ of less than 100 nM. For example, an antibody or antigen-binding fragment thereof that specifically binds to an antigen will bind to the antigen with a $K_D$ of up to 100 nM (e.g., between 1 pM and 100 nM). An antibody or antigen-binding fragment thereof that does not exhibit specific binding to a particular antigen or epitope thereof will exhibit a $K_D$ of greater than 100 nM (e.g., greater than 500 nm, 1 µM, 100 µM, 500 µM, or 1 mM) for that particular antigen or epitope thereof. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate. See, Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of immunoassay formats and conditions that can be used to determine specific immunoreactivity.

As used herein, the term "stabilized polypeptide trimer" or "stabilized trimer" refers, but is not limited to, a complex of three HIV envelope glycoproteins that have been modified with a polypeptide (e.g., an oligomerization domain, such as a trimerization domain, as described herein) that increases the association of the envelope glycoproteins of the trimer (e.g., reduces dissociation of the trimer into monomeric units) and increases resistance to perturbations including, but not limited to, nonionic detergents, high heat, high salt, and/or mildly acidic pH (see, e.g., Sanders et al., J. Virol. 76(17):8875-8889, 2002). The stabilized polypeptide trimer, for example, may be a homotrimer composed of three optimized clade C gp140 polypeptides, for example, a trimer of three optimized 459C polypeptides each having an amino acid sequence of SEQ ID NO: 11, 12, 13, or 14; or variants thereof composed of three clade C gp140 polypeptides each having at least 92% identity (e.g., at least 93%, 94%, 95%, 96%, 97%, 98%, or 99% identity) to SEQ ID NO: 11, 12, 13, or 14. At least one of the gp140 proteins of the trimer (e.g., one, two, or all three) includes a trimerization domain.

An "oligomerization domain" refers, but is not limited to, a polypeptide that can be used to increase the stability of an oligomeric envelope protein complex (e.g., a trimer of HIV gp140 envelope proteins). Oligomerization domains can be used to increase the stability of homooligomeric polypeptides (e.g., homotrimers), as well as heterooligomeric polypeptides (e.g., heterotrimers). Oligomerization domains are well known in the art, and include "trimerization domains." A trimerization domain refers to an oligomerization domain that stabilizes trimeric polypeptides (e.g., trimers consisting of one or more of the gp140 polypeptides of the invention). Examples of trimerization domains include, but are not limited to, the T4-fibritin "foldon" trimerization domain; the coiled-coil trimerization domain derived from GCN4 (Yang et al., J. Virol. 76(9):4634-4642, 2002); and the catalytic subunit of E. coli aspartate transcarbamoylase as a trimer tag (Chen et al., J. Virol. 78(9):4508-4516, 2004). A particular oligomerization domain includes the amino acid sequence of SEQ ID NO: 5 and variants having at least 90% sequence identity thereto.

A "subject" is a vertebrate, such as a mammal (e.g., a human). Mammals also include, but are not limited to, farm animals (such as cows), sport animals (e.g., horses), pets (such as cats and dogs), guinea pigs, rabbits, mice, rats, and monkeys (such as rhesus). A subject to be treated according to the methods described herein (e.g., a subject having an HIV infection or a subject at risk of an HIV infection, e.g., a fetus of an HIV-1-infected pregnant female, a newborn having an HIV-1-infected mother, a person who has or has had a needlestick injury or sexual exposure to an HIV-1-infected individual) may be one who has been diagnosed by a medical practitioner as having such a condition. Diagnosis may be performed by any suitable means. A subject in whom the risk of an HIV infection is to be reduced or prevented may or may not have received such a diagnosis. One skilled in the art will understand that a subject to be treated according to the invention may have been subjected to standard tests or may have been identified, without examination, as one at high risk due to the presence of one or more risk factors (e.g., a needle stick or known exposure to HIV or an HIV infected individual).

By "therapeutically effective amount" is meant an amount of a therapeutic agent that alone, or together with one or more additional (optional) therapeutic agents, produces beneficial or desired results upon administration to a mammal, such as a human. The therapeutically effective amount depends upon the context in which the therapeutic agent is applied. For example, in the context of administering a vaccine composition including a therapeutic agent such as a stabilized clade C gp140 trimer of the invention, the therapeutically effective amount of the vaccine composition is an amount sufficient to achieve a reduction in the level of HIV (e.g., as measured by a stabilization or decrease in HIV titer compared to a non-treated control), and/or an increase in the level of neutralizing anti-HIV antisera (e.g., as measured by an increase in serum neutralizing antibody levels relative to a non-treated control in a luciferase-based virus neutralization assay) as compared to a response obtained without administration of a composition of the invention (e.g., a vaccine composition), and/or to reduce or prevent the propagation of an infectious virus (e.g., HIV) in a subject (e.g., a human) having an increased risk of viral infection. Ideally, a therapeutically effective amount provides a therapeutic effect without causing a substantial cytotoxic effect in the subject. In general, a therapeutically effective amount of a composition administered to a subject (e.g., a human) will vary depending upon a number of factors associated with that subject, for example the overall health of the subject, the condition to be treated, or the severity of the condition. A therapeutically effective amount of a composition can be determined by varying the dosage of the product and measuring the resulting therapeutic response.

As used herein, and as well understood in the art, "treatment" is an approach for obtaining beneficial or desired results, such as clinical results. Beneficial or desired results can include, but are not limited to, alleviation or amelioration of one or more symptoms or conditions associated with a viral (e.g., retroviral, e.g., HIV, e.g., HIV-1) infection, including, without limitation, fever, muscle aches, coughing, sneezing, runny nose, sore throat, headache, chills, diarrhea, vomiting, rash, weakness, dizziness, bleeding under the skin, in internal organs, or from body orifices like the mouth, eyes, or ears, shock, nervous system malfunction, delirium, seizures, renal (kidney) failure, personality changes, neck stiffness, dehydration, seizures, lethargy, paralysis of the limbs, confusion, back pain, loss of sensation, impaired bladder and bowel function, and sleepiness that can progress into coma or death; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

By "V2 neutralizing antibodies" as used herein, is meant a neutralizing antibody that specifically binds the variable loop 2 and glycans (V2) region of an HIV envelope polypeptide (e.g., amino acid residues 157 to 196 of HIV-1 gp140 (see, e.g., WT 459C), as well as glycans in this region; the amino acid numbering corresponds to HXB2 reference numbering). A V2 neutralizing antibody may also be one that specifically binds a region adjacent the V2 region (e.g., one or more residues at an amino-terminal or carboxy-terminal region surrounding the V2 region).

By "V3 neutralizing antibodies" as used herein, is meant a neutralizing antibody that specifically binds the variable loop 3 and glycans (V3) regions of an HIV envelope polypeptide (e.g., amino acid residues 296 to 331 of HIV-1 gp140 (see, e.g., WT 459C) as well as glycans in this region; the amino acid numbering corresponds to HXB2 reference numbering). A V3 neutralizing antibody may also be one that specifically binds a region adjacent the V3 region (e.g., one or more residues at an amino-terminal or carboxy-terminal region surrounding the V3 region).

The term "vaccine," as used herein, is defined as material used to provoke an immune response (e.g., the production of neutralizing anti-HIV antisera). Administration of the vaccine to a subject may confer at least partial immunity against HIV infection (e.g., infection by HIV-1, such as Tier 1 and/or Tier 2 HIV).

The term "variant," as used herein, is meant a polypeptide having at least 85% sequence identity (e.g., at least 86%, 87%, 88%, 89%, 90%, 91%, 92%, 93%, 94%, 95%, 96%, 97%, 98%, or 99% identity) to the amino acid sequence of a reference polypeptide.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may, at times, be used interchangeably as the plasmid is the most commonly used form of vector.

The term "virus," as used herein, is defined as an infectious agent that is unable to grow or reproduce outside a host cell and that infects mammals (e.g., humans).

A "viral vector" is defined as a recombinantly produced virus or viral; particle that comprises a polynucleotide to be delivered into a host cell. Examples of viral vectors include retroviral vectors, adenovirus vectors, adeno-associated virus vectors (e.g., see PCT publication no. WO 2006/002203), alphavirus vectors and the like.

In aspects where gene transfer is mediated by a DNA viral vector, such as an adenovirus (Ad) or adeno-associated virus (MV), a vector construct refers to the polynucleotide comprising the viral genome or part thereof, and a transgene. Ads are a relatively well characterized, homogenous group of viruses, including over 50 serotypes (WO 95/27071). Ads are easy to grow and do not require integration into the host cell genome. Recombinant Ad-derived vectors, particularly those that reduce the potential for recombination and generation of wild-type virus, have also been constructed (WO 95/00655 and WO 95/11984). Vectors that contain both a promoter and a cloning site into which a polynucleotide can be operatively linked are known in the art. Such vectors are capable of transcribing RNA in vitro or in vivo. To optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation.

BRIEF DESCRIPTION OF THE DRAWINGS

The application file contains at least one drawing executed in color. Copies of this patent or patent application with color drawings will be provided by the Office upon request and payment of the necessary fee.

FIG. 1A is a schematic and alignment of amino acid sequences of epitope modified (e.g., SET) immunogens. Shown are sequence modifications used to generate variable loop 2 (V2) optimized (Opt) and alternate (Alt) V2-SET constructs. Color scheme indicates amino acids associated with bNAb neutralization sensitivity (blue), resistance (red), conflicting (pink), or no effect (black). Amino acids are shown as single letter abbreviations. Letter size indicates the probability that an amino acid will occur at a given site. Amino acid positions are listed utilizing the HXB2 reference numbering. Outside of the epitope region, only sensitive and neutral variants are included in the 459C Opt and Alt constructs to enhance epitope exposure in both cases. Inside the epitope, sensitive forms are presented in the epitope in the Opt construct, while common resistance forms are included in the Alt construct. The trivalent vaccine induced both greater breadth and potency in vaccinated guinea pigs. The V1 and V2 hypervariable regions were also modified.

FIG. 1B is a schematic and alignment of amino acid sequences of epitope modified (e.g., SET) immunogens. Shown are sequence modifications used to generate variable loop 3 (V3) optimized (Opt) and alternate (Alt) constructs. Color scheme indicates amino acids associated with bNAb neutralization sensitivity (blue), resistance (red), conflicting (pink), or no effect (black). Amino acids are shown as single letter abbreviations. Letter size indicates the probability that an amino acid will occur at a given site. Amino acid positions are listed utilizing the HXB2 reference numbering. Outside of the epitope region, only sensitive and neutral variants are included in the 459C Opt and Alt constructs. Inside the epitope sensitive forms are favored in the Opt construct, resistance forms are included in the Alt construct. The Opt form of the vaccine when given alone yielded responses with greater potency than 459C WT, the epitope was almost unchanged in this case suggesting an effect by the outside epitope mutations.

FIG. 3A is a schematic showing guinea pig vaccination regimen for the optimized stabilized trimers and cocktails of the same. Animals were vaccinated intramuscularly in the quadriceps with 100 μg total immunogen at weeks 0, 4, and 8 according to the listed vaccination schedule. The group size of vaccinated subjects is listed under 'n'.

FIG. 3B is a graph showing the magnitude and position of binding antibody responses from guinea pig sera to linear 15-mer peptides on peptide microarrays. Each dot represents an average MFI per single peptide that is positive for antibody binding within each vaccination group with standard deviation shown. Titles indicate vaccination regimen (459C WT). MFI: mean fluorescence intensity. Envelope regions are delineated by vertical lines.

FIG. 4A is a schematic showing a heat map comparison of clustering of the magnitude of tier 2 NAb titers elicited by guinea pigs vaccinated with variable loop 2 modified immunogens. The test pseudoviruses are listed below the maps; each row corresponds to a single guinea pig, and rows are clustered by vaccination regimen as listed to the right of the heat map. The highest ID50 responses are shown with the highest intensity color (dark red) and lower responses shown with the lowest intensity color (very light yellow). Negative responses shown in blue. The left side of the map includes average responses across all pseudoviruses per animal for all data (geometric means) as well as across only positive data (positive geometric means). Each map includes average responses across all pseudoviruses per animal for all data (Geomeans) as well as across only positive data (Positive Geomeans). Data from Cutoff 1 shown.

FIG. 4B is a schematic showing a heat map comparison of clustering of the magnitude of tier 2 NAb titers elicited by guinea pigs vaccinated with variable loop 3 modified immunogens. The test pseudoviruses are listed below the maps, each row corresponds to a single guinea pig, and rows are clustered by vaccination regimen as listed to the right of the heat map. The highest ID50 responses are shown with the highest intensity color (dark red) and lower responses shown with the lowest intensity color (very light yellow). Negative responses shown in blue. Each map includes average responses across all pseudoviruses per animal for all data (Geomeans) as well as across only positive data (Positive Geomeans). Data from Cutoff 1 shown.

FIG. 9D is a graph showing the total number of positive peptides bound by antibodies within V2, with each dot representing one animal and the red horizontal line at the mean. Vaccination regimen performed with 459C V2 Opt gp140.

FIG. 9E is a graph showing the total number of positive peptides bound by antibodies within V2, with each dot representing one animal and the red horizontal line at the mean. Vaccination regimen performed with 459C V2 Alt gp140.

FIG. 9F is a graph showing the total number of positive peptides bound by antibodies within V2, with each dot representing one animal and the red horizontal line at the mean. Vaccination regimen performed with 459C V3 Opt gp140.

FIG. 9G is a graph showing the total number of positive peptides bound by antibodies within V2, with each dot representing one animal and the red horizontal line at the mean. Vaccination regimen performed with 459C V3 Alt gp140.

FIG. 9K is a graph showing the total number of positive peptides bound by antibodies within V3, with each dot representing one animal and the red horizontal line at the mean. Vaccination regimen performed with 459C WT gp140.

FIG. 9L is a graph showing the total number of positive peptides bound by antibodies within V3, with each dot representing one animal and the red horizontal line at the mean. Vaccination regimen performed with 459C V2 Opt gp140.

FIG. 9M is a graph showing the total number of positive peptides bound by antibodies within V3, with each dot representing one animal and the red horizontal line at the mean. Vaccination regimen performed with 459C V2 Alt gp140.

FIG. 9N is a graph showing the total number of positive peptides bound by antibodies within V3, with each dot representing one animal and the red horizontal line at the mean. Vaccination regimen performed with 459C V3 Opt gp140.

FIG. 11A is a graph showing the results of a TZM.bl neutralization assay performed with guinea pig sera obtained after three vaccinations (week 12), tested against a clade C tier 1A neutralization-sensitive pseudovirus isolate. Neutralization data for every data point are animal-matched, MuLV negative control background subtracted. Values less than 10 set to 10. Horizontal red lines indicate mean titers. The x-axis immunogen names refer to the vaccination regimen.

FIG. 11B is a graph showing the results of a TZM.bl neutralization assay performed with guinea pig sera obtained after three vaccinations (week 12), tested against a clade B tier 1A neutralization-sensitive pseudovirus isolate. Neutralization data for every data point are animal-matched, MuLV negative control background subtracted. Values less than 10 set to 10. Horizontal red lines indicate mean titers. The x-axis immunogen names refer to the vaccination regimen.

FIG. 11C is a graph showing the results of a TZM.bl neutralization assay performed with guinea pig sera obtained after three vaccinations (week 12), tested against a clade B tier 1B neutralization-sensitive pseudovirus isolate. Neutralization data for every data point are animal-matched, MuLV negative control background subtracted. Values less than 10 set to 10. Horizontal red lines indicate mean titers. The x-axis immunogen names refer to the vaccination regimen.

FIG. 11D is a graph showing the results of a TZM.bl neutralization assay performed with guinea pig sera obtained after three vaccinations (week 12), tested against a clade C tier 1B neutralization-sensitive pseudovirus isolate. Neutralization data for every data point are animal-matched, MuLV negative control background subtracted. Values less than 10 set to 10. Horizontal red lines indicate mean titers. The x-axis immunogen names refer to the vaccination regimen.

FIG. 11E is a graph showing the results of a TZM.bl neutralization assay performed with guinea pig sera obtained after three vaccinations (week 12), tested against a clade A tier 1B neutralization-sensitive pseudovirus isolate. Neutralization data for every data point are animal-matched, MuLV negative control background subtracted. Values less than 10 set to 10. Horizontal red lines indicate mean titers. The x-axis immunogen names refer to the vaccination regimen.

FIG. 11F is a graph showing the results of a TZM.bl neutralization assay performed with guinea pig sera obtained after three vaccinations (week 12), tested against a clade C tier 1B neutralization-sensitive pseudovirus isolate. Neutralization data for every data point are animal-matched, MuLV negative control background subtracted. Values less than 10 set to 10. Horizontal red lines indicate mean titers. The x-axis immunogen names refer to the vaccination regimen.

FIG. 11G is a graph showing the results of a TZM.bl neutralization assay performed with guinea pig sera obtained after three vaccinations (week 12), tested against a clade B tier 1B neutralization-sensitive pseudovirus isolate. Neutralization data for every data point are animal-matched, MuLV negative control background subtracted. Values less than 10 set to 10. Horizontal red lines indicate mean titers. The x-axis immunogen names refer to the vaccination regimen.

FIG. 11H is a graph showing the results of a TZM.bl neutralization assay performed with guinea pig sera obtained after three vaccinations (week 12), tested against a clade B tier 1B neutralization-sensitive pseudovirus isolate. Neutralization data for every data point are animal-matched, MuLV negative control background subtracted. Values less than 10 set to 10. Horizontal red lines indicate mean titers. The x-axis immunogen names refer to the vaccination regimen.

FIG. 11I is a heat map illustration of the clustering of tier 1 TZM.bl NAb titers elicited by guinea pigs vaccinated with V2 modified immunogens. Test pseudoviruses are listed below the maps, each row corresponds to a single guinea pig, and rows are clustered by vaccination regimen, as listed to the right of the heat map. The highest ID50 responses are shown with the highest intensity color (dark red) and lower responses shown with the lowest intensity color (very light yellow). Negative responses shown in blue. All data generated utilizing cutoff 1 as defined in materials and methods.

FIG. 11J is a heat map illustration of the clustering of tier 1 TZM.bl NAb titers elicited by guinea pigs vaccinated with V3 modified immunogens. Test pseudoviruses are listed below the maps, each row corresponds to a single guinea pig, and rows are clustered by vaccination regimen, as listed to the right of the heat map. The highest ID50 responses are shown with the highest intensity color (dark red) and lower responses shown with the lowest intensity color (very light yellow). Negative responses shown in blue. All data generated utilizing cutoff 1 as defined in materials and methods.

FIG. 12A is a graph showing the results of a TZM.bl neutralization assay results of guinea pig sera obtained after three vaccinations (week 12), tested against clade C tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.

FIG. 12B is a graph showing the results of a TZM.bl neutralization assay results of guinea pig sera obtained after three vaccinations (week 12), tested against a clade C tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.

FIG. 12C is a graph showing the results of a TZM.bl neutralization assay results of guinea pig sera obtained after three vaccinations (week 12), tested against a clade 02_AG tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.

FIG. 12D is a graph showing the results of a TZM.bl neutralization assay results of guinea pig sera obtained after three vaccinations (week 12), tested against a clade 07_BC tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.

FIG. 12E is a graph showing the results of a TZM.bl neutralization assay results of guinea pig sera obtained after three vaccinations (week 12), tested against a clade 01_AE tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.

FIG. 12F is a graph showing the results of a TZM.bl neutralization assay results of guinea pig sera obtained after three vaccinations (week 12), tested against a clade C tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.

FIG. 12G is a graph showing the results of a TZM.bl neutralization assay results of guinea pig sera obtained after three vaccinations (week 12), tested against a clade C tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.

FIG. 15A is a graph showing the magnitude of neutralizing antibody titers elicited against tier 2 pseudoviruses in purified IgG from guinea pigs after immunization with HIV-1 Env gp140 epitope modified immunogens. Purified polyclonal IgG from vaccinated guinea pigs run against select tier 2 pseudoviruses and MuLV (negative control) as listed on the x-axis. Vaccination regimen listed in the title. Horizontal red lines indicate mean titers.

FIG. 15B is a heat map illustration of the clustering of tier 2 TZM.bl purified polyclonal NAb concentrations of vaccinated guinea pigs. Test pseudovirus listed below the maps, each row corresponds to a single guinea pig, and rows are clustered by vaccination regimen, as listed to the right of the heat map. The highest IC50 responses are shown with the highest intensity color (dark red) and lower responses shown with the lowest intensity color (very light yellow). Negative responses shown in blue. All data generated utilizing cutoff 1 (cutoff as described in materials and methods).

FIG. 16B is a graph comparing tier 2 NAb responses between 459C WT and the V2 Mixture vaccines. The graph shows the geometric means of NAb titers across all guinea pigs vaccinated with the same regimen and tested against the same pseudovirus with a single dot per vaccine per test pseudovirus. The dotted line at the arbitrary ID50 titer of 100 is added for visual emphasis. Dots in grey box are responses below the limit of detection for the assay and are aligned for visualization. Colors in key represent each vaccination regimen.

FIG. 16C is a graph comparing tier 2 NAb responses between 459C WT and the V2 Mixture vaccines. The graph shows the raw responses, with each dot corresponding to a single guinea pig. The dotted line at the arbitrary ID50 titer of 100 is added for visual emphasis. Dots in grey box are responses below the limit of detection for the assay and are aligned for visualization. Colors in key represent each vaccination regimen.

FIG. 17A is a graph showing the mapping of neutralizing antibody responses against variable loop 2 and 3 mutant, tier 2 pseudoviruses. Guinea pigs vaccinated with V2 Mixture and 459C WT alone were compared against natural Envs as well as T162I glycan mutants of matched pseudoviruses. Raw ID50 titers shown on the top graphs and data normalized to 459C WT shown on bottom graphs. Dotted line at a titer of 20 representing the limit of detection of the TZM.bl neutralization assay. Colors and shapes in key represent each vaccination regimen and natural or T162I mutant pseudovirus tested.

FIG. 17B is a graph showing the mapping of neutralizing antibody responses against variable loop 2 and 3 mutant, tier 2 pseudoviruses. Guinea pigs vaccinated with V2 Prime/Boost and 459C WT alone were compared against natural Envs as well as T162I glycan mutants of matched pseudoviruses. Raw ID50 titers shown on the top graphs and data normalized to 459C WT shown on bottom graphs. Dotted line at a titer of 20 representing the limit of detection of the TZM.bl neutralization assay. Colors and shapes in key represent each vaccination regimen and natural or T162I mutant pseudovirus tested.

FIG. 17C is the mapping of neutralizing antibody responses against variable loop 2 and 3 mutant, tier 2 pseudoviruses. Guinea pigs vaccinated with V2 Mixture and 459C WT alone were compared against an extended panel of natural Envs as well as T162I and N160[AK] glycan mutant pseudoviruses. Raw ID50 titers shown on the top graphs and data normalized to 459C WT shown on bottom graphs. Dotted line at a titer of 20 representing the limit of detection of the TZM.bl neutralization assay. Colors and shapes in key represent each vaccination regimen and natural or T162I mutant pseudovirus tested.

FIG. 17D is a graph showing the mapping of neutralizing antibody responses against variable loop 2 and 3 mutant, tier 2 pseudoviruses. Guinea pigs vaccinated with V3 Opt and 459C WT alone were compared against a panel of natural Envs as well as V3 glycan mutant pseudoviruses. Raw ID50 titers shown on the top graphs and data normalized to 459C WT shown on bottom graphs. Dotted line at a titer of 20 representing the limit of detection of the TZM.bl neutralization assay. Colors and shapes in key represent each vaccination regimen and natural or T162I mutant pseudovirus tested.

DETAILED DESCRIPTION OF THE INVENTION

Figure 2A:
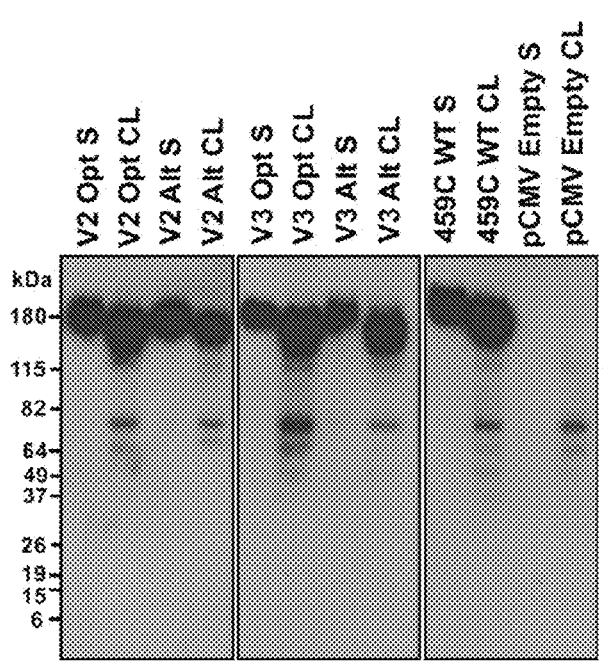
FIG. 2A is a photograph of a western blot showing expression levels of epitope modified (e.g., SET) HIV-1 gp140 Env polypeptides from small scale transfections. "CL" refers to a cell lysate and "S" refers to supernatant.
Figure 2B:
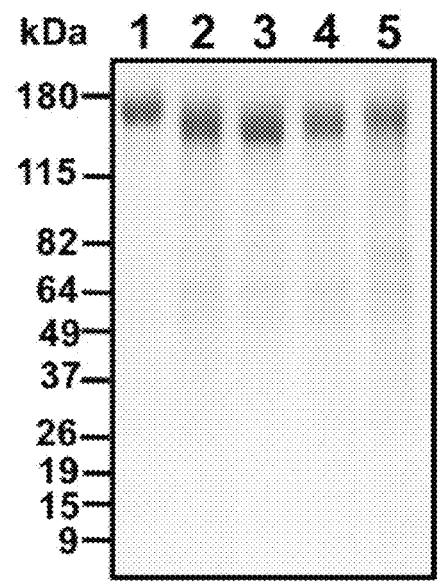
FIG. 2B is a photograph of a Coomassie stained SDS-PAGE gel showing purified gp140 Env. The lanes contain (1) 459C WT, (2) V2 Opt, (3) V2 Alt, (4) V3 Opt, and (5) V3 Alt HIV-1 Env gp140.
Figure 2C:
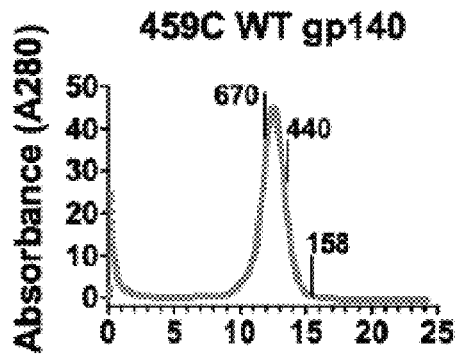
FIG. 2C is a graph showing the results of a gel filtration chromatography trace of 459C WT gp140 as run on a Superose 6 column. Molecular mass standards include thyoglobin (670 kDa), ferritin (440 kDa), and γ-globin (158 kDa).
Figure 2D:
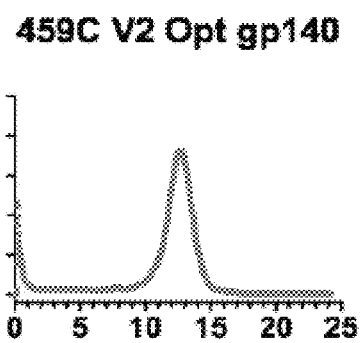
FIG. 2D is graph showing the results of a gel filtration chromatography trace of 459C V2 Opt gp140 as run on a Superose 6 column. Molecular mass standards are shown in FIG. 2C.
Figure 2E:
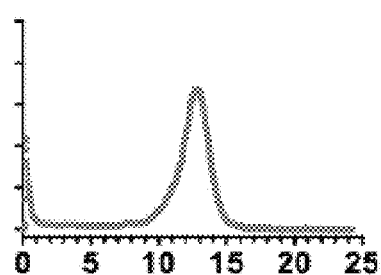
FIG. 2E is a graph showing the results of a gel filtration chromatography trace of 459C V2 Alt gp140 as run on a Superose 6 column. Molecular mass standards are shown in FIG. 2C.
Figure 2F:
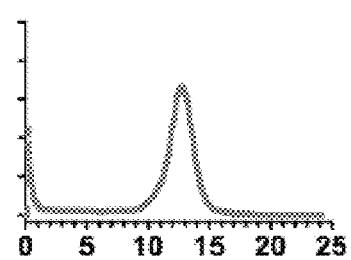
FIG. 2F is a graph showing the results of a gel filtration chromatography trace of 459C V3 Opt gp140 as run on a Superose 6 column. Molecular mass standards are shown in FIG. 2C.
Figure 2G:
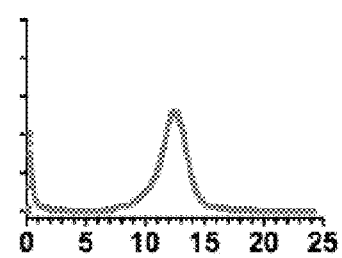
FIG. 2G is a graph showing the results of a gel filtration chromatography trace of 459C V3 Alt gp140 as run on a Superose 6 column. Molecular mass standards are shown in FIG. 2C.

The invention is based on the discovery that modifications to the V2 or V3 regions of human immunodeficiency virus (HIV) (e.g., HIV type 1 (HIV-1)) Env glycoproteins produce HIV immunogens that elicit robust nAb against HIV viruses, in particular Tier 2 HIV that are difficult to neutralize and represent circulating forms of the virus. These modified HIV Env glycoproteins can be used to prepare stabilized trimeric immunogens and combinations thereof that elicit a broad heterologous neutralizing antibody response in vivo against HIV (e.g., HIV-1, such as Tier 1 and Tier 2 HIV). Most antibodies induced by HIV are ineffective at preventing initiation or spread of infection, as they are either non-neutralizing or narrowly isolate-specific. One of the biggest challenges in HIV vaccine development is to design a HIV envelope immunogen that can induce protective, neutralizing antibodies effective against the diverse HIV strains that characterize the global pandemic. Indeed, the generation of "broadly neutralizing" antibodies that recognize relatively conserved regions on the envelope glycoprotein are rare. For example, difficulties in generating broadly neutralizing antibodies (bNAbs) arise from the extensive sequence diversity of circulating strains of HIV-1 (Gaschen, Science 296:2354-2360, 2002). The compositions of the invention, as a signature-based vaccine design, address an unmet need for effective HIV therapies.

Polypeptides of the Invention

The invention features optimized HIV clade C gp140 Env polypeptides. We have bioinformatically designed a series of unique, epitope modified trimers utilizing the previously described early clade C HIV-1 Env 459C gp140Fd trimer (Bricault et al., J. Virol. 89(5):2507-19, 2015) as the backbone upon which to introduce amino acid modification. For the construction of the immunogens, bNAbs targeting distinct regions of Env, including the variable loop 2 (V2) and variable loop 3 (V3) have been tested against a panel of 219 unique pseudovirions (DeCamp et al., J. Virol. 88:2489-2507, 2014; Lacerda et al., Virol. J. 10:347, 2013; Yoon et al., Nucleic Acids Res. 43:W213-W219, 2015). We designed two sets of polyvalent vaccine that incorporated the vaccine antigens that could be used in combination, either for the V2 glycan binding antibodies, or for the V3 glycan binding antibodies. For each set, the first antigen was the natural 459c expressed as a soluble trimer. The second was a modified version of the 459C WT trimer containing relevant amino acids and hypervariable loop region characteristics that were statistically robustly associated with the greatest neutralization sensitivity (optimized, Opt). Some of the signature residues are inside the antibody binding sites, while some are outside of the binding site. We hypothesized that those Env signatures outside the antibody binding sites were important for epitope accessibility and protein expression. So for the third antigen in each set we made a modified version of the 459c opt protein that retained all of the sensitivity signatures and hypervariable loop characteristics associated with sensitivity to the antibody class outside of the epitope, to maintain enhanced epitope exposure. Within the binding region we specifically introduced commonly found amino acids that were associated with neutralization resistance (alternate, Alt). The reason for including resistance signatures in the antibody binding site was to design a trivalent vaccine that represented common natural variants of the epitope region that are relevant to antibody binding, to select for antibodies that could better interact with common epitope variants. Soluble Env gp140 trimers, as compared to Env gp120 monomers, more closely mimic the antigenic properties of circulating virions, and generate more robust neutralizing antibody responses, so all three polypeptides were expressed as soluble Env gp140 trimers. Polypeptides of the invention may include:

(a) polypeptide encoding a human immunodeficiency virus (HIV) envelope (Env) glycoprotein mutations of amino having an asparagine residue at position 33, a lysine residue at position 49, a glutamic acid residue at position 130, and a threonine residue at position 132 relative to the sequence of HXBX2 Chronic Clone B; and/or (b) a HIV Env glycoprotein having an asparagine residue at position 156, a serine residue at position 158, an asparagine residue at position 160, a methionine residue at position 161, a threonine residue at position 162, a threonine residue at position 163, a glutamic acid residue at position 164, a lysine residue at position 165, an arginine residue at position 166, an aspartic acid residue at position 167, a lysine residue at position 168, a lysine residue at position 169, a lysine residue at position 170, a lysine residue at position 171, a valine residue at position 172, and a serine residue at position 173 relative to the sequence of HXBX2 Chronic Clone B; and/or (c) a HIV Env glycoprotein having a tyrosine residue at position 177, a tyrosine residue at position 223, an isoleucine residue at position 297, a serine residue at position 306, an aspartic acid residue at position 322, a lysine residue at position 335, a serine residue at position 636, an arginine residue at position 644, and an asparagine residue at position 677 relative to the sequence of HXBX2 Chronic Clone B.

(d) a HIV Env glycoprotein having an asparagine residue at position 33, a glutamic acid residue at position 49, an aspartic acid residue at position 130, and a lysine residue at position 132 relative residue to the sequence of HXBX2 Chronic Clone B; and/or (e) a HIV Env glycoprotein having an asparagine residue at position 156, a threonine residue at position 158, an asparagine residue at position 160, an isoleucine residue at position 161, a threonine residue at position 162, a threonine residue at position 163, a serine residue at position 164, a valine residue at position 165, a lysine residue at position 166, a glycine residue at position 167, a lysine residue at position 168, an arginine residue at position 169, a glutamine residue at position 170, a glutamine residue at position 171, a glutamic acid residue at position 172, and a histidine residue at position 173 relative to the sequence of HXBX2 Chronic Clone B; and/or (f) a HIV Env glycoprotein having a tyrosine residue at position 177, a tyrosine residue at position 223, a valine residue at position 297, a serine residue at position 306, a glutamic acid residue at position 322, a lysine residue at position 335, a serine residue at position 636, an arginine residue at position 644, and an asparagine residue at position 677 relative to the sequence of HXBX2 Chronic Clone B.

(g) a HIV Env glycoprotein having an aspartic acid residue at position 62, a valine residue at position 85, a lysine residue at position 160, a threonine residue at position 162, an isoleucine residue at position 184, a threonine residue at position 240, an asparagine residue at position 276, and a threonine residue at position 278 relative to the sequence of HXBX2 Chronic Clone B; and/or (h) a HIV Env glycoprotein having an asparagine residue at position 295, a threonine residue at position 297, a glycine residue at position 300, an asparagine residue at position 301, a threonine residue at position 303, an arginine residue at position 304, an isoleucine residue at position 307, an isoleucine residue at position 323, a glycine residue at position 324, an aspartic acid residue at position 325, an isoleucine residue at position 326, an arginine residue at position 327, a glutamine residue at position 328, a histidine residue at position 330, an asparagine residue at position 332, and a serine residue at position 334 relative to the sequence of HXBX2 Chronic Clone B; and/or (i) a HIV Env glycoprotein having an alanine residue at position 336, an asparagine residue at position 339, a threonine residue at position 341, a glutamine residue at position 344, an alanine residue at position 346, an asparagine residue at position 392, a threonine residue at position 394, and a serine residue at position 668 relative to the sequence of HXBX2 Chronic Clone B.

(j) a HIV Env glycoprotein having an aspartic acid residue at position 62, a valine residue at position 85, an asparagine residue at position 160, a threonine residue at position 162, an isoleucine residue at position 184, a threonine residue at position 240, an asparagine residue at position 276, and a serine residue at position 278 relative to the sequence of HXBX2 Chronic Clone B; and/or (k) a HIV Env glycoprotein having a threonine residue at position 295, an isoleucine residue at position 297, a serine residue at position 300, an asparagine residue at position 301, a threonine residue at position 303, an arginine residue at position 304, a valine residue at position 307, an isoleucine residue at position 323, a glycine residue at position 324, an asparagine residue at position 325, an isoleucine residue at position 326, an arginine residue at position 327, a lysine residue at position 328, a tyrosine residue at position 330, a glutamic acid residue at position 332, and an asparagine residue at position 334 relative to the sequence of HXBX2 Chronic Clone B; and/or (l) a HIV Env glycoprotein having a threonine residue at position 336, an asparagine residue at position 339, a threonine residue at position 341, an asparagine residue at position 344, a serine residue at position 346, an asparagine residue at position 392, a serine residue at position 394, and a serine residue at position 668 relative to the sequence of HXBX2 Chronic Clone B.

Additionally, polypeptides of the invention include, for example, an optimized polypeptide including (a) an amino acid sequence having at least 92% identity (e.g., at least 93%, 94%, 95%, 96%, 97%, 98%, 99%, or 100% identity) to SEQ ID NOs: 1, 11, or 19 (459C V2 Opt-based polypeptides); (b) an amino acid sequence having at least 92% identity (e.g., at least 93%, 94%, 95%, 96%, 97%, 98%, 99%, or 100% identity) to SEQ ID NOs: 2, 12, or 20 (459C V2 Alt-based polypeptides); (c) an amino acid sequence having at least 92% identity (e.g., at least 93%, 94%, 95%, 96%, 97%, 98%, 99%, or 100% identity) to SEQ ID NOs: 3, 13, or 21 (459C V3 Opt-based polypeptides); or (d) an amino acid sequence having at least 92% identity (e.g., at least 93%, 94%, 95%, 96%, 97%, 98%, 99%, or 100% identity) to SEQ ID NOs: 4, 14, or 22 (459C V3 Alt-based polypeptides).

These polypeptides may have, or may be modified to include, one or more of the following domains and/or mutations. A clade C gp140 Env polypeptide constituent of a stabilized trimer of the invention may include a T4-fibritin "foldon" trimerization domain sequence to support stable trimer formation, such as an amino acid sequence having at least 90% identity (e.g., at least 91%, 92%, 93%, 94%, 95%, 96%, 97%, 98%, 99%, or 100% identity) to SEQ ID NO: 5. Such optimized clade C gp140 Env polypeptides include the 459C V2 Opt gp140-foldon (gp140Fd) polypeptide (SEQ ID NO: 11), 459C V2 Alt gp140-foldon (gp140Fd) polypeptide (SEQ ID NO: 12), 459C V3 Opt gp140-foldon (gp140Fd) polypeptide (SEQ ID NO: 13), 459C V3 Alt gp140-foldon (gp140Fd) polypeptide (SEQ ID NO: 14), and variants thereof, which each include a C-terminal trimerization domain, and may include a C-terminal histidine tag (SEQ ID NO: 29). The optimized gp140 Env polypeptides may also include cleavage site mutations to enhance stability, for example, by eliminating cleavage by a peptidase. The optimized gp140 Env polypeptides may additionally have a signal/leader sequence at the N-terminus of the polypeptide to maximize protein expression, such as an amino acid sequence having at least 90% identity (e.g., at least 91%, 92%, 93%, 94%, 95%, 96%, 97%, 98%, 99%, or 100% identity) to SEQ ID NO: 17. Further, the optimized gp140 Env polypeptides may include a Factor Xa cleavage site (SRIEGR), which may, for example, be incorporated upstream of (N-terminal to) the trimerization domain.

Stabilized Trimers of the Invention

The invention also features stabilized HIV clade C gp140 Env polypeptide trimers. Stabilized trimers of the invention feature optimized clade C gp140 Env polypeptides, such as the optimized clade C gp140 polypeptides of the invention described above. As discussed herein below, the stabilized trimers of the invention can be either homotrimers (e.g., trimers composed of three identical polypeptides) or heterotrimers (e.g., trimers composed of three polypeptides that are not all identical). The stabilized trimer of the invention may be a stabilized homotrimer that includes, for example, three optimized gp140 polypeptides. Exemplary homotrimers of the invention include Trimers 1, 2, 3, and 4 described in Table 1 below.

In particular, a trimer of the invention includes the following: a trimer of V2 Opt polypeptides (SEQ ID NOs: 1, 11, or 19), a trimer of V2 Alt polypeptides (SEQ ID NOs: 2, 12, or 20), a trimer of V3 Opt polypeptides (SEQ ID NOs: 3, 13, or 21), or a trimer of V3 Alt polypeptides (SEQ ID NOs: 4, 14, or 22).

Alternatively, the stabilized trimer of the invention may be a stabilized heterotrimer. For example, the stabilized trimer may be a stabilized heterotrimer that includes a combination of two different optimized clade C gp140 polypeptides (e.g., polypeptides having the sequence of SEQ ID NO: 11 and SEQ ID NO: 12; SEQ ID NO: 11 and SEQ ID NO: 13; and SEQ ID NO: 12 and SEQ ID NO: 14), such as Trimers 5-10 described in Table 1 below. The optimized gp140 polypeptides of the invention may also be combined with a WT clade C gp140 polypeptide, such as Trimers 11-12 described in Table 1 below. In some instances, the stabilized trimer may be a stabilized heterotrimer that includes a combination of three different optimized clade C gp140 polypeptides (e.g., combinations of polypeptides having the sequence of SEQ ID NO: 11, SEQ ID NO: 12, SEQ ID NO: 13, and SEQ ID NO: 14) or a WT clade C gp140 sequence (WT 459C), such as Trimers 26-34 described in Table 1 below.

TABLE 1

Optimized gp140 Trimers of the Invention

| Exemplary Trimer | Constituent Polypeptides | | |
|---|---|---|---|
| | Polypeptide 1 | Polypeptide 2 | Polypeptide 3 |
| Trimer 1 | SEQ ID NO: 11 | SEQ ID NO: 11 | SEQ ID NO: 11 |
| Trimer 2 | SEQ ID NO: 12 | SEQ ID NO: 12 | SEQ ID NO: 12 |
| Trimer 3 | SEQ ID NO: 13 | SEQ ID NO: 13 | SEQ ID NO: 13 |
| Trimer 4 | SEQ ID NO: 14 | SEQ ID NO: 14 | SEQ ID NO: 14 |
| Trimer 5 | SEQ ID NO: 11 | SEQ ID NO: 11 | SEQ ID NO: 12 |
| Trimer 6 | SEQ ID NO: 11 | SEQ ID NO: 12 | SEQ ID NO: 12 |
| Trimer 7 | SEQ ID NO: 11 | SEQ ID NO: 11 | SEQ ID NO: 13 |
| Trimer 8 | SEQ ID NO: 11 | SEQ ID NO: 13 | SEQ ID NO: 13 |
| Trimer 9 | SEQ ID NO: 11 | SEQ ID NO: 11 | SEQ ID NO: 14 |
| Trimer 10 | SEQ ID NO: 11 | SEQ ID NO: 14 | SEQ ID NO: 14 |
| Trimer 11 | SEQ ID NO: 11 | SEQ ID NO: 11 | WT 459C |
| Trimer 12 | SEQ ID NO: 11 | WT 459C | WT 459C |
| Trimer 13 | SEQ ID NO: 12 | SEQ ID NO: 12 | SEQ ID NO: 13 |
| Trimer 14 | SEQ ID NO: 12 | SEQ ID NO: 13 | SEQ ID NO: 13 |
| Trimer 15 | SEQ ID NO: 12 | SEQ ID NO: 13 | SEQ ID NO: 13 |
| Trimer 16 | SEQ ID NO: 12 | SEQ ID NO: 14 | SEQ ID NO: 14 |
| Trimer 17 | SEQ ID NO: 12 | SEQ ID NO: 14 | SEQ ID NO: 14 |
| Trimer 18 | SEQ ID NO: 12 | SEQ ID NO: 12 | WT 459C |
| Trimer 19 | SEQ ID NO: 12 | WT 459C | WT 459C |
| Trimer 20 | SEQ ID NO: 13 | SEQ ID NO: 13 | SEQ ID NO: 14 |
| Trimer 21 | SEQ ID NO: 13 | SEQ ID NO: 14 | SEQ ID NO: 14 |
| Trimer 22 | SEQ ID NO: 13 | SEQ ID NO: 13 | WT 459C |
| Trimer 23 | SEQ ID NO: 13 | WT 459C | WT 459C |
| Trimer 24 | SEQ ID NO: 14 | SEQ ID NO: 14 | WT 459C |
| Trimer 25 | SEQ ID NO: 14 | WT 459C | WT 459C |
| Trimer 26 | SEQ ID NO: 11 | SEQ ID NO: 12 | SEQ ID NO: 13 |
| Trimer 27 | SEQ ID NO: 11 | SEQ ID NO: 12 | SEQ ID NO: 14 |
| Trimer 28 | SEQ ID NO: 11 | SEQ ID NO: 12 | WT 459C |
| Trimer 29 | SEQ ID NO: 11 | SEQ ID NO: 13 | SEQ ID NO: 14 |
| Trimer 30 | SEQ ID NO: 11 | SEQ ID NO: 13 | WT 459C |
| Trimer 31 | SEQ ID NO: 11 | SEQ ID NO: 14 | WT 459C |
| Trimer 32 | SEQ ID NO: 12 | SEQ ID NO: 13 | WT 459C |
| Trimer 33 | SEQ ID NO: 12 | SEQ ID NO: 14 | WT 459C |
| Trimer 34 | SEQ ID NO: 13 | SEQ ID NO: 14 | WT 459C |

The polypeptides of the trimers described above may also have a signal peptide at the N-terminus (e.g., a signal peptide having the sequence of SEQ ID NO: 17).

Nucleic Acid Molecules of the Invention

The invention also features nucleic acid molecules encoding the optimized HIV clade C gp140 Env polypeptides described above. The nucleic acid molecules of the invention can encode one or more of the optimized Env polypeptides (e.g., V2 Opt, V2 Alt, V3 Opt, and/or V3 Alt). The nucleic acid molecules have a nucleotide sequence with at least 90% (e.g., at least 91%, 92%, 93%, 94%, 95%, 96%, 97%, 98%, 99% or 100%) sequence identity to, all or a portion of any one of (a) SEQ ID NOs: 7, 11, 19, or 25 (459C V2 Opt-based polypeptides); (b) SEQ ID NOs: 8, 12, 20, or 26 (459C V2 Alt-based polypeptides); (c) SEQ ID NOs: 9, 13, 27 or 35 (459C V3 Opt-based polypeptides); (d) SEQ ID NOs: 10, 14, 28 or 36 (459C V3 Alt-based polypeptides); (e) SEQ ID NO: 6 (Trimerization Domain); or (f) SEQ ID NO: 18 (Leader signal sequence), or a complementary sequence thereof. Alternatively, an isolated nucleic acid molecule has a nucleotide sequence that encodes a gp140 polypeptide with at least 92% (e.g., at least 93%, 94%, 95%, 96%, 97%, 98%, 99% or 100%) sequence identity to an amino acid sequence including (a) SEQ ID NOs: 1, 11, or 19 (459C V2 Opt); (b) SEQ ID NOs: 2, 12, or 20 (459C V2 Alt-based polypeptides); (c) SEQ ID NOs: 3, 13, or 21 (459C V3 Opt-based polypeptides); (d) SEQ ID NOs: 4, 14, or 22 (459C V3 Alt-based polypeptides); (e) SEQ ID NO: 5 (Trimerization Domain); or (f) SEQ ID NO: 17 (Leader signal sequence).

The nucleic acid molecules of the invention may be further optimized, such as by codon optimization, for expression in a targeted mammalian subject (e.g., human). As discussed below, vectors (e.g., viral vectors, such as an adenovirus or poxvirus vector) of the invention can include one or more of these nucleic acid molecules. Accordingly, vaccines of the invention may include one or more of these vectors. The stabilized clade C gp140 Env trimer polypeptides of the invention, as well as vaccines, nucleic acids, and vectors that incorporate one or more optimized clade C gp140 Env polypeptides, can be recombinantly expressed in a cell or organism, or can be directly administered to a subject (e.g., a human) infected with, or at risk of becoming infected with, HIV (e.g., HIV-1).

Vectors of the Invention

The invention features vectors including one or more of the nucleic acid molecules of the invention described above. The vector can be, for example, a carrier (e.g., a liposome), a plasmid, a cosmid, a yeast artificial chromosome, or a virus (e.g., an adenovirus vector or a poxvirus vector) that includes one or more of the nucleic acid molecules of the invention.

An adenovirus vector of the invention can be derived from a recombinant adenovirus serotype 11 (Ad11), adenovirus serotype 15 (Ad15), adenovirus serotype 24 (Ad24), adenovirus serotype 26 (Ad26), adenovirus serotype 34 (Ad34), adenovirus serotype 35 (Ad35), adenovirus serotype 48 (Ad48), adenovirus serotype 49 (Ad49), adenovirus serotype 50 (Ad50), Pan9 (AdC68), or a chimeric variant thereof (e.g., adenovirus serotype 5 HVR48 (Ad5HVR48)). A poxvirus vector of the invention may be derived, for example, from modified vaccinia virus Ankara (MVA). These vectors can include additional nucleic acid sequences from several sources.

Vectors of the invention can be constructed using any recombinant molecular biology technique known in the art. The vector, upon transfection or transduction of a target cell or organism, can be extrachromosomal or integrated into the host cell chromosome. The nucleic acid component of a vector can be in single or multiple copy number per target cell, and can be linear, circular, or concatamerized. The vectors can also include internal ribosome entry site (IRES) sequences to allow for the expression of multiple peptide or polypeptide chains from a single nucleic acid transcript (e.g., a polycistronic vector, e.g., a bi- or tri-cistronic vector).

Vectors of the invention can also include gene expression elements that facilitate the expression of the encoded polypeptide(s) of the invention (e.g., the polypeptides of SEQ ID NO: 11 (459C V2 Opt gp140Fd), SEQ ID NO: 12 (459C V2 Alt gp140Fd), SEQ ID NO: 13 (459C V3 Opt gp140Fd), and/or SEQ ID NO: 14 (459C V3 Alt gp140Fd) or polypeptides having amino acids sequences with at least 92%, 93%, 94%, 95%, 96%, 97%, 98%, or 99% sequence identity to SEQ ID NOs: 11, 12, 13, or 14). Gene expression elements include, but are not limited to, (a) regulatory sequences, such as viral transcription promoters and their enhancer elements, such as the SV40 early promoter, Rous sarcoma virus LTR, and Moloney murine leukemia virus LTR; (b) splice regions and polyadenylation sites such as those derived from the SV40 late region; and (c) polyadenylation sites such as in SV40. Also included are plasmid origins of replication, antibiotic resistance or selection genes, multiple cloning sites (e.g., restriction enzyme cleavage loci), and other viral gene sequences (e.g., sequences encoding viral structural, functional, or regulatory elements, such as the HIV long terminal repeat (LTR)).

Exemplary vectors are described below.

Adenovirus Vectors

Recombinant adenoviruses offer several significant advantages for use as vectors for the expression of, for example, one or more of the optimized clade C gp140 Env polypeptides of the invention. The viruses can be prepared to high titer, can infect non-replicating cells, and can confer high-efficiency transduction of target cells following contact with a target cell population, tissue, or organ (e.g., in vivo, ex vivo, or in vitro). Furthermore, adenoviruses do not integrate their DNA into the host genome. Thus, their use as an expression vector has a reduced risk of inducing spontaneous proliferative disorders. In animal models, adenoviral vectors have generally been found to mediate high-level expression for approximately one week. The duration of transgene expression (e.g., expression of a nucleic acid molecule of the invention) from an adenovirus vector can be prolonged by using, for example, cell or tissue-specific promoters. Other improvements in the molecular engineering of the adenovirus vector itself have produced more sustained transgene expression and less inflammation. This is seen with so-called "second generation" vectors harboring specific mutations in additional early adenoviral genes and "gutless" vectors in which virtually all the viral genes are deleted utilizing a Cre-Lox strategy (see, e.g., Engelhardt et al., *Proc. Natl. Acad. Sci. USA* 91:6196, 1994, and Kochanek et al., *Proc. Natl. Acad. Sci. USA* 93:5731, 1996, each herein incorporated by reference).

The rare serotype and chimeric adenoviral vectors disclosed in International Patent Application Publications WO 2006/040330 and WO 2007/104792, each incorporated by reference herein, are particularly useful as vectors of the invention. For example, recombinant adenovirus serotype 11 (Ad11), adenovirus serotype 15 (Ad15), adenovirus serotype 24 (Ad24), adenovirus serotype 26 (Ad26), adenovirus serotype 34 (Ad34), adenovirus serotype 35 (Ad35), adenovirus serotype 48 (Ad48), adenovirus serotype 49 (Ad49), adenovirus serotype 50 (Ad50), Pan9 (AdC68), or a chimeric variant thereof (e.g., adenovirus serotype 5 HVR48 (Ad5HVR48) can encode and/or deliver one or more of the optimized clade C gp140 Env polypeptides of the invention to facilitate formation and presentation of gp140 Env trimer formation. In some embodiments, one or more recombinant adenovirus vectors can be administered to the subject in order to express the clade C gp140 Env polypeptides for formation of stabilized trimers of the invention, such as those disclosed in International Patent Application Publication WO 2014/107744, incorporated by reference herein.

Adeno-Associated Virus (AAV) Vectors

Adeno-associated viruses (AAV), derived from non-pathogenic parvoviruses, can also be used to facilitate delivery and/or expression of one or more of the optimized clade C gp140 Env polypeptides of the invention. These vectors evoke almost no anti-vector cellular immune response and produce transgene expression lasting months in most experimental systems.

Stabilized trimers of the invention may be produced upon expression of the clade C gp140 Env polypeptides described herein using an AAV vector that includes a nucleic acid molecule of the invention that encodes one or more (e.g., 1, 2, or 3 or more) of the clade C gp140 Env polypeptide(s) described above.

Retrovirus Vectors

Retroviruses are useful for the expression of optimized clade C gp140 Env polypeptides of the invention. Unlike adenoviruses, the retroviral genome is based in RNA. When a retrovirus infects a cell, it will introduce its RNA together with several enzymes into the cell. The viral RNA molecules from the retrovirus will produce a double-stranded DNA copy, called a provirus, through a process called reverse transcription. Following transport into the cell nucleus, the proviral DNA is integrated in a host cell chromosome, permanently altering the genome of the transduced cell and any progeny cells that may derive from this cell. The ability to permanently introduce a gene into a cell or organism is the defining characteristic of retroviruses used for gene therapy. Retroviruses, which include lentiviruses, are a family of viruses including human immunodeficiency virus (HIV) that includes several accessory proteins to facilitate viral infection and proviral integration. Current "third-generation" lentiviral vectors feature total replication incompetence, broad tropism, and increased gene transfer capacity for mammalian cells (see, e.g., Mangeat and Trono, *Human Gene Therapy* 16(8):913, 2005; Wiznerowicz and Trono, *Trends Biotechnol.* 23(1):42, 2005; and Chira et al., *Oncotarget* 6(31):30675, 2015, each herein incorporated by reference).

Stabilized trimers of the invention may be produced upon expression of the clade C gp140 Env polypeptides described herein using a retrovirus vector that includes a nucleic acid molecule of the invention that encodes one or more (e.g., 1, 2, or 3 or more) clade C gp140 Env polypeptide(s) of the invention.

Other Viral Vectors

Besides adenoviral and retroviral vectors, other viral vectors and techniques are known in the art that can be used to facilitate delivery and/or expression of one or more of the optimized clade C gp140 Env polypeptides of the invention in other cells (e.g., a blood cell, such as a lymphocyte) or subject (e.g., a human) in order to promote formation of the trimers of the invention. These viruses include poxviruses (e.g., vaccinia virus and modified vaccinia virus Ankara (MVA); see, e.g., U.S. Pat. Nos. 4,603,112 and 5,762,938, each incorporated by reference herein), herpesviruses, togaviruses (e.g., Venezuelan Equine Encephalitis virus; see, e.g., U.S. Pat. No. 5,643,576, incorporated by reference herein), picornaviruses (e.g., poliovirus; see, e.g., U.S. Pat. No. 5,639,649, incorporated by reference herein), baculoviruses, and others described by Wattanapitayakul and Bauer (*Biomed. Pharmacother.* 54:487, 2000, incorporated by reference herein).

Naked DNA and Oligonucleotides

Naked DNA or oligonucleotides encoding one or more of the optimized clade C gp140 Env polypeptides of the invention can also be used to express these polypeptides in a cell or a subject (e.g., a human) in order to promote formation of the trimers of the invention. A description of the use of naked DNA or oligonucleotides as a delivery vector can be found in, e.g., Cohen, *Science* 259:1691-1692, 1993; Fynan et al., *Proc. Natl. Acad. Sci. USA,* 90:11478, 1993; and Wolff et al., *Bio Techniques* 11:474485, 1991, each herein incorporated by reference. This is the simplest method of non-viral transfection. Methods for delivery of naked DNA, such as electroporation and the use of a "gene gun," which shoots DNA-coated gold particles into a cell using high pressure gas and carrier particles (e.g., gold), can also be used.

Lipoplexes and Polyplexes

To improve the delivery of a nucleic acid encoding one or more of the optimized clade C gp140 Env polypeptides of the invention into a cell or subject in order to promote formation of the trimers of the invention, lipoplexes (e.g., liposomes) and polyplexes can be used to protect the nucleic acid from undesirable degradation during the transfection process. The nucleic acid molecules can be covered with lipids in an organized structure like a micelle or a liposome. When the organized structure is complexed with the nucleic acid molecule it is called a lipoplex. There are three types of lipids: anionic (negatively-charged), neutral, or cationic (positively-charged). Lipoplexes that utilize cationic lipids have proven utility for gene transfer. Cationic lipids, due to their positive charge, naturally complex with the negatively-charged nucleic acid. Also as a result of their charge they interact with the cell membrane, endocytosis of the lipoplex occurs, and the nucleic acid is released into the cytoplasm. The cationic lipids also protect against degradation of the nucleic acid by the cell.

Complexes of polymers with nucleic acids are called polyplexes. Most polyplexes consist of cationic polymers and their production is regulated by ionic interactions. One large difference between the methods of action of polyplexes and lipoplexes is that polyplexes cannot release their nucleic acid load into the cytoplasm, so, to this end, co-transfection with endosome-lytic agents (to lyse the endosome that is made during endocytosis), such as inactivated adenovirus, must occur. However, this is not always the case; polymers, such as polyethylenimine, have their own method of endosome disruption, as does chitosan and trimethylchitosan.

Exemplary cationic lipids and polymers that can be used in combination with one or more of the nucleic acid molecules encoding one or more of the optimized clade C gp140 Env polypeptides of the invention to form lipoplexes or polyplexes include, but are not limited to, polyethylenimine, lipofectin, lipofectamine, polylysine, chitosan, trimethylchitosan, and alginate.

Hybrid Methods

Several hybrid methods of gene transfer combine two or more techniques. Virosomes, for example, combine lipoplexes (e.g., liposomes) with an inactivated virus. This approach has been shown to result in more efficient gene transfer in respiratory epithelial cells compared to either viral or liposomal methods alone. Other methods involve mixing other viral vectors with cationic lipids or hybridizing viruses. Each of these methods can be used to facilitate transfer of one or more of the nucleic acid molecules of the invention encoding one or more of the optimized clade C gp140 Env polypeptides of the invention into a cell or subject in order to promote formation of the trimers of the invention.

Dendrimers

Dendrimers may be also be used to transfer one or more of the nucleic acid molecules of the invention encoding one or more of the optimized clade C gp140 Env polypeptide(s) of the invention into a cell or subject in order to promote formation of the trimers of the invention. A dendrimer is a highly branched macromolecule with a spherical shape. The surface of the particle may be functionalized in many ways, and many of the properties of the resulting construct are determined by its surface. In particular, it is possible to construct a cationic dendrimer (i.e., one with a positive surface charge). When in the presence of genetic material (e.g., a nucleic acid molecule of the invention), charge complimentarity leads to a temporary association of the nucleic acid with the cationic dendrimer. On reaching its destination the dendrimer-nucleic acid complex is then taken into the cell via endocytosis, resulting in the subsequent expression of one or more of the optimized clade C gp140 Env polypeptide(s) of the invention.

Compositions of the Invention

Compositions of the invention include DNA vectors containing a heterologous nucleic acid molecule encoding an antigenic or therapeutic gene product, or fragment thereof, from HIV Env (e.g., all or a portion of the nucleic acid molecule of SEQ ID NOs: 7, 8, 9, 10 15, 16, 17, 25, 26, 27, 28, 37, 38, 39, or 40, or a variant thereof having at least 90% (e.g., at least 91%, 92%, 93%, 94%, 95%, 96%, 97%, 98%, 99% or 100%) sequence identity to SEQ ID NOs: 7, 8, 9, 10 15, 16, 17, 25, 26, 27, 28, 37, 38, 39, or 40, and complements thereof). Additional compositions of the invention include an immunogenic polypeptide, or fragment thereof, from HIV Env (e.g., all or a portion of the polypeptide of SEQ ID NOs: 1, 2, 3, 4, 9, 10, 11, 12, 13, 19, 20, 21, 22, 24, 25, 27, 28, 29, 30, or 31, or a variant thereof having at least 90% (e.g., at least 91%, 92%, 93%, 94%, 95%, 96%, 97%, 98%, 99% or 100%) sequence identity to SEQ ID NOs: 1, 2, 3, 4, 9, 10, 11, 12, 13, 19, 20, 21, 22, 24, 25, 27, 28, 29, 30, or 31). The compositions of the invention may also include a HIV Env antibody (e.g., an anti-Env antibody) capable of binding HIV Env and epitopes derived thereof, such as epitopes containing one or more of residues of any one of SEQ ID NOs: 1, 2, 3, 4, 9, 10, 11, 12, 13, 14, 19, 20, 21, 22, 30, 31, 32, 33, 34, 35, or 36. The antibody may be generated by immunization of a host with a polypeptide of any one of SEQ ID NOs: 1, 2, 3, 4, 9, 10, 11, 12, 13, 14, 19, 20, 21, 22, 30, 31, 32, 33, 34, 35, or 36, or a trimer of such polypeptides.

Any one of the stabilized clade C gp140 Env trimers of the invention, such as those described above, can be included in a composition of the invention (e.g., a pharmaceutical composition). Accordingly, the invention features a composition including at least one of the optimized clade C gp140 Env trimers described above (e.g., at least 1, 2, 3, 4, or more different types of optimized clade C gp140 Env trimers may be included in a single composition or vaccine).

For example, the composition may be a monovalent composition including only optimized clade C 459C V2 Opt trimers (e.g., stabilized 459C V2 Opt homotrimers of the invention having three polypeptides each including the amino acid sequence of SEQ ID NO: 11, or a variant thereof having at least 92% sequence identity (e.g., at least 93%, 94%, 95%, 96%, 97%, 98%, or 99% or more sequence identity) to SEQ ID NO: 11), only optimized clade C 459C V2 Alt trimers (e.g., stabilized 459C V2 Alt homotrimers of the invention having three polypeptides each including the amino acid sequence of SEQ ID NO: 12, or a variant thereof having at least 92% sequence identity (e.g., at least 93%, 94%, 95%, 96%, 97%, 98%, or 99% or more sequence identity) to SEQ ID NO: 12), only optimized clade C 459C V3 Opt trimers (e.g., stabilized 459C V3 Opt homotrimers of the invention having three polypeptides each including the amino acid sequence of SEQ ID NO: 13, or a variant thereof having at least 92% sequence identity (e.g., at least 93%, 94%, 95%, 96%, 97%, 98%, or 99% or more sequence identity) to SEQ ID NO: 13), or only optimized clade C 459C V3 Alt trimers (e.g., stabilized 459C V3 Alt homotrimers of the invention having three polypeptides each including the amino acid sequence of SEQ ID NO: 14, or a variant thereof having at least 92% sequence identity (e.g., at least 93%, 94%, 95%, 96%, 97%, 98%, or 99% or more identity) to SEQ ID NO: 14). The monovalent composition may be prepared for use as a prime or a boost composition (e.g., V2 Opt gp140 or V3 Opt gp140 ("prime"), WT gp140 and V2 Alt gp140 or V3 Alt gp140 ("boost 1"), and WT gp140 and V2 Alt gp140 or V3 Alt gp140 ("boost 2")).

In other examples, the composition may be a multivalent composition (e.g., a bivalent, trivalent, or quadrivalent composition) including two or more different types of optimized clade C trimers as in Table 1. The compositions may contain one or more different homotrimers or one or more different heterotrimers.

For example, the composition may be a bivalent composition including two different types of optimized clade C gp140 trimers of the invention (from Table 1) (e.g., combinations of homotrimers of 459C V2 Opt (SEQ ID NOs: 1, 11, 19, or 30) and 459C V2 Alt (SEQ ID NOs: 2, 12, 20, or 31), or 459C V3 Opt (SEQ ID NOs: 3, 13, or 21) and 459C V3 Alt (SEQ ID NOs: 4, 14, or 22)).

In yet other examples, the composition may be a monovalent or multivalent composition including one or more heterotrimers (e.g., Trimers 4-10 in Table 1 above) of the invention. The composition can also include a homotrimer or a heterotrimer described in U.S. provisional application Ser. No. 61/749,737, incorporated herein by reference.

In some examples, the multivalent composition is a trivalent composition including three different types of optimized clade C gp140 trimers of the invention (e.g., combinations of homotrimers of 459C V2 Opt (SEQ ID NOs: 1, 11, 19, or 30), 459C V2 Alt (SEQ ID NOs: 2, 12, 20, or 31), and 459C V3 Opt (SEQ ID NOs: 3, 13, or 21) homotrimers). The composition can also include a homotrimer or a heterotrimer described in U.S. provisional application Ser. No. 61/749,737, incorporated herein by reference.

In some examples, the multivalent composition is a trivalent composition including combinations of homotrimers of 459C WT gp140, 459C V2 Opt, and 459C V2 Alt ("V2 mixture") or 459C WT gp140, 459C V3 Opt, and 459C V3 Alt ("V3 mixture"). The composition can also include a homotrimer or a heterotrimer described in U.S. provisional application Ser. No. 61/749,737, incorporated herein by reference.

In some examples, the multivalent composition is a quadrivalent composition including four different types of optimized clade C gp140 trimers, such as a composition that includes 459C V2 Opt, 459C V2 Alt, and 459C V3 Opt homotrimers of the invention in combination with another gp140 trimer (e.g., WT 459C)("QuadC mixture"). The composition can also include a homotrimer or a heterotrimer described in U.S. provisional application Ser. No. 61/749,737, incorporated herein by reference.

The compositions may be sterilized by conventional sterilization techniques, or may be sterile filtered. The resulting aqueous solutions may be packaged for use as is, or lyophilized, the lyophilized preparation may be administered in powder form or combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of any one or more of the optimized clade C gp140 Env nucleic acids required to support formation of one or more of the stabilized trimers of the invention and/or one or more of the stabilized clade C trimers of the invention and, if desired, one or more immunomodulatory agents, such as in a sealed package of tablets or capsules, or in a suitable dry powder inhaler (DPI) capable of administering one or more doses.

Any one of the compositions of the invention may further include a pharmaceutically acceptable carrier, excipient, or diluent, and/or an adjuvant.

Carriers, Excipients, Diluents

Therapeutic formulations of the compositions of the invention (e.g., vaccines, vectors, stabilized trimer(s), nucleic acid molecules, etc.) may be prepared using standard methods known in the art by mixing the active ingredient having the desired degree of purity with optional physiologically acceptable carriers, excipients, or stabilizers (Remington's Pharmaceutical Sciences (20$^{th}$ edition), ed. A. Gennaro, 2000, Lippincott, Williams & Wilkins, Philadelphia, Pa.). Acceptable carriers include saline or buffers, such as phosphate, citrate, and other organic acids; antioxidants, including ascorbic acid; low molecular weight (less than about 10 residues) polypeptides; proteins, such as serum albumin, gelatin or immunoglobulins; hydrophilic polymers, such as polyvinylpyrrolidone, amino acids, such as glycine, glutamine, asparagines, arginine, or lysine; monosaccharides, disaccharides, and other carbohydrates including, e.g., glucose, mannose, or dextrins; chelating agents, such as EDTA; sugar alcohols, such as mannitol or sorbitol; salt-forming counterions, such as sodium; and/or nonionic surfactants, such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of about 0.005 to about 0.02%.

Adjuvants

Any one of the compositions of the invention (e.g., vaccines, vectors, stabilized trimer(s), nucleic acid molecules, etc.) can be formulated to include, be administered concurrently with, and/or be administered in series with, one or more pharmaceutically acceptable adjuvants to increase the immunogenicity of the composition (e.g., upon administration to a subject in need thereof, e.g., a subject infected with HIV or at risk of an HIV infection). Adjuvants approved for human use include aluminum salts (alum). These adjuvants have been useful for some vaccines including, e.g., hepatitis B, diphtheria, polio, rabies, and influenza. Other useful adjuvants include Complete Freund's Adjuvant (CFA), Incomplete Freund's Adjuvant (IFA), muramyl dipeptide (MDP), synthetic analogues of MDP, N-acetylmuramyl-L-alanyl-D-isoglutamyl-L-alanine-2-[1,2-dipalmitoyl-s-gly-cero-3-(hydroxyphosphoryloxy)]ethylamide (MTP-PE) and compositions containing a metabolizable oil and an emulsifying agent, wherein the oil and emulsifying agent are present in the form of an oil-in-water emulsion having oil droplets substantially all of which are less than one micron in diameter.

Vaccines of the Invention

The invention features vaccines including at least one of the compositions of the invention described above. The vaccine may be used for treating or reducing the risk of a human immunodeficiency virus (HIV) infection in a subject in need thereof. For example, the vaccine may elicit production of neutralizing anti-HIV antisera (e.g., neutralizing anti-HIV-1 antisera) after administration to the subject. The anti-HIV antisera may also be able to neutralize HIV (e.g., HIV-1), for example, selected from any one or more of clade A, clade B, and clade C. The vaccine of the invention may contain the trimers of the invention as part of a prime-boost regimen (e.g., WT 459C gp140 (SEQ ID NOs: 16 or 23)+V2 Opt (SEQ ID NOs: 1, 11, or 19)+V2 Alt (SEQ ID NOs: 2, 12, or 20)("Trimer 24" from Table 1) as both a prime and a boost; or V2 Opt as a prime and WT 459C gp140+V2 Alt as a boost).

Any one of the vaccines of the invention may further include a pharmaceutically acceptable carrier, excipient, or diluent, and/or an adjuvant.

Antibodies of the Invention

Antibodies of the invention include those that are generated by immunizing a host (e.g., a mammalian host, such as a human) with the polypeptides of SEQ ID NOs: 1, 2, 3, 4, 9, 10, 11, 12, 13, 14, 19, 20, 21, 22, 30, 31, 32, 33, 34, 35, or 36. The antibodies can be prepared recombinantly and, if necessary, humanized, for subsequent administration to a human recipient if the host in which the anti-HIV antibodies are generated is not a human.

Anti-HIV antibodies of the invention are capable of specifically binding to a HIV Env polypeptide, in particular, the epitope of the antibodies is the optimized V2 and/or V3 regions of gp140, and are capable of inhibiting a HIV-mediated activity (e.g., viral spread, infection, and or cell fusion) in a subject (e.g., a human). The result of such binding may be, for example, a reduction in viral titer (e.g., viral load), by about 1% (e.g., 2%, 3%, 4%, 5%, 6%, 7%, 8%, 9%, 10%, 20%, 30%, 40%, 50%, 60%, 70%, 80%, or 90%) or more, after administration of an antibody of the invention to a subject infected with HIV. The anti-HIV antibodies of the invention may selectively bind to an epitope comprising all, or a portion of, the HIV envelope protein. In particular, the anti-HIV antibodies of the invention may selectively bind to an epitope comprising all, or a portion of, any one of SEQ ID NOs: 1, 2, 3, 4, 9, 10, 11, 12, 13, 14, 19, 20, 21, 22, 30, 31, 32, 33, 34, 35, or 36. The antibodies of the invention can therefore be used to prevent or treat an HIV infection.

The specific binding of an antibody or antibody fragment of the invention to a HIV envelope protein can be determined by any of a variety of established methods. The affinity can be represented quantitatively by various measurements, including the concentration of antibody needed to achieve half-maximal inhibition of viral spread (e.g., viral titer) in vitro ($IC_{50}$ and the equilibrium constant ($K_D$) of the antibody-HIV envelope complex dissociation. The equilibrium constant, $K_D$, that describes the interaction of HIV envelope with an antibody of the invention is the chemical equilibrium constant for the dissociation reaction of a HIV envelope-antibody complex into solvent-separated HIV envelope and antibody molecules that do not interact with one another.

Antibodies of the invention are those that specifically bind to a HIV envelope protein (e.g., the gp140 region of HIV, in particular, the epitope of the antibodies is the optimized V2 and/or V3 regions of gp140) with a $K_D$ value of less than 1 µM (e.g., 900 nM, 800 nM, 700 nM, 600 nM, 500 nM, 400 nM, 300 nM, 200 nM, 100 nM, 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, 5 nM, 4 nM, 3 nM, 2 nM, 1 nM, 990 pM, 980 pM, 970 pM, 960 pM, 950 pM, 940 pM, 930 pM, 920 pM, 910 pM, 900 pM, 890 pM, 880 pM, 870 pM, 860 pM, 850 pM, 840 pM, 830 pM, 820 pM, 810 pM, 800 pM, 790 pM, 780 pM, 770 pM, 760 pM, 750 pM, 740 pM, 730 pM, 720 pM, 710 pM, 700 pM, 690 pM, 680 pM, 670 pM, 660 pM, 650 pM, 640 pM, 630 pM, 620 pM, 610 pM, 600 pM, 590 pM, 580 pM, 570 pM, 560 pM, 550 pM, 540 pM, 530 pM, 520 pM, 510 pM, 500 pM, 490 pM, 480 pM, 470 pM, 460 pM, 450 pM, 440 pM, 430 pM, 420 pM, 410 pM, 400 pM, 390 pM, 380 pM, 370 pM, 360 pM, 350 pM, 340 pM, 330 pM, 320 pM, 310 pM, 300 pM, 290 pM, 280 pM, 270 pM, 260 pM, 250 pM, 240 pM, 230 pM, 220 pM, 210 pM, 200 pM, 190 pM, 180 pM, 170 pM, 160 pM, 150 pM, 140 pM, 130 pM, 120 pM, 110 pM, 100 pM, 90 pM, 80 pM, 70 pM, 60 pM, 50 pM, 40 pM, 30 pM, 20 pM, 10 pM, 5 pM, or 1 pM).

Antibodies of the invention can also be characterized by a variety of in vitro binding assays. Examples of experiments that can be used to determine the $K_D$ or $IC_{50}$ of a HIV antibody include, e.g., surface plasmon resonance, isothermal titration calorimetry, fluorescence anisotropy, and ELISA-based assays, among others. ELISA represents a particularly useful method for analyzing antibody activity, as such assays typically require minimal concentrations of antibodies. A common signal that is analyzed in a typical ELISA assay is luminescence, which is typically the result of the activity of a peroxidase conjugated to a secondary antibody that specifically binds a primary antibody (e.g., a HIV antibody of the invention). Antibodies of the invention are capable of binding HIV and epitopes derived thereof, such as epitopes containing one or more of residues of any one of SEQ ID NOs: 1, 2, 3, 4, 9, 10, 11, 12, 13, 14, 19, 20, 21, 22, 30, 31, 32, 33, 34, 35, or 36, as well as isolated peptides derived from HIV that structurally pre-organize various residues in a manner that may simulate the conformation of these amino acids in the native protein. For instance, antibodies of the invention may bind peptides containing the amino acid sequence of any one of SEQ ID NOs: 1, 2, 3, 4, 9, 10, 11, 12, 13, 14, 19, 20, 21, 22, 30, 31, 32, 33, 34, 35, or 36, or a peptide containing between about 10 and about 30 continuous or discontinuous amino acids of any one of SEQ ID NOs: 1, 2, 3, 4, 9, 10, 11, 12, 13, 14, 19, 20, 21, 22, 30, 31, 32, 33, 34, 35, or 36. In a direct ELISA experiment, this binding can be quantified, e.g., by analyzing the luminescence that occurs upon incubation of an HRP substrate (e.g., 2,2'-azino-di-3-ethylbenzthiazoline sulfonate) with an antigen-antibody complex bound to a HRP-conjugated secondary antibody.

Methods of Making the Antibodies of the Invention

Antibodies of the invention may be produced through methods including, but not limited to, immunizing a non-human mammal. Examples of non-human mammals that can be immunized in order to produce anti-HIV Env antibodies of the invention include rabbits, mice, rats, goats, guinea pigs, hamsters, horses, and sheep, as well as non-human primates. For instance, established procedures for immunizing primates are known in the art (see, e.g., WO 1986/6004782; incorporated herein by reference). Immunization represents a robust method of producing monoclonal or polyclonal antibodies by exploiting the antigen specificity of B lymphocytes. For example, monoclonal antibodies can be prepared by the Kohler-Millstein procedure (described, e.g., in EP 0110716; incorporated herein by reference), in which spleen cells from a non-human animal (e.g., a primate) immunized with a peptide that presents an HIV Env-derived antigen (e.g., a peptide containing the amino acid sequence of any one of SEQ ID NOs: 1, 2, 3, 4, 9, 10, 11, 12, 13, 14, 19, 20, 21, 22, 30, 31, 32, 33, 34, 35, or 36). A clonally-expanded B lymphocyte produced by immunization can be isolated from the serum of the animal and subsequently fused with a myeloma cell in order to form a hybridoma. Hybridomas are particularly useful agents for antibody production, as these immortalized cells can provide a lasting supply of an antigen-specific antibody. Antibodies from such hybridomas can subsequently be isolated using techniques known in the art, e.g., by purifying the antibodies from the cell culture medium by affinity chromatography, using reagents such as Protein A or Protein G.

Methods of Treatment Using Compositions of the Invention

In Vivo Administration

The invention features methods for the in vivo administration of a therapeutically effective amount of one or more of the compositions of the invention (e.g., vaccines, vectors, stabilized trimer(s), optimized polypeptides, and nucleic acid molecules) to a subject (e.g., a human, e.g., a human infected with HIV or a human at risk of an HIV infection) in need thereof. Upon administering one or more of the compositions of the invention (e.g., a stabilized trimer-containing composition) to the subject, the composition elicits protective or therapeutic immune responses (e.g., cellular or humoral immune responses, e.g., neutralizing anti-HIV antisera production, e.g., anti-HIV antisera that neutralizes HIV selected from clade A, clade B, and/or clade C HIV) directed against the viral immunogens, in particular, anti-HIV tier 2 nAbs.

The method may be used to treat or reduce the risk of an HIV infection (e.g., an HIV-1 infection) in a subject in need thereof. The subject may be infected with HIV (e.g., HIV-1) or may be at risk of exposure to HIV (e.g., HIV-1). The compositions of the invention can be administered to a subject infected with HIV to treat AIDS. Examples of symptoms of diseases caused by a viral infection, such as AIDS, that can be treated using the compositions of the invention include, for example, fever, muscle aches, coughing, sneezing, runny nose, sore throat, headache, chills, diarrhea, vomiting, rash, weakness, dizziness, bleeding under the skin, in internal organs, or from body orifices like the mouth, eyes, or ears, shock, nervous system malfunction, delirium, seizures, renal (kidney) failure, personality changes, neck stiffness, dehydration, seizures, lethargy, paralysis of the limbs, confusion, back pain, loss of sensation, impaired bladder and bowel function, and sleepiness that can progress into coma or death. These symptoms, and their resolution during treatment, may be measured by, for example, a physician during a physical examination or by other tests and methods known in the art.

In cases in which the subject is infected with HIV, the method may be used to reduce an HIV-mediated activity (e.g., infection, fusion (e.g., target cell entry and/or syncytia formation), viral spread, etc.) and/or to decrease HIV titer in the subject. HIV-mediated activity and/or HIV titer may be decreased, for example, by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more compared to that of a control subject (e.g., an untreated subject or a subject treated with a placebo). In some instances, the method can result in a reduced HIV titer as measured by a reduction of proviral DNA level in tissue of the subject relative to an amount of proviral DNA level in tissue of the subject before treatment, an untreated subject, or a subject treated with a placebo. For example, the proviral DNA level in tissue (e.g., lymph node tissue, gastrointestinal tissue, and/or peripheral blood) may be reduced to below about 1,000 DNA copies/$10^6$ cells (e.g., below about 100 DNA copies/$10^6$ cells, e.g., below about 10 DNA copies/$10^6$ cells, e.g., below about 1 DNA copy/$10^6$ cells). In some instances, the method can result in a reduced HIV titer as measured by a reduction of plasma viral load of the subject relative to an amount of plasma viral load of the subject before treatment, an untreated subject, or a subject treated with a placebo. For example, plasma viral load may be reduced to less than 3,500 RNA copies/ml (e.g., less than 2,000 RNA copies/ml, e.g., less than 400 RNA copies/ml, e.g., less than 50 RNA copies/ml, e.g., less than 1 RNA copy/ml).

One or more of the compositions of the invention may also be administered in the form of a vaccine for prophylactic treatment of a subject (e.g., a human) at risk of an HIV infection.

The compositions can be formulated, for example, for administration intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, by gavage, in creams, or in lipid compositions. The methods of treatment include administering a composition of the invention to a subject in need thereof by one of the routes described above.

A chosen method of administration can vary depending on various factors (e.g., the components of the composition being administered and the severity of the condition being treated). Formulations suitable for oral or nasal administration may consist of liquid solutions, such as an effective amount of the composition dissolved in a diluent (e.g., water, saline, or PEG-400), capsules, sachets, tablets, or gels, each containing a predetermined amount of the chimeric Ad5 vector composition of the invention. The pharmaceutical composition may also be an aerosol formulation for inhalation, for example, to the bronchial passageways. Aerosol formulations may be mixed with pressurized, pharmaceutically acceptable propellants (e.g., dichlorodifluoromethane, propane, or nitrogen). In particular, administration by inhalation can be accomplished by using, for example, an aerosol containing sorbitan trioleate or oleic acid, for example, together with trichlorofluoromethane, dichlorofluoromethane, dichlorotetrafluoroethane, or any other biologically compatible propellant gas.

Immunogenicity of the composition of the invention may be significantly improved if it is co-administered with an immunostimulatory agent or adjuvant. Suitable adjuvants well-known to those skilled in the art include, for example, aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Choi, DDA, cytokines, and other adjuvants and derivatives thereof.

Compositions according to the invention described herein may be formulated to release the composition immediately upon administration (e.g., targeted delivery) or at any predetermined time period after administration using controlled or extended release formulations. Administration of the composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window at the site of release (e.g., the gastrointestinal tract); or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, for example, appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

The compositions of the invention may be administered to provide pre-infection prophylaxis or may be administered for treatment after a subject has been diagnosed with an HIV infection or a disease with an etiology traceable to an HIV infection (e.g., AIDS). The composition may be administered, for example, 1, 2, 3, 4, 5, 6, 7, 8, 9, 10, 15, 20, 30, 35, 40, 45, 50, 55, or 60 minutes, 2, 4, 6, 10, 15, or 24 hours, 2, 3, 5, or 7 days, 2, 4, 6 or 8 weeks, or even 3, 4, or 6 months pre-infection or pre-diagnosis, or may be administered to the subject 15-30 minutes or 1, 2, 3, 4, 5, 6, 7, 8, 9, 10, 12, 20, 24, 48, or 72 hours, 2, 3, 5, or 7 days, 2, 4, 6 or 8 weeks, 3, 4, 6, or 9 months, 1, 2, 3, 4, 5, 6, 7, 8, 9, 10, 15, or 20 years or longer post-diagnosis or post-infection. The subject can be administered a single dose of the composition(s) (or, e.g., 2, 3, 4, 5, 6, 7, 8, 9, 10, or more doses) or the subject can be administered at least one dose (e.g., 1, 2, 3, 4, 5, 6, 7, 8, 9, 10, or more doses) daily, weekly, monthly, or yearly.

The administration period may be defined (e.g., 1-4 weeks, 1-12 months, 1-20 years) or may be for the life of the subject. The composition(s) may also be administered to said subject as a prime or a boost composition or in a prime-boost regimen. For example, the composition (e.g., a vaccine) of the invention can be administered as a boost following administration of an additional composition (e.g., vaccine) as a prime. The prime and/or the boost in this regimen may include one or more of the composition(s) of the invention (e.g., any one of the stabilized trimers, the compositions, the vaccines, the nucleic acid molecules, and/or the vectors of the invention). The subject can be administered the first boost ("Boost 1") 1-8 weeks (e.g., 1-4 weeks, such as 4 weeks) after administering the initial dose ("Prime"), and an optional second boost ("Boost 2") can be administered 1-4 weeks after Boost 1 (see, e.g., Table 2).

TABLE 2

Optimized gp140 Trimer Vaccination Regimens

| Name | Prime | Boost 1 | Boost 2 (optional) |
|---|---|---|---|
| WT 459C | WT 459C | WT 459C | WT 459C |
| V2 Opt | V2 Opt | V2 Opt | V2 Opt |
| V2 Alt | V2 Alt | V2 Alt | V2 Alt |
| V3 Opt | V3 Opt | V3 Opt | V3 Opt |
| V3 Alt | V3 Alt | V3 Alt | V3 Alt |
| V2 Opt + V2 Alt | V2 Opt + V2 Alt | V2 Opt + V2 Alt | V2 Opt + V2 Alt |
| V3 Opt + V3 Alt | V3 Opt + V3 Alt | V3 Opt + V3 Alt | V3 Opt + V3 Alt |
| V2 Mixture | WT 459C + V2 Opt + V2 Alt | WT 459C + V2 Opt + V2 Alt | WT 459C + V2 Opt + V2 Alt |
| V3 Mixture | WT 459C + V3 Opt + V3 Alt | WT 459C + V3 Opt + V3 Alt | WT 459C + V3 Opt + V3 Alt |
| V2 Prime/ Boost | V2 Opt | WT 459C + V2 Alt | WT 459C + V2 Alt |
| V3 Prime/ Boost | V3 Opt | WT 459C + V3 Alt | WT 459C + V3 Alt |

When treating disease (e.g., AIDS), the compositions of the invention may be administered to the subject either before the occurrence of symptoms or a definitive diagnosis or after diagnosis or symptoms become evident. For example, the composition may be administered, for example, immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

The compositions (e.g., vaccines, vectors, stabilized trimer(s), nucleic acids, or other composition thereof described herein) of the invention can be administered in combination with one or more additional therapeutic agents, for example, for treating an HIV infection (e.g., an HIV-1 infection) in a subject. Such additional therapeutic agents can include, for example, a broadly neutralizing antibody (bnAb), e.g., those described in PCT Application No. PCT/US14/58383, WO 2012/030904, and WO 2013/055908, each of which is incorporated by reference herein in its entirety.

Exemplary bnAbs that can be administered in combination with the compositions of the invention include PGT121, PGT122, PGT123, PGT124, PGT125, PGT126, PGT127, PGT128, PGT130, PGT131, PGT132, PGT133, PGT134, PGT135, PGT136, PGT137, PGT138, PGT139, PGT141, PGT142, PGT143, PGT144, PGT145, PGT151, PGT152, PGT153, PGT154, PGT155, PGT156, PGT157, PGT158, 10-1074, a derivative or clonal relative thereof, or a combination thereof. Preferably, the N332 glycan-dependent antibody can be PGT121, or a derivative or clonal relative thereof (e.g., 10-1074). Further bnAbs that can administered in combination with the compositions of the invention include, for example, a CD4 binding site (CD4bs)-specific antibody (e.g., 3BNC117 or VRC07-523) or a V2 glycan-dependent antibody (e.g., CAP256-VRC26).

The additional therapeutic agent can also be an antiretroviral therapy (ART), which may, e.g., be selected from any one or more of the following, or combinations thereof: efavirenz, emtricitabine, and tenofovir disoproxil fumarate (Atripla); emtricitabine, rilpivirine, and tenofovir disoproxil fumarate (Complera); elvitegravir, cobicistat, emtricitabine, and tenofovir disoproxil fumarate (Stribild); lamivudine and zidovudine (Combivir); emtricitabine, FTC (Emtriva); lamivudine, 3TC (Epivir); abacavir and lamivudine (Ebzicom); zalcitabine, dideoxycytidine, ddC (Hivid); zidovudine, azidothymidine, AZT, ZDV (Retrovir); abacavir, zidovudine, and lamivudine (Trizivir); tenofovir disoproxil fumarate and emtricitabine (Truvada); enteric coated didanosine, ddI EC (Videx EC); didanosine, dideoxyinosine, ddI (Videx); tenofovir disoproxil fumarate, TDF (Viread); stavudine, d4T (Zerit); abacavir sulfate, ABC (Ziagen); Rilpivirine (Edurant); Etravirine (Intelence); delavirdine, DLV (Rescriptor); efavirenz, EFV (Sustiva); nevirapine, NVP (Viramune or Viramune XR); amprenavir, APV (Agenerase); tipranavir, TPV (Aptivus); indinavir, IDV (Crixivan); saquinavir (Fortovase); saquinavir mesylate, SQV (Invirase); lopinavir and ritonavir, LPV/RTV (Kaletra); Fosamprenavir Calcium, FOS-APV (Lexiva); ritonavir, RTV (Norvir); Darunavir (Prezista); atazanavir sulfate, ATV (Reyataz); nelfinavir mesylate, NFV (Viracept); enfuvirtide, T-20 (Fuzeon); maraviroc (Selzentry); raltegravir, RAL (Isentress); and dolutegravir (Tivicay).

The additional therapeutic agent can also be an immunomodulator. The immunomodulator may, e.g., be selected from any one or more of the following, or combinations thereof: AS-101, Bropirimine, Acemannan, CL246,738, EL10, FP-21399, Gamma Interferon, Granulocyte Macrophage Colony Stimulating Factor, HIV Core Particle Immunostimulant, IL-2, Immune Globulin Intravenous, IMREG-1, IMREG-2, Imuthiol Diethyl Dithio Carbamate, Alpha-2 Interferon, Methionine-Enkephalin, MTP-PE Muramyl-Tripeptide, Granulocyte Colony Stimulating Factor, Remune, CD4 (e.g., recombinant soluble CD4), rCD4-IgG hybrids, SK&F106528 Soluble T4, Thymopentin, Tumor Necrosis Factor, and Infliximab.

The additional therapeutic agent can also be a reservoir activator. The reservoir activator may, e.g., be selected from any one or more of the following, or combinations thereof: histone deacytelase (HDAC) inhibitors (e.g., romidepsin, vorinostat, and panobinostat), immunologic activators (e.g., cytokines and TLR agonists), and dedicated small molecule drugs.

Administration of an additional therapeutic agent may be prior to, concurrent with, or subsequent to the administration of the composition or vaccine of the invention.

Dosages

The dose of a composition of the invention (e.g., a vaccine including one or more of the stabilized clade C gp140 Env trimers of the invention) or the number of treatments using a composition of the invention may be increased or decreased based on the severity of, occurrence of, or progression of, the HIV infection and/or disease related to the HIV infection (e.g., AIDS) in the subject (e.g., based on the severity of one or more symptoms of HIV infection/AIDS described above).

The stabilized clade C gp140 Env trimer compositions of the invention can be administered in a therapeutically effective amount that provides an immunogenic and/or protective effect against HIV or target protein(s) of HIV (e.g., gp160 and/or gp140). The subject may, for example, be administered a polypeptide composition of the invention (e.g., stabilized clade C gp140 Env trimers of the invention) in a non-vectored form. The polypeptide composition administered may include between approximately 1 μg and 1 mg of stabilized Env trimers, e.g., between 50 μg and 300 μg of stabilized Env trimers, e.g., 100 μg of stabilized Env trimers of the invention. The multivalent formulation of the trimer composition may include trimers administered in equal amounts or in disproportionate amounts.

Alternatively, the subject may be administered, in the form of a viral vector, at least about $1\times10^3$ viral particles (vp)/dose or between $1\times10^1$ and $1\times10^{14}$ vp/dose, preferably between $1\times10^3$ and $1\times10^{12}$ vp/dose, and more preferably between $1\times10^5$ and $1\times10^{11}$ vp/dose.

Viral particles include nucleic acid molecules encoding one or more of the optimized clade C gp140 Env polypeptides of the invention and are surrounded by a protective coat (a protein-based capsid with hexon and fiber proteins). Viral particle number can be measured based on, for example, lysis of vector particles, followed by measurement of the absorbance at 260 nm (see, e.g., Steel, *Curr. Opin. Biotech.*, 1999).

The dosage administered depends on the subject to be treated (e.g., the age, body weight, capacity of the immune system, and general health of the subject being treated), the form of administration (e.g., as a solid or liquid), the manner of administration (e.g., by injection, inhalation, dry powder propellant), and the cells targeted (e.g., epithelial cells, such as blood vessel epithelial cells, nasal epithelial cells, or pulmonary epithelial cells). The composition is preferably administered in an amount that provides a sufficient level of the stabilized clade C gp140 Env trimer gene product (e.g., a level of stabilized clade C gp140 Env trimer that elicits an immune response without undue adverse physiological effects in the subject caused by the immunogenic trimer).

In addition, single or multiple administrations of the compositions of the invention may be given (pre- or post-infection and/or pre- or post-diagnosis) to a subject (e.g., one administration or administration two or more time (e.g., as a prime-boost regimen)). For example, subjects who are particularly susceptible to, for example, HIV infection may require multiple treatments to establish and/or maintain protection against the virus. Levels of induced immunity provided by the pharmaceutical compositions described herein can be monitored by, for example, measuring amounts of neutralizing anti-HIV secretory and serum antibodies. The dosages may then be adjusted or repeated as necessary to trigger the desired level of immune response. For example, the immune response triggered by a single administration (prime) of a composition of the invention may not be sufficiently potent and/or persistent to provide effective protection. Accordingly, in some embodiments, repeated administration (boost), such that a prime-boost regimen is established, may significantly enhance humoral and cellular responses to the antigen of the composition. The prime-boost composition may be the same or different.

Alternatively, as applies to recombinant therapy, the efficacy of treatment can be determined by monitoring the level of the one or more optimized clade C gp140 Env trimers expressed by or present in a subject (e.g., a human) following administration of the compositions of the invention. For example, the blood or lymph of a subject can be tested for the immunogenic trimer(s) using, for example, standard assays known in the art (see, e.g., Human Interferon-Alpha Multi-Species ELISA kit (Product No. 41105) and the Human Interferon-Alpha Serum Sample kit (Product No. 41110) from Pestka Biomedical Laboratories (PBL), Piscataway, N.J.).

A single dose of one or more of the compositions of the invention may achieve protection, pre-infection or pre-diagnosis. In addition, a single dose administered post-infection or post-diagnosis can function as a treatment according to the invention.

A single dose of one or more of the compositions of the invention can also be used to achieve therapy in subjects being treated for a disease. Multiple doses (e.g., 2, 3, 4, 5, or more doses) can also be administered, if necessary, to these subjects.

Ex Vivo Transfection and Transduction

The invention also features methods for the ex vivo transfection or transduction of cells, tissue, or organs, followed by administration of these cells, tissues, or organs into a subject (e.g., human) to allow for the expression of one or more of the optimized clade C gp140 Env polypeptides of the invention that have immunogenic properties. In one embodiment, the cells, tissue(s), or organ(s) are autologous to the treated subject. Cells can be transfected or transduced ex vivo with, for example, one or more nucleic acid molecules or vectors of the invention to allow for the temporal or permanent expression of one or more of the optimized clade C gp140 Env polypeptides in the treated subject. Upon administering these modified cells to the subject, the one or more nucleic acid molecules or vectors of the invention will lead to the expression of optimized clade C gp140 Env polypeptides capable of eliciting protective or therapeutic immune responses (e.g., cellular or humoral immune responses, e.g., production of neutralizing anti-HIV antisera) directed against the clade C gp140 immunogenic trimer or trimers that form.

Cells that can be isolated and transfected or transduced ex vivo according to the methods of invention include, but are not limited to, blood cells, skin cells, fibroblasts, endothelial cells, skeletal muscle cells, hepatocytes, prostate epithelial cells, and vascular endothelial cells. Stem cells are also appropriate cells for transduction or transfection with a vector of the invention. Totipotent, pluripotent, multipotent, or unipotent stem cells, including bone marrow progenitor cells, hematopoietic stem cells (HSC), and mesenchymal stem cells (MSCs) (e.g., bone marrow (BM) or umbilical cord MSCs) can be isolated and transfected or transduced with, for example, a nucleic acid molecule or vector of the invention, and administered to a subject according to the methods of the invention.

The method of transfection or transduction has a strong influence on the strength and longevity of protein expression (e.g., stabilized clade C gp140 trimer expression) in the transfected or transduced cell, and subsequently, in the subject (e.g., human) receiving the cell. The invention features the use of vectors that are temporal (e.g., adenoviral vectors) or long-lived (e.g., retroviral vectors) in nature. Regulatory sequences (e.g., promoters and enhancers) are known in the art that can be used to regulate protein expression. The type of cell being transfected or transduced also has a strong bearing on the strength and longevity of protein expression. For example, cell types with high rates of turnover can be expected to have shorter periods of protein expression.

Methods for Optimizing HIV Envelope Protein Domains to Improve Immunogenicity

The methods of the invention also feature methods for optimizing HIV envelope glycoproteins to enhance their immunogenicity. Using these methods, we have generated HIV Env gp140 polypeptides having modified regions involved in neutralization sensitivity of a class of antibodies, either V2 glucan or V3 glycan (see, e.g., Example 1). The relevant sites are statistically defined based on HIV-1 evolution and neutralization sensitivity; some are in the well-documented epitope regions, other are outside the epitope and are most likely to be related to epitope accessibility. These modified HIV Env gp140 polypeptides exhibit improved immunogenicity when tested as immunogens based on their ability to elicit broadly neutralizing anti-HIV antibodies with breadth. These methods can also be applied to other regions of the Env protein, including, but not limited to, the V1 region or the CD4 binding site, to optimize the immunogenicity of HIV Env polypeptides having these modified regions.

Figure 18A:
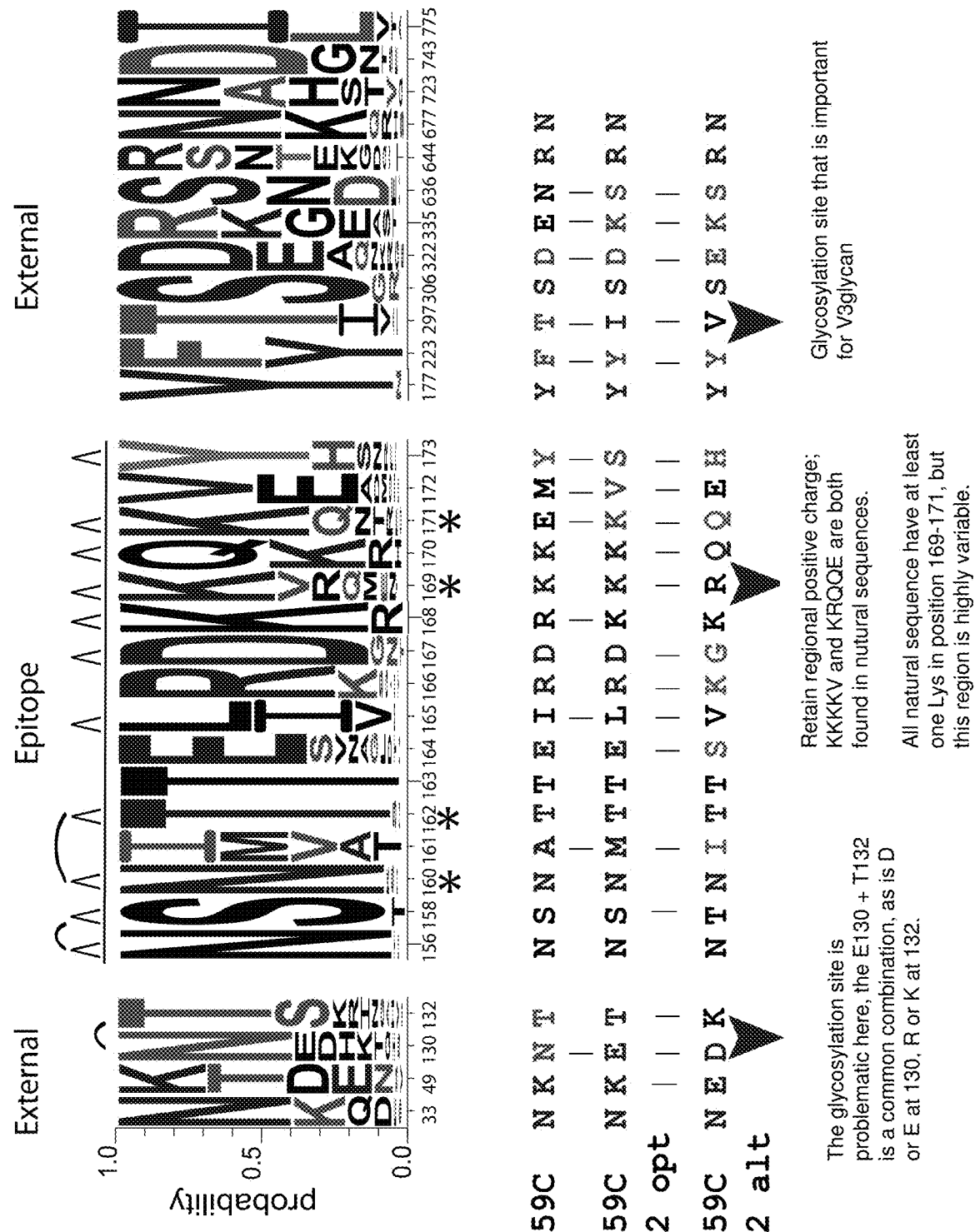
FIG. 18A is a schematic and alignment of V2 glycan amino acid signatures incorporated into the V2 construct designs, their frequency in the HIV M group globally circulating virus, and the amino acid substitutions made into the WT 459C protein to create the Opt and Alt forms. Color scheme indicates amino acids associated with bNAb neutralization sensitivity (blue), resistance (red), conflicting (pink), or no effect (black). Amino acids are shown as single letter abbreviations. Letter size indicates the probability that an amino acid will occur at a given site. Amino acid position listed utilizing HXB2 reference numbering. Arrows with explanations for specific residue modifications are included.
Figure 18B:
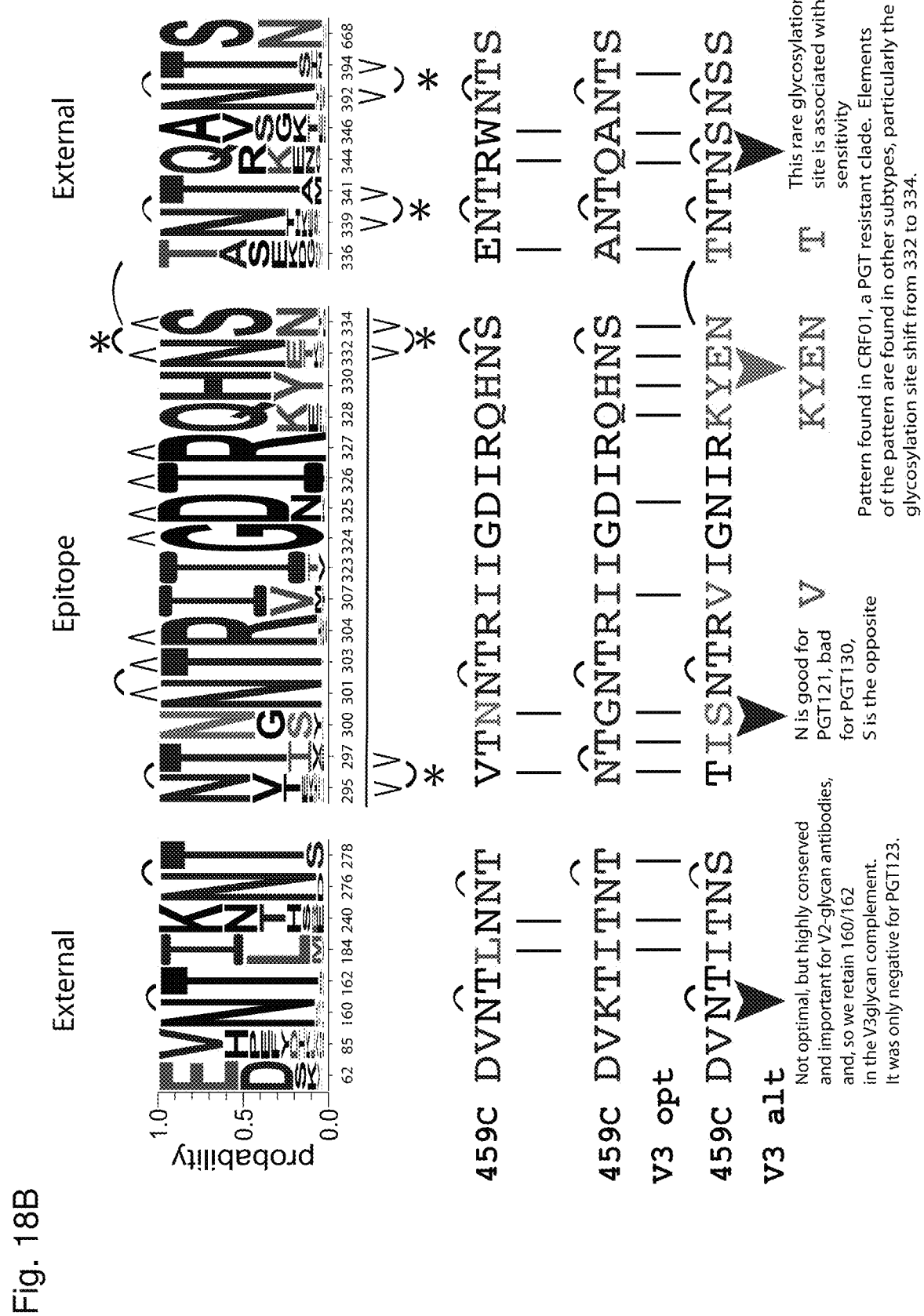
FIG. 18B is a schematic and alignment of V3 glycan amino acid signatures incorporated into the V3 construct designs, their frequency in the HIV M group globally circulating virus, and the amino acid substitutions made into the WT 459C protein to create the Opt and Alt forms. Color scheme indicates amino acids associated with bNAb neutralization sensitivity (blue), resistance (red), conflicting (pink), or no effect (black). Amino acids are shown as single letter abbreviations. Letter size indicates the probability that an amino acid will occur at a given site. Amino acid position listed utilizing HXB2 reference numbering. Arrows with explanations for specific residue modifications are included.

The process involves the use of a phylogenetically-corrected optimization method that identifies amino acids within the domain to be optimized that are associated with sensitivity and resistance to neutralizing antibodies. A first step involves identifying patterns in HIV Env protein sequences that are highly associated with amino acids signatures for resistance and sensitivity for distinct classes of HIV neutralizing antibodies. For example, the process identified a glycosylation site at N160 (V2 glycan) as part of a signature of resistance and sensitivity for distinct classes of HIV neutralizing antibodies, and, in the V3 region, the process identified a glycosylation site at N332 (V3 glycan) as part of a signature of resistance and sensitivity for distinct classes of HIV neutralizing antibodies (see Example 1). These are known to be highly characteristic of these epitopes. The process also involves defining many other patterns in Env proteins associated with antibody sensitivity, including sites both within and outside of the epitope, retention or loss of carbohydrate addition motifs in the protein sequence, and the occurrence of insertions and deletions in the protein sequence that can impact antibody sensitivity (FIGS. 18A-18B).

The signature-based vaccine design method is based in part on the premise that capturing relevant variability within the targeted epitopes in a vaccine may yield antibodies with greater breadth. By including common resistance and sensitivity mutations within the antibody binding site in different Envs in our trivalent vaccine, we have created a polyvalent vaccine that can select for antibodies that tolerate the spectrum of common diversity in the targeted epitope. In addition signatures outside of the epitope are likely to be important for enhancing epitope accessibility, and so its sensitivity.

Antibody binding sites are defined using published structures of neutralizing antibody/Env interactions for representative antibodies in each class described above. Other factors that are incorporated into the design of optimized antigenic epitopes include patterns in hypervariable loop diversity that are directly associated with antibody sensitivity, and amino acid signatures outside of the antibody contact region that, when mutated, are associated with enhanced sensitivity, under the premise that these mutations will enhance exposure and accessibility of the epitope to the antibodies being elicited. Such mutations outside the epitope may impact epitope exposure by influencing expression levels of Env, conformational attributes of the trimer, carbohydrate modifications, or the time between different key transition states in the structure of the Env protein.

Kits

The invention also features kits that include a pharmaceutical composition containing a composition, vaccine, vector, nucleic acid molecule, stabilized trimer, or optimized viral polypeptide of the invention, and a pharmaceutically-acceptable carrier, in a therapeutically effective amount for preventing or treating a viral infection (e.g., HIV infection). The kits can include instructions directing a clinician (e.g., a physician or nurse) in methods for administering the composition contained therein.

The kits may include multiple packages of single-dose pharmaceutical composition(s) containing an effective amount of a composition, vaccine, vector, nucleic acid molecule, stabilized trimer, or optimized viral polypeptide of the invention. Optionally, instruments or devices necessary for administering the pharmaceutical composition(s) may be included in the kits. For instance, a kit of this invention may provide one or more pre-filled syringes containing an effective amount of a vaccine, vector, stabilized trimer, or optimized viral polypeptide of the invention. Furthermore, the kits may also include additional components, such as instructions or schedules for administration of the composition to a patient infected with or at risk of being infected with a virus.

It will be apparent to those skilled in the art that various modifications and variations can be made in the compositions, methods, and kits of the invention without departing from the spirit or scope of the invention. Thus, it is intended that the invention cover the modifications and variations of this invention provided they come within the scope of the appended claims and their equivalents.

EXAMPLES

The invention is illustrated by the following examples, which are in no way intended to be limiting of the invention.

Example 1. Materials and Methods

Signature-Based Epitope Modified HIV-1 Envelope Immunogen Design

We rationally designed a series of unique, epitope modified trimers (i.e., Signature-based Epitope Targeted (SET) HIV-1 Env gp140 immunogens) utilizing the previously described early clade C HIV-1 Env 459C gp140Fd Env (Bricault et al., *J. Virol.* 89(5):2507-19, 2015; see also International Patent Application Publication WO 2015/051270, incorporated herein by reference) as the backbone upon which to introduce amino acid modification. For the construction of the immunogens, bNAbs targeting distinct regions of Env, including the variable loop 2 (V2) and variable loop 3 (V3) have been tested against a panel of 219 unique pseudoviruses (DeCamp et al., *J. Virol.* 88:2489-2507, 2014; Lacerda et al., *Virol. J.* 10:347, 2013; Yoon et al., *Nucleic Acids Res.* 43:W213-W219, 2015). Within this panel, bNAbs to V1/V2/glycans included PG9, PG16, PGT142, PGT143, PGT145, CH01, and CAP256, and bNAbs to V3/glycans included PGT121, PGT123, PGT125, PGT126, PGT127, PGT128, PGT130, PGT135, 10.1074, 10.996, and 2G12. From this functional neutralization data, sequence signatures were rationally derived and defined as the most common amino acid at each position within the epitope associated with neutralization sensitivity or resistance to each family of bNAbs. Amino acids were considered to be part of an antibody's neutralization sequence signature if they served as direct contact residues between the bNAb and Env as defined by structural and/or mutational studies and influenced neutralization from non-direct contact, peripheral regions of the Env as determined by functional neutralization data (DeCamp et al., *J. Virol.* 88:2489-2507, 2014; Lacerda et al., *Virol. J.* 10:347, 2013; Yoon et al., *Nucleic Acids Res.* 43:W213-W219, 2015; Kwong et al., *Nature* 393:648-659, 1998; Calarese et al., *Science* 300:2065-2071, 2003; Ofek et al., *J. Virol.* 78:10724-10737, 2004; Cardoso et al., *Immunity* 22:163-173, 2005; Zhou et al., *Science* 329:811-817, 2010; Diskin et al., *Science* 334:1289-1293, 2011; Pejchal et al., *Science* 334:1097-1103, 2011; McLellan et al., Nature: 1-10, 2011; Scheid et al., *Science* 333:1633-1637, 2011; Mouquet et al., *Proc. Natl. Acad. Sci. USA:* 109:e3268-77, 2012; Falkowska et al., *J. Virol.* 86:4394-4403, 2012; Julien et al., *PLoS Pathog.* 9:e1003342, 2013; Pancera et al., *Nat. Struct. Mol. Biol.* 20:804-813, 2013).

In designing the immunogens, we focused on two key regions of the envelope protein, including V2 and glycans and V3 and glycans. The SET trivalent vaccines contain the 459C wildtype (WT) env and two modified versions of 459C: an "optimized" version (Opt) and an "alternate" version (Alt). The Opt and Alt immunogens were engineered by incorporating amino acid signature sequences associated with neutralization sensitivity and resistance to bNAbs that target the variable loop 2 (V2) or variable loop 3 (V3) epitope. The concept was to generate a modified version of the 459C WT trimer containing amino acids associated with the greatest neutralization sensitivity (optimized, Opt) and a version with the greatest neutralization resistance (alternate, Alt) to the panel of bNAbs for each epitope.

In designing the SET immunogens, internal direct antibody-antigen contact sites as well as external amino acid signature sequences were considered. External sites are not within antigen contact sites but were still statistically associated with bNAb sensitivity when large pseudovirus panels were evaluated. For both Opt and Alt constructs, non-contact amino acids were engineered to be associated with neutralization sensitivity, with the intent of maximizing epitope exposure. Additionally, hypervariable region characteristics statistically associated with bNAb sensitivity were defined. Hypervariable regions are the sections within variable loops of Env that evolve rapidly by amino acid insertions and deletions. Hypervariable regions are not part of the direct contact surface of V2 or V3 bNAbs, but are strongly associated with patterns of neutralization sensitivity and resistance to these bNAbs.

In contrast, within the antibody contact surface, we attempted to capture the relevant epitope diversity in our trivalent SET vaccines. The Opt construct contained amino acids associated with the greatest neutralization sensitivity to V2 or V3 bNAbs, while the Alt construct included amino acids associated with resistance that were nevertheless common in the circulating population, with the goal of facilitating selection of somatic mutations during affinity maturation that would enable antibodies to tolerate these common HIV-1 sequence variants. The trivalent V2-SET antigen cocktail (459C WT, Opt, Alt) thus maximized inclusion of common amino acid variants that impact V2 bNAb sensitivity. The combination of epitope regions and optimization schemes resulted in four new trimers to be designed and synthesized as genes; V2 Opt (SEQ ID NO: 19), V2 Alt (SEQ ID NO: 20), V3 Opt (SEQ ID NO: 21), and V3 Alt (SEQ ID NO: 22) (FIGS. 1A-1B and FIGS. 18A-18B). The optimized and alternate versions of the 459C WT trimer were designed to be used together, either in mixtures or sequential prime/boost vaccination regimens, to increase the sequence diversity the immune system experiences within a given epitope.

In designing the V2-SET immunogens, bNAbs V2 and glycans (V2) were considered (FIG. 1A). Vaccines that included any V2/glycan modified epitope are considered "V2-SET" vaccines (e.g., V2-SET immunogens). We hypothesized that 459C WT, V2 Opt, and V2 Alt, either in trivalent mixtures or as sequential prime/boost vaccination regimens, would increase the sequence diversity the immune system experiences within a given epitope and, thus, generate NAb responses with greater breadth. Multivalent vaccines using the SET immunogens include two "V2-SET trivalent" vaccines ("V2 Mixture" and "V2 Prime/Boost") as described herein.

Plasmids, Cell Lines, Protein Production, and Antibodies

The codon-optimized synthetic genes of the epitope modified HIV-1 Env gp140Fd trimers (e.g., V2-SET HIV-1 Env gp140 immunogens) were produced by GENEART® (Life Technologies). All constructs contained a consensus leader signal sequence peptide (SEQ ID NO: 17), as well as a C-terminal foldon trimerization tag (SEQ ID NO: 5) followed by a His-tag (SEQ ID NO: 29) as described previously (Frey et al., *Proc. Natl. Acad. Sci. USA* 105:3739-3744, 2008 and Nkolola et al., *J. Virol.* 84:3270-3279, 2010). HIV-1 Env C97ZA012 (SEQ ID NO: 41), 92UG037 (SEQ ID NO: 42), PVO.4 (SEQ ID NO: 45), and Mosaic (MosM, SEQ ID NO: 43) gp140Fd were produced as described previously (Nkolola et al., *J. Virol.* 88:9538-9552, 2014 and Nkolola et al., *J. Virol.* 84:3270-3279, 2010). Preliminary expression of each epitope modified 459C gp140 construct was tested by small-scale transfection of 293T cells with LIPOFECTAMINE® 3000 (Life Technologies). Cells were lysed with CELLLYTIC™ M (Sigma-Aldrich) to probe intracellular protein expression and cell supernatant was used to probe secreted protein expression. Western blots were run on an IBLOT® Dry Blotting System (Life Technologies) and an anti-penta-his antibody conjugated to horseradish peroxidase (HRP) (Abcam) was utilized for detecting expressed protein utilizing Amersham ECL Prime Western Blotting Detection Reagent (GE Life Sciences) as the developer. Large scale protein production conducted as described previously (Bricault et al., *J. Virol.* 89:2507-2519, 2015 and Kovacs et al., *Proc. Natl. Acad. Sci. USA* 109: 12111-12116, 2012). Soluble two-domain CD4 was produced as described previously (Freeman et al., *Structure* 18:1632-1641, 2010). 10-1074 was provided by Michel Nussenzweig (Rockefeller University, New York, N.Y.). PG16 was purchased from Polymun Scientific. Gp70 V1/V2 HIV-1 envelope scaffolds including ConC, Case A2, CN54, and A244 V1/V2 were purchased from Immune Technology Corp.

Surface Plasmon Resonance Binding Analysis

Surface plasmon resonance experiments were conducted on a BIACORE® 3000 (GE Healthcare) at 25° C. utilizing HBS-EP [10 mM Hepes (pH 7.4), 150 mM NaCl, 3 mM EDTA, 0.005% P20] (GE Healthcare) as the running buffer. Immobilization of CD4 (1,000 RU) or protein A (Thermo-Scientific) to CM5 chips was performed following the standard amine coupling procedure as recommended by the manufacturer (GE Healthcare). Protein-protein interactions (e.g., interactions of antibodies with envelope constructs) were analyzed using single-cycle kinetics consisting of four cycles of a 1-min association phase and a 4-min dissociation phase without regeneration between injections, followed by an additional cycle of a 1-min association phase and a 15-min dissociation phase, at a flow rate of 50 µL/min. Immobilized IgGs were captured at about 500 RU for 10-1074 and about 3,000 RU for PG16. Soluble gp140 was then passed over the surface at increasing concentrations from 62.5 nM to 1,000 nM. Regeneration was conducted with 35 mM NaOH, 1.3 M NaCl (pH 12) at 100 µL/min followed by 5-min equilibration in the HBS-EP buffer. Identical injections over blank surfaces were subtracted from the binding data for analysis. All samples were run in duplicate and yielded similar sensorgram traces. Single curves of the duplicates are shown in all figures.

Guinea Pig Vaccinations

Outbred female Hartley guinea pigs (Elm Hill) were used for all vaccination studies and were housed at the Animal Research Facility of Beth Israel Deaconess Medical Center under approved Institutional Animal Care and Use Committee (IACUC) protocols.

Guinea pigs (n=5-15/group) were immunized with Env gp140 immunogens intramuscularly in the quadriceps bilaterally at 4-week intervals (weeks 0, 4, or 8) for a total of 3 injections. Vaccine formulations for each guinea pig consisted of a total of 100 µg of immunogen (e.g., trimer, Env gp140) per injection formulated in 15% EMULSIGEN® (vol/vol) oil-in-water emulsion (MVP Laboratories) and 50 µg CpG (Midland Reagent Company) as adjuvants. In multivalent vaccination regimens, the total amount of injected protein was maintained at 100 µg and divided equally among total the number of immunogens in the mixture. Vaccination groups included HIV-1 Env gp140 versions of: 459C wild type only (459C WT; SEQ ID NO: 23) (n=15), 459C V2 optimized only (V2 Opt; SEQ ID NO: 19) (n=5), 459C V2 alternate only (V2 Alt; SEQ ID NO: 20) (n=5), 459C V3 optimized only (V3 Opt; SEQ ID NO: 21) (n=10), 459C V3 alternate only (V3 Alt; SEQ ID NO: 22) (n=10), 459C V2 Opt+459C V2 Alt (V2 Opt+V2 Alt) (n=5), 459C V3 Opt+459C V3 Alt (V3 Opt+V3 Alt) (n=5), 459C WT+459C V2 Opt+459C V2 Alt (V2 Mixture) (n=5), 459C WT+459C V3 Opt+459C V3 Alt (V3 Mixture) (n=5), 459C V2 Opt prime with two boosts of [459C WT+459C V2 Alt] (V2 Prime/Boost) (n=5), and 459C V3 Opt prime with two boosts of [459C WT+459C V3 Alt] (V3 Prime/Boost) (n=5). To compare the benefit of the rationally designed V2-SET immunogens over 459C WT alone to mixtures of naturally occurring sequences over 459C WT alone, we tested mixtures of non-SET Env sequences in guinea pigs. Vaccination groups included a clade C only, trivalent mixture (459C+ 405C (SEQ ID NO: 44)+C97ZA012 gp140, "3C Mixture" and "3C") (n=5) and a multiclade, quadrivalent mixture that includes a clade A, B, C, and mosaic Env gp140 (92UG037+ PVO.4+C97ZA012+Mosaic gp140, respectively; "ABCM Mixture" and "ABCM") (n=5) utilizing the same vaccination scheme as with the V2-SET vaccines. To test the generalizability of the V2-SET vaccine strategy, we used a second adjuvant and a lengthened vaccination schedule where we compared the 459C WT (n=10) and the V2 Mixture (n=10) formulated with 10 µg Monophosphoryl lipid A (MPLA) (InvivoGen) adjuvant with vaccinations at weeks 0, 4, and 24. Serum samples were obtained from the vena cava of anesthetized animals four weeks after each immunization as well as prior to vaccination for week 0, naïve sera.

Endpoint ELISAs

Serum binding antibodies against gp140 and V1N2 scaffolds were measured by endpoint enzyme-linked immunosorbant assays (ELISAs) as described previously (Nkolola et al., *J. Virol.* 84:3270-3279, 2010). Briefly, ELISA plates (Thermo Scientific) were coated with individual gp140s or V1/V2 scaffolds and incubated overnight. Guinea pig sera were then added in serial dilutions and later detected with an HRP-conjugated goat anti-guinea pig secondary antibody (Jackson ImmunoResearch Laboratories). Plates were developed and read using the SPECTRAMAX® Plus ELISA plate reader (Molecular Devices) and SOFTMAX® Pro-4.7.1 software. End-point titers were considered positive at the highest dilution that maintained an absorbance >2-fold above background values.

Peptide Microarrays

REPLITOPE™ Antigen Collection HIV Ultra slides (JPT Peptide Technologies GmbH) arrays were generated, conducted, and analyzed using methods as described previously (Stephenson et al., *J. Immunol. Methods* 416:105-123, 2015). These slides contain linear 15-mer peptides that were designed utilizing the HIV global sequence database and designed to provide coverage of HIV-1 global sequence as described in detail previously (Stephenson et al., *J. Immunol. Methods* 416:105-123, 2015).

Briefly, microarray slides were incubated with guinea pig sera diluted 1/200 in SUPERBLOCK® T20 (TBS) Blocking Buffer (Thermo Scientific). Binding antibody responses were detected with Alexa Fluor 647-conjugated AffiniPure Goat Anti-Guinea Pig IgG (H+L) (Jackson ImmunoResearch Laboratories). Slides were placed in the individual chambers and incubated with diluted sera. Slides were then washed followed by an incubation in the dark for 1 hour with ALEX FLUOR® 647-conjugated AffiniPure Goat Anti-Guinea Pig IgG (H+L) (Jackson ImmunoResearch Laboratories). Slides were then washed and dried. All batches of slides were run in parallel with a control slide incubated with the secondary antibody only for background subtraction.

Microarray Slide Scanning and Determination of Positivity

Slides were scanned with a GENEPIX® 4300A scanner (Molecular Devices), using 635 nm and 532 nm lasers at 500 PMT and 100 Power settings. The fluorescent intensity for each feature (peptide spot) was calculated using GENEPIX® Pro 7 software and GENEPIX® Array List as described previously (Stephenson et al., *J. Immunol. Methods* 416:105-123, 2015). A slide containing signal from the secondary antibody only was subtracted from all experimental slides to remove background. The threshold values for positivity was calculated as the point at which the chance that signal is noise as low as possible ($P<10^{-16}$). As guinea pigs notoriously have high background in serum responses (Bricault et al., *J. Virol.* 89:2507-2519, 2015 and Liao et al., *J. Virol.* 87:4185-4201, 2013), $P<10^{-16}$ was used for the cutoff for all analyses. For each batch of slides run together, the highest $P<10^{-16}$ value from all arrays run was chosen as the cutoff for all slides within that batch to ensure that positive signals were real. All values that fell below the $P<10^{-16}$ cutoff were set to equal zero and all samples that were greater than the cutoff value were maintained as their raw, positive signal.

Microarray Data Analysis

The magnitude, or fluorescent intensity, of antibody binding to individual envelope peptides was determined. To calculate average magnitude of responses, the fluorescent intensity of all animals within a group was averaged together. Percent positive peptides was determined by envelope region (e.g. V1, V2, etc.). Each peptide with a positive signal was scored as a single positive peptide. These positive responses were then added together to be the total number of positive peptides, which was then divided by the total number of peptides within each region, and multiplied by 100 [Percent peptide set positive=(total positive peptides within an Env region/total number of peptides within an Env region)*100]. These values were then averaged together for each animal, by group, to determine the average percent positive peptides per Env region.

The peak positive antibody binding responses to linear V2 and V3 Env peptides were further analyzed comparing the 459C WT and the V2-SET vaccines. Peptides with the highest magnitude binding responses were analyzed comparing geometric means over animals separately against each 15-mer peptide start position. Geometric means were calculated for each vaccination group resulting in a single point per vaccine per peptide sequence.

TZM.Bl Neutralization Assay with Serum

Functional neutralizing antibody responses against HIV-1 Env pseudoviruses were measured using the TZM.bl neutralization assay, a luciferase-based virus neutralization assay in TZM.bl cells as described previously (Wei et al., *Antimicrob. Agents Chemother.* 46, 1896-1905, 2002, and Sarzotti-Kelsoe et al., *J. Immunol. Methods* 409:147-160, 2014). ID50 was calculated as the serum dilution that resulted in a 50% reduction in relative luminescence units of TZM.bl cells compared to virus-only control wells after the subtraction of a cell-only control. Briefly, serial dilutions of sera were incubated with pseudoviruses and then overlaid with TZM.bl cells. Murine leukemia virus (MuLV) was included as a negative control in all assays. For graphing data, response=Post-MuLV, if Post-MuLV>0, 0 otherwise, where 'Post' is post-vaccination sera (week 12 sera) and 'MuLV' is the responses seen for animal-matched MuLV negative control (week 12 sera). HIV-1 Env pseudoviruses, including tier 1 isolates from clade A (DJ263.8), clade B (SF162.LS, BaL.26, SS1196.1, 6535.3), and clade C (MW965.26, TV1.21, ZM109F.PB4). A previously selected global panel of tier 2 HIV-1 Env pseudoviruses were also tested including clade A (398.F1), clade AC (246_F3), clade B (TRO.11, X2278), clade C (Ce1176, Ce0217, 25710), clade G (X1632), CRF01_AE (CNE8, CNE55), and CRF07_BC (BJOX200, CH119) (DeCamp et al., *J. Virol.* 88:2489-2507, 2014). Pseudoviruses were prepared as described previously (Sarzotti-Kelsoe et al., *J. Immunol. Methods* 409:147-160, 2014 and Montefiori, *Curr. Protoc. Immunol.* Chapter 12:Unit 12.11, 2005).

Rational Selection of Tier 2 Pseudoviruses

A total of 20 tier 2 pseudoviruses were used in the TZM.bl neutralization assay: the standardized global panel of 12 HIV-1 reference strains independently selected to represent global diversity (DeCamp et al., *J. Virol.* 88:2489-2507, 2014) and a panel of 8 additional tier 2 pseudoviruses selected to assess tier 2 NAbs among heterologous pseudoviruses that resembled the SET vaccines in the relevant epitope regions. These selected pseudoviruses were sensitive to human sera (falling in the top quartile of geometric mean serological reactivity of the tier 2 panel), were sensitive to the relevant bNAb monoclonals (Yoon et al., *Nucleic Acids Res.* 43:W213-W219, 2015), had glycosylation patterns and variable loop signatures associated with neutralization sensitivity, and were close in sequence to the SET vaccines in the neutralization signature positions. The 8 additional pseudoviruses were added as an a priori attempt to increase the chances of getting a positive signal, but when tested were found to be very comparable in sensitivity to the global panel. For example, detectable neutralization was observed in 51% of the neutralization assays testing sera elicited by 459C WT using the global pseudovirus panel and in 51% of the assays using the selected panel of 8. Similarly, 82% of the V2 Mixture responses were positive using the global panel, and 80% were positive in the selected panel. The rationally selected tier 2 pseudoviruses included clade C strains (Du156.12, CT349_39_16, 234_F1_15_57, CNE58, and CA240_A5.5), CRF 02_AG (T250_4), CRF 07_BC (CNE20), and CRF 01_AE (C3347_C11).

TZM.Bl Neutralization Assay with Purified, Polyclonal IgG

For purification of guinea pig polyclonal IgG from sera, High-Capacity Protein A Agarose (Thermo Scientific) was utilized following manufacturer's instructions. After purification by protein A, polyclonal IgG samples were buffer exchanged into 1× phosphate buffered saline, pH 7.4 (Gibco) utilizing a EMD Millipore AMICON™ Ultra-15 Centrifugal Filter Unit (Millipore) at 4° C. Samples were then run in the TZM.bl neutralization assay as described for serum samples.

Mutant Pseudoviruses

Mutant pseudoviruses were generated with point mutations in variable loop 2 and 3 glycans to map NAb responses targeting these epitopes. Point mutations aiming to abrogate V2 antibody neutralization were selected to minimize disruptions in the virus backbone by representing mutations that occur most commonly in nature. A T162I mutation was introduced into X1632, T250-4, BJOX2000, X2278, TRO.11, Du156.12, and CNE58 to knock out the glycan at position 160. A N160A mutations was introduced into TRO.11, Du156.12 to knock out a glycan at position 160. T303I and [S/T]334N mutations were introduced into 398-F1, X2278, CNE58, Ce1176, Du156.12 to knock out glycans at positions 301 and 332.

Statistical Analysis of Neutralization Data

Neutralization data were analyzed using the R package (Sarah Stowell. *Using R for Statistics*. Apress, 2014) and GraphPad PRISM™ version 6.00 software (GraphPad Software, San Diego Calif. USA). Three distinct thresholds were tested with the goals of being both conservative in terms of trying to remove background noise due to non-specific neutralization while trying to avoid discounting low, but persistent and vaccine specific, positive signals as has been described previously (Bricault et al., *J. Virol.* 89:2507-2519, 2015 and Liao et al., *J. Virol.* 87:4185-4201, 2013). The three cutoffs utilized to determine positivity were as follows:
Cutoff 1: Response=Post, if Post>MuLV+10; 10 otherwise,
Cutoff 2: Response=Post-MuLV, if Post-MuLV>10, 10 otherwise,
Cutoff 3: Response=Post, if Post>3*MuLV, 10 otherwise, where 'Post' is post-vaccination sera (week 12 sera, 4 weeks-post last vaccination), 'MuLV' is the responses seen for animal-matched MuLV negative control (week 12 sera, 4 weeks-post last vaccination), and lowest background below cutoffs set to 10, as was done in the past (Bricault et al., *J. Virol.* 89:2507-2519, 2015) for statistical comparisons of below the cutoff threshold. Cutoff 1 is more inclusive and would be more informative for tier 2 studies with low, positive neutralizing antibody magnitudes, cutoff 2 is more restrictive, but removes non-specific neutralization signal as determined by the MuLV control, and Cutoff 3 is the most restrictive and reflects what is frequently used in published neutralization studies involving mostly tier 1 pseudoviruses. For samples that are MuLV subtracted, cutoff 2 was utilized for displaying the data.

Generalized Linear Model Analysis.

Generalized Linear Model (GLM) is a generalization of linear regression, which allows for response variables with other than normal error distribution models, including binary and continuous distributions that are other than normal. GLM analysis was performed in R, using glmer4 package. Specifically, a mixed effect linear model was utilized for analyses. For tier 1 analyses, the GLM analysis included both random (animal, pseudovirion) and fixed effects (vaccine given and tier).

Fixed effects Vaccine and tier (tier 1A and 1B) interacting:

$$\log 10(\text{Response}) \sim \text{Tier}*\text{Vaccine}+(1|\text{Env})+(1|\text{Animal})$$

Fixed effects Vaccine and Tier NOT interacting:

$$\log 10(\text{Response}) \sim \text{Tier}+\text{Vaccine}+(1|\text{Env})+(1|\text{Animal}),$$

where 1|Animal is the notation for treating an animal as a random effect. Vaccine*Tier is the notation for an interaction between the vaccine and the tier of the test Env. As there was no statistical difference between the 2 models (ANOVA p=0.8397), a simpler, no interaction model g1 was utilized for analysis that included tier 1 neutralization data.

Tier 2 analysis with GLM is more complicated. When using GLMs, the data are assumed to be well modeled by one of a range of probability distributions, such as normal, binomial, Poisson, and gamma distributions. Unlike the tier 1 responses, the tier 2 responses, have a high proportion of censored data (below cutoff, not-detected responses), making the data a poor fit for all standard distributions tested. Given this, the whole body of the tier 2 data (detected and not-detected together) was analyzed by standard nonparametric statistical methods (see below) rather than a GLM. We found the GLM was, however, appropriate to use for analyzing the breadth of tier 2 response (binomial distribution: detected/not-detected).

Magnitude of Neutralization Response

All (detected and not-detected) responses were also analyzed by a permutation test (Parrish et al., *PNAS*. 110: 6626-6633, 2013) to assess the differences between vaccines. The SET (e.g., V2-SET) vaccine regimens V2 Mixture and V2 Prime/Boost were each separately compared to 459C WT, and the non-parametric test we applied estimated the probability that the improvement in responses by the given SET (e.g., V2-SET) vaccine relative to WT could be this high by the chance alone. The algorithm included three essential steps:

1. For each pseudovirus, the responses elicited by the WT and the given SET (e.g., V2-SET) vaccine were combined and the median was calculated. Then the count of responses elicited by the SET (e.g., V2-SET) vaccine that were above this median was calculated; this number was summed across all 20 pseudoviruses and the result was regarded as the rank-sum of the observed SET (e.g., V2-SET) responses above the median.

2. 10,000 randomized data sets were then created, where the vaccine category was randomly reassigned between vaccinated animals, keeping the responses linked to the tested pseudovirus. For each randomized data set the procedure described in Step 1 was repeated, recalculating the count of the responses randomly designated as "SET" (e.g., V2-SET) were above the median (the rank-sum) for the randomized data.

3. The fraction of occurrences in the randomized data of rank-sum values from the Step 2 that were equal to or less than that observed rank-sum in the actual data (Step 1) provided an estimate of the probability for of observing the actual rank-sum by the chance alone.

The responses elicited by the 459C WT and each of the SET (e.g., V2-SET) regimens were also compared separately for each pseudovirus using the Wilcoxon one-sided test. To better visualize the differences in the magnitude of response between vaccine regimens we compared the geometric means of response per pseudovirus across all animals vaccinated with a particular immunogen and tested on that pseudovirus, resulting in one data point per immunogen per pseudovirus. These geometric means were initially compared by the Friedman paired test to detect statistical differences between different immunogens, followed by the Wilcoxon paired test to compare SET (e.g., V2-SET) immunogens to the 459C WT.

Wilcoxon paired tested comparing geometric means per animal across all pseudoviruses was utilized to determine differences in the magnitude of neutralization responses. When all data was considered, Friedman paired test was utilized to detect statistical differences. Non-parametric resampling was also utilized to probe differences among vaccines. For each pseudovirus, WT and epitope modified immunogen categories are randomly reassigned between animals 10,000 times. The proportion of randomized datasets with greater than observed fraction of modified vaccine responses above the median is a non-parametric p-value.
Breadth of Neutralization Response The breadth of neutralization response was assessed by counting for each animal a proportion of 20 pseudoviruses with detectable neutralization and then applying the restrictive Wilcoxon rank-sum test to compare the differences in distributions of responses per animal between the 459C WT and the SET vaccines. Simple over-arching differences in breadth of neutralization responses were assessed by the inclusive Fisher's exact test and the vaccine groups were compared using GLM (see above) fitted with a binomial distribution to determine whether the difference between detected and non-detected responses was explained by the vaccine given.

The 3C Mixture was analyzed against a panel of 9 C clade pseudoviruses (9 of 18) and a panel of 9 non-C clade pseudoviruses (18 of the original 20 were tested). The C clade pseudoviruses, as well as the CRF07 recombination viruses which are almost entirely C clade in the Env protein, are highlighted with red Cs below the heat map for the 3C Mixture (Du156.12 and CT349_39_16 were not tested due to lack of virus). Data for the 3C Mixture are reported as follows: all data, responses to C clade pseudoviruses only, and responses to non-C clade pseudoviruses only. As our hypothesis was that trivalent vaccines that include 459C WT (3C and V2-SET) should improve the breadth of responses elicited by 459C WT alone, the one-sided test was used for 3C, 3C on only C clade pseudoviruses and V2-SET. For ABCM, not containing 459C, and for 3C tested on non-C clade pseudoviruses, no hypothesis existed, thus a two-sided test was used.

Example 2: Generation of Signature-Based Epitope Targeted (SET) HIV-1 Envelope Immunogens We designed a series of novel variable loop 2 SET (V2-SET) Env gp140 immunogens utilizing a previously described early clade C HIV-1 Env 459C gp140 (Bricault et al., *J. Virol.* 89:2507-2519, 2015) as the backbone. We chose 459C WT as it was a phylogenetically central clade C sequence and elicited a greater magnitude of tier 1 NAbs in guinea pigs than other single Env we had previously tested. As described in the methods, we focused on the V2/glycan (FIG. 1A) epitopes to create V2-SET immunogens. The trivalent immunogen design included a 459C WT Env and two modified versions of 459C, Opt and Alt. The Opt and Alt vaccines were designed to be administered together to encompass natural sequence variation in Env regions that influence neutralization sensitivity to V2/glycan targeted bNAbs, considering both direct and non-direct bNAb amino acid contact sites in their design. The design of these variants is described herein.

Each epitope modified gp140 immunogen (e.g., V2-SET immunogens) was screened for expression in 293T cells by transient transfection for secreted as well as intracellular protein production. The V2 Opt, V2 Alt, V3 Opt, V3 Alt, and WT 459C gp140 proteins all expressed both as intracellular and as secreted proteins (FIG. 2A). These data suggest that the V2 Opt, V2 Alt, V3 Opt, and V3 Alt gp140 successfully expressed as secreted proteins.

Example 3: Biochemical Properties of Epitope Modified Env Trimers

The V2 Opt, V2 Alt, V3 Opt, and V3 Alt gp140 proteins were then expressed in larger scale production and assessed for their homogeneity and relative stability. Large scale preparations of Env immunogens were produced in 293T cells and purified by a nickel nitrilotriacetic acid (NiNTA) column followed by size exclusion chromatography. Each of the purified Env proteins ran as a single, symmetrical peak as measured by size exclusion chromatography, and as a single band on SDS-PAGE (FIGS. 2B-2G). These data suggest that the variable loop epitope modified HIV-1 Env immunogens express as relatively stable, homogeneous preparations of secreted gp140.

Figure 6A:
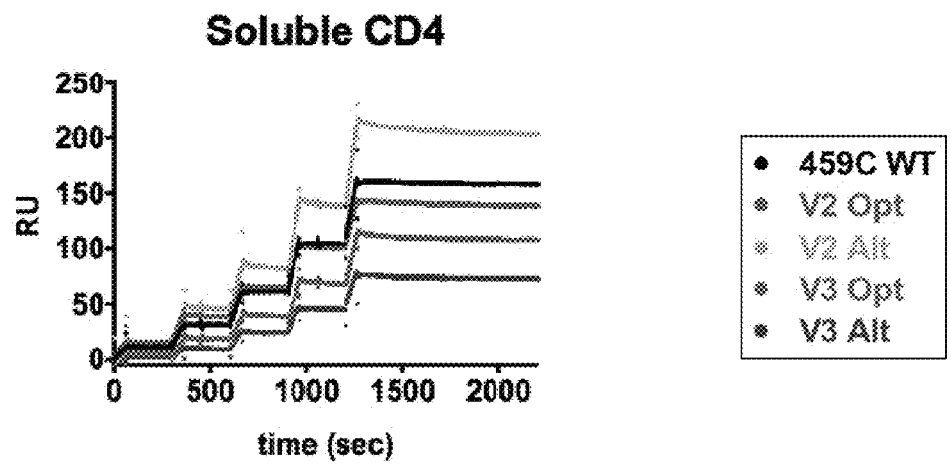
FIG. 6A is a graph showing an assessment of the presentation of the CD4 binding site by soluble CD4 binding to epitope modified (e.g., SET) Env gp140s as assessed by surface plasmon resonance. gp140 was flowed over the chip at concentrations of 62.5 to 1000 nM using single cycle kinetics and IgG captured by protein A. Sensorgram colors correspond to each gp140 as listed in the key. RU: response units.
Figure 6B:
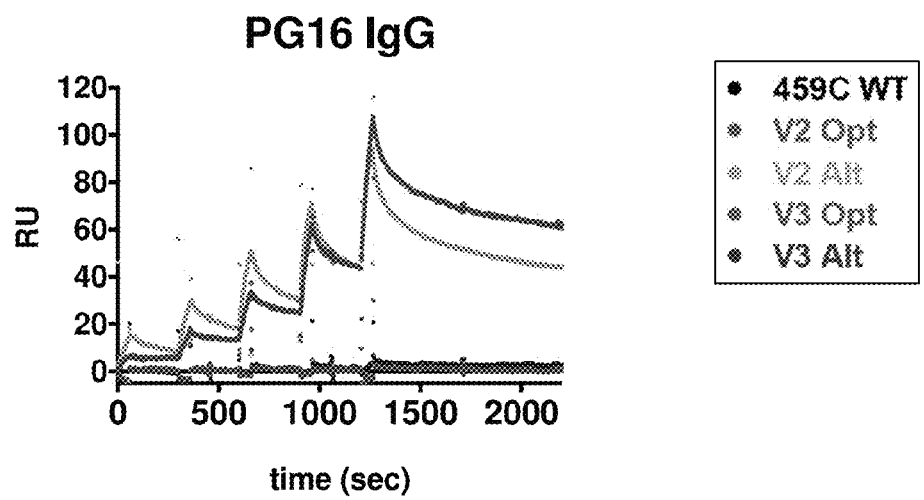
FIG. 6B is a graph showing an assessment of the presentation of the V2/glycan binding site with PG16 binding to epitope modified (e.g., SET) Env gp140s as assessed by surface plasmon resonance. gp140 was flowed over the chip at concentrations of 62.5 to 1000 nM using single cycle kinetics and IgG captured by protein A. Sensorgram colors correspond to each gp140 as listed in the key. RU: response units.
Figure 6C:
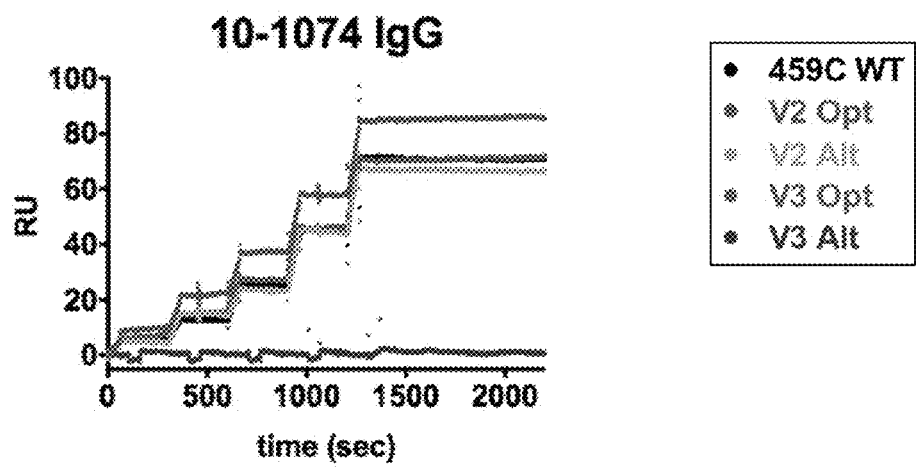
FIG. 6C is a graph showing an assessment of the presentation of the V3/glycan binding site by 10-1074 binding to epitope modified (e.g., SET) Env gp140s as assessed by surface plasmon resonance. gp140 was flowed over the chip at concentrations of 62.5 to 1000 nM using single cycle kinetics and IgG captured by protein A. Sensorgram colors correspond to each gp140 as listed in the key. RU: response units.
Figure 7A:
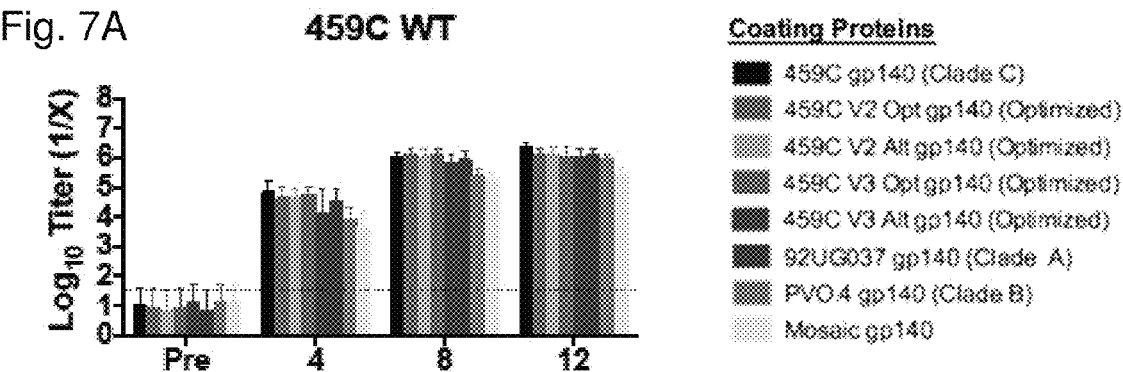
FIG. 7A is a graph showing a group of endpoint ELISAs of sera from guinea pigs vaccinated with HIV-1 459C WT gp140 that is tested against a panel of gp140 antigens. Colors correspond to ELISA coating trimers as listed. The horizontal dotted line indicates background and error bars indicate standard deviation for all endpoint ELISAs.
Figure 7B:
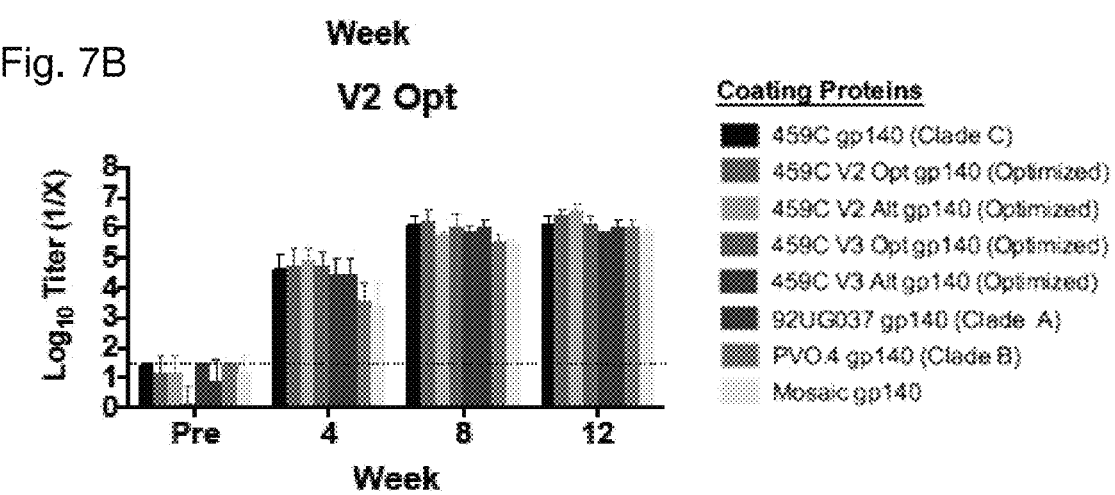
FIG. 7B a graph showing a group of endpoint ELISAs of sera from guinea pigs vaccinated with HIV-1 V2 Opt gp140 that is tested against a panel of gp140 antigens. Colors correspond to ELISA coating trimers as listed. The horizontal dotted line indicates background and error bars indicate standard deviation for all endpoint ELISAs.
Figure 7C:
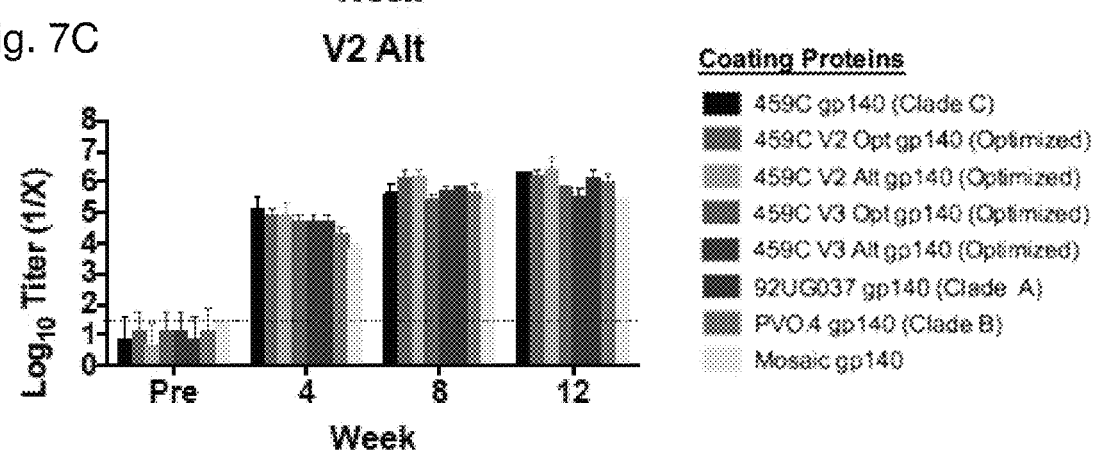
FIG. 7C is a graph showing a group of endpoint ELISAs of sera from guinea pigs vaccinated with HIV-1 V2 Alt gp140 that is tested against a panel of gp140 antigens. Colors correspond to ELISA coating trimers as listed. The horizontal dotted line indicates background and error bars indicate standard deviation for all endpoint ELISAs.
Figure 7D:
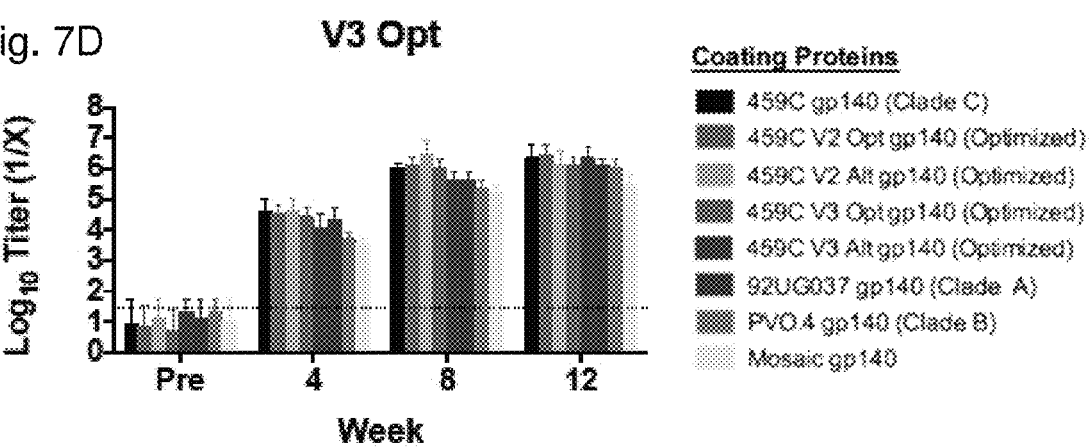
FIG. 7D is a graph showing a group of endpoint ELISAs of sera from guinea pigs vaccinated with HIV-1 V3 Opt gp140 that is tested against a panel of gp140 antigens. Colors correspond to ELISA coating trimers as listed. The horizontal dotted line indicates background and error bars indicate standard deviation for all endpoint ELISAs.
Figure 7E:
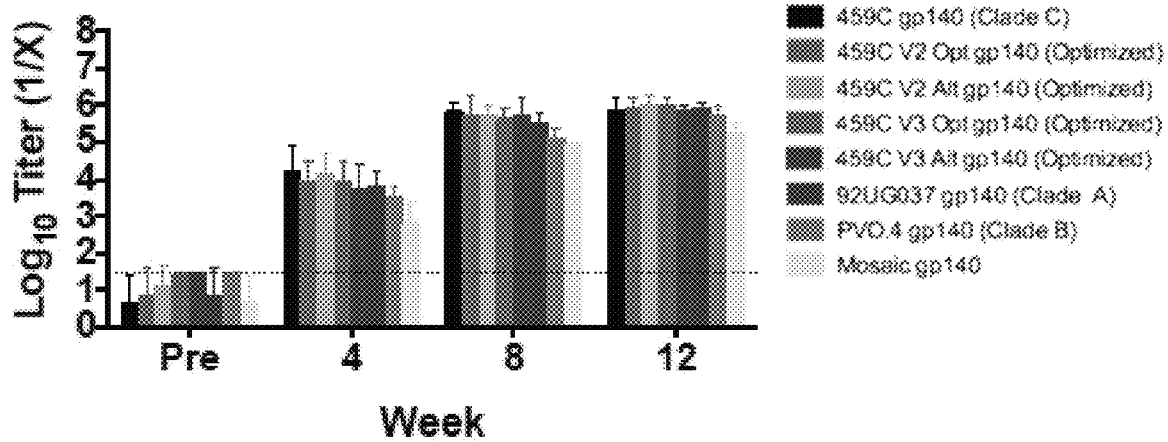
FIG. 7E is a graph showing a group of endpoint ELISAs of sera from guinea pigs vaccinated with HIV-1 V3 Alt gp140 that is tested against a panel of gp140 antigens. Colors correspond to ELISA coating trimers as listed. The horizontal dotted line indicates background and error bars indicate standard deviation for all endpoint ELISAs.
Figure 7F:
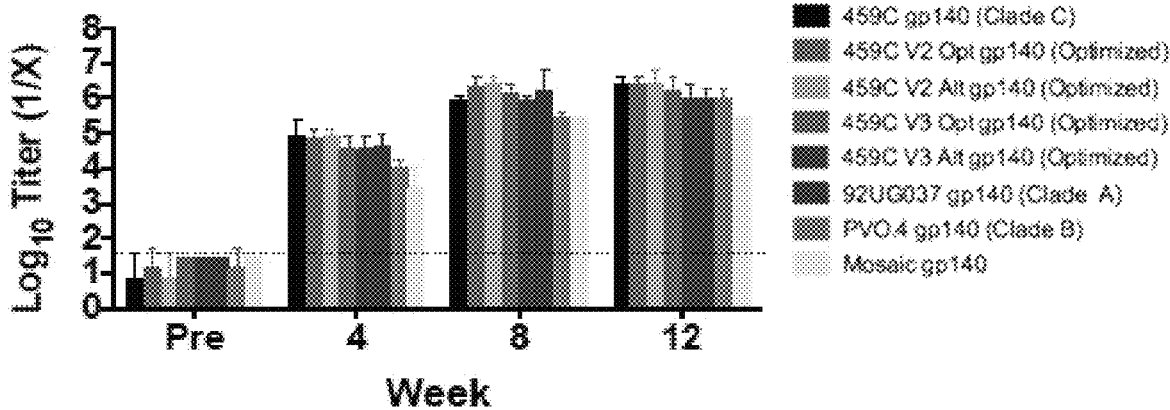
FIG. 7F is a graph showing a group of endpoint ELISAs of sera from guinea pigs vaccinated with HIV-1 V2 Opt gp140+V2 Alt gp140 that is tested against a panel of gp140 antigens. Colors correspond to ELISA coating trimers as listed. The horizontal dotted line indicates background and error bars indicate standard deviation for all endpoint ELISAs.
Figure 7G:
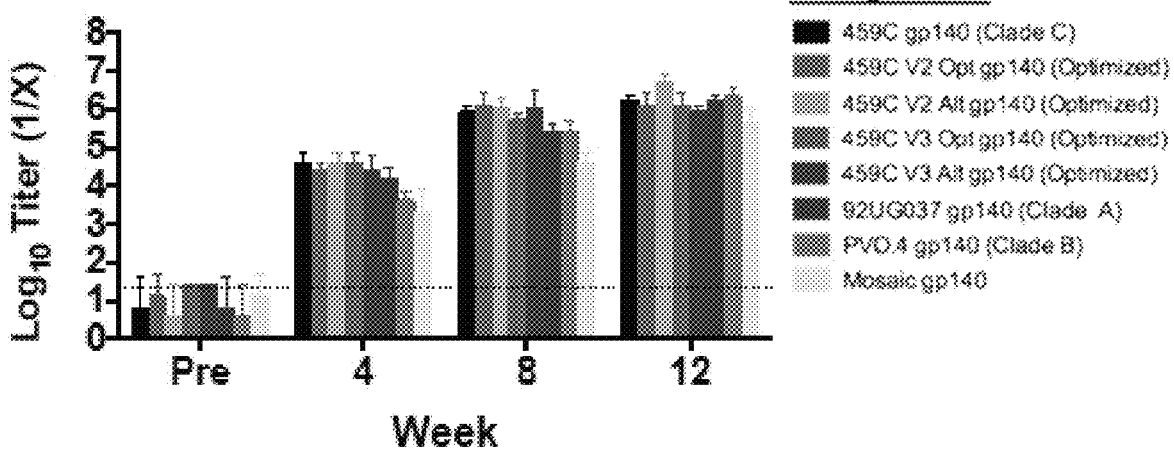
FIG. 7G is a graph showing a group of endpoint ELISAs of sera from guinea pigs vaccinated with HIV-1 V3 Opt gp140+V3 Alt gp140 that is tested against a panel of gp140 antigens. Colors correspond to ELISA coating trimers as listed. The horizontal dotted line indicates background and error bars indicate standard deviation for all endpoint ELISAs.
Figure 7H:
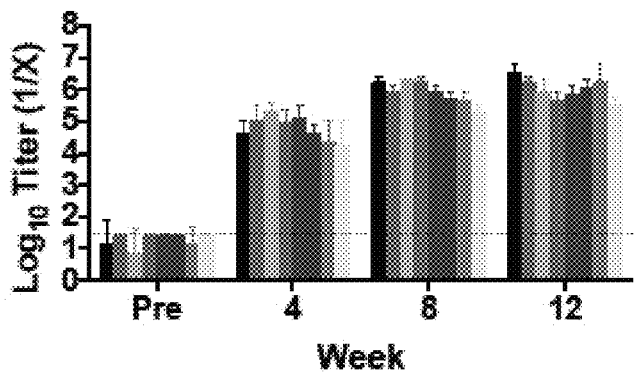
FIG. 7H is is a graph showing a group of endpoint ELISAs of sera from guinea pigs vaccinated with HIV-1 V2 mixture gp140 that is tested against a panel of gp140 antigens. Colors correspond to ELISA coating trimers as listed. The horizontal dotted line indicates background and error bars indicate standard deviation for all endpoint ELISAs.
Figure 7I:
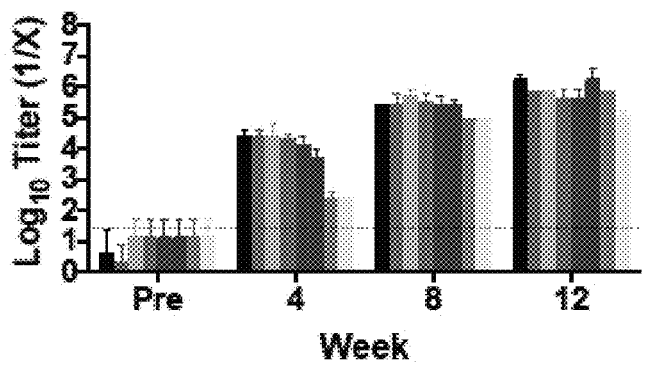
FIG. 7I is a graph showing a group of endpoint ELISAs of sera from guinea pigs vaccinated with HIV-1 V3 mixture gp140 that is tested against a panel of gp140 antigens. Colors correspond to ELISA coating trimers as listed. The horizontal dotted line indicates background and error bars indicate standard deviation for all endpoint ELISAs.
Figure 7J:
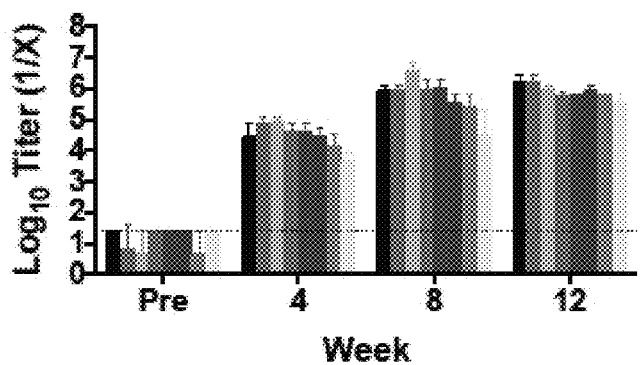
FIG. 7J is a graph showing a group of endpoint ELISAs of sera from guinea pigs vaccinated with HIV-1 V2 Prime/Boost that is tested against a panel of gp140 antigens. Colors correspond to ELISA coating trimers as listed. The horizontal dotted line indicates background and error bars indicate standard deviation for all endpoint ELISAs.
Figure 7K:
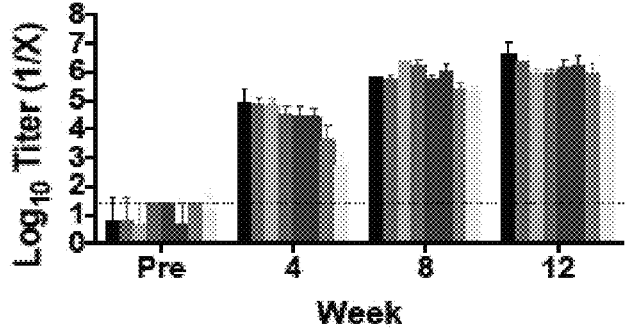
FIG. 7K is a graph showing a group of endpoint ELISAs of sera from guinea pigs vaccinated with HIV-1 V3 Prime/Boost that is tested against a panel of gp140 antigens. Colors correspond to ELISA coating trimers as listed. The horizontal dotted line indicates background and error bars indicate standard deviation for all endpoint ELISAs.
Figure 8A:
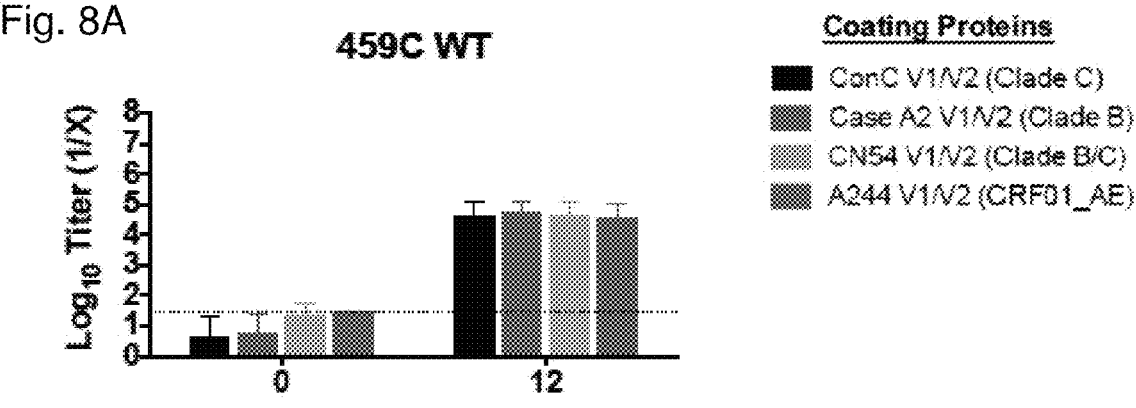
FIG. 8A is a graph showing a group of endpoint ELISAs of sera that is tested in guinea pigs vaccinated with HIV-1 459C WT gp140 in endpoint ELISAs against a panel of V1/V2 gp70 scaffolds as listed. Colors correspond to ELISA coating V1/V2 scaffolds as listed. The horizontal dotted line indicates background and error bars indicate standard deviation for all endpoint ELISAs.
Figure 8B:
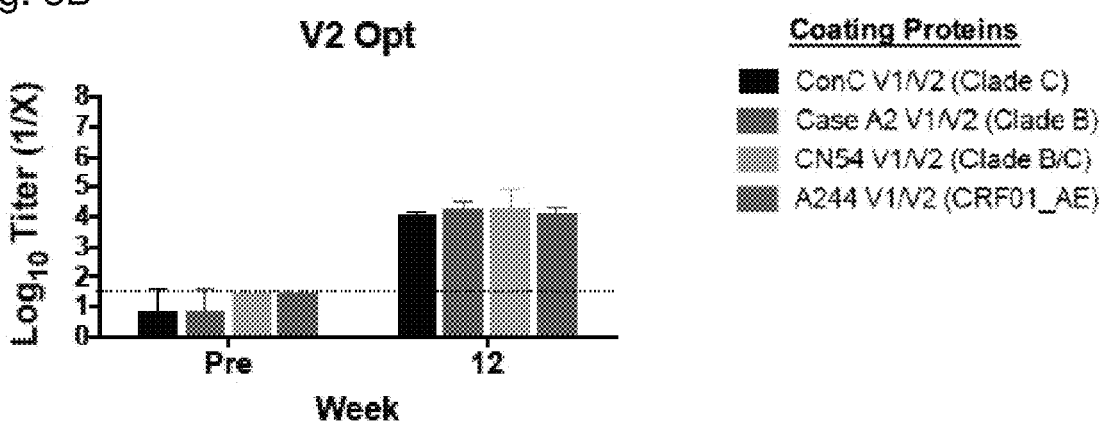
FIG. 8B is a graph showing a group of endpoint ELISAs of sera that is tested in guinea pigs vaccinated with HIV-1 V2 Opt gp140 in endpoint ELISAs against a panel of V1/V2 gp70 scaffolds as listed. Colors correspond to ELISA coating V1/V2 scaffolds as listed. The horizontal dotted line indicates background and error bars indicate standard deviation for all endpoint ELISAs.
Figure 8C:
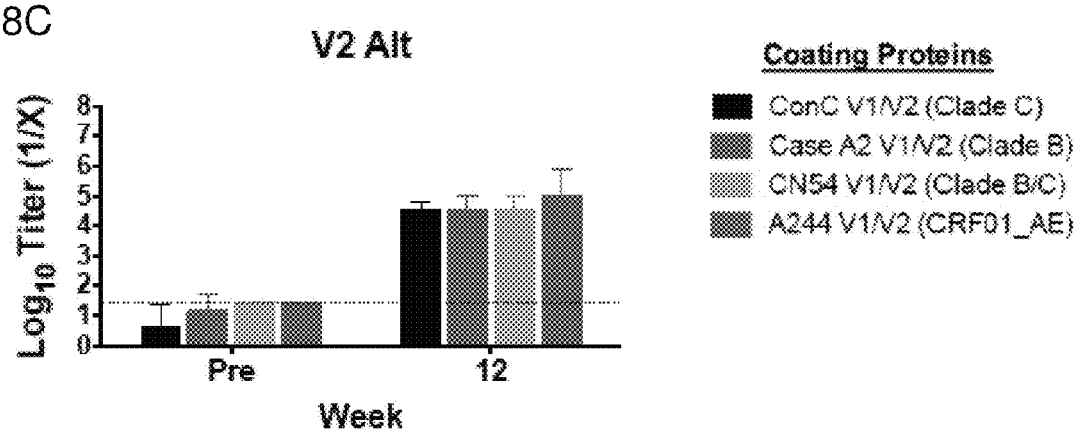
FIG. 8C is a graph showing a group of endpoint ELISAs of sera that is tested in guinea pigs vaccinated with HIV-1 V2 Alt gp140 in endpoint ELISAs against a panel of V1/V2 gp70 scaffolds as listed. Colors correspond to ELISA coating V1/V2 scaffolds as listed. The horizontal dotted line indicates background and error bars indicate standard deviation for all endpoint ELISAs.
Figure 8D:
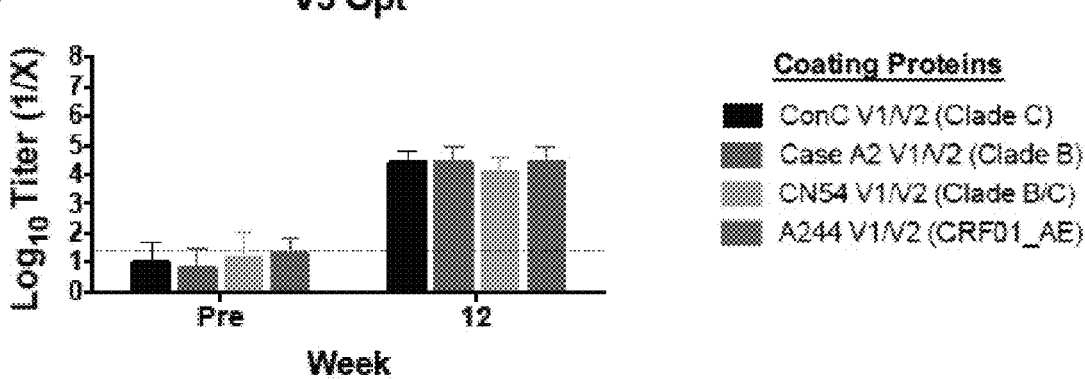
FIG. 8D is a graph showing a group of endpoint ELISAs of sera that is tested in guinea pigs vaccinated with HIV-1 V3 Opt gp140 in endpoint ELISAs against a panel of V1/V2 gp70 scaffolds as listed. Colors correspond to ELISA coating V1/V2 scaffolds as listed. The horizontal dotted line indicates background and error bars indicate standard deviation for all endpoint ELISAs.
Figure 8E:
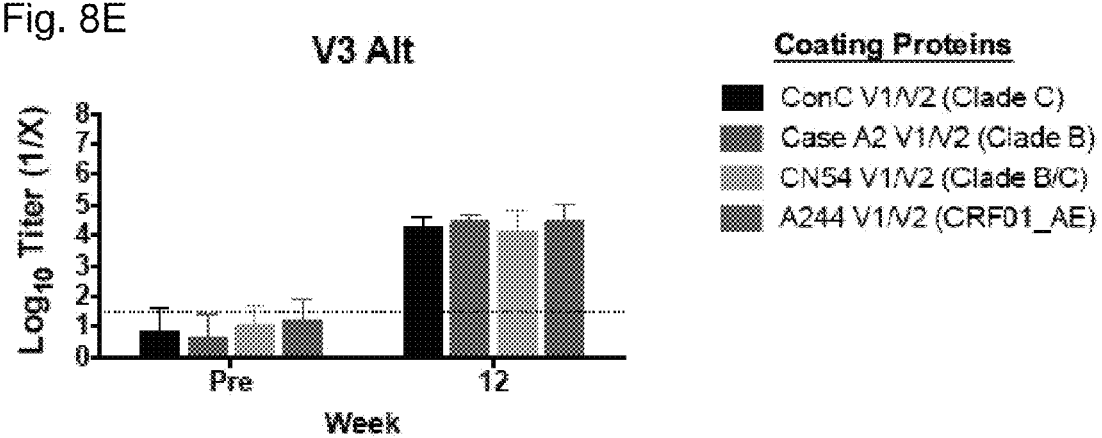
FIG. 8E is a graph showing a group of endpoint ELISAs of sera that is tested in guinea pigs vaccinated with HIV-1 V3 Alt gp140 in endpoint ELISAs against a panel of V1/V2 gp70 scaffolds as listed. Colors correspond to ELISA coating V1/V2 scaffolds as listed. The horizontal dotted line indicates background and error bars indicate standard deviation for all endpoint ELISAs.
Figure 8F:
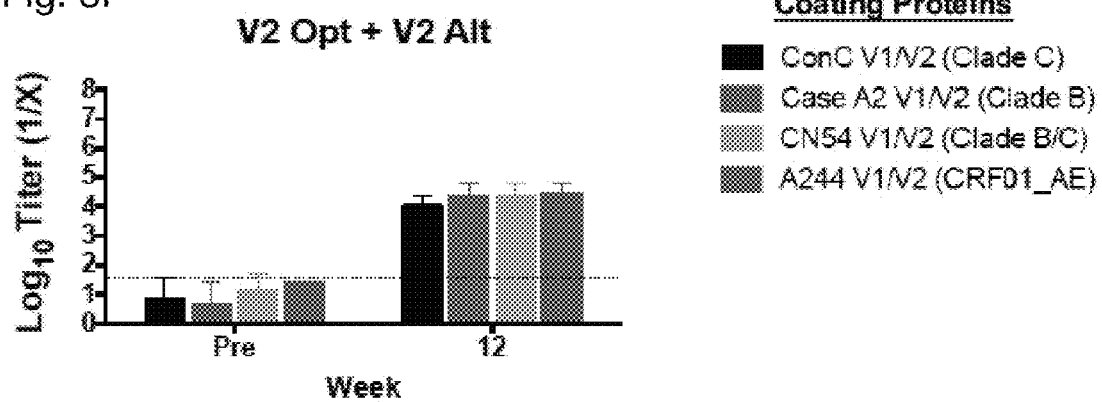
FIG. 8F is a graph showing a group of endpoint ELISAs of sera that is tested in guinea pigs vaccinated with HIV-1 V2 Opt gp140+V2 Alt gp140 in endpoint ELISAs against a panel of V1/V2 gp70 scaffolds as listed. Colors correspond to ELISA coating V1/V2 scaffolds as listed. The horizontal dotted line indicates background and error bars indicate standard deviation for all endpoint ELISAs.
Figure 8G:
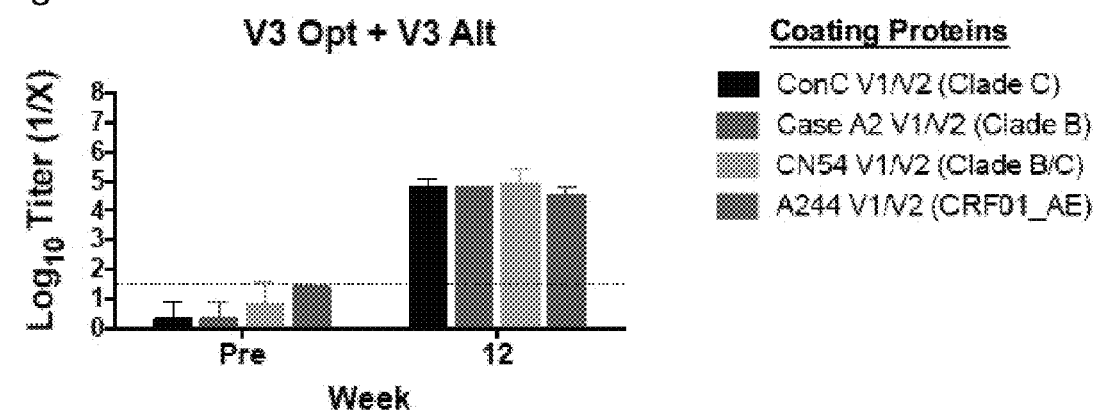
FIG. 8G is a graph showing a group of endpoint ELISAs of sera that is tested in guinea pigs vaccinated with HIV-1 V3 Opt gp140+V3 Alt gp140 in endpoint ELISAs against a panel of V1/V2 gp70 scaffolds as listed. Colors correspond to ELISA coating V1/V2 scaffolds as listed. The horizontal dotted line indicates background and error bars indicate standard deviation for all endpoint ELISAs.
Figure 8H:
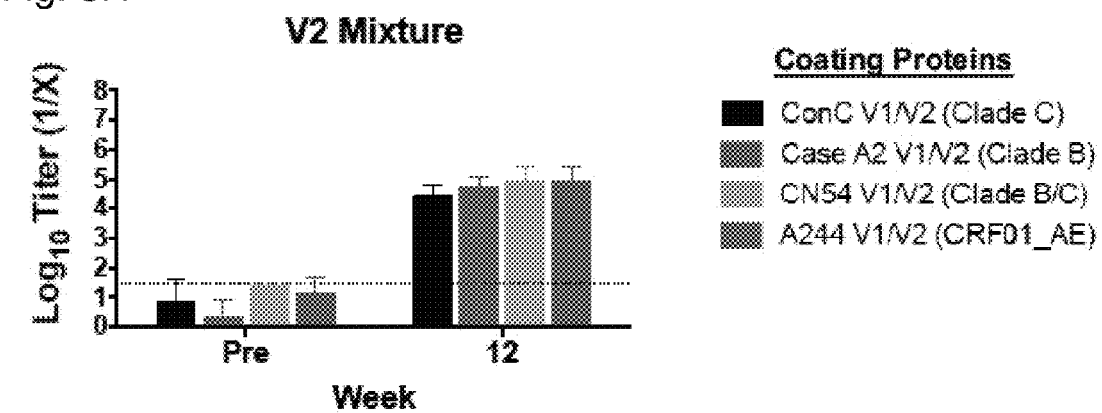
FIG. 8H is a graph showing a group of endpoint ELISAs of sera that is tested in guinea pigs vaccinated with HIV-1 V2 mixture gp140 in endpoint ELISAs against a panel of V1/V2 gp70 scaffolds as listed. Colors correspond to ELISA coating V1/V2 scaffolds as listed. The horizontal dotted line indicates background and error bars indicate standard deviation for all endpoint ELISAs.
Figure 8I:
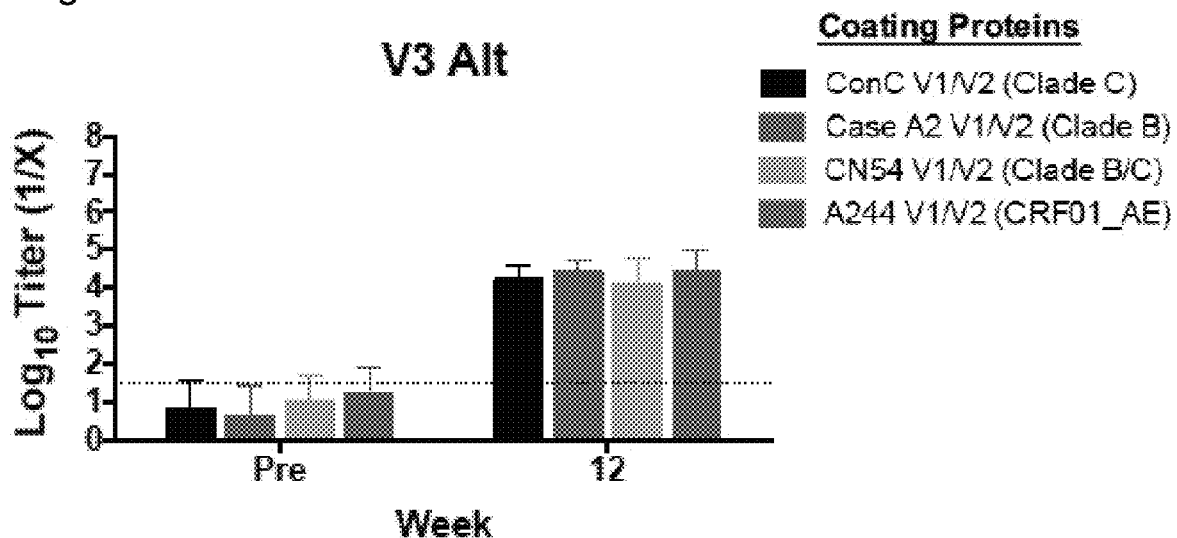
FIG. 8I is a graph showing a group of endpoint ELISAs of sera that is tested in guinea pigs vaccinated with HIV-1 V3 mixture gp140 in endpoint ELISAs against a panel of V1/V2 gp70 scaffolds as listed. Colors correspond to ELISA coating V1/V2 scaffolds as listed. The horizontal dotted line indicates background and error bars indicate standard deviation for all endpoint ELISAs.
Figure 8J:
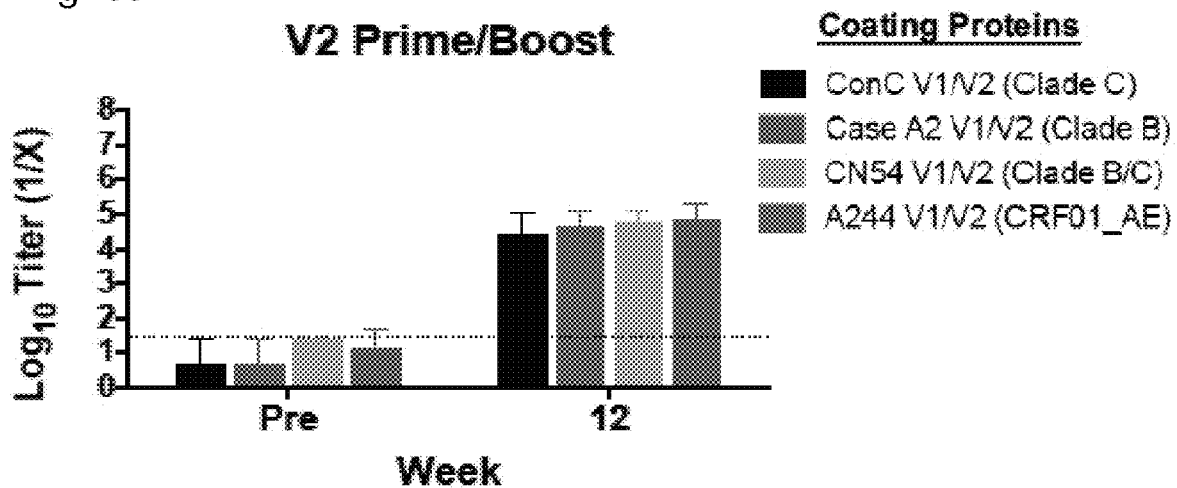
FIG. 8J is a graph showing a group of endpoint ELISAs of sera that is tested in guinea pigs vaccinated with HIV-1 V2 Prime/Boost gp140 in endpoint ELISAs against a panel of V1/V2 gp70 scaffolds as listed. Colors correspond to ELISA coating V1/V2 scaffolds as listed. The horizontal dotted line indicates background and error bars indicate standard deviation for all endpoint ELISAs.
Figure 8K:
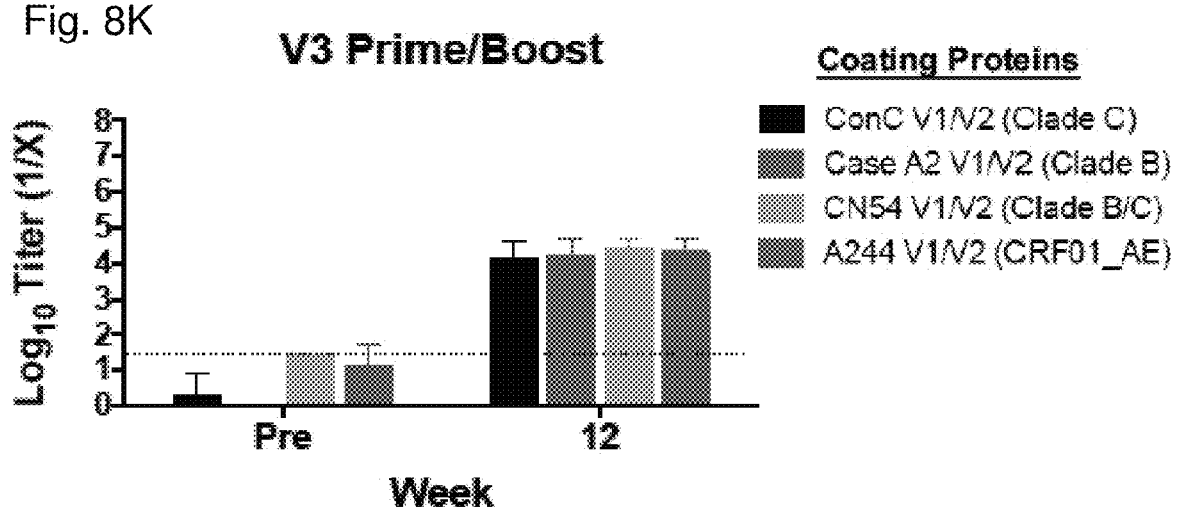
FIG. 8K is a graph showing a group of endpoint ELISAs of sera that is tested in guinea pigs vaccinated with HIV-1 V3 Prime/Boost gp140 in endpoint ELISAs against a panel of V1/V2 gp70 scaffolds as listed. Colors correspond to ELISA coating V1/V2 scaffolds as listed. The horizontal dotted line indicates background and error bars indicate standard deviation for all endpoint ELISAs.

The antigenic properties of the epitope modified Env immunogens (e.g., V2-SET immunogens) were probed utilizing surface plasmon resonance and known bNAbs. We first assessed the presentation of the CD4bs within the immunogens using a soluble, two-domain CD4 (Ryu et al., *Nature* 348:419-426, 1990 and Kwong et al., *Nature* 393:648-659, 1998). CD4 bound to all of the gp140s (FIG. 6A), suggesting that the CD4bs is presented in all proteins. Immunogens were then tested against a V2/glycan dependent PG16 (Doores et al., *J. Virol.* 84:10510-10521, 2010; Julien et al., *PLoS Pathog.* 9:e1003342, 2013; Pancera et al., *Nat. Struct. Mol. Biol.* 20:804-813, 2013; Walker et al., *Science* 326:285-289, 2009; Pancera et al., *J. Virol.* 84:8098-8110, 2010; McLellan et al., *Nature:* 1-10, 2011). V2 Opt and V2 Alt bound to PG16, while the WT and V3 immunogens did not bind PG16 suggesting that the V2-SET modifications increased exposure of this epitope compared to the wild type and V3 modified gp140 immunogens (FIG. 6B). The V3/glycan-dependent bNAb 10-1074 (Mouquet et al., *Proc. Natl. Acad. Sci. USA* 109:E3268-77, 2012; Julien et al., *PLoS Pathog.* 9:e1003342, 2013) was assessed and found to bind to WT and V2-SET gp140s similarly, as expected, as this epitope was not modified in these immunogens, while binding to V3 Opt at a slightly increased magnitude, and showing no binding to V3 Alt (FIG. 6C). This suggests that the V3 modifications improved the exposure of this epitope in the Opt gp140, while eliminating this epitope in the Alt gp140. These data suggest that each Env gp140 (e.g., V2 SET Env gp140 immunogens) has unique antigenic properties from one another within the CD4bs, V2/glycan, and V3/glycan epitopes.

Example 4: Immunization Regimens

Figure 3C:
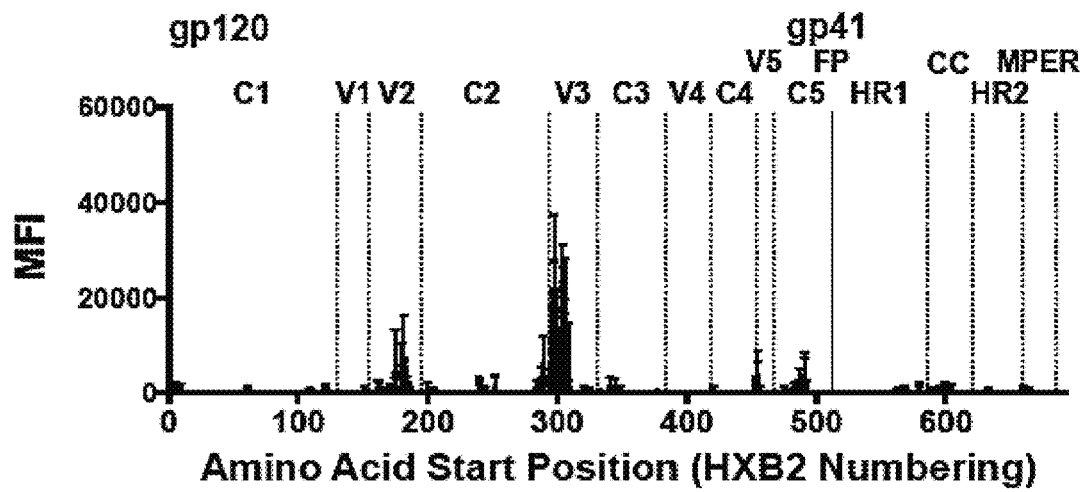
FIG. 3C is a graph showing the magnitude and position of binding antibody responses from guinea pig sera to linear 15-mer peptides on peptide microarrays. Each dot represents an average MFI per single peptide that is positive for antibody binding within each vaccination group with standard deviation shown. Titles indicate vaccination regimen (V2 Opt). MFI: mean fluorescence intensity. Envelope regions are delineated by vertical lines.
Figure 3D:
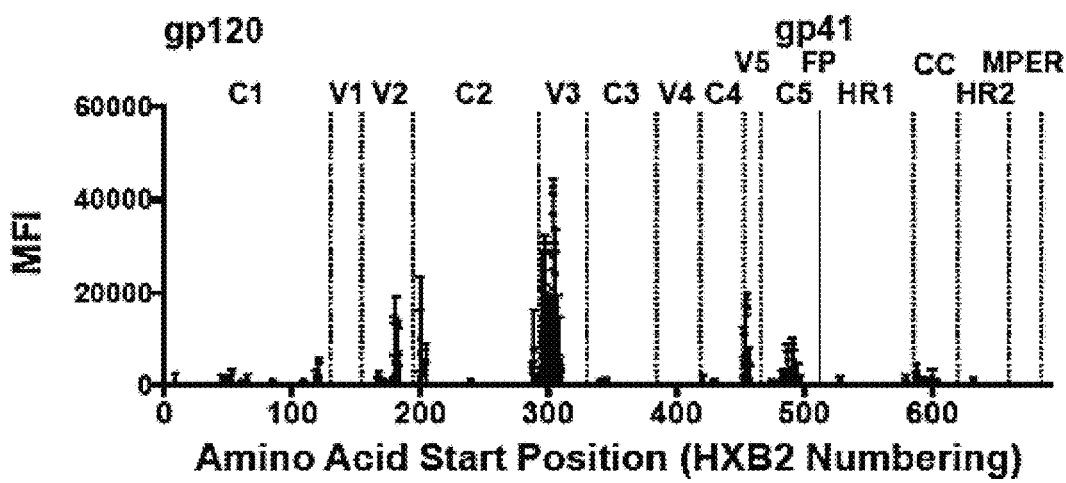
FIG. 3D is a graph showing the magnitude and position of binding antibody responses from guinea pig sera to linear 15-mer peptides on peptide microarrays. Each dot represents an average MFI per single peptide that is positive for antibody binding within each vaccination group with standard deviation shown. Titles indicate vaccination regimen (V2 Alt). MFI: mean fluorescence intensity. Envelope regions are delineated by vertical lines.
Figure 3E:
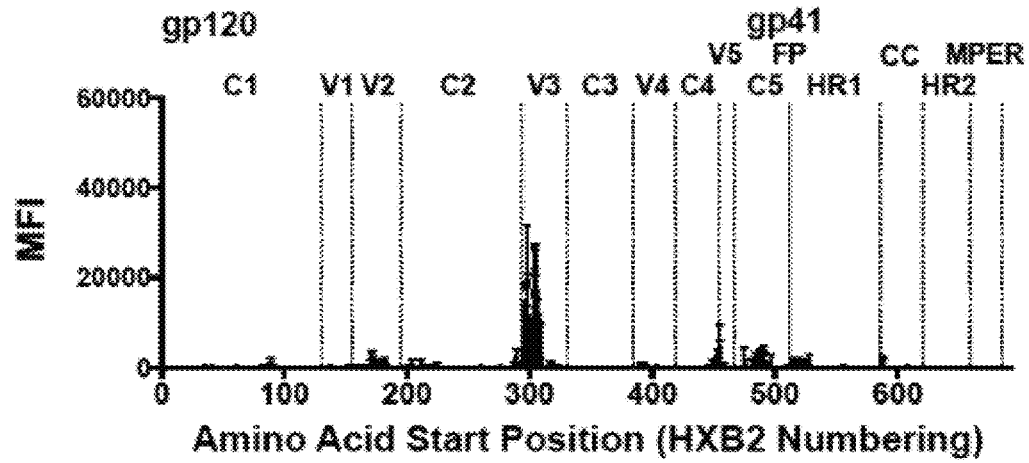
FIG. 3E is a graph showing the magnitude and position of binding antibody responses from guinea pig sera to linear 15-mer peptides on peptide microarrays. Each dot represents an average MFI per single peptide that is positive for antibody binding within each vaccination group with standard deviation shown. Titles indicate vaccination regimen (V3 Opt). MFI: mean fluorescence intensity. Envelope regions are delineated by vertical lines.
Figure 3F:
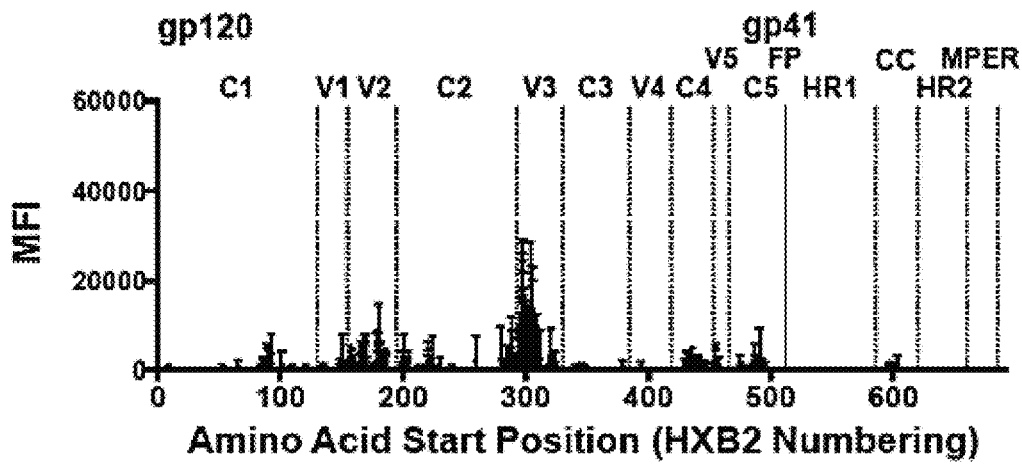
FIG. 3F is a graph showing the magnitude and position of binding antibody responses from guinea pig sera to linear 15-mer peptides on peptide microarrays. Each dot represents an average MFI per single peptide that is positive for antibody binding within each vaccination group with standard deviation shown. Titles indicate vaccination regimen (V3 Alt). MFI: mean fluorescence intensity. Envelope regions are delineated by vertical lines.
Figure 3G:
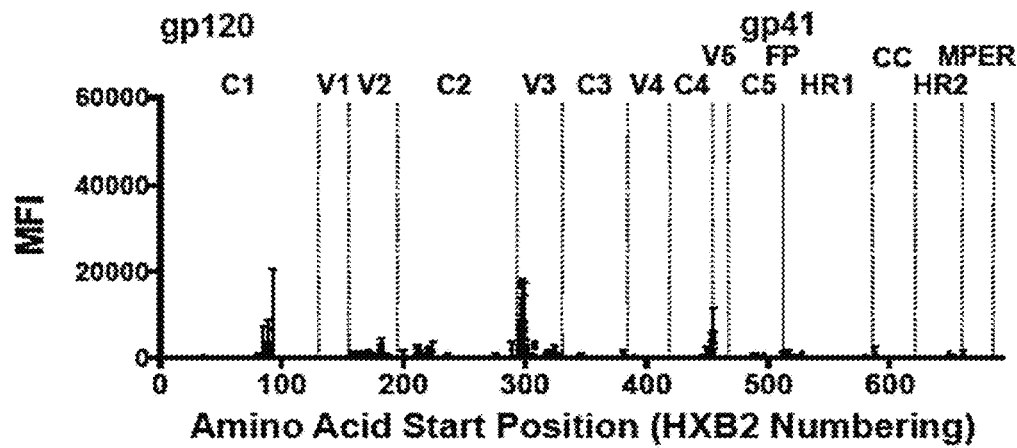
FIG. 3G is a graph showing the magnitude and position of binding antibody responses from guinea pig sera to linear 15-mer peptides on peptide microarrays. Each dot represents an average MFI per single peptide that is positive for antibody binding within each vaccination group with standard deviation shown. Titles indicate vaccination regimen (V2 Mixture). MFI: mean fluorescence intensity. Envelope regions are delineated by vertical lines.
Figure 3H:
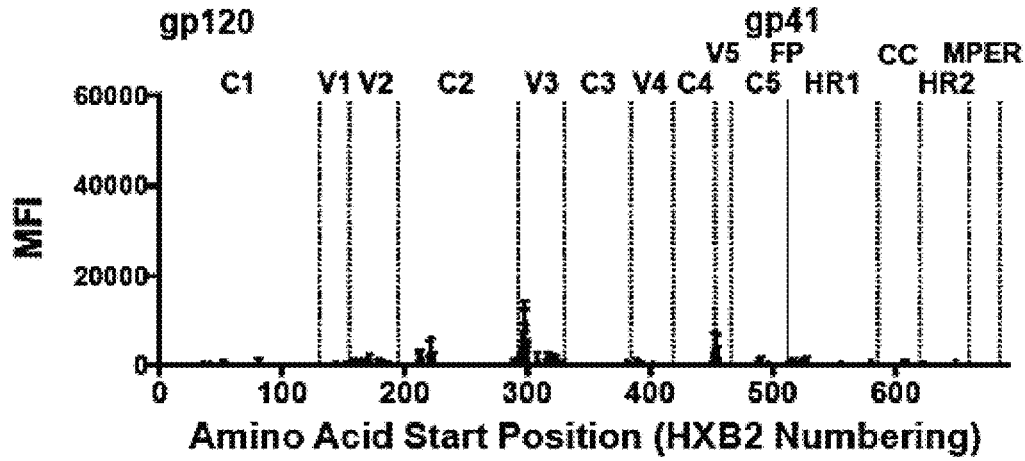
FIG. 3H is a graph showing the magnitude and position of binding antibody responses from guinea pig sera to linear 15-mer peptides on peptide microarrays. Each dot represents an average MFI per single peptide that is positive for antibody binding within each vaccination group with standard deviation shown. Titles indicate vaccination regimen (V2 Prime/Boost). MFI: mean fluorescence intensity. Envelope regions are delineated by vertical lines.

To assess the immunogenicity of these SET gp140s (e.g., V2-SET immunogens), we immunized guinea pigs three times at monthly intervals, and animals were bled 4 weeks after each vaccination (FIG. 3A). Five groups of guinea pigs were vaccinated with single immunogens, including 459C WT, V2 Opt, V2 Alt, V3 Opt, and V3 Alt alone (n=5-15 animals/group). Additionally, guinea pigs were vaccinated with mixtures of gp140 Envs including V2 Opt+V2 Alt, WT+V2 Opt+V2 Alt (V2 Mixture), V3 Opt+V3 Alt, WT+V3 Opt+V3 Alt (V3 Mixture), as well as sequential prime/boost vaccination, with V2 Opt, WT, and V2 Alt (V2 Prime/Boost), as well as V3 Opt, WT, and V3 Alt (V3 Prime/Boost) (n=5 animals/group).

15 guinea pigs were vaccinated with 459C WT, as controls. To test the immunogenicity of the V2-SET immunogens separately, two groups of guinea pigs were vaccinated with single SET immunogens, V2 Opt and V2 Alt (n=5 animals/group). Additionally, three groups of guinea pigs were vaccinated with cocktails of WT, Opt, and Alt immunogens including a V2-SET bivalent mixture (V2 Opt+V2 Alt), V2-SET trivalent mixture (459C WT+V2 Opt+V2 Alt; "V2 Mixture") and sequential prime/boost, with V2 Opt as a prime followed by a mixture of WT and V2 Alt ("V2 Prime/Boost") (n=5 animals/group). All animals were vaccinated at weeks 0, 4, and 8 intramuscularly in the quadriceps and given a total of 100 µg of immunogen (divided equally among immunogens in the multivalent vaccination groups) formulated in CpG/Emulsigen.

Example 5: Binding Antibodies Responses by ELISA

Binding antibody responses were assessed utilizing an ELISA and a panel of coating proteins including all of the epitope modified immunogens (e.g., V2-SET Envs) and a multi-clade panel of gp140 Envs (FIGS. 7A-7K). All vaccination regimens elicited similarly high magnitude and breadth of binding antibody responses with similar kinetics. Additionally, all sera were tested against a multi-clade panel of V1V2 gp70 scaffolds (Pinter et al., Vaccine 16:1803-1811, 1998 and Kayman et al., J. Virol. 68:400-410, 1994)) to assess the magnitude of V1/V2 binding antibodies elicited by each vaccine (FIGS. 8A-8K). At week 12, all vaccines showed a similar magnitude of binding antibodies to all four V1/V2 scaffolds, suggesting that animals are successfully generating cross reactive binding antibodies to this loop. While all vaccines successfully elicited binding antibodies against gp140 gp140 Envs and V1N2 scaffolds, no differences among vaccines was detected by binding ELISA.

Example 6: Mapping Binding Antibody Responses by Linear Peptide Microarray

Figure 9A:
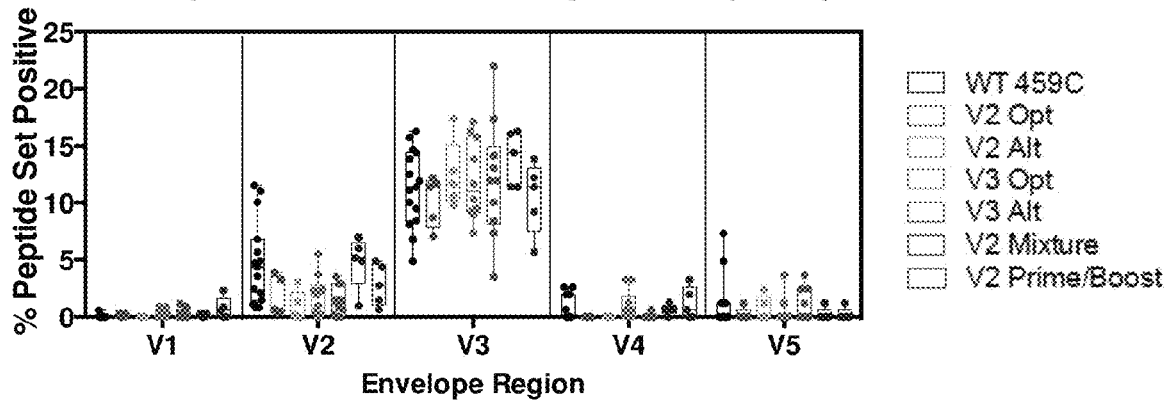
FIG. 9A is a graph showing the percent positive peptide responses of antibody responses from guinea pig sera to linear peptides by envelope region. Percent positive peptides is defined as [(positive peptides within a region/total number of peptides within a region)*100]. Box and whisker plots used to represent the data, with each animal shown as an individual dot per region. Graph colors represent vaccination strategies as listed in key.
Figure 9B:
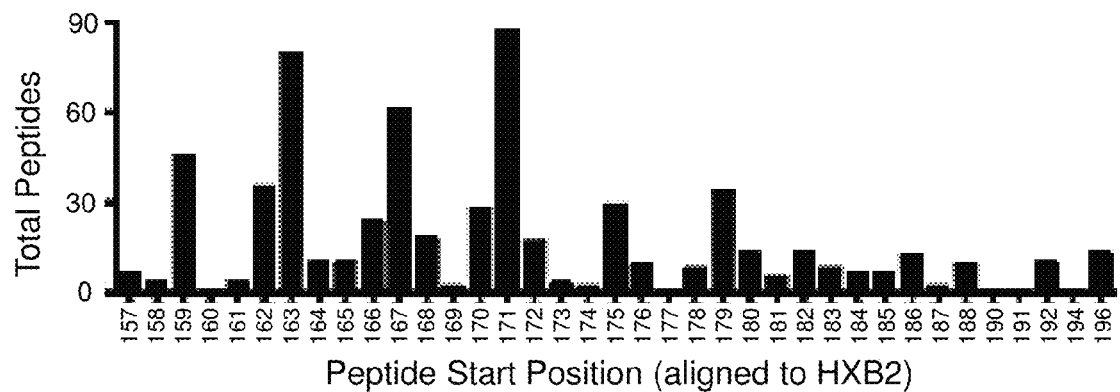
FIG. 9B is a graph showing the total positive peptides of antibody responses from guinea pig sera to linear peptides within V2. Bar graph depicts the total number of peptides on the array for each start position.
Figure 9C:
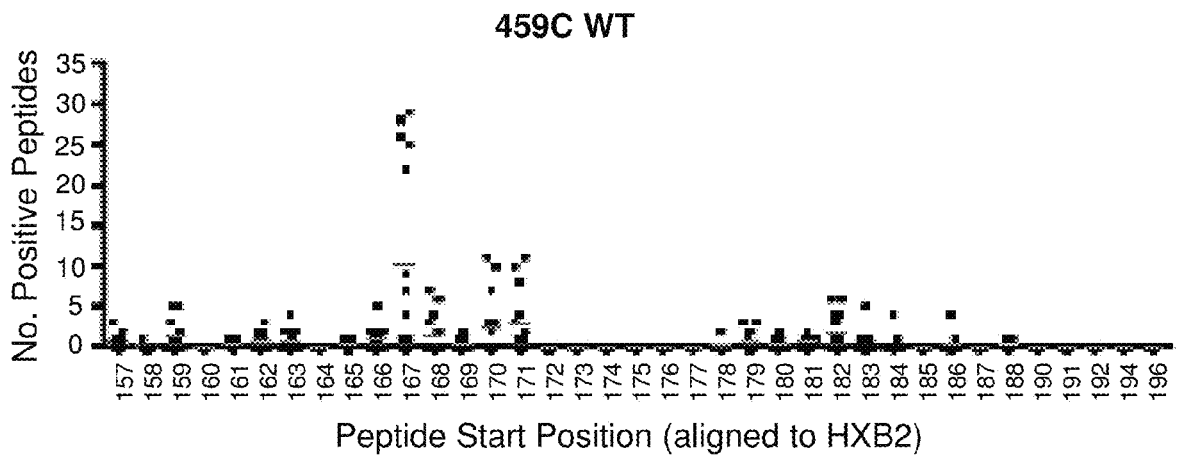
FIG. 9C is a graph showing the total number of positive peptides bound by antibodies within V2, with each dot representing one animal and the red horizontal line at the mean. Vaccination regimen performed with 459C WT gp140.
Figure 9H:
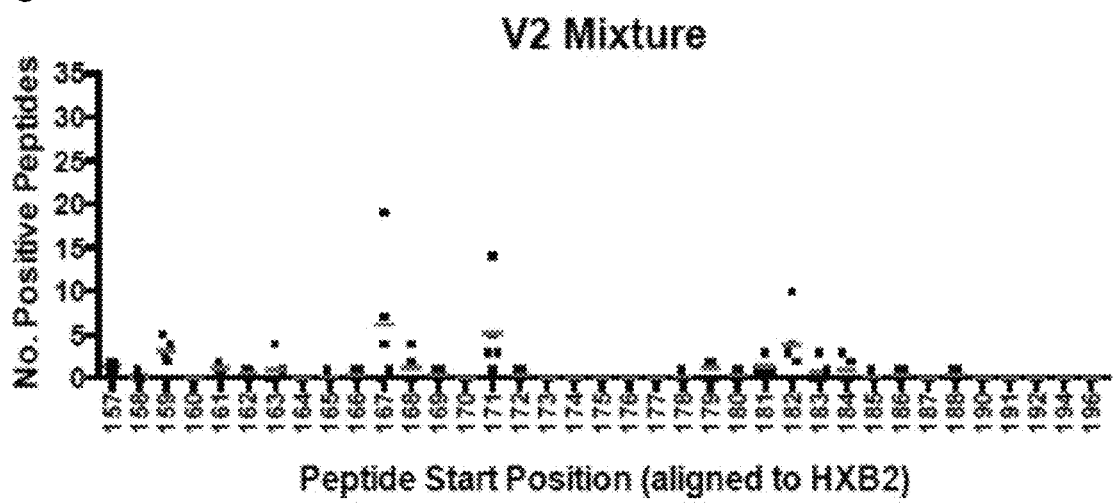
FIG. 9H is a graph showing the total number of positive peptides bound by antibodies within V2, with each dot representing one animal and the red horizontal line at the mean. Vaccination regimen performed with 459C V2 Mixture gp140.
Figure 9I:
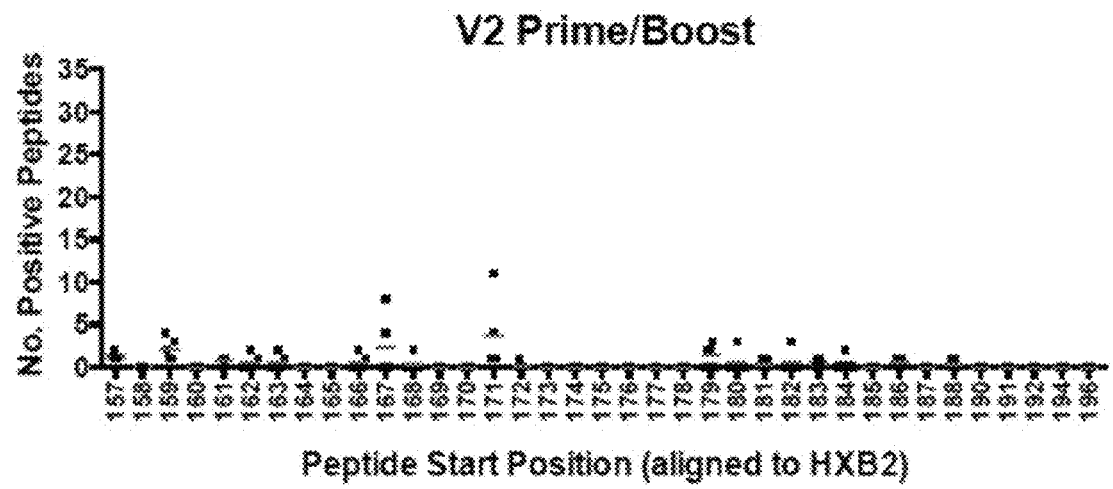
FIG. 9I is a graph showing the total number of positive peptides bound by antibodies within V2, with each dot representing one animal and the red horizontal line at the mean. Vaccination regimen performed with 459C V2 Prime/Boost gp140.
Figure 9J:
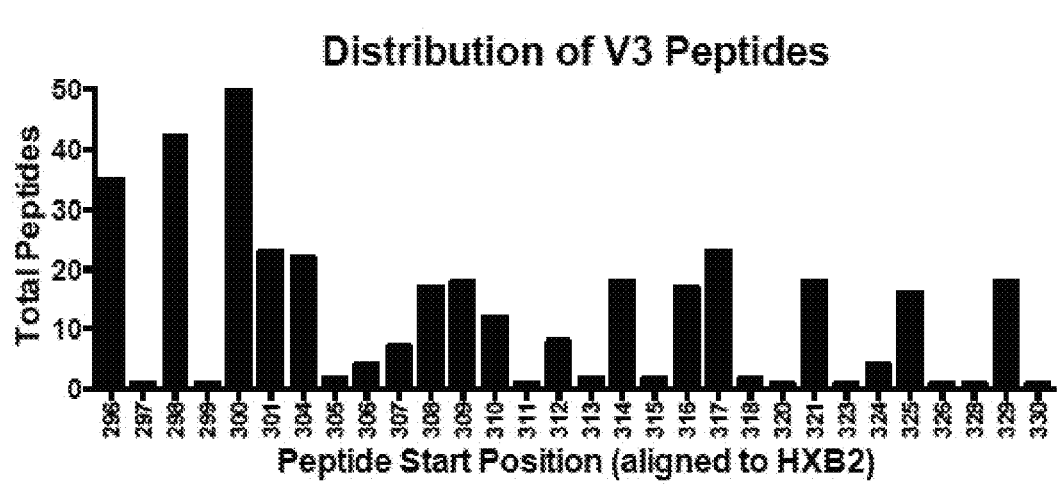
FIG. 9J is a graph showing the total positive peptides of antibody responses from guinea pig sera to linear peptides within V3. Bar graph depicts the total number of peptides on the array for each start position.
Figure 9O:
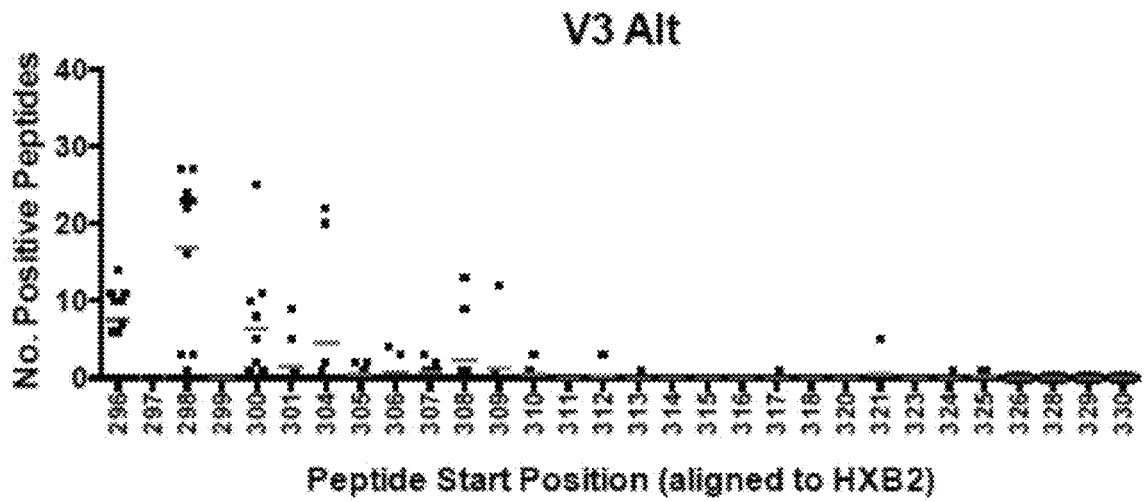
FIG. 9O is a graph showing the total number of positive peptides bound by antibodies within V3, with each dot representing one animal and the red horizontal line at the mean. Vaccination regimen performed with 459C V3 Alt gp140.
Figure 9P:
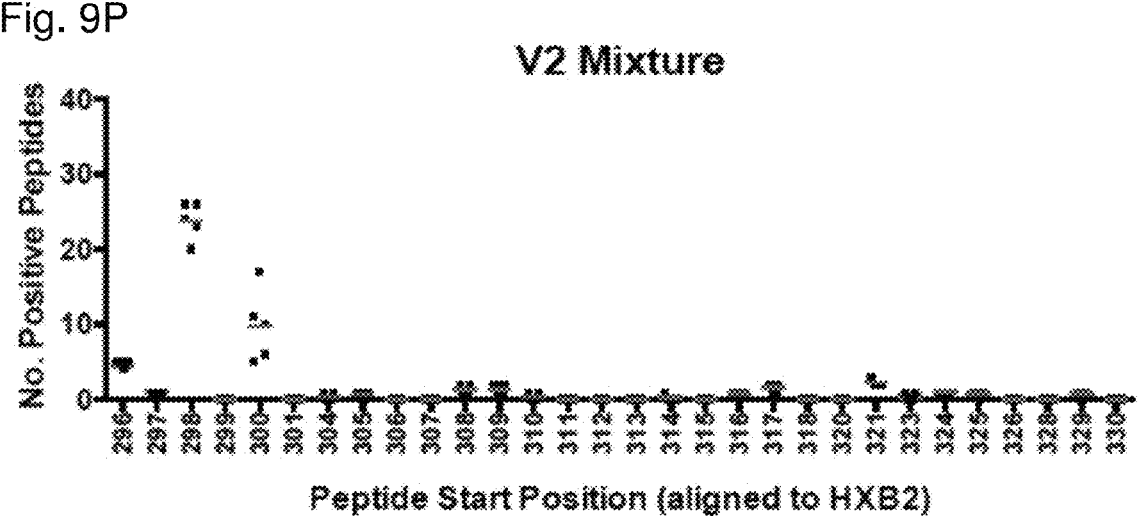
FIG. 9P is a graph showing the total number of positive peptides bound by antibodies within V3, with each dot representing one animal and the red horizontal line at the mean. Vaccination regimen performed with 459C V2 Mixture gp140.
Figure 9Q:
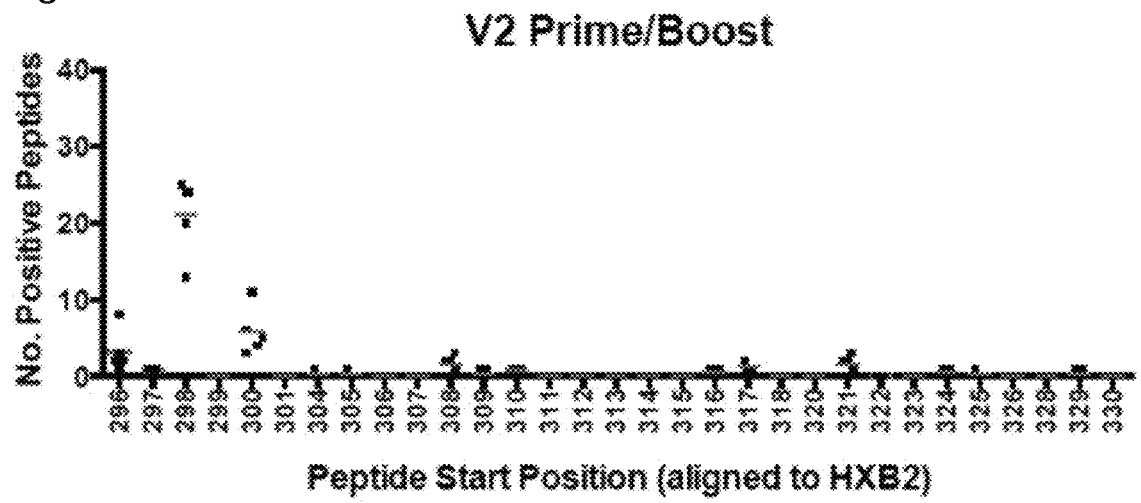
FIG. 9Q is a graph showing the total number of positive peptides bound by antibodies within V3, with each dot representing one animal and the red horizontal line at the mean. Vaccination regimen performed with 459C V2 Prime/Boost gp140.
Figure 10:
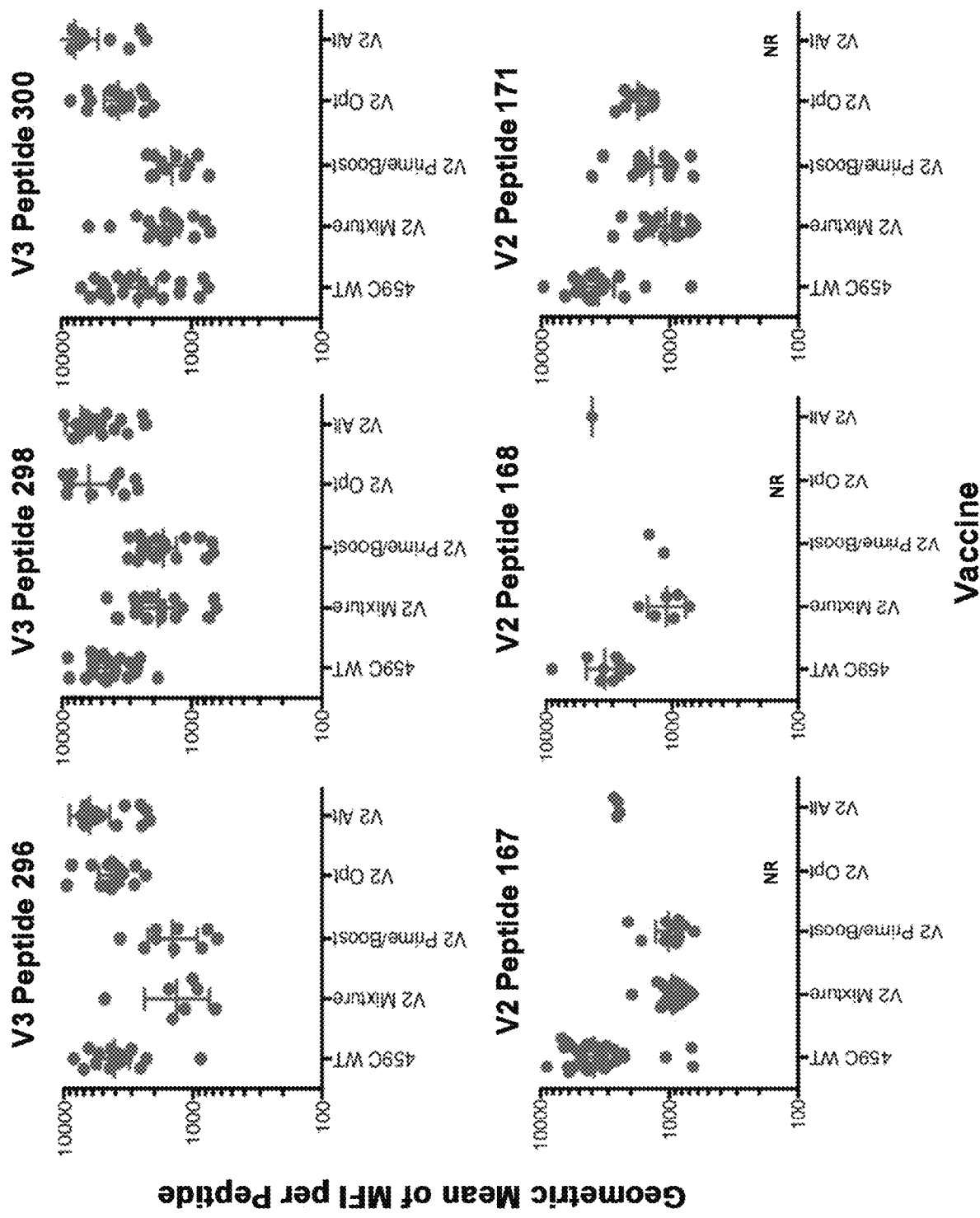
FIG. 10 is a series of graphs comparing the Dominant Linear Peptide Binding Antibody Responses in Variable Loops 2 and 3. Dominant linear peptide binding responses raised by V2-SET vaccines. Each dot denotes the geometric mean of all positive peptides at the listed Env amino acid start position (standard HXB2 numbering) per guinea pig that were positive for antibody binding, with a single dot per vaccinated guinea pig. Graph titles denote the variable loop and start peptide position. X-axis denotes the V2-SET vaccine given. Red bars show standard deviation. NR: no response.
Figure 12A:
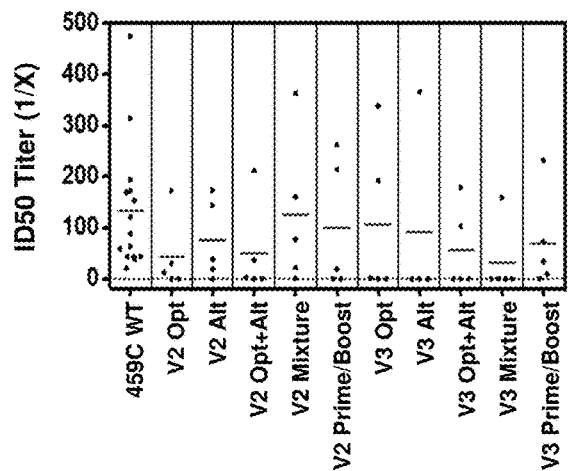
FIG. 12H is a graph showing the results of a TZM.bl neutralization assay results of guinea pig sera obtained after three vaccinations (week 12), tested against a clade C tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.
Figure 12B:
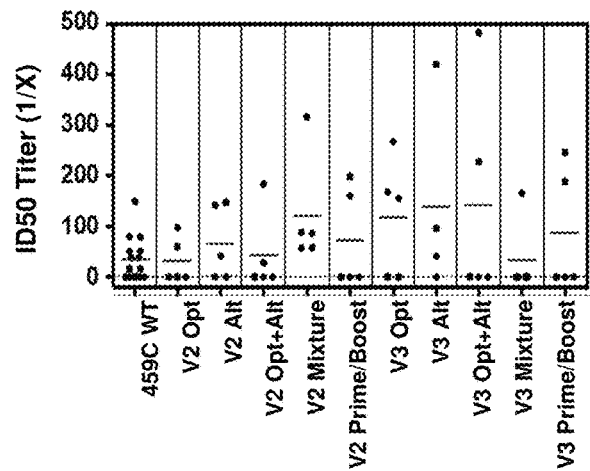
Figure 12C:
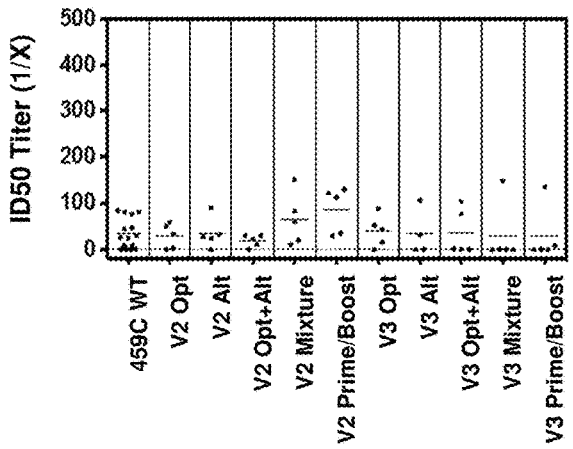
Figure 12D:
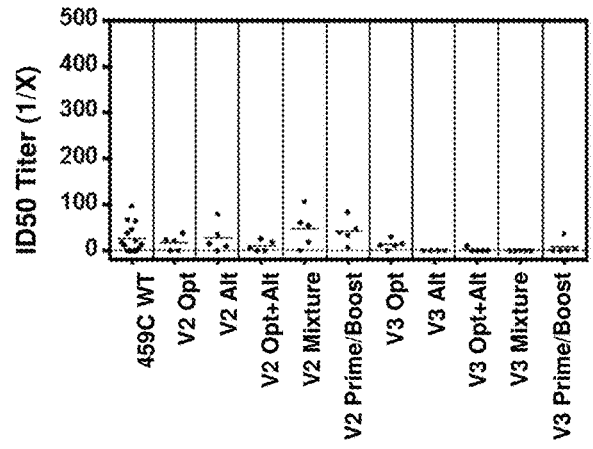
Figure 12E:
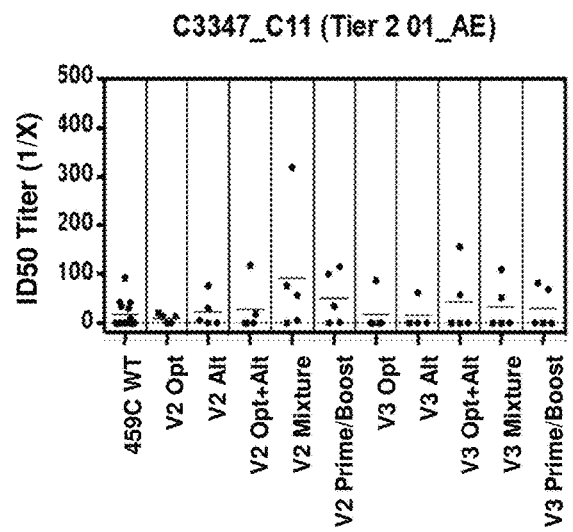
Figure 12F:
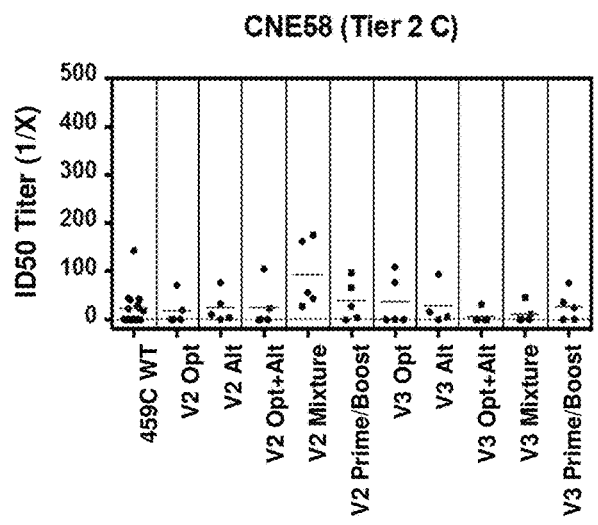
Figure 12G:
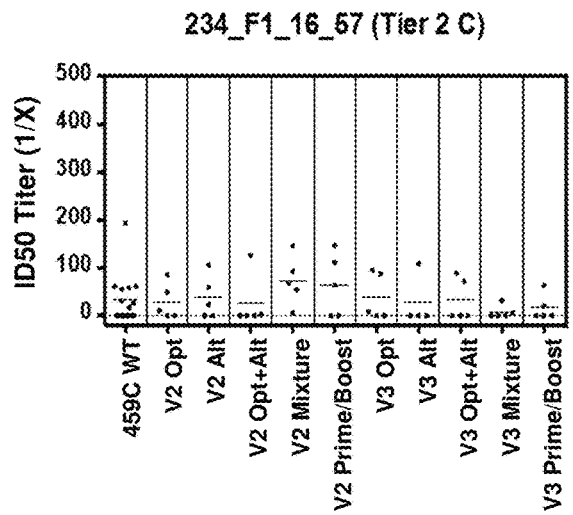
Figure 12H:
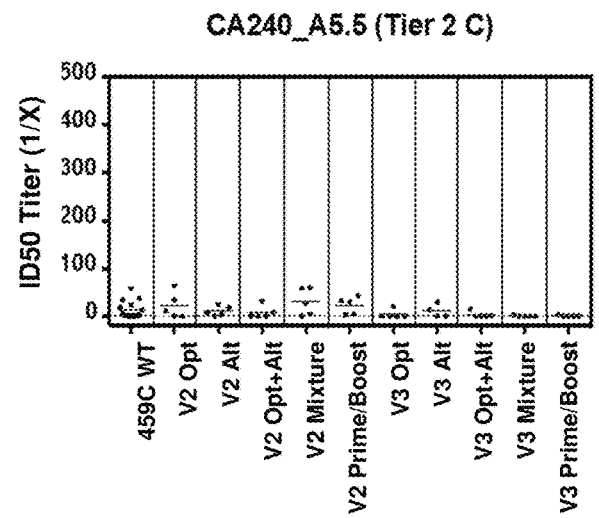
Figure 13A:
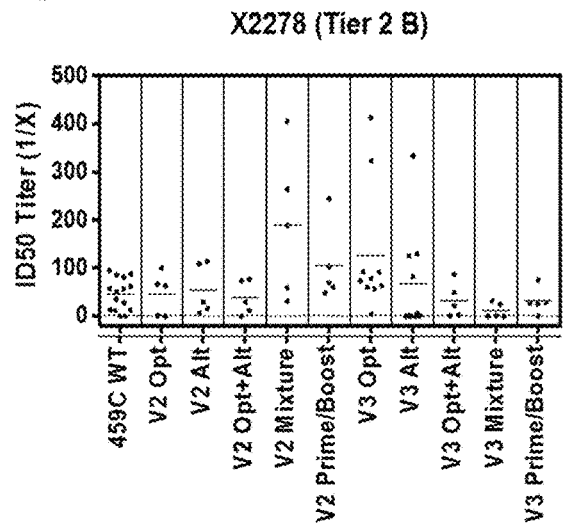
FIG. 13A is a graph showing the results of a TZM.bl neutralization assay results of guinea pig sera obtained after three vaccinations (week 12), tested against a clade B tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.
Figure 13B:
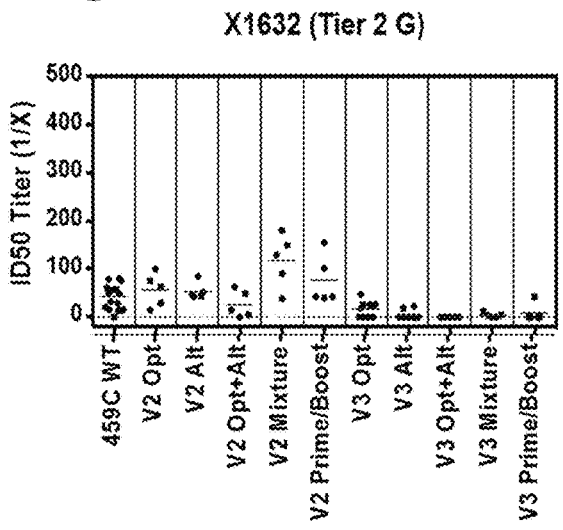
FIG. 13B is a graph showing the results of a TZM.bl neutralization assay results of guinea pig sera obtained after three vaccinations (week 12), tested against a clade G tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.
Figure 13C:
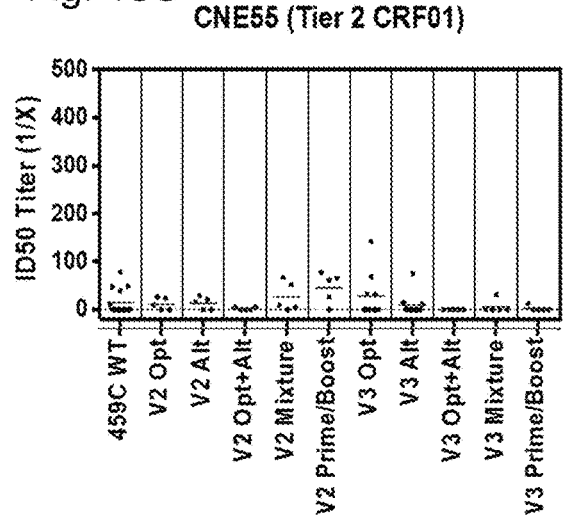
FIG. 13C is a graph showing the results of a TZM.bl neutralization assay results of guinea pig sera obtained after three vaccinations (week 12), tested against a clade CRF01 tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.
Figure 13D:
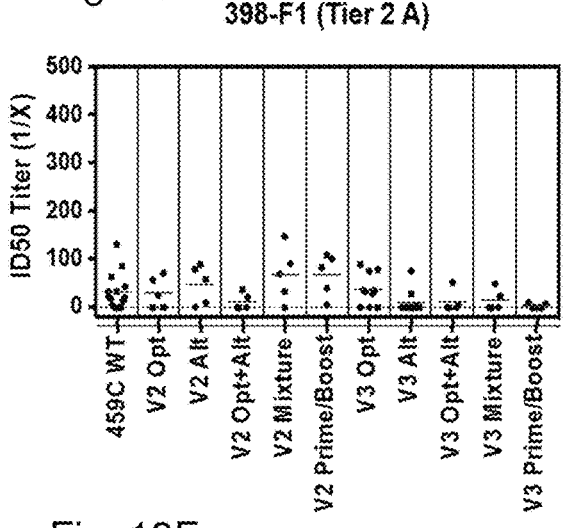
FIG. 13D is a graph showing the results of a TZM.bl neutralization assay results of guinea pig sera obtained after three vaccinations (week 12), tested against a clade A tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.
Figure 13E:
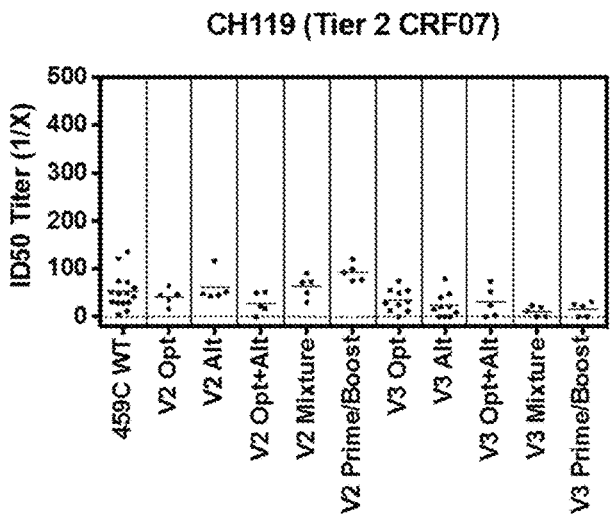
FIG. 13E is a graph showing the results of a TZM.bl neutralization assay results of guinea pig sera obtained after three vaccinations (week 12), tested against a clade CRF07 tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.
Figure 13F:
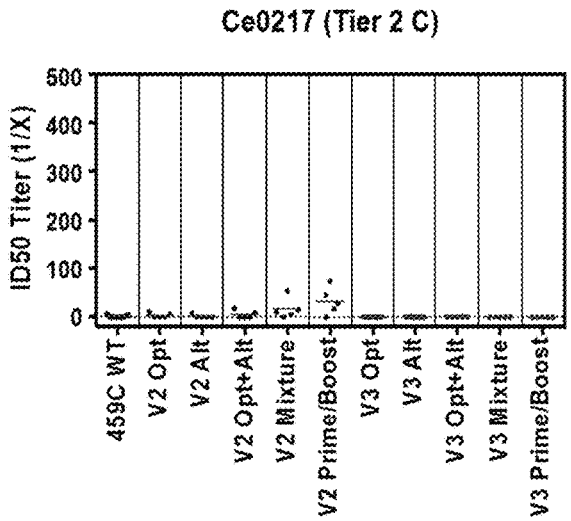
FIG. 13F is a graph showing the results of a TZM.bl neutralization assay results of guinea pig sera obtained after three vaccinations (week 12), tested against a clade C tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.
Figure 13G:
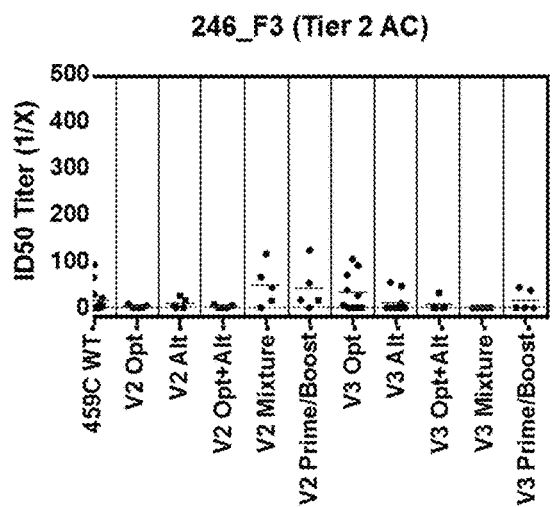
FIG. 13G is a graph showing the results of a TZM.bl neutralization assay results of guinea pig sera obtained after three vaccinations (week 12), tested against a clade AC tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.
Figure 13H:
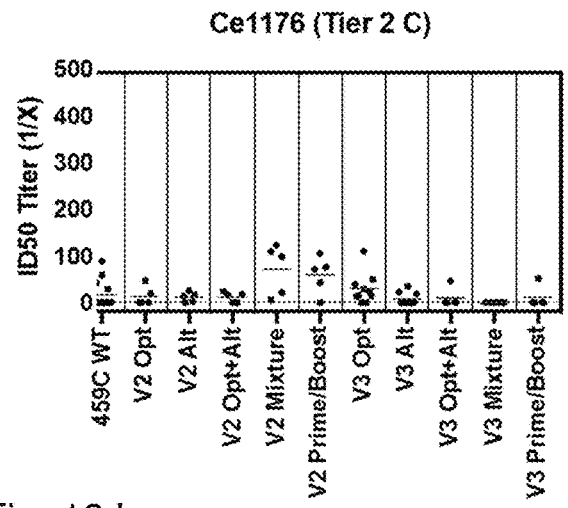
FIG. 13H is a graph showing the results of a TZM.bl neutralization assay results of guinea pig sera obtained after three vaccinations (week 12), tested against a clade C tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.
Figure 13I:
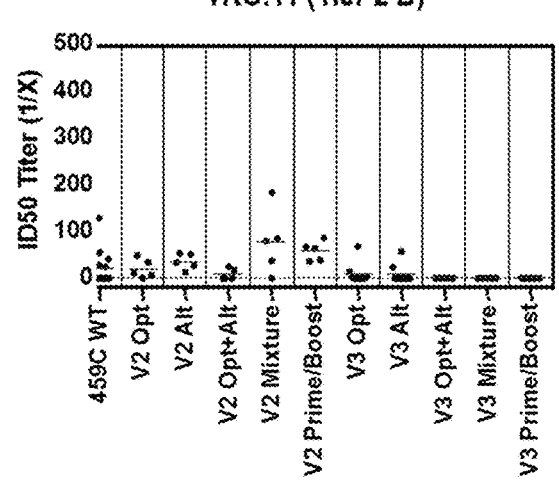
FIG. 13I is a graph showing the results of a TZM.bl neutralization assay results of guinea pig sera obtained after three vaccinations (week 12), tested against a clade B tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.
Figure 13J:
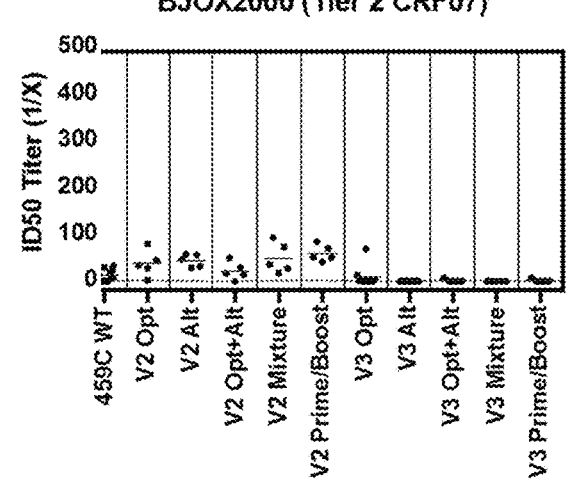
FIG. 13J is a graph showing the results of a TZM.bl neutralization assay results of guinea pig sera obtained after three vaccinations (week 12), tested against a clade CRF07 tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.
Figure 13K:
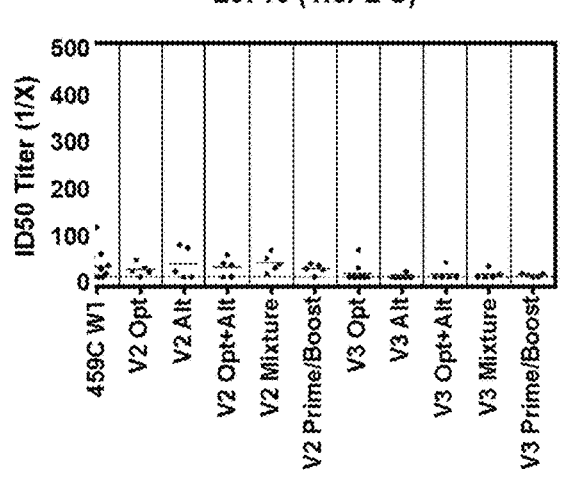
FIG. 13K is a graph showing the results of a TZM.bl neutralization assay results of guinea pig sera obtained after three vaccinations (week 12), tested against a clade C tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.
Figure 13L:
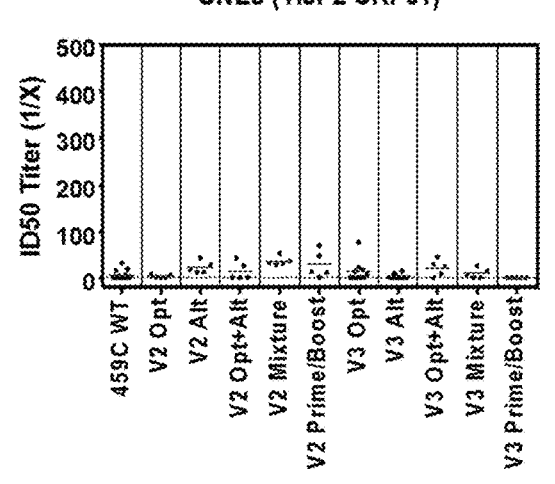
FIG. 13L is a graph showing the results of a TZM.bl neutralization assay results of guinea pig sera obtained after three vaccinations (week 12), tested against a clade CRF01 tier 2 neutralization-resistant pseudovirus. Neutralization data for every data point are animal-matched, MuLV negative control background subtracted. Horizontal red lines indicate mean titers. The title refers to the tested pseudovirus, its tier, and the clade or recombinant form.
Figure 14A:
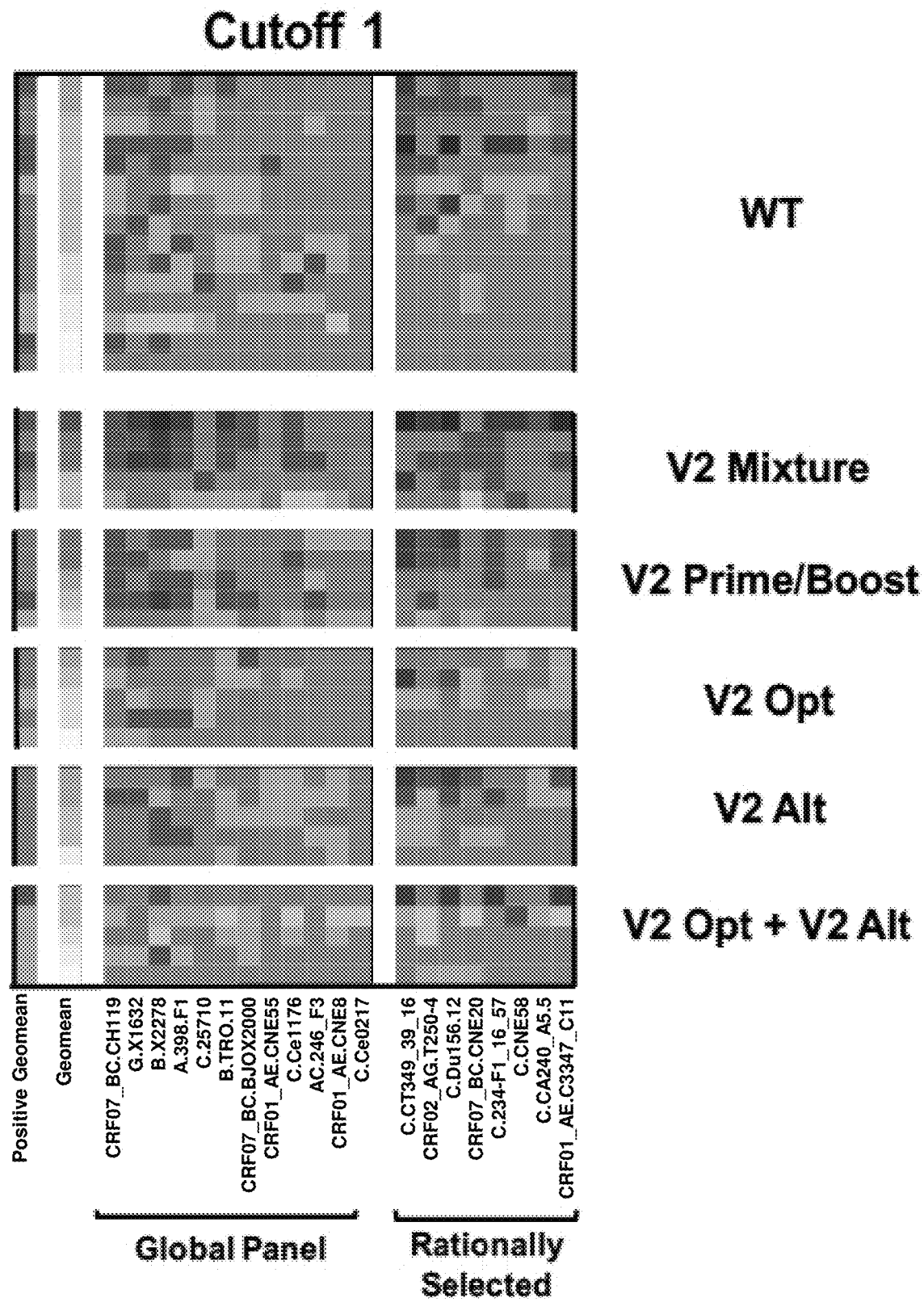
FIG. 14A is a heat map illustration of the clustering of NAb titers against tier 2 pseudoviruses elicited by guinea pigs vaccinated with variable loop 2 modified immunogens using cutoff 1 (cutoff as described in materials and methods). Test pseudoviruses are listed below the maps including a rationally selected tier 2 panel. Each row corresponds to a single guinea pig, and rows are clustered by vaccination regimen, as listed to the right of the heat map. The highest ID50 responses are shown with the highest intensity color (dark red) and lower responses shown with the lowest intensity color (very light yellow). Negative responses shown in blue. The left side of the map includes average responses across all pseudoviruses per animal for all data (geometric means) as well as across only positive data (positive geometric means). [Cutoff 1: Response=Post, if Post >MuLV+10; 10 otherwise], where 'Post' is post-vaccination sera (4 weeks-post last vaccination), 'MuLV' is the responses seen for animal-matched MuLV negative control, and lowest background below cutoffs set to 10. Each map includes average responses across all pseudoviruses per animal for all data (Geomeans) as well as across only positive data (Positive Geomeans).
Figure 14B:
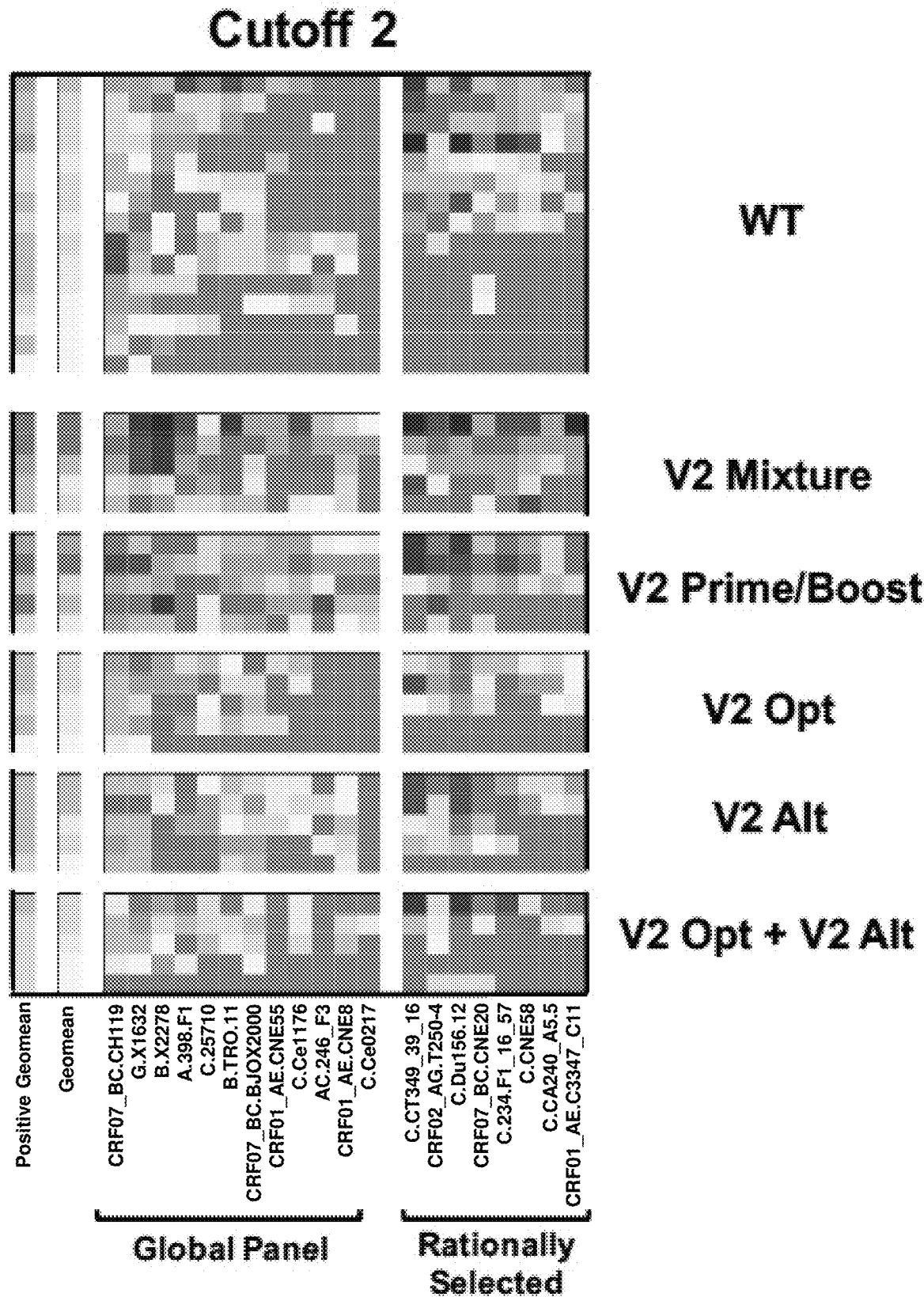
FIG. 14B is a heat map illustration of the clustering of NAb titers against tier 2 pseudoviruses elicited by guinea pigs vaccinated with variable loop 2 modified immunogens using cutoff 2 (cutoff as described in materials and methods). Test pseudoviruses are listed below the maps including a rationally selected tier 2 panel. Each row corresponds to a single guinea pig, and rows are clustered by vaccination regimen, as listed to the right of the heat map. The highest ID50 responses are shown with the highest intensity color (dark red) and lower responses shown with the lowest intensity color (very light yellow). Negative responses shown in blue. The left side of the map includes average responses across all pseudoviruses per animal for all data (geometric means) as well as across only positive data (positive geometric means). [Cutoff 2: Response=Post–MuLV, if Post-MuLV >10, 10 otherwise], where 'Post' is post-vaccination sera (4 weeks-post last vaccination), 'MuLV' is the responses seen for animal-matched MuLV negative control, and lowest background below cutoffs set to 10. Each map includes average responses across all pseudoviruses per animal for all data (Geomeans) as well as across only positive data (Positive Geomeans).
Figure 14C:
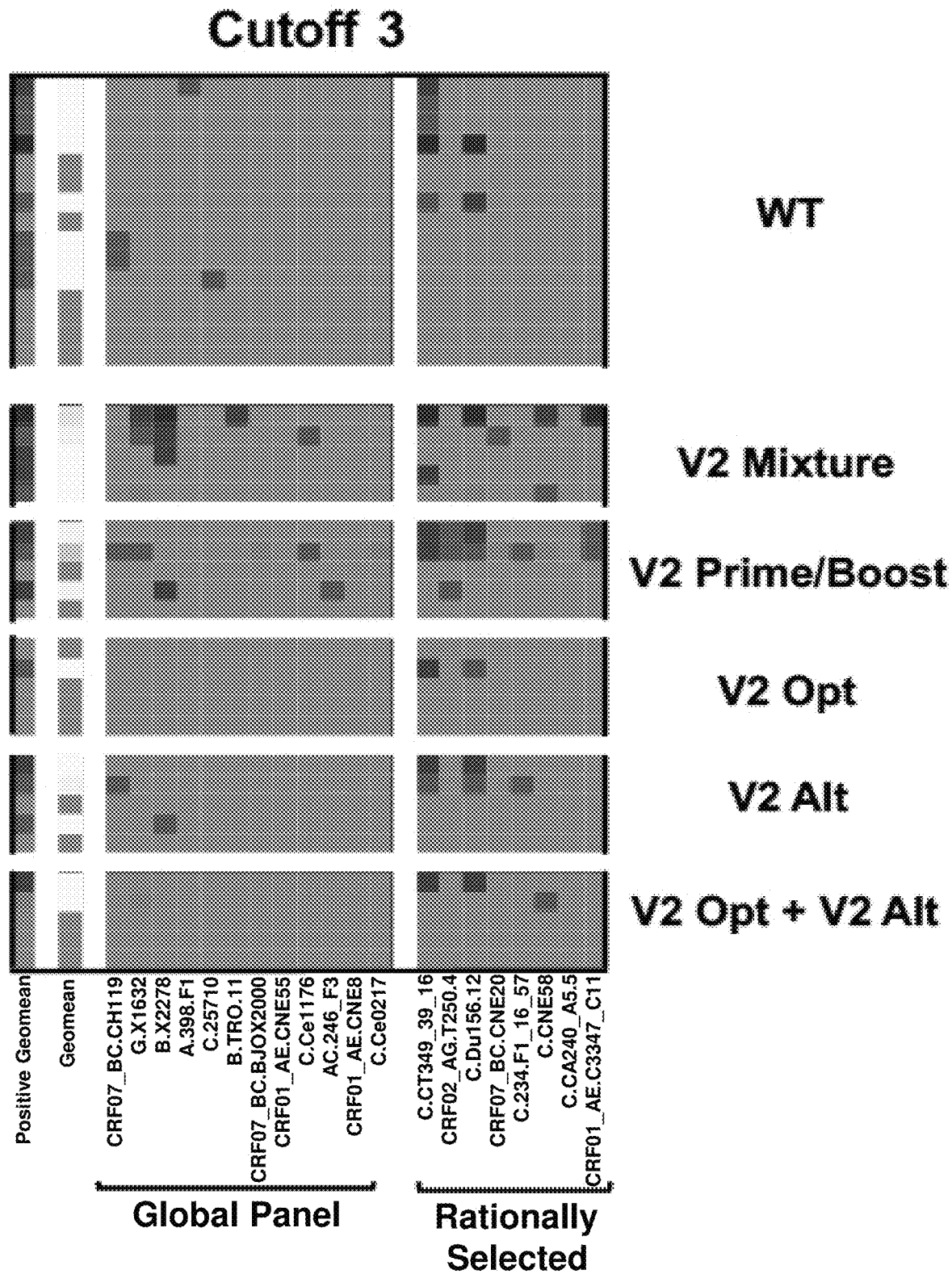
FIG. 14C is a heat map illustration of the clustering of NAb titers against tier 2 pseudoviruses elicited by guinea pigs vaccinated with variable loop 2 modified immunogens using cutoff 3 (cutoff as described in materials and methods). Test pseudoviruses are listed below the maps including a rationally selected tier 2 panel. Each row corresponds to a single guinea pig, and rows are clustered by vaccination regimen, as listed to the right of the heat map. The highest ID50 responses are shown with the highest intensity color (dark red) and lower responses shown with the lowest intensity color (very light yellow). Negative responses shown in blue. The left side of the map includes average responses across all pseudoviruses per animal for all data (geometric means) as well as across only positive data (positive geometric means). [Cutoff 3: Response=Post, if Post >3*MuLV, 10 otherwise], where 'Post' is post-vaccination sera (4 weeks-post last vaccination), 'MuLV' is the responses seen for animal-matched MuLV negative control, and lowest background below cutoffs set to 10. Each map includes average responses across all pseudoviruses per animal for all data (Geomeans) as well as across only positive data (Positive Geomeans).

We utilized microarray chips containing linear peptides corresponding to the entire HIV-1 Env sequence to map linear binding antibody responses. We assessed binding antibody responses from guinea pigs vaccinated with each single gp140, as well as V2 Mixture, V2 Prime/Boost, and V3 Alt elicited a lower magnitude of binding antibodies to linear V3 peptides at peptides starting with amino acids 296, 298, and 300 than 459C WT alone (Mann-Whitney U, $p=0.007$, $p=0.001$ and $p=0.007$, respectively) (FIGS. 3B-3H, Table 3). Interestingly, while differences in magnitude of linear binding responses were seen, all vaccines elicited binding responses to similar number of total linear peptides with in all variable loops and against similar regions of V2 and V3 (FIGS. 9A-9Q). These data suggest that guinea pigs vaccinated with V2 Mixture and V2 Prime/Boost elicit a lower magnitude of linear binding antibody responses to both V2 and V3 than guinea pigs vaccinated with the 459C WT immunogen.

TABLE 3

Comparison of the Peak Magnitude of Antibodies Binding to Linear Peptides in Variable Loop 3

| Test | Comparison | P value |
|---|---|---|
| Mann-Whitney U | WT ≅ V2 Opt | 0.30 |
| | WT ≅ V2 Alt | 0.74 |
| | WT > V3 Opt | 0.007* |
| | WT ≅ V3 Alt | 0.55 |
| | WT > V2 Mixture | 0.007* |
| | WT > V2 Prime/Boost | 0.001* |

*Significant compared by Mann-Whitney U pairwise comparisons ($p < 0.05$)

We next utilized microarray chips containing linear peptides corresponding to the entire HIV-1 Env sequence to map linear binding antibody responses. We assessed binding antibody responses from guinea pigs vaccinated with each single V2-SET immunogen, as well as the V2-SET trivalent vaccines (V2 Mixture, V2 Prime/Boost). When comparing peak magnitude binding responses across vaccines, V2 Mixture and V2 Prime/Boost elicited a lower magnitude of binding antibodies than did 459C WT against linear V2 and V3 peptides ($p<0.0001$ for V2 peptides 167 and 171 and $p<0.0001$ for V3 peptide 298, across V2-SET trivalent vaccines compared to 459C WT) (FIGS. 3B-3D, 3G, and 3H, FIG. 10, Table 4). These data demonstrate that V2 Mixture and V2 Prime/Boost elicited a lower magnitude of binding antibody responses against linear V2 and V3 epitopes than did 459C WT, suggesting that the V2-SET trivalent vaccines shifted the binding responses, at least in part, away from linear epitopes.

TABLE 4

Comparison of the Magnitude of Antibodies Binding to Linear Peptides in Variable Loop 2 and 3 Elicited by V2-SET Vaccines

| | | | Vaccine Compared to 459C WT Alone | | | |
|---|---|---|---|---|---|---|
| Test | Loop | Position | V2 Mixture | V2 Prime/Boost | V2 Opt | V2 Alt |
| Wilcoxon Rank-Sum | V3 | 296 | 0.0018 | <0.0001 | 0.41 | 0.039 |
| | | 298 | <0.0001 | <0.0001 | 0.11 | 0.010 |
| | | 300 | 0.017 | 0.0078 | 0.10 | <0.0001 |
| Wilcoxon Rank-Sum | V2 | 167 | <0.0001 | <0.0001 | nd | 0.0087 |
| | | 168 | 0.0002 | 0.018 | nd | nd |
| | | 171 | <0.0001 | <0.0001 | nd | nd | nd: Not enough data points to generate data

Example 7: Assessing Heterologous, Tier 1 Neutralizing Antibodies

We first wanted to assess the magnitude and breadth of NAbs elicited by each vaccination regimen (e.g., using the V2-SET immunogens) against tier 1, laboratory-adapted neutralization sensitive, pseudoviruses in the TZM.bl neutralization assay (Seaman et al., *J. Virol.* 84:1439-1452, 2010, Sarzotti-Kelsoe et al., *J. Immunol. Methods* 409:147-160, 2014). All vaccination regimens elicited high magnitude tier 1 NAbs against a panel of tier 1A and 1B pseudoviruses from clade A, B, and C after MuLV control subtraction (FIGS. 11A-11H). Neutralization data were further grouped by vaccination regimen and compared for magnitude of responses compared to 459C WT vaccinated animals (FIGS. 11I-11J). A generalized linear model with a mixed-effect linear model found that the vaccine given and the elicitation of tier 1A or tier 1B responses were not related (p=0.8397) (Table 5). Additionally, animals vaccinated with 459C WT gp140 elicited a higher magnitude of tier 1 NAbs than the epitope modified vaccines, including a statistically superior magnitude of NAbs than V2 Opt (p=$1.15^{-02}$), V2 Alt (p=$7.44^{-03}$), V2 Opt+V2 Alt (p=$1.21^{-02}$), V2 Prime/Boost (p=$7.06^{-05}$), V3 Alt (p=$1.98^{-20}$), V3 Opt+V3 Alt (p=$4.53^{-03}$), V3 Mixture (p=$3.39^{-02}$), and V3 Prime/Boost (p=$3.14^{-02}$) (Table 5), with the largest statistical differences seen between WT and either V2 Prime/Boost or V3 Alt. These data suggest that guinea pigs vaccinated with 459C WT gp140 elicited a greater magnitude of tier 1 NAbs than the animals vaccinated with epitope modified immunogens.

TABLE 5

Comparison of Magnitude of Tier 1 Sera Neutralizing Titers by Generalized Linear Model Analysis (Cutoff 1)

| Vaccine | Comparison Across All Pseudoviruses to 459C WT | |
|---|---|---|
| | Estimate | P value |
| V2 Opt | 0.601 | 1.16e−02* |
| V2 Alt | 0.579 | 7.44e−03* |
| V2 Opt + V2 Alt | 0.660 | 1.21e−02* |
| V2 Mixture | 0.694 | 5.16e−02 |
| V2 Prime/Boost | 0.426 | 7.06e−05** |
| V3 Opt | 0.787 | 8.88e−02 |
| V3 Alt | 0.196 | 1.97e−20** |
| V3 Opt + V3 Alt | 0.557 | 4.53e−03* |
| V3 Mixture | 0.664 | 3.39e−02* |
| V3 Prime/Boost | 0.659 | 3.14e−02* |

*Significant by pairwise comparisons (p < 0.05)
**Significant after Bonferroni correction Example 8: Assessing Heterologous, Tier 2 Neutralizing Antibodies We next assessed the ability of the vaccination regimens (e.g., using the V2-SET immunogens) to neutralize 20 heterologous tier 2 pseudoviruses, including the standard global panel of 12 pseudoviruses (DeCamp et al., *J. Virol.* 88:2489-2507, 2014) as well as 8 additional rationally selected heterologous tier 2 viruses with partial homology to the vaccine immunogens, as described herein (FIGS. 12A-12H and 13A-13L).

We assessed the ability of the vaccine-elicited antibodies to neutralize tier 2, neutralization resistant pseudoviruses. We first tested sera against a panel of rationally selected tier 2 pseudoviruses (Example 1)(as described in materials and methods) as well as the standard global panel of pseudoviruses (DeCamp et al., *J. Virol.* 88:2489-2507, 2014). 459C WT was chosen as the backbone for the V2-SET modification (Bricault et al., *J. Virol.* 89(5):2507-19, 2015). In our previous work, we tested 459C WT vaccinated guinea pigs against a single tier 2 pseudovirus, Du422.1 and observed low neutralizing antibody titers in 459C WT vaccinated animals. Here we expanded these observations by showing that the 459C WT immunogen elicited low but detectable NAb responses above background to a median of 11 (range 1-15) tier 2 pseudoviruses from our panel of 20 tier 2 pseudoviruses (including the 12 virus global panel) (DeCamp et al., *J. Virol.* 88:2489-2507, 2014) (FIGS. 4A-4B, 5, 6A-6B, 7A-7B, 8A-8C, 15A-15H, 16A-16L, 17A-17C). Thus, the 459C WT immunogen induced low levels of tier 2 NAbs in guinea pigs. We also found that epitope modified (e.g., V2-SET) immunogens were capable of eliciting heterologous tier 2 NAb against both panels (FIGS. 12A-12H and FIGS. 13A-13L).

Figure 4B:
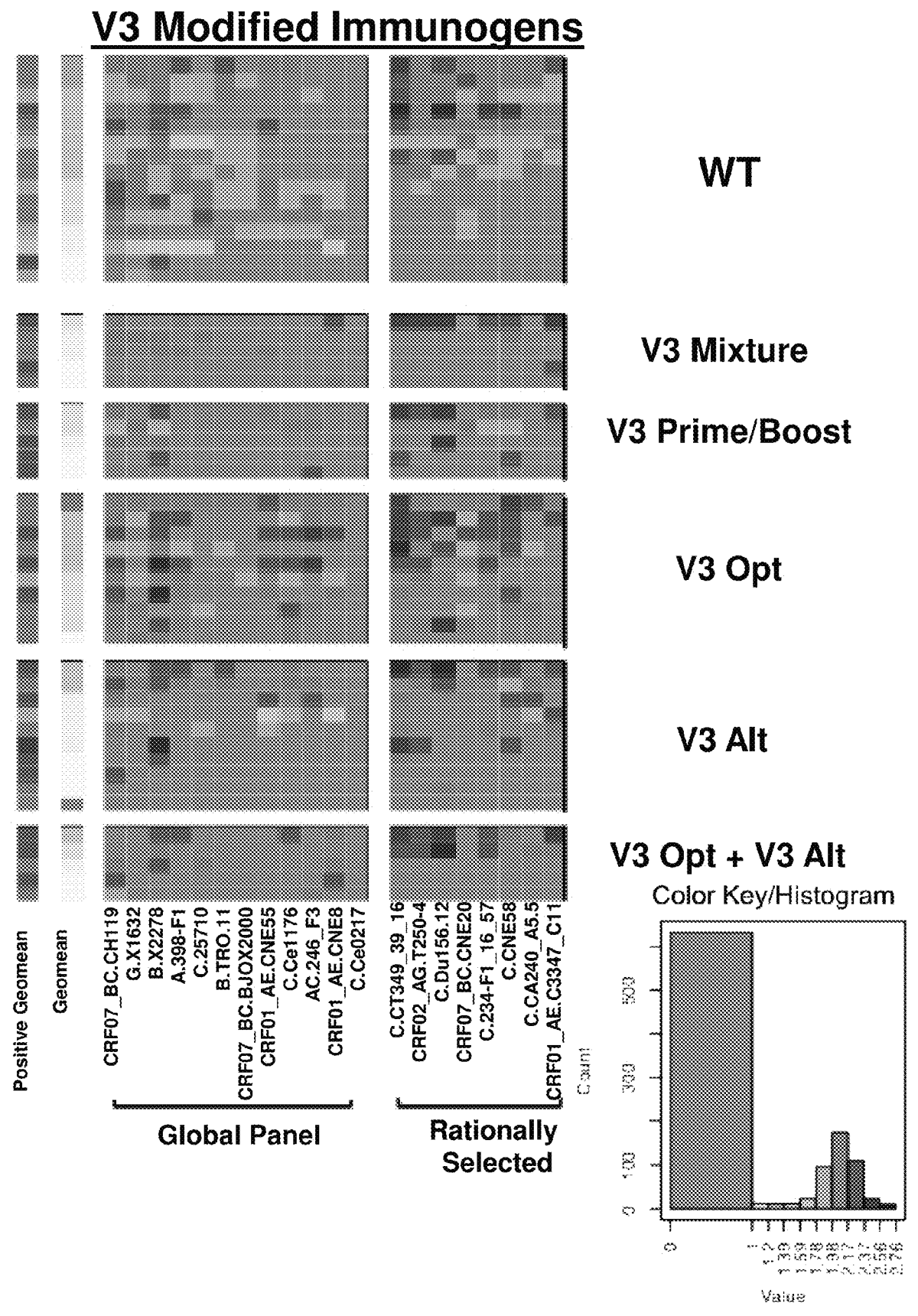

Furthermore, we assessed whether the epitope modified (e.g., V2-SET) immunogens augmented the magnitude of tier 2 NAbs compared with the 459C WT gp140 immunogen alone (FIGS. 4A-4B). We found that V2 Mixture and V2 Prime/Boost vaccinations elicited a magnitude of tier 2 NAbs which were statistically superior to 459C WT alone (Wilcoxon paired test, p=$9.5^{-07}$ and p=$1.9^{-06}$, respectively, cutoff 1, cutoff as described in materials and methods) (Table 6). The V2 Mixture and the V2 Prime/Boost elicited the greatest magnitude of NAbs, which were comparable to each other (Wilcoxon paired test, p=1.8e-01, cutoff 1). Additionally, the V2 Mixture vaccine elicited a superior magnitude of tier 2 NAbs to 11 of 20 pseudoviruses and V2 Prime/Boost to 8 of 20 pseudoviruses compared to 459C WT alone (FIGS. 5A-5B; Table 7). These data suggest that the V2 Mixture and V2 Prime/Boost vaccines were capable of eliciting a statistically superior magnitude of heterologous, tier 2 NAbs compared with 459C WT alone.

Geometric means of NAb titers across all guinea pigs vaccinated with the same regimen and tested against the same pseudovirus were calculated, producing a single data point per vaccine per test pseudovirus (see FIGS. 6A-6D and 8A-8C, Table 6). For 11 vaccination regimens and 20 pseudoviruses this translated to 11 sets of data, each consisting of 20 data points. Friedman paired test was used first to detect differences across multiple vaccine sets. Comparisons were made over 459C WT, V2 Mixture, V2 Prime/Boost, V2 Opt, V2 Alt, V2 Opt+V2 Alt vaccination regimens. After significance was established, the pairwise comparison with WT, as well as between V2 Mixture and V2 Prime/Boost was made where "≅" means comparable responses, "<" means significantly lower responses.

TABLE 6

Comparison of Magnitude of Tier 2 Sera Neutralizing Titers Across Vaccines (Cutoff 1)

| Test | Comparison | P value |
|---|---|---|
| Friedman Paired | Sera of all 459C WT and all V2 vaccinated animals | 5.6e−14 |
| | Sera of all 459C WT and all V3 vaccinated animals | 1.6e−06 |

| Test | Comparison of Geometric Means | P value |
|---|---|---|
| Wilcoxon Paired | WT ≅ V2 Opt | 7.2e−01 |
| | WT < V2 Alt | 2.0e−03* |
| | WT ≅ V2 Opt + V2 Alt | 9.9e−01 |
| | WT < V2 Mixture | 9.5e−07* |
| | WT < V2 Prime/Boost | 1.9e−06* |
| | V2 Mixture ≅ V2 Prime/Boost | 1.8e−01 |
| | WT ≅ V3 Opt | 9.5e−02 |
| | WT ≅ V3 Alt | 9.9e−01 |
| | WT ≅ V3 Opt + V3 Alt | 9.9e−01 |

TABLE 6-continued

Comparison of Magnitude of Tier 2 Sera Neutralizing
Titers Across Vaccines (Cutoff 1)

| | | |
|---|---|---|
| | WT ≅ V3 Mixture | 9.9e−01 |
| | WT ≅ V3 Prime/Boost | 9.9e−01 |

*Significant by pairwise comparisons (p < 0.05)

TABLE 7

Comparison of Tier 2 Neutralizing Titers
for V2 Multivalent Vaccination Regimens

| Test | Comparison | Cutoff | P value |
|---|---|---|---|
| Non-parametric Resampling | WT < V2 Mixture | 1 | 6.0e−03* |
| | | 2 | 5.0e−03* |
| | WT < V2 Prime/Boost | 1 | 8.0e−03* |
| | | 2 | 5.0e−03* |

| Test | Number of Pseudoviruses Statistically Superior to WT | | No. of Pseudoviruses (of 20 total) |
|---|---|---|---|
| Wilcoxon | WT < V2 Mixture | 1 | 11 |
| | WT < V2 Prime/Boost | 1 | 8 |

*Significant by pairwise comparisons (p < 0.05)

TABLE 8

Comparison of Breadth of Tier 2 Sera
Neutralizing Titers Across Vaccines

| Test | Comparison | Cutoff | P value | |
|---|---|---|---|---|
| Linear Model Binomial Distribution | Response differences sera among all vaccines tested | 1 | 1.0e−06 | |
| | | 2 | 1.0e−06 | |
| | | 3 | 4.0e−03 | |

| Test | Comparison | Cutoff | P value | Odds Ratio |
|---|---|---|---|---|
| Fisher's Exact | WT ≅ V2 Opt | 1 | 5.0e−01 | 1.00 |
| | WT < V2 Alt | 1 | 5.0e−03* | 1.88 |
| | WT ≅ V2 Opt + V2 Alt | 1 | 9.0e−01 | 0.76 |
| | WT < V2 Mixture | 1 | 3.5e−08[b] | 4.1 |
| | | 2 | 4.13e−08[b] | 4.1 |
| | | 3 | 8.98e−08[b] | 4.9 |
| | WT < V2 Prime/Boost | 1 | 1.06e−07[b] | 3.8 |
| | | 2 | 1.06e−07[b] | 3.8 |
| | | 3 | 4.02e−06[b] | 6.1 |

| Test | Comparison | Cutoff | P value |
|---|---|---|---|
| Wilcoxon Rank-Sum | WT < V2 Mixture | 1 & 2 | 0.003[b] |
| | | 3 | 0.007[b] |
| | WT < V2 Prime/Boost | 1 & 2 | 0.01[b] |
| | | 3 | 0.10 |

[a]Cutoff 1 and 2 use the same threshold for positivity, so the positive/negative counts are the same. Cutoff 3 is distinct and much more conservative. See methods.
[b]Significant by pairwise comparisons (p < 0.05)

We also assessed differences in the breadth of tier 2 NAb responses elicited by each of the epitope modified (V2-SET) vaccines compared to 459C WT. We found that V2 Mixture and V2 Prime/Boost elicited a breadth of tier 2 NAbs which was superior to that of 459C WT alone (Fisher's exact test, $p=3.5^{-08}$ and $p=1.1^{-07}$, respectively, cutoff 1) (Table 8). Additionally, we determined the statistical breadth differences among 459C WT and V2 modified (e.g., V2-SET) vaccines utilizing more stringent cutoffs and found that statistical significance held true across all three cutoff stringencies (GLM, $1.0^{-06}$, cutoff 2; $4.0^{-03}$, cutoff 3) (Table 8). We further confirmed that the vaccination regimens, V2 Mixture and V2 Prime/Boost, elicited a statistically superior breadth of NAbs compared to 459C WT across cutoffs of increasing-stringency (Wilcoxon paired test, $p=4.13^{-08}$, $p=1.06^{-07}$, respectively, cutoff 2; $p=8.98^{-08}$, $p=4.02^{-06}$, respectively, cutoff 3) (FIGS. 14A-14C and 19; Table 8). These data suggest that V2 Mixture and V2 Prime/Boost vaccines elicited the greatest breadth of tier 2 NAbs compared to 459C WT alone.

Several statistical measures (as described herein) were utilized to determine whether the V2-SET trivalent vaccines augmented the magnitude and breadth of heterologous tier 2 NAbs as compared with the 459C WT immunogen (FIGS. 5A-5D, 12A-12H, 13A-13L, and 14A-14C). Using three different cutoffs for positivity, the V2 Mixture and V2 Prime/Boost vaccinations elicited a modestly improved magnitude of tier 2 NAbs as compared to 459C WT alone (p=9.5e-07 and p=1.9e-06 respectively, one-sided paired Wilcoxon test) (FIGS. 5A-5D, Table 6). Furthermore, for one-third of the tested pseudoviruses the increase in the magnitude of response was more than 3-fold greater with the V2 Mixture compared with 459C WT, with many ID50 titers in the 100-500 range. Comparing raw NAb responses to each pseudovirus separately, the V2 Mixture vaccine elicited a greater magnitude of tier 2 NAbs to 11 of 20 pseudoviruses and V2 Prime/Boost to 8 of 20 pseudoviruses compared to 459C WT (Wilcoxon one-sided test) (FIGS. 5A-5D).

Figure 5A:
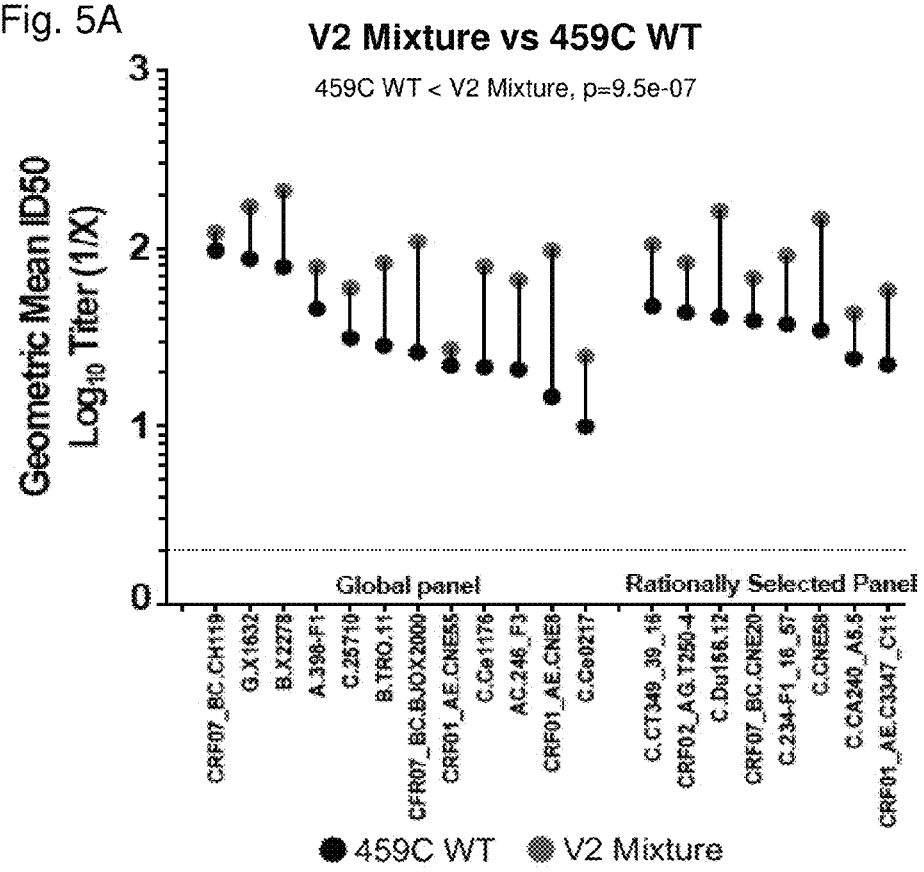
FIG. 5A is a graph showing a comparison of tier 2 neutralizing antibody responses by V2 modified, multivalent Env vaccinations as compared to 459C WT only. Geometric means of NAb titers with each guinea pig vaccination regimen represented as a single dot against each tier 2 pseudovirus including the global panel and rationally selected pseudoviruses with comparing V2 Mixture against 459C WT. Dotted line at a titer of 20 representing the limit of detection of the TZM.bl neutralization assay. Colors in key represent each vaccination regimen. Results are shown for cutoff 1. The resulting p-values are shown on the graphs, and "<" is statistically lower, "~" is statistically indistinguishable, and ">" is statistically higher. Geometric means were analyzed by Wilcoxon paired rank test, one-sided for V2-SET vaccines.
Figure 5B:
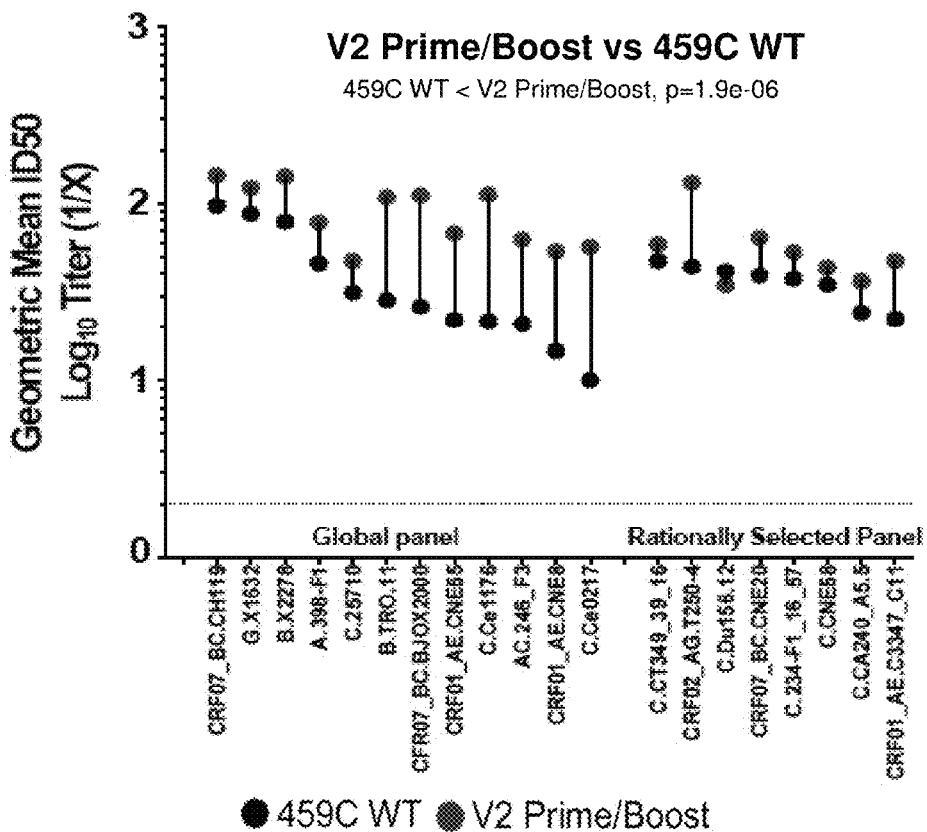
FIG. 5B is a graph showing a comparison of tier 2 neutralizing antibody responses by V2 modified, multivalent Env vaccinations as compared to 459C WT only. Geometric means of NAb titers with each guinea pig vaccination regimen represented as a single dot against each tier 2 pseudovirus including the global panel and rationally selected pseudoviruses with comparing V2 Prime/Boost against 459C WT. Dotted line at a titer of 20 representing the limit of detection of the TZM.bl neutralization assay. Colors in key represent each vaccination regimen. Results are shown for cutoff 1. The resulting p-values are shown on the graphs, and "<" is statistically lower, "~" is statistically indistinguishable, and ">" is statistically higher. Geometric means were analyzed by Wilcoxon paired rank test, one-sided for V2-SET vaccines.
Figure 5C:
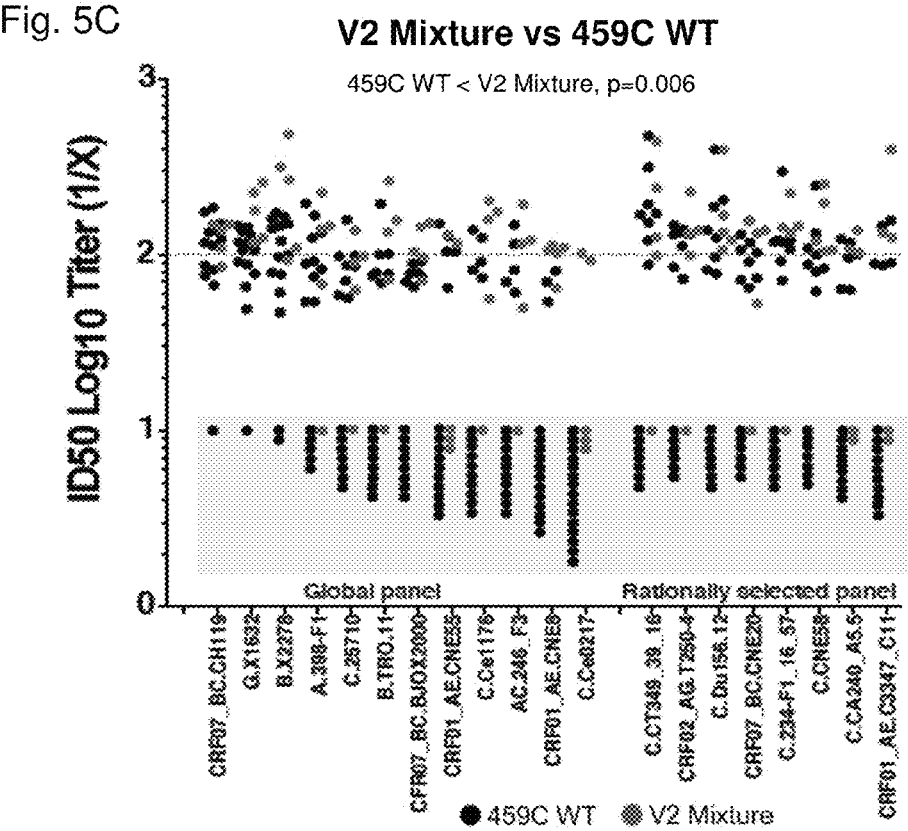
FIG. 5C is a graph showing the raw responses, with each dot corresponding to a single guinea pig. The dotted line at the arbitrary ID50 titer of 100 is added for visual emphasis. Dots in grey box are responses below the limit of detection for the assay and are aligned for visualization. Title denotes which vaccines are being compared. Colors in key represent each vaccination regimen. Results are shown for cutoff 1. The resulting p-values are shown on the graphs, and "<" is statistically lower, "~" is statistically indistinguishable, and ">" is statistically higher. Raw data was analyzed by permutation test.
Figure 5D:
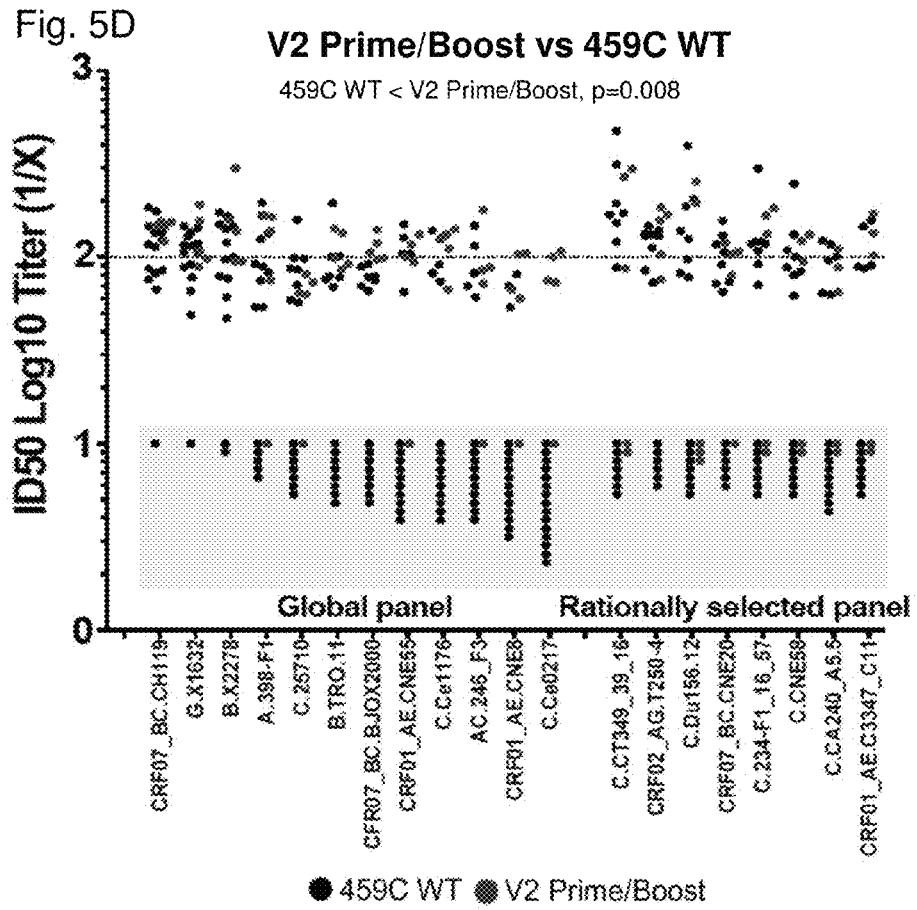
FIG. 5D is a graph showing the raw responses, with each dot corresponding to a single guinea pig. The dotted line at the arbitrary ID50 titer of 100 is added for visual emphasis. Dots in grey box are responses below the limit of detection for the assay and are aligned for visualization. Title denotes which vaccines are being compared. Colors in key represent each vaccination regimen. Results are shown for cutoff 1. The resulting p-values are shown on the graphs, and "<" is statistically lower, "~" is statistically indistinguishable, and ">" is statistically higher. Raw data was analyzed by permutation test.
Figure 5E:
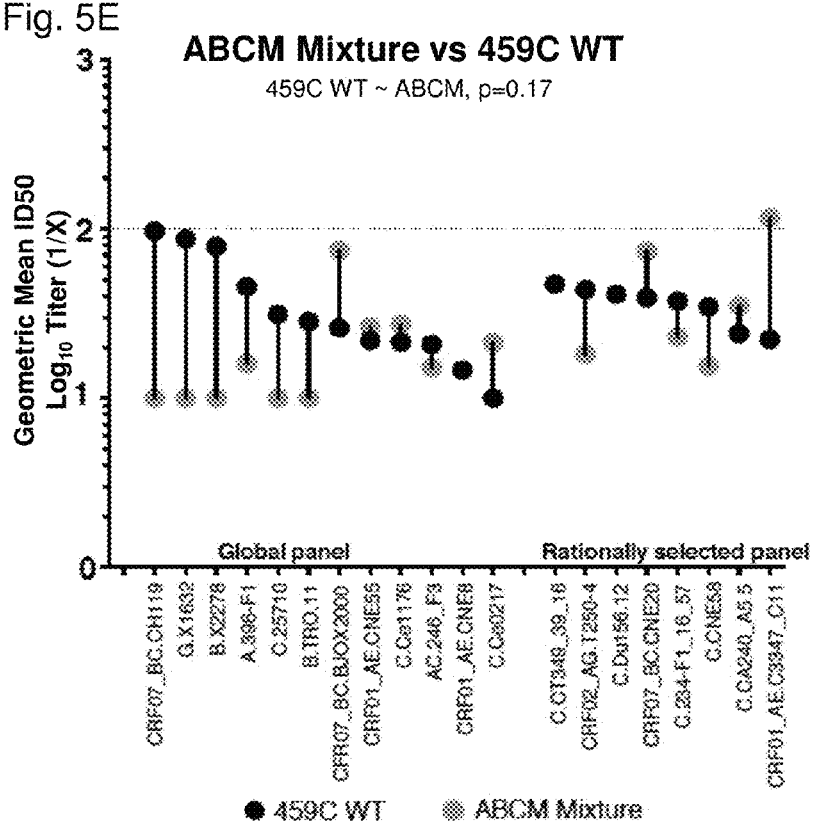
FIG. 5E is a graph showing a comparison of tier 2 neutralizing antibody responses by ABCM multivalent Env vaccinations as compared to 459C WT only. Geometric means of NAb titers with each guinea pig vaccination regimen represented as a single dot against each tier 2 pseudovirus including the global panel and rationally selected pseudoviruses with comparing ABCM Mixture against 459C WT. Colors in key represent each vaccination regimen. The dotted line at the arbitrary $ID_{50}$ titer of 100 is added for visual emphasis. Colors in key represent each vaccination regimen. Results are shown for cutoff 1. The resulting p-values are shown on the graphs, and "<" is statistically lower, "~" is statistically indistinguishable, and ">" is statistically higher. Geometric means were analyzed by two-sided Wilcoxon paired rank test for ABCM.
Figure 5F:
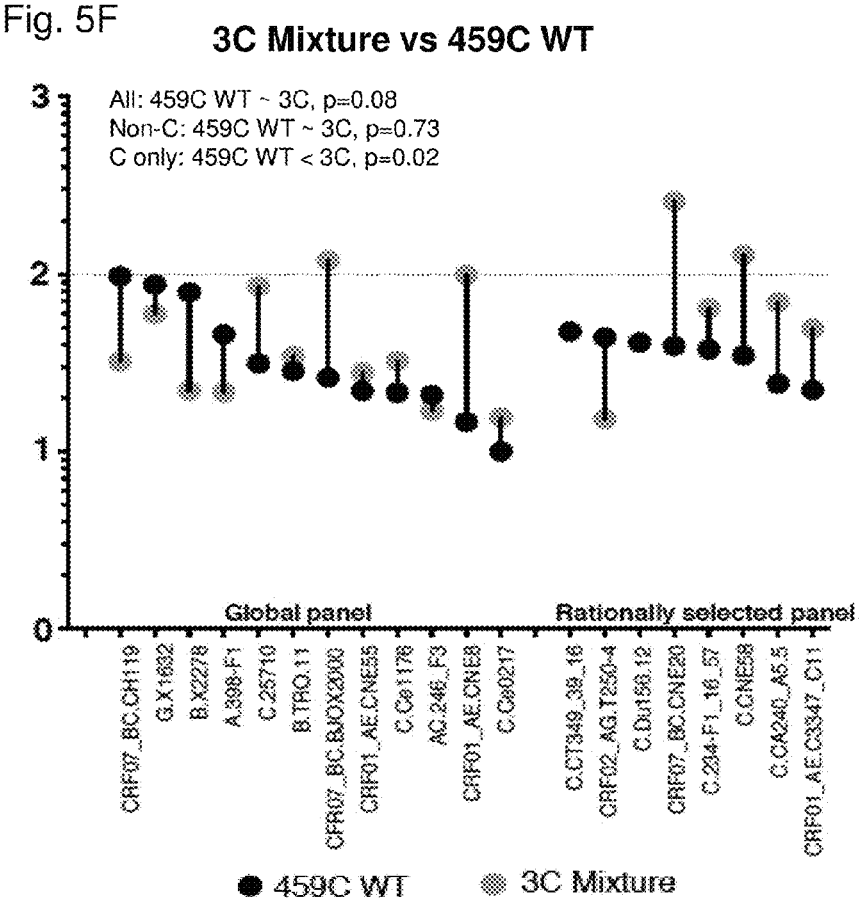
FIG. 5F is a graph showing a comparison of tier 2 neutralizing antibody responses by 3C, multivalent Env vaccinations as compared to 459C WT only. Geometric means of NAb titers with each guinea pig vaccination regimen represented as a single dot against each tier 2 pseudovirus including the global panel and rationally selected pseudoviruses with comparing 3C Mixture against 459C WT. Colors in key represent each vaccination regimen. The dotted line at the arbitrary ID50 titer of 100 is added for visual emphasis. Colors in key represent each vaccination regimen. Results are shown for cutoff 1. The resulting p-values are shown on the graphs, and "<" is statistically lower, "~" is statistically indistinguishable, and ">" is statistically higher. Geometric means were analyzed by Wilcoxon paired rank test, one-sided for V2-SET vaccines and 3C. Clade C pseudoviruses are highlighted in red for the 3C Mixture.
Figure 5G:
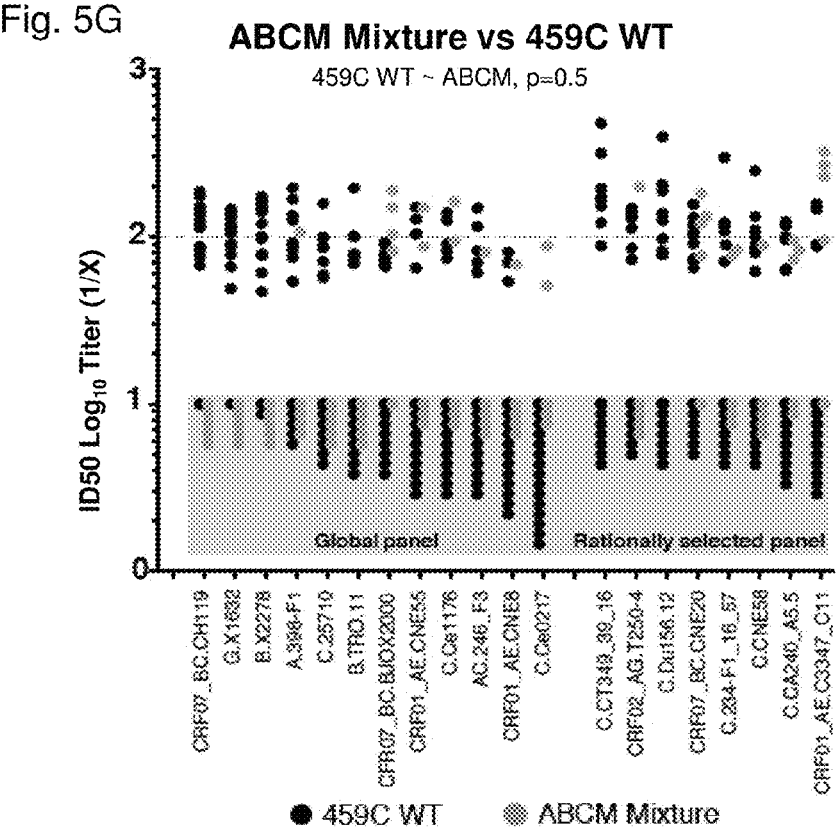
FIG. 5G is a graph showing the raw responses, with each dot corresponding to a single guinea pig. The dotted line at the arbitrary ID50 titer of 100 is added for visual emphasis. Dots in grey box are responses below the limit of detection for the assay and are aligned for visualization. Title denotes which vaccines are being compared. Colors in key represent each vaccination regimen. Results are shown for cutoff 1. The resulting p-values are shown on the graphs, and "<" is statistically lower, "~" is statistically indistinguishable, and ">" is statistically higher. Raw data was analyzed by permutation test.
Figure 5H:
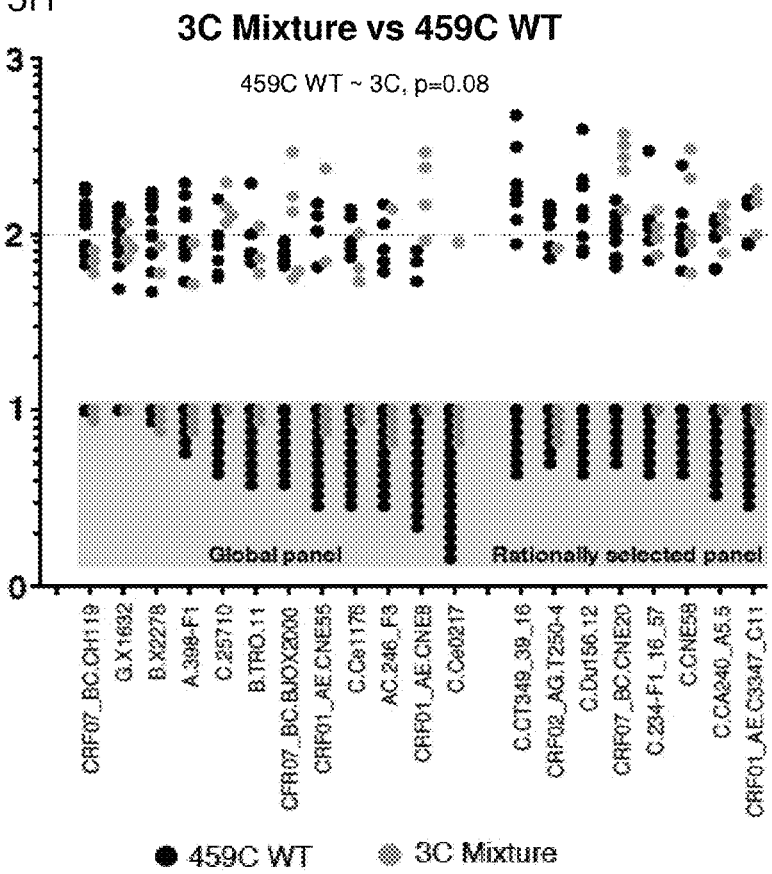
FIG. 5H is a graph showing the raw responses, with each dot corresponding to a single guinea pig. The dotted line at the arbitrary ID50 titer of 100 is added for visual emphasis. Dots in grey box are responses below the limit of detection for the assay and are aligned for visualization. Title denotes which vaccines are being compared. Colors in key represent each vaccination regimen. Results are shown for cutoff 1. The resulting p-values are shown on the graphs, and "<" is statistically lower, "~" is statistically indistinguishable, and ">" is statistically higher. Raw data was analyzed by permutation test.
Figure 19:
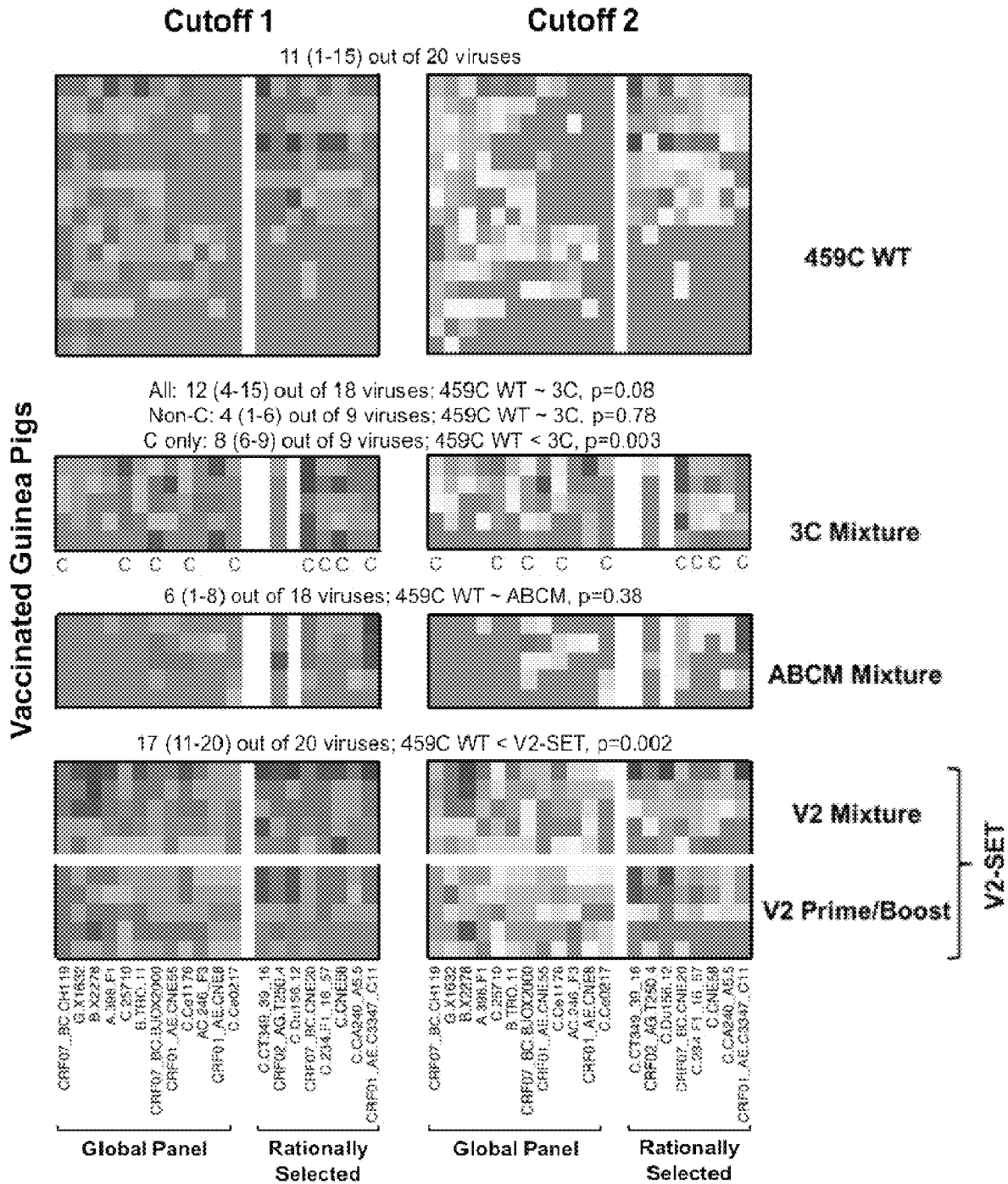
FIG. 19 is a schematic showing a heat map of tier 2 NAb responses elicited by 459C WT, V2-SET, 3C Mixture, and ABCM Mixture vaccines across three cutoffs for positivity are shown. The V2-SET, 3C, and ABCM vaccination regimens include immunogens as described in the methods. Each column represents a tested tier 2 pseudovirus, ordered left to right by sensitivity, and listed below the maps. Each row corresponds to a single guinea pig, rows are organized by vaccination regimen as listed to the right of the heat map, and ordered from top to bottom by the breadth of the response within each group. The highest ID50 responses are shown with the highest intensity color (dark red) and lower responses shown with the lowest intensity color (very light yellow). Negative responses are shown in blue for contrast. Cutoffs described in methods. 'MuLV' is the responses seen for animal-matched MuLV negative control. Responses that are undetectable are set to 10. One value is reported above the heat map for cutoff 1 and 2 as the calculations of breadth are identical. Cutoff 3 is shown separately. The 3C Mixture is analyzed against all viruses, clade C viruses only, and non-clade C viruses only as described in methods. Clade C pseudoviruses highlighted with red Cs. In vaccines comparisons "<" is statistically less broad, "~" is statistically indistinguishable, and ">" is significantly more broad.
Figure 19:
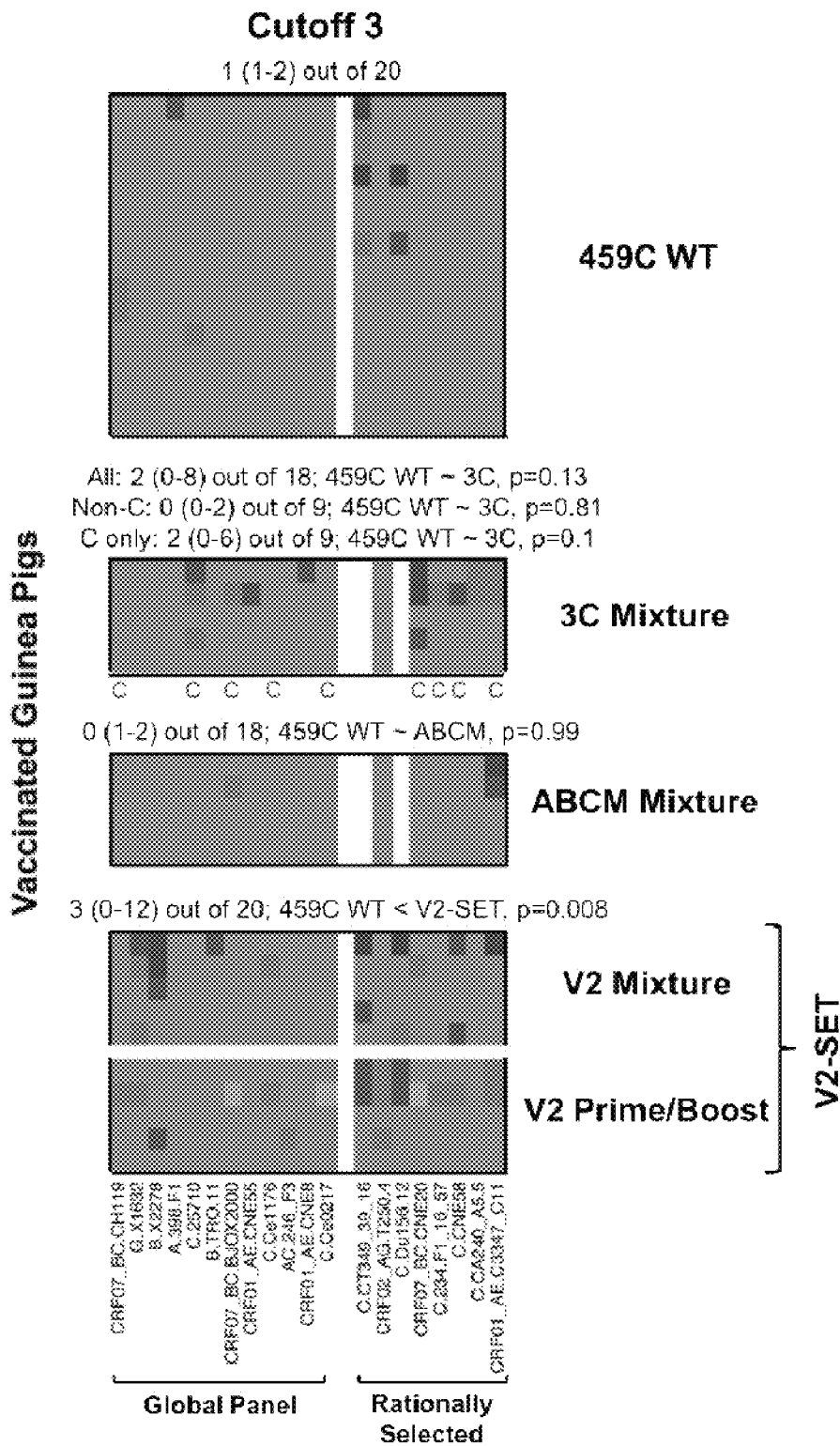

We next explored whether the improved tier 2 NAb responses observed with the trivalent V2-SET vaccines was due to the SET rational design or simply reflected the multivalency of the V2-SET vaccine cocktail as compared with the single 459C WT immunogen by assessing the immunogenicity of two non-SET Env immunogen cocktails. We first evaluated a trivalent clade C vaccine (3C Mixture), which included 459C WT plus two additional natural clade C gp140s. The 3C Mixture did not increase the overall breadth (FIG. 19) or potency (FIGS. 5F and 5H) of tier 2 NAbs compared to 459C WT alone against the panel of 20 pseudoviruses. However, when only clade C and CRF07 (mainly clade C in Env) were assessed, more C clade pseudoviruses were recognized in the 3C vaccinated animals (p=0.003) and the NAb magnitudes were slightly more potent (p=0.02) than 459C WT alone. This increase was less than that observed with the V2-SET vaccines, and the 3C vaccine did not enhance responses against non-clade clade C pseudoviruses. We also evaluated a quadrivalent global vaccine, which did not include 459C WT but included natural sequence Env gp140s from clades A, B, and C and a Mosaic Env gp140 (Nkolola et al., J. Virol. 88:9538-9552, 2014) (ABCM Mixture). This ABCM vaccine induced fewer and lower tier 2 NAb responses than did 459C WT alone (FIGS. 19, 5E, and 5G). Taken together, these data suggest that the improvement in NAb responses achieved with the trivalent V2-SET vaccine was not simply due to the trivalent nature of the vaccine cocktail.

In contrast to the V2 epitope modified (e.g., V2-SET) immunogens, we found that the V3 epitope modified (e.g., V3-SET) immunogens did not afford the same tier 2 neutralization benefit over 459C WT. With the exception of V3 Opt, which showed a modest trend towards being superior to 459C WT (Wilcoxon paired test, p=9.5e-02, cutoff 1) (Table 6), the V3 vaccines were equivalent to 459C WT alone (Wilcoxon paired test, p=0.99, cutoff 1). We further compared only positive NAb responses for 459C WT to V3 Opt to determine if there was a benefit of V3 Opt over 459C WT.

By generalized linear model analysis (p=3.0e-03, cutoff 1) and Wilcoxon paired test (p=1.0e-03, cutoff 1) V3 Opt positive NAbs were greater than WT responses (Table 9). Finally, by Wilcoxon test, the V3 Opt vaccine elicited a superior magnitude of tier 2 NAbs to 8 of 20 pseudoviruses compared to 459C WT alone, showing an advantage for V3 Opt over WT. These data suggest the V3 Alt vaccine, and all mixtures containing it, did not afford a benefit over the wild type 459C alone, but that V3 Opt alone had a slight advantage for the magnitude of NAbs elicited.

The breadth of tier 2 NAb responses elicited by the V2-SET vaccines was similarly significantly improved compared to 459C WT (FIGS. 5A-5D and 14A-14C). Sera from 459C WT vaccinated guinea pigs neutralized a median of 11 (range 1-15) of the 20 pseudoviruses, while sera from V2 Mixture neutralized a median of 17 (range 11-20) and V2 Prime/Boost a median of 16 (range 11-20) of the 20 pseudoviruses tested. Using a generalized linear model, the observed differences in breadth were explained by the differences between vaccines, as the V2-SET trivalent vaccine groups elicited a greater breadth of NAbs than 459C WT alone (p=0.003 for V2 Mixture vs. 459C WT, p=0.01 for V2 Prime/Boost vs. 459C WT, one-sided Wilcoxon rank-sum), with this advantage existing across a high stringency cutoff for V2 Mixture (Table 8).

TABLE 9

Comparison of Positive Titers of Sera Neutralizing Tier 2 Pseudoviruses of V3 Opt to 459C Only

| Test | Comparison | Cutoff | P value |
| --- | --- | --- | --- |
| Gaussian Mixed Effect | WT < V3 Opt | 1 | 3.0e−03* |
| Generalized Linear Model | | 2 | 1.9e−01 |
| Wilcoxon Paired | WT < V3 Opt | 1 | 1.0e−03* |
| Wilcoxon | WT < V3 Opt | 1 | 8 |

*Significant by pairwise comparisons (p < 0.05)

As these tier 2 neutralizing titers were of modest magnitude, we wanted to confirm our results utilizing purified IgG (FIGS. 5A-5D and 14A-14C). For generating these data, we selected the six pseudoviruses that showed the highest responses and the MuLV negative control to ensure removal of non-specific background. We ran the three vaccines (e.g., V2-SET immunogens) that elicited the highest magnitude of tier 2 NAbs (V2 Mixture, V2 Prime/Boost, and V3 Opt) as well as animals vaccinated with the wild type 459C vaccine against these pseudoviruses (FIG. 15A). IgG from vaccinated animals successfully neutralized tier 2 pseudoviruses, thus confirming the serum neutralization data. We further characterized these responses by heat map (FIG. 15B) and by statistical testing (Table 10), which confirmed that V2 Mixture and V3 Opt elicited a superior breadth of tier 2 NAbs compared to 459C WT only (Fisher's Exact, p=0.01 and p=0.01, respectively), and that V2 Prime/Boost showed a trend to superiority over 459C WT only (Fisher's Exact, p=0.13).

Figure 16A:
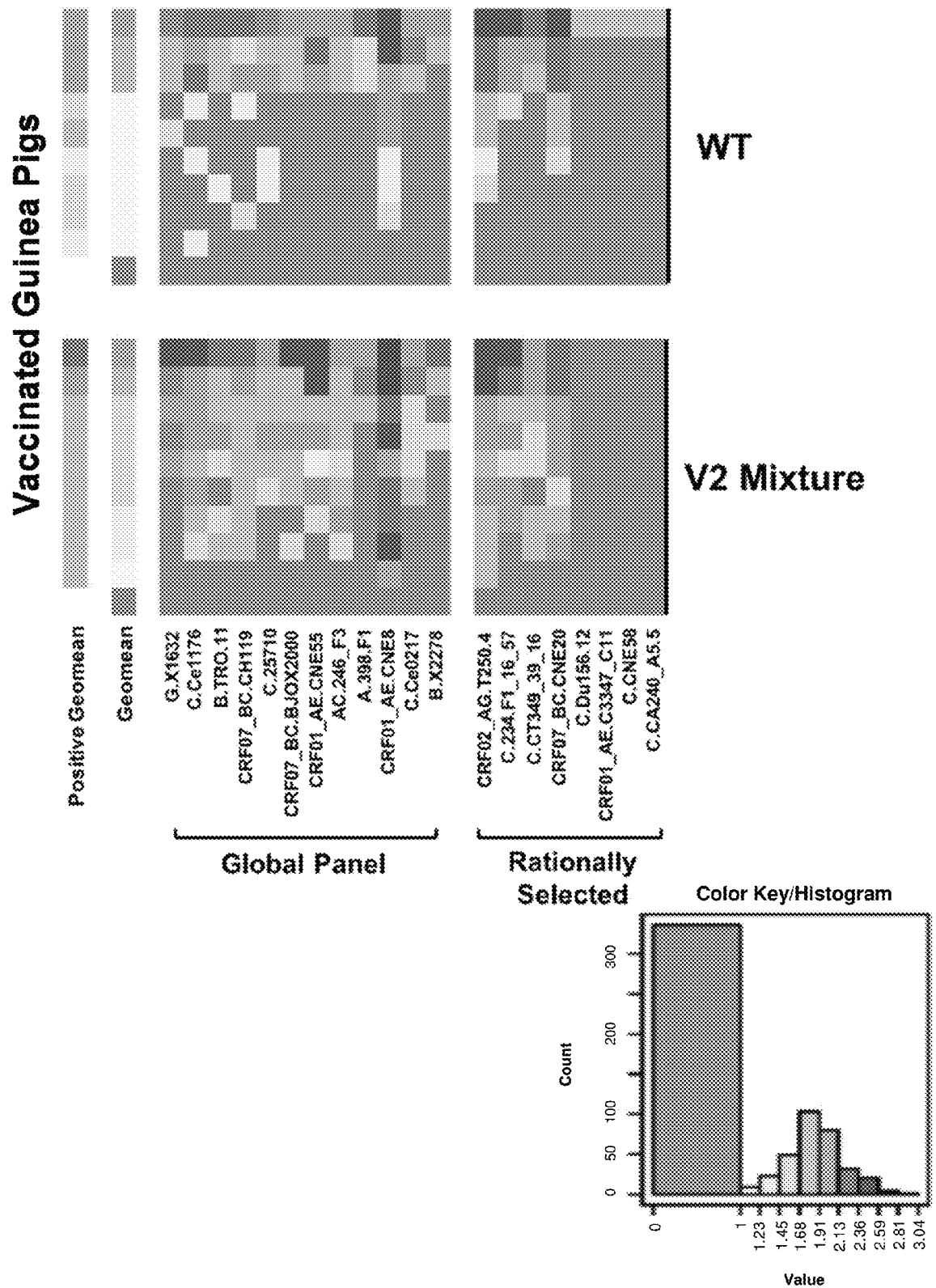
FIG. 16A is a heat map illustration comparing the magnitude of NAbs elicited against tier 2 pseudoviruses by vaccination with 459C WT and V2 Mixture. The test pseudoviruses are listed below the maps, with each row corresponding to a single guinea pig, and rows clustered by vaccination regimen are listed to the right of the heat map. The highest $ID_{50}$ responses are shown with the highest intensity color (dark red) and low positive responses shown with the lowest intensity color (very light yellow). Negative responses are shown in blue. The left side of the map includes geometric means of the responses across all pseudoviruses per animal for all data and positive (detected) data only.
Figures 16B, 16C:
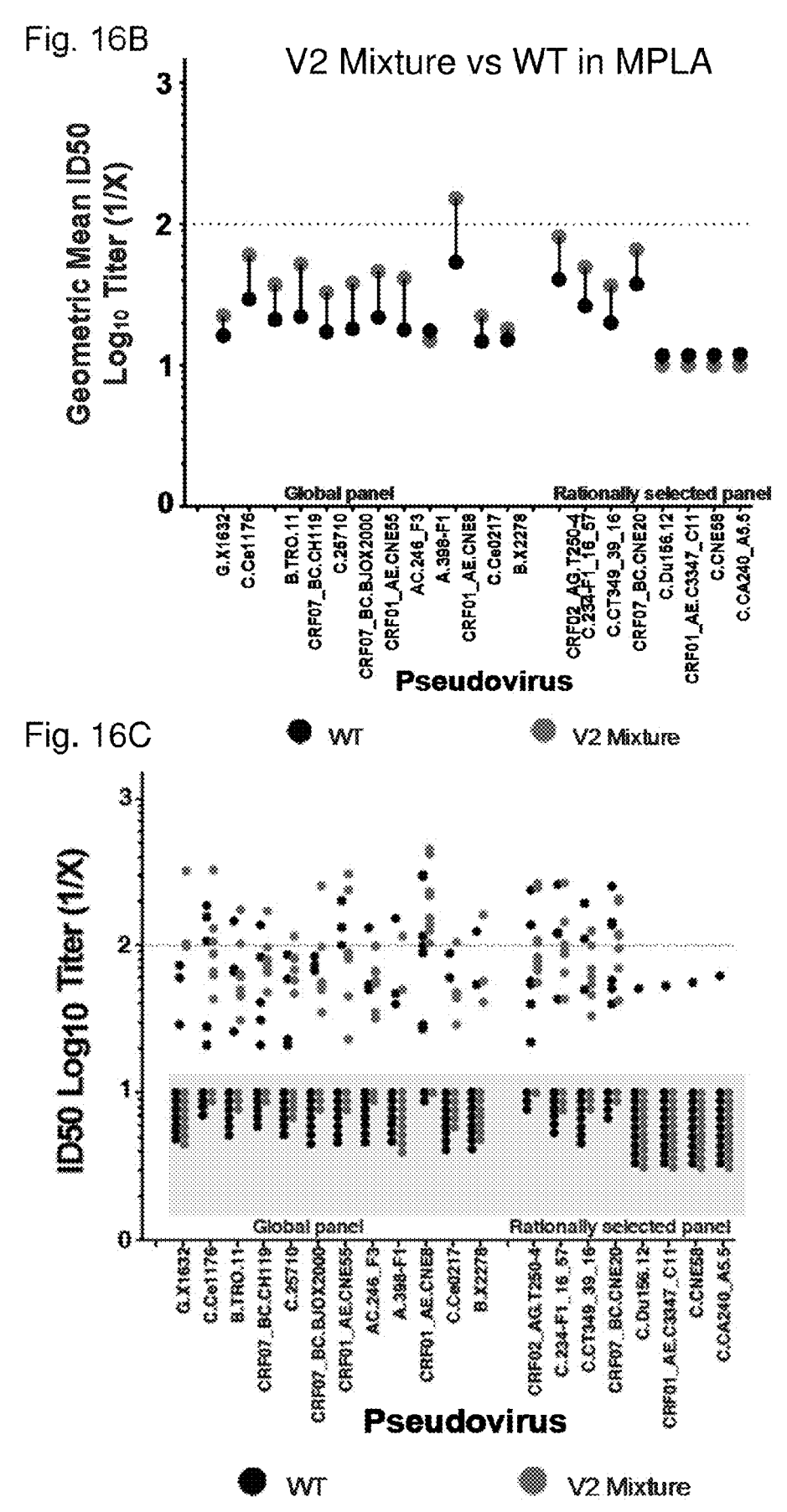

We next compared the V2 Mixture with the 459C WT immunogen using a different adjuvant, MPLA (Nkolola et al., *Vaccine*. 32:2109-2116, 2014), and a more extensive vaccination schedule in guinea pigs. Consistent with the prior observations, the V2 Mixture demonstrated an increased potency relative to 459C WT against heterologous tier 2 pseudoviruses (p=0.0001, Wilcoxon rank-sum test) (FIGS. 16A-16C). The breadth of response per guinea pig in the V2 Mixture was also modestly increased compared to 459C WT alone, as V2 Mixture neutralized median of 12 (range 0-17) while 459C WT only neutralized a median of 4.5 (range 1-18) of the 20 pseudoviruses tested (p=0.0004, Fisher's exact test). Similar statistical differences were observed when using the more restrictive cutoff 2 and cutoff 3 for positivity.

TABLE 10

Comparison of Magnitude of Tier 2 Purified IgG Neutralizing Titers Across Vaccines

| Test | Comparison | | P value |
| --- | --- | --- | --- |
| Linear Model Binomial Distribution | Response differences among purified polyclonal IgG from all vaccines tested | | 0.07 |

| Test | Comparison | Odds Ratio | P value |
| --- | --- | --- | --- |
| Fisher's Exact | WT < V2 Mixture | 3.3 | 0.01* |
| | WT ≅ V2 Prime/Boost | 1.8 | 0.13 |
| | WT < V3 Opt | 2.4 | 0.01* |

*Significant by pairwise comparisons (p < 0.05)

Example 9: Mapping Neutralizing Antibody Responses with Variable Loop Glycan Mutant Pseudoviruses Finally, we mapped NAb responses elicited by epitope modified vaccines using pseudoviruses with glycan knock out mutations in V2 and V3. We found that a T162I mutation in the V2 of X1632, T250-4, and BJOX2000 diminished the neutralization advantage of V2 Mixture and V2 Prime/Boost over 459C WT alone (FIGS. 17A-17D, Table 11). This glycan knock out mutation also resulted in an increased sensitivity to neutralization by vaccine sera in these pseudoviruses. This same advantage was not seen against additional V2 and V3 glycan mutants when assessed against further vaccine sera, largely due to skewing of negative responses. These data suggest that part of the neutralization advantage of V2 Mixture and V2 Prime/Boost over 459C WT maps to NAb targeting V2.

To explore whether the observed improvement in heterologous tier 2 NAb activity with our V2-SET vaccines over the 459C WT immunogen targeted the V2 epitope, we mapped NAb responses elicited by the V2-SET vaccines using pseudoviruses with a glycan deletion mutations in V2. These glycan deletions resulted in an overall unexpected global increase in sensitivity of these pseudoviruses to neutralization. Nevertheless, we found that a T162I mutation in V2 of the HIV viral isolates X1632, T250-4, and BJOX2000, which eliminates the critical glycosylation site at N160, diminished or abrogated the neutralization advantage of V2 Mixture and V2 Prime/Boost over 459C WT (FIGS. 17A-17D, Table 10). These data suggest that the neutralization advantage of the V2-SET trivalent vaccines over 459C WT at least partially targeted the V2 epitope.

TABLE 11

Comparison of Magnitude of Tier 2 Sera Neutralizing Titers Against Natural and Variable Loop 2 and 3 Mutant Pseudoviruses

| Test | Pseudovirus | Comparison | P value |
| --- | --- | --- | --- |
| Wilcoxon Paired | X1632 natural | 459C WT < WT + V2 Opt + V2 Alt | 0.07 |
| | X1632 T162I | 459C WT ≅ WT + V2 Opt + V2 Alt | 0.20 |

TABLE 11-continued

Comparison of Magnitude of Tier 2 Sera Neutralizing Titers Against Natural and Variable Loop 2 and 3 Mutant Pseudoviruses

| Test | Pseudovirus | Comparison | P value |
|---|---|---|---|
| | T250-4 natural | 459C WT < WT + V2 Opt + V2 Alt | 0.004* |
| | T250-4 T162I | 459C WT ≅ WT + V2 Opt + V2 Alt | 0.30 |
| | BJOX2000 natural | 459C WT < WT + V2 Opt + V2 Alt | 0.01* |
| | BJOX2000 T162I | 459C WT ≅ WT + V2 Opt + V2 Alt | 0.09 |
| Wilcoxon Paired | X1632 natural | 459C WT ≅ V2 Prime/Boost | 0.29 |
| | X1632 T162I | 459C WT ≅ V2 Prime/Boost | 0.15 |
| | T250-4 natural | 459C WT < V2 Prime/Boost | 0.048* |
| | T250-4 T162I | 459C WT ≅ V2 Prime/Boost | 0.23 |
| | BJOX2000 natural | 459C WT < V2 Prime/Boost | 0.009* |
| | BJOX2000 T162I | 459C WT ≅ V2 Prime/Boost | 0.40 |
| Wilcoxon Paired | 398-F1 natural | 459C WT ≅ V3 Opt | 0.17 |
| | 398-F1 T303I/S334N | 459C WT ≅ V3 Opt | 0.50 |
| | CNE58 natural | 459C WT ≅ V3 Opt | 0.16 |
| | CNE58 T303I/T334N | 459C WT ≅ V3 Opt | 0.44 |

*Significant by pairwise comparison (p < 0.05)

Conclusion

In this study, we show that bioinformatically designed HIV-1 V2-SET Env vaccines elicited lower magnitude of linear binding antibodies but greater magnitude and breadth of tier 2 NAbs as compared with the parental 459C WT immunogen in guinea pigs. In contrast, minimal to no improvement in tier 2 NAbs was observed with two other non-SET Env vaccine cocktails. Although the tier 2 NAb titers induced by the V2-SET vaccines were modest, our findings demonstrate the proof-of-concept that HIV-1 Env immunogens can be improved by bioinformatic optimization of bNAb epitopes.

We report the generation of rationally designed, epitope modified variable loop 2 and 3 HIV-1 Env gp140 immunogens (e.g., HIV-1 V2-SET Env immunogens) containing modified amino acid signature sequences associated with bNAb neutralization sensitivity or resistance. We found that the V2 Mixture and the V2 Prime/Boost regimens (e.g., V2-SET trivalent immunogens) elicited a lower magnitude of linear binding antibodies to V2 and V3 than 459C WT alone. We further found that vaccines containing combinations of WT, V2 Opt and V2 Alt, given as cocktails or sequential prime/boost regimens were capable of eliciting a greater magnitude and breadth of heterologous tier 2 NAbs than 459C WT alone. Similar findings were observed with purified IgG as well as with a second adjuvant, and the augmented heterologous tier 2 NAb responses at least partially mapped to V2. These data suggest that there is an immunological advantage to using a cocktail of HIV-1 Env 459C WT, V2 Opt, and V2 Alt epitope modified immunogens. Further, these data suggest that bioinformatic optimization of HIV-1 Env using bNAb-derived neutralization sequences can improve vaccine immunogenicity.

It is known that soluble forms of HIV-1 Env immunogens tend to expose the immunodominant V3 loop more readily than closed, native envelope proteins (Sanders et al., *Science* 349:aac4223, 2015; Kovacs et al., *Proc. Natl. Acad. Sci. USA* 109:12111-12116, 2012; Kovacs et al., *Proc. Natl. Acad. Sci. USA* 111:18542-18547, 2014). Moreover, specific point mutations in the SOSIP gp140 construct (de Taeye et al., *Cell* 163:1702-1715, 2015) or full length gp160 (Dev et al., *Science* 353:172-175, 2016 and Chen et al., *Science* 349:191-195, 2015) can reduce the exposure of, and response to (e.g., non-neutralizing Ab responses to), V3. It is possible that the sequence modifications in the V2 Opt and Alt vaccines (e.g., V2-SET immunogens) may result in reduced exposure of immunodominant linear epitopes in V2 and V3 than the 459C WT counterpart, resulting in a lower linear V3-directed response than for 459C WT. The multivalent V2 vaccination regimens may result in an increased elicitation of antibodies to structural epitopes rather than linear epitopes.

The optimized Env immunogens described here can be incorporated into the context of a SOSIP construct (de Taeye et al., *Cell* 163:1702-1715, 2015) or a gp160 immunogen (Dev et al., *Science* 353:172-175, 2016 and Chen et al., *Science* 349:191-195, 2015), e.g., to further reduce responses to the immunodominant V3 in the wild type and epitope modified immunogens and to increase the magnitude of heterologous tier 2 responses.

Similarly, the V2 Mixture and V2 Prime/Boost vaccines appear to target V2 in a distinct manner from the 459C WT vaccine. While responses to linear V2 peptides in the microarray were diminished in these vaccines compared to 459C WT alone, binding responses to V1/V2 scaffolds were identical across vaccines as measured by ELISA. Furthermore, these V2 multivalent vaccines lost their neutralization advantage over 459C WT against select V2 glycan knock out pseudoviruses. These data suggest that exposing the immune system to sequence diversity within V2 results in a decrease in linear V2-directed antibodies and an increase in NAbs that target a structural epitope in V2 capable of neutralizing tier 2 pseudoviruses.

Previously conducted HIV-1 vaccine studies have also reported limited tier 2 NAbs but, in most cases, the tier 2 NAb responses have largely been limited the autologous virus. A potential limitation in select studies was the use of a single Env immunogen (Sanders et al., *Science* 349: aac4223, 2015; de Taeye et al., *Cell* 163:1702-1715, 2015; Crooks et al., *PLoS Pathog.* 11:e1004932, 2015; Townsley et al., *J. Virol.* 90:8644-60, 2016). By limiting exposure of the immune system to a single Env immunogen, B cells are only exposed to a single antigenic surface, likely resulting in a limited breadth of NAb responses due to immune focusing on one sequence. In contrast, some of these studies did use a multivalent vaccination strategy but failed to achieve neutralization breadth (e.g., broad tier 2 NAbs) (Bradley et al., *Cell Reports* 14:43-54, 2016; Hessell et al., *J. Immunol.* 196:3064-3078, 2016). It is possible that breadth was not achieved due to the characteristics of the specific immunogens utilized, the vaccination platform used, or the length of vaccination regimens was not long enough to achieve NAb breadth.

A vaccination strategy of this invention combines two features to elicit tier 2 NAbs against a moderate breadth of viruses compared to other vaccination regimens. First, we used a phylogenetically central 459C WT strain as the parental sequence for the SET immunogen designs. 459C WT alone elicited low but reproducible NAbs against a subset of tier 2 pseudoviruses. Second, our immunogens were rationally designed in an attempt to maximize exposure of bNAb epitopes by including substitutions associated with neutralization sensitivity both inside and outside the bNAb epitopes. The V2 and V3 Env immunogens were rationally designed to present bNAb epitopes associated with both neutralization sensitivity and resistance within a single epitope. By using patterns in Env sensitivity to existing bNAbs to guide our design, we attempted to mimic natural variation in Env regions that bind or influence binding to bNAbs. Third, we tried to represent the most relevant forms of the epitope diversity, including both common sensitivity and resistance forms within the epitope. These immunogens can be administered as a trivalent antigen mixture to encompass the most relevant global sequence diversity within a single epitope. This sequence diversity within a single Env region exposes B cells to epitope diversity, which may serve drive affinity maturation towards a more conserved epitope, resulting in more cross reactive NAbs. Rational immunogen design paired with multivalency promoted a tier 2 neutralization breadth not achieved by previous vaccination regimens. As naturally circulating strains of HIV-1 encompass a large sequence diversity, it is important that elicited NAbs are effective against a large breadth of viral sequences.

We were able to elicit a modest breadth of heterologous tier 2 Nabs. Lengthening our vaccination regimens to include longer rest periods and/or more vaccinations may provide for a greater amount of affinity maturation and increased NAb titers. Additionally, the use of different adjuvants and/or different Env vaccination platforms may also increase the magnitude and breadth of NAb responses.

In summary, our data demonstrate that a mixture of bioinformatically designed V2-SET HIV-1 Env immunogens expand the magnitude and breadth of heterologous tier 2 NAbs as compared with the 459C WT immunogen.

Example 10. Administration of a HIV-1 Vaccine to a Human Subject

Compositions of the invention may be administered to human subjects, pre- or post-exposure to a HIV, according to the methods of the invention. The human subject may be one identified as being at high risk for infection, such as an individual who has or will be traveling to a region where HIV infection is prevalent and who would be at risk of HIV-1 transmission following sexual exposure to an HIV-1-infected individual or at risk of HIV-1 transmission following a needlestick.

For example, a women of child-bearing age identified as having a risk of HIV-1 infection may be administered a DNA vaccine containing a nucleic acid molecule encoding a HIV-1 nucleic acid of the invention (e.g., 459C V2 Opt Env ("459C V2 Opt gp140 NT," SEQ ID NO: 7)), e.g., in an adenoviral vector at about $1 \times 10^3$ viral particles (vp)/dose to about $1 \times 10^{14}$ vp/dose.

The patient is then monitored for presentation of symptoms of HIV-1 infection or the resolution of symptoms. If necessary, a second or additional dose of the DNA vaccine can be administered.

Example 11. Administration of an Immunogenic HIV-1 Env Polypeptide to a Human Subject A human subject identified as having a risk of HIV-1 infection may be administered a HIV-1 immunogen of the invention (e.g., 459C V2 Opt gp140 polypeptide (SEQ ID NO: 1)) or a nucleic acid molecule encoding this polypeptide (e.g., SEQ ID NO: 7), e.g., in an adenoviral vector at about $1 \times 10^3$ viral particles (vp)/dose to about $1 \times 10^{14}$ vp/dose. The patient is then monitored for presentation of symptoms of HIV-1 infection or the resolution of symptoms. If necessary, a second dose of the DNA vaccine can be administered. The second dose may be V2 Opt gp140 or WT gp140+V2 Alt gp140.

Example 12. Administration of Anti-HIV Antibodies to a Human Subject at Risk of HIV Infection A human subject identified as having a risk of HIV infection (e.g., due to travel to a region where HIV infection is prevalent, or the subject being a pregnant woman or a woman of childbearing age) may be administered an anti-HIV antibody that binds to an epitope within the 459C V2 Opt (SEQ ID NO: 1) polypeptide (e.g., the antibody may have been generated against the 459C V2 Opt polypeptide of SEQ ID NO: 1) at a dose of between 1-1,000 mg as a prophylactic therapy. The subject may be administered the anti-HIV antibody as a prophylactic therapy prior to or post-exposure to a HIV. The patient can then be monitored for presentation of symptoms of HIV infection or the resolution of symptoms. If necessary, a second dose or additional doses of the anti-HIV antibody can be administered.

Example 13. Administration of Anti-HIV Antibodies to a Human Subject Presenting Symptoms of HIV Infection A human subject identified as presenting symptoms of HIV may be administered an anti-HIV antibody that binds to an epitope within the 459C V2 Opt (SEQ ID NO: 1) polypeptide (e.g., the antibody may have been generated against the 459C V2 Opt polypeptide of SEQ ID NO: 1) at a dose of between 1-1,000 mg. The subject (e.g., a male or female subject, such as a pregnant woman or a woman of childbearing age) may have recently traveled to a region where HIV infection is prevalent. After diagnosis of HIV infection by a medical practitioner, the subject can be administered a dose of the anti-HIV antibody. The patient can then be monitored for resolution of symptoms. If necessary, a second or additional dose of the anti-HIV antibody can be administered.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

APPENDIX

Clone: HXB2 (Chronic Clade B) Sequence
(SEQ ID NO: 46)
MRVKEKYQHLWRWGWRWGTMLLGMLMICSATEKLWVTVYYGVPVWKEATT

TLFCASDAKAYDTEVHNVWATHACVPTDPNPQEVVLVNVTENFNMWKNDM

VEQMHEDIISLWDQSLKPCVKLTPLCVSLKCTDLKNDTNTNSSSGRMIME

KGEIKNCSFNISTSIRGKVQKEYAFFYKLDIIPIDNDTTSYKLTSCNTSV

-continued

ITQACPKVSFEPIPIHYCAPAGFAILKCNNKTFNGTPCTNVSTVQCTHG
IRPVVSTQLLLNGSLAEEEVVIRSVNFTDNAKTIIVQLNTSVEINCTRPN
NNTRKRIRIQRGPGRAFVTIGKIGNMRQAHCNISRAKWNNTLKQIASKLR
EQFGNNKTIIFKQSSGGDPEIVTHSFNCGGEFFYCNSTQLFNSTWFNSTV
VSTEGSNNTEGSDTITLPCRIKQIINMWQKVGKAMYAPPISGQIRCSSNI
TGLLLTRDGGNSNNESEIFRPGGGDMRDNWRSELYKYKVVKIEPLGVAPT
KAKRRVVQREKRAVGIGALFLGFLGAAGSTMGAASMTLTVQARQLLSGIV

-continued

QQQNNLLRAIEAQQHLLQLTVWGIKQLQARILAVERYLKDQQLLGIWGCS
GKLICTTAVPWNASWSNKSLEQIWNHTTVVMEWDREINNYTSLIHSLIEE
SQNQQEKNEQELLELDKWASLWNWFNITNWLWYIKLFIMIVGGLVGLRIV
FAVLSIVNRVRQGYSPLSFQTHLPTPRGPDRPEGIEEEGGERDRDRSIRL
VNGSLALIWDDLRSLCLFSYHRLRDLLLIVTRIVELLGRRGWEALKYWWN
LLQYVVSQELKNSAVSLLNATAIAVAEGTDRVIEVVQGACRAIRHIPRRI
RQGLERILL

---

The invention claimed is:

1. An isolated polypeptide comprising:

A)
(a) a human immunodeficiency virus (HIV) envelope (Env) glycoprotein comprising an asparagine residue at position 33, a lysine residue at position 49, a glutamic acid residue at position 130, and a threonine residue at position 132 relative to the sequence of HXB2 (GenBank Accession No. AF033819.3); and/or
(b) a HIV Env glycoprotein comprising an asparagine residue at position 156, a serine residue at position 158, an asparagine residue at position 160, a methionine residue at position 161, a threonine residue at position 162, a threonine residue at position 163, a glutamic acid residue at position 164, a lysine residue at position 165, an arginine residue at position 166, an aspartic acid residue at position 167, a lysine residue at position 168, a lysine residue at position 169, a lysine residue at position 170, a lysine residue at position 171, a valine residue at position 172, and a serine residue at position 173 relative to the sequence of HXB2 (GenBank Accession No. AF033819.3); and/or
(c) a HIV Env glycoprotein comprising a tyrosine residue at position 177, a tyrosine residue at position 223, an isoleucine residue at position 297, a serine residue at position 306, an aspartic acid residue at position 322, a lysine residue at position 335, a serine residue at position 636, an arginine residue at position 644, and an asparagine residue at position 677 relative to the sequence of HXB2 (GenBank Accession No. AF033819.3); or B)
(a) a HIV Env glycoprotein comprising an asparagine residue at position 33, a glutamic acid residue at position 49, an aspartic acid residue at position 130, and a lysine residue at position 132 relative residue to the sequence of HXB2 (GenBank Accession No. AF033819.3); and/or
(b) a HIV Env glycoprotein comprising an asparagine residue at position 156, a threonine residue at position 158, an asparagine residue at position 160, an isoleucine residue at position 161, a threonine residue at position 162, a threonine residue at position 163, a serine residue at position 164, a valine residue at position 165, a lysine residue at position 166, a glycine residue at position 167, a lysine residue at position 168, an arginine residue at position 169, a glutamine residue at position 170, a glutamine residue at position 171, a glutamic acid residue at position 172, and a histidine residue at position 173 relative to the sequence of HXB2 (GenBank Accession No. AF033819.3); and/or
(c) a HIV Env glycoprotein comprising a tyrosine residue at position 177, a tyrosine residue at position 223, a valine residue at position 297, a serine residue at position 306, a glutamic acid residue at position 322, a lysine residue at position 335, a serine residue at position 636, an arginine residue at position 644, and an asparagine residue at position 677 relative to the sequence of HXB2 (GenBank Accession No. AF033819.3); or C)
(a) a HIV Env glycoprotein comprising an aspartic acid residue at position 62, a valine residue at position 85, a lysine residue at position 160, a threonine residue at position 162, an isoleucine residue at position 184, a threonine residue at position 240, an asparagine residue at position 276, and a threonine residue at position 278 relative to the sequence of HXB2 (GenBank Accession No. AF033819.3); and/or
(b) a HIV Env glycoprotein comprising an asparagine residue at position 295, a threonine residue at position 297, a glycine residue at position 300, an asparagine residue at position 301, a threonine residue at position 303, an arginine residue at position 304, an isoleucine residue at position 307, an isoleucine residue at position 323, a glycine residue at position 324, an aspartic acid residue at position 325, an isoleucine residue at position 326, an arginine residue at position 327, a glutamine residue at position 328, a histidine residue at position 330, an asparagine residue at position 332, and a serine residue at position 334 relative to the sequence of HXB2 (GenBank Accession No. AF033819.3); and/or (c) a HIV Env glycoprotein comprising an alanine residue at position 336, an asparagine residue at position 339, a threonine residue at position 341, a glutamine residue at position 344, an alanine residue at position 346, an asparagine residue at position 392, a threonine residue at position 394, and a serine residue at position 668 relative to the sequence of HXB2 (GenBank Accession No. AF033819.3); or D)
(a) a HIV Env glycoprotein comprising an aspartic acid residue at position 62, a valine residue at position 85, an asparagine residue at position 160, a threonine residue at position 162, an isoleucine residue at position 184, a threonine residue at position 240, an asparagine residue at position 276, and a serine residue at position 278 relative to the sequence of HXB2 (GenBank Accession No. AF033819.3); and/or (b) a HIV Env glycoprotein comprising a threonine residue at position 295, an isoleucine residue at position 297, a serine residue at position 300, an asparagine residue at position 301, a threonine residue at position 303, an arginine residue at position 304, a valine residue at position 307, an isoleucine residue at position 323, a glycine residue at position 324, an asparagine residue at position 325, an isoleucine residue at position 326, an arginine residue at position 327, a lysine residue at position 328, a tyrosine residue at position 330, a glutamic acid residue at position 332, and an asparagine residue at position 334 relative to the sequence of HXB2 (GenBank Accession No. AF033819.3); and/or (c) a HIV Env glycoprotein comprising a threonine residue at position 336, an asparagine residue at position 339, a threonine residue at position 341, an asparagine residue at position 344, a serine residue at position 346, an asparagine residue at position 392, a serine residue at position 394, and a serine residue at position 668 relative to the sequence of HXB2 (GenBank Accession No. AF033819.3); or E) an amino acid sequence having at least 85% sequence identity to the amino acid sequence of SEQ ID NO: 33; or F) an amino acid sequence having at least 85% sequence identity to the amino acid sequence of SEQ ID NO: 34; or G) an amino acid sequence having at least 97% sequence identity to the amino acid sequence of SEQ ID NO: 35; or H) an amino acid sequence having at least 94% sequence identity to the amino acid sequence of SEQ ID NO: 36.

2. The isolated polypeptide of claim 1, wherein the polypeptide of E):
   i) has at least 86%, 87%, 88%, 89%, 90%, 91%, 92%, 93%, 94%, 95%, 96%, 97%, 98%, 99%, or 100% sequence identity to the amino acid sequence of SEQ ID NO: 33; and/or
   ii) further comprises a sequence having at least 50, 100, 150, 200, 250, 300, 350, 400, 450, 500, 550, 600, 650, 700, or more consecutive amino acids of the sequence of SEQ ID NO: 1, or a variant thereof having a sequence with at least 92%, 93%, 94%, 95%, 96%, 97%, 98%, or 99% sequence identity to a sequence comprising at least 50, 100, 150, 200, 250, 300, 350, 400, 450, 500, 550, 600, 650, 700, or more consecutive amino acids of the sequence of SEQ ID NO: 1; and/or
   iii) further comprises:
      (a) an asparagine residue at position 33, a lysine residue at position 49, a glutamic acid residue at position 130, and a threonine residue at position 132 relative to the sequence of HXB2 (GenBank Accession No. AF033819.3); and/or
      (b) an asparagine residue at position 156, a serine residue at position 158, an asparagine residue at position 160, a methionine residue at position 161, a threonine residue at position 162, a threonine residue at position 163, a glutamic acid residue at position 164, a lysine residue at position 165, an arginine residue at position 166, an aspartic acid residue at position 167, a lysine residue at position 168, a lysine residue at position 169, a lysine residue at position 170, a lysine residue at position 171, a valine residue at position 172, and a serine residue at position 173 relative to the sequence of HXB2 (GenBank Accession No. AF033819.3); and/or
      (c) a tyrosine residue at position 177, a tyrosine residue at position 223, an isoleucine residue at position 297, a serine residue at position 306, an aspartic acid residue at position 322, a lysine residue at position 335, a serine residue at position 636, an arginine residue at position 644, and an asparagine residue at position 677 relative to the sequence of HXB2 (GenBank Accession No. AF033819.3).

3. The isolated polypeptide of claim 1, wherein:
I) the polypeptide further comprises:
   a) a trimerization domain;
   b) a histidine tag; and/or
   (c) a leader signal sequence at the amino terminus of the polypeptide; and/or
II) the polypeptide is an HIV gp140 polypeptide and/or is derived from a clade C HIV envelope glycoprotein.

4. The isolated polypeptide of claim 3, wherein:
a) the trimerization domain:
   i) has at least 90%, 91%, 92%, 93%, 94%, 95%, 96%, 97%, 98%, 99%, or 100% sequence identity to the amino acid sequence of SEQ ID NO: 5; and/or
   ii) is at the carboxy-terminus of the polypeptide; and/or
b) the histidine tag:
   i) is at the carboxy-terminus of the trimerization domain; and/or
   ii) comprises one to twenty contiguous histidine residues; and/or
c) the leader signal sequence has at least 90% sequence identity to the amino acid sequence of SEQ ID NO: 17.

5. A stabilized trimer comprising three polypeptides of claim 1, wherein:
I)
   a) the polypeptides are gp140 polypeptides; and/or
   b) each of the polypeptides comprises an amino acid sequence having at least 92%, 93%, 94%, 95%, 96%, 97%, 98%, 99%, or 100% sequence identity to the amino acid sequence of any one of SEQ ID NO: 11 to 14; or
II)
   a) each polypeptide of the trimer is the same; or
   b) each polypeptide of the trimer is different; or
   c) two polypeptides of the trimer are the same; or
   d) two polypeptides of the trimer are different.

6. A composition comprising
the polypeptide of claim 1 or
a stabilized trimer comprising three of the polypeptides.

7. The composition of claim 6, comprising
a population of the stabilized trimer, wherein the population comprises a homogenous population of said stabilized trimer or a heterogenous population of said stabilized trimer.

8. An immunogenic composition comprising the composition of claim 6 and a pharmaceutically acceptable carrier, excipient, or diluent and/or an adjuvant.

9. A method of treating or reducing the risk of a human immunodeficiency virus (HIV) infection in a subject in need thereof comprising administering the immunogenic composition of claim 8 to the subject.

10. The method of claim 9, wherein the composition elicits production of neutralizing anti-HIV antisera after administration to said subject, wherein the anti-HIV antisera is capable of neutralizing HIV selected from any one or more of clade A, clade B, and clade C; and/or wherein the HIV is a heterologous, tier 2 neutralization resistant strain of HIV-1.

11. A method of producing a plurality of neutralizing anti-HIV polyclonal antibodies in a subject comprising administering an amount of a composition comprising the polypeptide of claim 1 or a stabilized trimer thereof to the subject, wherein the composition elicits the production of said neutralizing anti-HIV polyclonal antibodies in the subject.

12. The method of claim 11, wherein the method further comprises collecting the plurality of polyclonal antibodies from antisera of the subject.

13. A kit comprising the polypeptide of claim 1 or a stabilized trimer comprising the polypeptide, and, optionally, instructions for use.

14. The isolated polypeptide of claim 1, wherein the polypeptide of F):
   i) has at least 86%, 87%, 88%, 89%, 90%, 91%, 92%, 93%, 94%, 95%, 96%, 97%, 98%, 99%, or 100% sequence identity to the amino acid sequence of SEQ ID NO: 34; and/or
   ii) further comprises a sequence having at least 50, 100, 150, 200, 250, 300, 350, 400, 450, 500, 550, 600, 650, 700, or more consecutive amino acids of the sequence of SEQ ID NO: 2, or a variant thereof having a sequence with at least 92%, 93%, 94%, 95%, 96%, 97%, 98%, or 99% sequence identity to a sequence comprising at least 50, 100, 150, 200, 250, 300, 350, 400, 450, 500, 550, 600, 650, 700, or more consecutive amino acids of the sequence of SEQ ID NO: 2; and/or
   iii) further comprises:
      (a) an asparagine residue at position 33, a glutamic acid residue at position 49, an aspartic acid residue at position 130, and a lysine residue at position 132 relative residue to the sequence of HXB2 (GenBank Accession No. AF033819.3); and/or
      (b) an asparagine residue at position 156, a threonine residue at position 158, an asparagine residue at position 160, an isoleucine residue at position 161, a threonine residue at position 162, a threonine residue at position 163, a serine residue at position 164, a valine residue at position 165, a lysine residue at position 166, a glycine residue at position 167, a lysine residue at position 168, an arginine residue at position 169, a glutamine residue at position 170, a glutamine residue at position 171, a glutamic acid residue at position 172, and a histidine residue at position 173 relative to the sequence of HXB2 (GenBank Accession No. AF033819.3); and/or
      (c) a tyrosine residue at position 177, a tyrosine residue at position 223, a valine residue at position 297, a serine residue at position 306, a glutamic acid residue at position 322, a lysine residue at position 335, a serine residue at position 636, an arginine residue at position 644, and an asparagine residue at position 677 relative to the sequence of HXB2 (GenBank Accession No. AF033819.3).

15. The isolated polypeptide of claim 1, wherein the polypeptide of G):
   i) has at least 98%, 99%, or 100% sequence identity to the amino acid sequence of SEQ ID NO: 35;
   ii) further comprises a sequence having at least 50, 100, 150, 200, 250, 300, 350, 400, 450, 500, 550, 600, 650, 700, or more consecutive amino acids of the sequence of SEQ ID NO: 3, or a variant thereof having a sequence with at least 92%, 93%, 94%, 95%, 96%, 97%, 98%, or 99% sequence identity to a sequence comprising at least 50, 100, 150, 200, 250, 300, 350, 400, 450, 500, 550, 600, 650, 700, or more consecutive amino acids of the sequence of SEQ ID NO: 3; and/or
   iii) further comprises:
      (a) an aspartic acid residue at position 62, a valine residue at position 85, a lysine residue at position 160, a threonine residue at position 162, an isoleucine residue at position 184, a threonine residue at position 240, an asparagine residue at position 276, and a threonine residue at position 278 relative to the sequence of HXB2 (GenBank Accession No. AF033819.3); and/or
      (b) an asparagine residue at position 295, a threonine residue at position 297, a glycine residue at position 300, an asparagine residue at position 301, a threonine residue at position 303, an arginine residue at position 304, an isoleucine residue at position 307, an isoleucine residue at position 323, a glycine residue at position 324, an aspartic acid residue at position 325, an isoleucine residue at position 326, an arginine residue at position 327, a glutamine residue at position 328, a histidine residue at position 330, an asparagine residue at position 332, and a serine residue at position 334 relative to the sequence of HXB2 (GenBank Accession No. AF033819.3); and/or
      (c) an alanine residue at position 336, an asparagine residue at position 339, a threonine residue at position 341, a glutamine residue at position 344, an alanine residue at position 346, an asparagine residue at position 392, a threonine residue at position 394, and a serine residue at position 668 relative to the sequence of HXB2 (GenBank Accession No. AF033819.3).

16. The isolated polypeptide of claim 1, wherein the polypeptide of H):
   i) has at least 95%, 96%, 97%, 98%, 99%, or 100% sequence identity to the amino acid sequence of SEQ ID NO: 36; and/or
   ii) further comprises a sequence having at least 50, 100, 150, 200, 250, 300, 350, 400, 450, 500, 550, 600, 650, 700, or more consecutive amino acids of the sequence of SEQ ID NO: 4, or a variant thereof having a sequence with at least 92%, 93%, 94%, 95%, 96%, 97%, 98%, or 99% sequence identity to a sequence comprising at least 50, 100, 150, 200, 250, 300, 350, 400, 450, 500, 550, 600, 650, 700, or more consecutive amino acids of the sequence of SEQ ID NO: 4; and/or
   iii) further comprises:
      (a) an aspartic acid residue at position 62, a valine residue at position 85, an asparagine residue at position 160, a threonine residue at position 162, an isoleucine residue at position 184, a threonine residue at position 240, an asparagine residue at position 276, and a serine residue at position 278 relative to the sequence of HXB2 (GenBank Accession No. AF033819.3); and/or
      (b) a threonine residue at position 295, an isoleucine residue at position 297, a serine residue at position 300, an asparagine residue at position 301, a threonine residue at position 303, an arginine residue at position 304, a valine residue at position 307, an isoleucine residue at position 323, a glycine residue at position 324, an asparagine residue at position 325, an isoleucine residue at position 326, an arginine residue at position 327, a lysine residue at position 328, a tyrosine residue at position 330, a glutamic acid residue at position 332, and an asparagine residue at position 334 relative to the sequence of HXB2 (GenBank Accession No. AF033819.3); and/or
      (c) a threonine residue at position 336, an asparagine residue at position 339, a threonine residue at position 341, an asparagine residue at position 344, a serine residue at position 346, an asparagine residue at position 392, a serine residue at position 394, and a serine residue at position 668 relative to the sequence of HXB2 (GenBank Accession No. AF033819.3).

17. The isolated polypeptide of claim 1, wherein the polypeptide is A) or E) and comprises an amino acid sequence having at least 92%, 93%, 94%, 95%, 96%, 97%, 98%, 99%, or 100% sequence identity to the amino acid sequence of SEQ ID NO: 11 or 19.

18. The isolated polypeptide of claim 1, wherein the polypeptide is B) or F) and comprises an amino acid sequence having at least 92%, 93%, 94%, 95%, 96%, 97%, 98%, 99%, or 100% sequence identity to the amino acid sequence of SEQ ID NO: 12 or 20.

19. The isolated polypeptide of claim 1, wherein the polypeptide is C) or G) and comprises an amino acid sequence having at least 92%, 93%, 94%, 95%, 96%, 97%, 98%, 99%, or 100% sequence identity to the amino acid sequence of SEQ ID NO: 13 or 21.

20. The isolated polypeptide of claim 1, wherein the polypeptide is D) or H) and comprises an amino acid sequence having at least 92%, 93%, 94%, 95%, 96%, 97%, 98%, 99%, or 100% sequence identity to the amino acid sequence of SEQ ID NO: 14 or 22.

21. The composition of claim 6, wherein:
   A) the heterogeneous population of said stabilized trimers comprises two or more different stabilized trimers, wherein each polypeptide of the stabilized trimer in the heterologous population has the amino acid sequence of SEQ ID NO: 11, 12, 13, or 14, and/or further comprises one or more stabilized trimers comprising three polypeptides each of which has at least 90%, 91%, 92%, 93%, 94%, 95%, 96%, 97%, 98%, 99%, or 100% sequence identity to the amino acid sequence of SEQ ID NO: 16; or
   B) each polypeptide of the stabilized trimer in the homologous population has the amino acid sequence of SEQ ID NO: 11, 12, 13, or 14; or
   C) the population comprises one or more of three different stabilized trimers, wherein:
      i) a first said stabilized trimer comprises three polypeptides having at least 92%, 93%, 94%, 95%, 96%, 97%, 98%, 99%, or 100% sequence identity to the amino acid sequence of SEQ ID NO: 30, a second said stabilized trimer comprises three polypeptides having at least 92%, 93%, 94%, 95%, 96%, 97%, 98%, 99%, or 100% sequence identity to the amino acid sequence of SEQ ID NO: 31, and a third said stabilized trimer comprises three polypeptides having at least 92%, 93%, 94%, 95%, 96%, 97%, 98%, 99%, or 100% sequence identity to the amino acid sequence of SEQ ID NO: 32; or
      ii) a first said stabilized trimer comprises three polypeptides having at least 92%, 93%, 94%, 95%, 96%, 97%, 98%, 99%, or 100% sequence identity to the amino acid sequence of SEQ ID NO: 13, a second said stabilized trimer comprises three polypeptides having at least 92%, 93%, 94%, 95%, 96%, 97%, 98%, 99%, or 100% sequence identity to the amino acid sequence of SEQ ID NO: 14, and a third said stabilized trimer comprises three polypeptides having at least 92%, 93%, 94%, 95%, 96%, 97%, 98%, 99%, or 100% sequence identity to the amino acid sequence of SEQ ID NO: 16; or
   D) the population comprises one or more of two different stabilized trimers, wherein:
      i) a first said stabilized trimer comprises three polypeptides having at least 92%, 93%, 94%, 95%, 96%, 97%, 98%, 99%, or 100% sequence identity to the amino acid sequence of SEQ ID NO: 11 and a second said stabilized trimer comprises three polypeptides having at least 92%, 93%, 94%, 95%, 96%, 97%, 98%, 99%, or 100% sequence identity to the amino acid sequence of SEQ ID NO: 12; or
      ii) a first said stabilized trimer comprises three polypeptides having at least 92%, 93%, 94%, 95%, 96%, 97%, 98%, 99%, or 100% sequence identity to the amino acid sequence of SEQ ID NO: 13 and a second said stabilized trimer comprises three polypeptides having at least 92%, 93%, 94%, 95%, 96%, 97%, 98%, 99%, or 100% sequence identity to the amino acid sequence of SEQ ID NO: 14.

22. The composition of claim 6, wherein the composition comprises the polypeptide, and wherein the polypeptide comprises an amino acid sequence with at least 92% sequence identity to the amino acid sequence of any one of SEQ ID NOs: 11-14, 19-22, 33, and 34 or comprises an amino acid sequence with at least 99% sequence identity to the amino acid sequence of SEQ ID NO: 35 or 36.

23. The composition of claim 22, wherein the polypeptide comprises an amino acid sequence with at least 99% sequence identity to the amino acid sequence of any one of SEQ ID NOs: 11-14, 19-22, 33, and 34.

24. The composition of claim 22, wherein the polypeptide comprises an amino acid sequence with 100% sequence identity to the amino acid sequence of any one of SEQ ID NOs: 11-14, 19-22, and 33-36.

25. An immunogenic composition comprising the composition of claim 22.

26. An immunogenic composition comprising the composition of claim 23.

27. An immunogenic composition comprising the composition of claim 24.

28. A method of treating or reducing the risk of an HIV infection in a subject in need thereof comprising administering the immunogenic composition of claim 25 to the subject.

29. A method of treating or reducing the risk of an HIV infection in a subject in need thereof comprising administering the immunogenic composition of claim 26 to the subject.

30. A method of treating or reducing the risk of an HIV infection in a subject in need thereof comprising administering the immunogenic composition of claim 27 to the subject.

* * * * *

SEQUENCE LISTING

<160> NUMBER OF SEQ ID NOS: 46

<210> SEQ ID NO 1
<211> LENGTH: 645
<212> TYPE: PRT
<213> ORGANISM: Artificial Sequence
<220> FEATURE:
<223> OTHER INFORMATION: Synthetic construct

<400> SEQUENCE: 1

Val Gly Asn Leu Trp Val Thr Val Tyr Tyr Gly Val Pro Val Trp Arg
1               5                   10                  15

Glu Ala Lys Thr Thr Leu Phe Cys Ala Ser Asp Ala Lys Ala Tyr Asp
                20                  25                  30

Arg Glu Val His Asn Val Trp Ala Thr His Ala Cys Val Pro Thr Asp
            35                  40                  45

Pro Asn Pro Gln Glu Ile Val Leu Glu Asn Val Thr Glu Asn Phe Asn
        50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Glu Cys Thr Ala Phe Asn Ser Ser Ser His Thr Asn Ser
            100                 105                 110

Ser Ile Ala Met Gln Glu Met Lys Asn Cys Ser Phe Asn Met Thr Thr
        115                 120                 125

Glu Leu Arg Asp Lys Lys Lys Val Ser Ala Leu Phe Tyr Lys Leu
    130                 135                 140

Asp Ile Val Pro Leu Asn Lys Asn Gly Arg Gln Tyr Arg Leu Ile Asn
145                 150                 155                 160

Cys Asn Thr Ser Thr Leu Thr Gln Ala Cys Pro Lys Val Ser Phe Asp
                165                 170                 175

Pro Ile Pro Ile His Tyr Cys Thr Pro Ala Gly Tyr Ala Ile Leu Lys
            180                 185                 190

Cys Asn Asn Lys Thr Phe Asn Gly Thr Gly Pro Cys Asn Asn Val Ser
        195                 200                 205

Thr Val Gln Cys Thr His Gly Ile Lys Pro Val Val Ser Thr Gln Leu
    210                 215                 220

Leu Leu Asn Gly Ser Leu Ala Glu Glu Asp Ile Ile Arg Ser Glu
225                 230                 235                 240

Asn Leu Thr Asn Asn Ala Lys Thr Ile Ile Val His Leu Asn Glu Ser
                245                 250                 255

Val Glu Ile Val Cys Ile Arg Pro Asn Asn Asn Thr Arg Lys Ser Ile

```
            260                 265                 270
Arg Ile Gly Pro Gly Gln Thr Phe Tyr Ala Asn Asn Asp Ile Ile Gly
            275                 280                 285

Asp Ile Arg Gln Ala His Cys Asn Ile Ser Lys Glu Lys Trp Asn Asn
290                 295                 300

Thr Leu His Arg Val Trp Lys Lys Leu Val Glu His Phe Pro Asn Lys
305                 310                 315                 320

Thr Thr Ile Arg Phe Asp Arg His Ser Gly Gly Asp Leu Glu Ile Thr
                325                 330                 335

Thr His Ser Phe Asn Cys Gly Gly Glu Phe Phe Tyr Cys Asn Thr Ser
            340                 345                 350

Gly Leu Phe Asn Ile Thr Tyr Asn Ser Asn Tyr Thr Tyr Asn Asp Thr
        355                 360                 365

Lys His Asn Gly Thr Lys Val Ile Thr Leu Pro Cys Arg Ile Lys Gln
    370                 375                 380

Ile Ile Asn Met Trp Gln Glu Val Gly Arg Ala Met Tyr Ala Pro Pro
385                 390                 395                 400

Ile Ala Gly Asn Ile Thr Cys Thr Ser Asn Ile Thr Gly Leu Leu Leu
                405                 410                 415

Thr Arg Asp Gly Gly Asn Asn Ser Thr Glu Thr Glu Thr Phe Arg Pro
            420                 425                 430

Gly Gly Gly Asp Met Arg Asp Asn Trp Arg Ser Glu Leu Tyr Lys Tyr
        435                 440                 445

Lys Val Val Glu Ile Lys Pro Leu Gly Ile Ala Pro Thr Gly Ala Lys
    450                 455                 460

Arg Arg Val Val Glu Arg Glu Lys Arg Ala Val Gly Ile Gly Ala Val
465                 470                 475                 480

Phe Leu Gly Phe Leu Gly Ala Ala Gly Ser Thr Met Gly Ala Ala Ser
                485                 490                 495

Ile Thr Leu Thr Val Gln Ala Arg Gln Leu Leu Ser Gly Ile Val Gln
            500                 505                 510

Gln Gln Ser Asn Leu Leu Lys Ala Ile Glu Ala Gln Gln His Leu Leu
        515                 520                 525

Gln Leu Thr Val Trp Gly Ile Lys Gln Leu Gln Thr Arg Val Leu Ala
    530                 535                 540

Ile Glu Arg Tyr Leu Lys Asp Gln Gln Leu Leu Gly Leu Trp Gly Cys
545                 550                 555                 560

Ser Ala Lys Leu Ile Cys Thr Thr Ala Val Pro Trp Asn Ser Ser Trp
                565                 570                 575

Ser Asn Lys Ser Glu Thr Glu Ile Trp Asn Asn Met Thr Trp Met Gln
            580                 585                 590

Trp Asp Arg Glu Ile Ser Asn Tyr Thr Asn Thr Ile Tyr Arg Leu Leu
        595                 600                 605

Glu Glu Ser Gln Asn Gln Gln Glu Lys Asn Glu Asn Asp Leu Leu Ala
    610                 615                 620

Leu Asp Lys Trp Asn Ser Leu Trp Asp Trp Phe Gly Ile Ser Asn Trp
625                 630                 635                 640

Leu Trp Tyr Ile Arg
                645

<210> SEQ ID NO 2
<211> LENGTH: 645
<212> TYPE: PRT
<213> ORGANISM: Artificial Sequence
```

<220> FEATURE:
<223> OTHER INFORMATION: Synthetic construct

<400> SEQUENCE: 2

```
Val Gly Asn Leu Trp Val Thr Val Tyr Tyr Gly Val Pro Val Trp Arg
1               5                   10                  15

Glu Ala Glu Thr Thr Leu Phe Cys Ala Ser Asp Ala Lys Ala Tyr Asp
            20                  25                  30

Arg Glu Val His Asn Val Trp Ala Thr His Ala Cys Val Pro Thr Asp
        35                  40                  45

Pro Asn Pro Gln Glu Ile Val Leu Glu Asn Val Thr Glu Asn Phe Asn
    50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asp Cys Lys Ala Phe Asn Ser Ser His Thr Asn Ser
            100                 105                 110

Ser Ile Ala Met Gln Glu Met Lys Asn Cys Thr Phe Asn Ile Thr Thr
        115                 120                 125

Ser Val Lys Gly Lys Arg Gln Gln Glu His Ala Leu Phe Tyr Lys Leu
    130                 135                 140

Asp Ile Val Pro Leu Asn Lys Asn Gly Arg Gln Tyr Arg Leu Ile Asn
145                 150                 155                 160

Cys Asn Thr Ser Thr Leu Thr Gln Ala Cys Pro Lys Val Ser Phe Asp
                165                 170                 175

Pro Ile Pro Ile His Tyr Cys Thr Pro Ala Gly Tyr Ala Ile Leu Lys
            180                 185                 190

Cys Asn Asn Lys Thr Phe Asn Gly Thr Gly Pro Cys Asn Asn Val Ser
        195                 200                 205

Thr Val Gln Cys Thr His Gly Ile Lys Pro Val Val Ser Thr Gln Leu
    210                 215                 220

Leu Leu Asn Gly Ser Leu Ala Glu Glu Asp Ile Ile Ile Arg Ser Glu
225                 230                 235                 240

Asn Leu Thr Asn Asn Ala Lys Thr Ile Ile Val His Leu Asn Glu Ser
                245                 250                 255

Val Glu Ile Val Cys Val Arg Pro Asn Asn Asn Thr Arg Lys Ser Ile
            260                 265                 270

Arg Ile Gly Pro Gly Gln Thr Phe Tyr Ala Asn Asn Glu Ile Ile Gly
        275                 280                 285

Asp Ile Arg Gln Ala His Cys Asn Ile Ser Lys Glu Lys Trp Asn Asn
    290                 295                 300

Thr Leu His Arg Val Trp Lys Lys Leu Val Glu His Phe Pro Asn Lys
305                 310                 315                 320

Thr Thr Ile Arg Phe Asp Arg His Ser Gly Gly Asp Leu Glu Ile Thr
                325                 330                 335

Thr His Ser Phe Asn Cys Gly Gly Glu Phe Phe Tyr Cys Asn Thr Ser
            340                 345                 350

Gly Leu Phe Asn Ile Thr Tyr Asn Ser Asn Tyr Thr Tyr Asn Asp Thr
        355                 360                 365

Lys His Asn Gly Thr Lys Val Ile Thr Leu Pro Cys Arg Ile Lys Gln
    370                 375                 380

Ile Ile Asn Met Trp Gln Glu Val Gly Arg Ala Met Tyr Ala Pro Pro
385                 390                 395                 400
```

```
Ile Ala Gly Asn Ile Thr Cys Thr Ser Asn Ile Thr Gly Leu Leu Leu
                405                 410                 415

Thr Arg Asp Gly Gly Asn Asn Ser Thr Glu Thr Glu Thr Phe Arg Pro
            420                 425                 430

Gly Gly Gly Asp Met Arg Asp Asn Trp Arg Ser Glu Leu Tyr Lys Tyr
            435                 440                 445

Lys Val Val Glu Ile Lys Pro Leu Gly Ile Ala Pro Thr Gly Ala Lys
        450                 455                 460

Arg Arg Val Val Glu Arg Glu Lys Arg Ala Val Gly Ile Gly Ala Val
465                 470                 475                 480

Phe Leu Gly Phe Leu Gly Ala Ala Gly Ser Thr Met Gly Ala Ala Ser
                485                 490                 495

Ile Thr Leu Thr Val Gln Ala Arg Gln Leu Leu Ser Gly Ile Val Gln
            500                 505                 510

Gln Gln Ser Asn Leu Leu Lys Ala Ile Glu Ala Gln Gln His Leu Leu
        515                 520                 525

Gln Leu Thr Val Trp Gly Ile Lys Gln Leu Gln Thr Arg Val Leu Ala
    530                 535                 540

Ile Glu Arg Tyr Leu Lys Asp Gln Gln Leu Leu Gly Leu Trp Gly Cys
545                 550                 555                 560

Ser Ala Lys Leu Ile Cys Thr Thr Ala Val Pro Trp Asn Ser Ser Trp
                565                 570                 575

Ser Asn Lys Ser Glu Thr Glu Ile Trp Asn Asn Met Thr Trp Met Gln
            580                 585                 590

Trp Asp Arg Glu Ile Ser Asn Tyr Thr Asn Thr Ile Tyr Arg Leu Leu
        595                 600                 605

Glu Glu Ser Gln Asn Gln Gln Glu Lys Asn Glu Asn Asp Leu Leu Ala
    610                 615                 620

Leu Asp Lys Trp Asn Ser Leu Trp Asp Trp Phe Gly Ile Ser Asn Trp
625                 630                 635                 640

Leu Trp Tyr Ile Arg
                645

<210> SEQ ID NO 3
<211> LENGTH: 645
<212> TYPE: PRT
<213> ORGANISM: Artificial Sequence
<220> FEATURE:
<223> OTHER INFORMATION: Synthetic construct

<400> SEQUENCE: 3

Val Gly Asn Leu Trp Val Thr Val Tyr Tyr Gly Val Pro Val Trp Arg
1               5                   10                  15

Glu Ala Lys Thr Thr Leu Phe Cys Ala Ser Asp Ala Lys Ala Tyr Asp
            20                  25                  30

Arg Glu Val His Asn Val Trp Ala Thr His Ala Cys Val Pro Thr Asp
        35                  40                  45

Pro Asn Pro Gln Glu Ile Val Leu Glu Asn Val Thr Glu Asn Phe Asn
    50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Ala Phe Asn Ser Ser Ser His Thr Asn Ser
            100                 105                 110
```

```
Ser Ile Ala Met Gln Glu Met Lys Asn Cys Ser Phe Lys Ala Thr Thr
            115                 120                 125

Glu Ile Arg Asp Arg Lys Lys Glu Met Tyr Ala Leu Phe Tyr Lys Leu
    130                 135                 140

Asp Ile Val Pro Ile Asn Lys Asn Gly Arg Gln Tyr Arg Leu Ile Asn
145                 150                 155                 160

Cys Asn Thr Ser Thr Leu Thr Gln Ala Cys Pro Lys Val Ser Phe Asp
                165                 170                 175

Pro Ile Pro Ile His Tyr Cys Thr Pro Ala Gly Phe Ala Ile Leu Lys
            180                 185                 190

Cys Asn Asn Lys Thr Phe Asn Gly Thr Gly Pro Cys Thr Asn Val Ser
            195                 200                 205

Thr Val Gln Cys Thr His Gly Ile Lys Pro Val Val Ser Thr Gln Leu
    210                 215                 220

Leu Leu Asn Gly Ser Leu Ala Glu Glu Asp Ile Ile Arg Ser Glu
225                 230                 235                 240

Asn Leu Thr Asn Asn Ala Lys Thr Ile Ile Val His Leu Asn Glu Ser
                245                 250                 255

Val Glu Ile Asn Cys Thr Arg Pro Gly Asn Asn Thr Arg Lys Ser Ile
            260                 265                 270

Arg Ile Gly Pro Gly Gln Thr Phe Tyr Ala Asn Asn Asp Ile Ile Gly
    275                 280                 285

Asp Ile Arg Gln Ala His Cys Asn Ile Ser Glu Ala Lys Trp Asn Asn
            290                 295                 300

Thr Leu His Gln Val Ala Lys Lys Leu Val Glu His Phe Pro Asn Lys
305                 310                 315                 320

Thr Thr Ile Arg Phe Asp Arg His Ser Gly Gly Asp Leu Glu Ile Thr
                325                 330                 335

Thr His Ser Phe Asn Cys Gly Gly Glu Phe Phe Tyr Cys Asn Thr Ser
            340                 345                 350

Gly Leu Phe Asn Ile Thr Tyr Asn Ser Asn Tyr Thr Tyr Asn Asp Thr
    355                 360                 365

Lys His Asn Gly Thr Lys Val Ile Thr Leu Pro Cys Arg Ile Lys Gln
    370                 375                 380

Ile Ile Asn Met Trp Gln Glu Val Gly Arg Ala Met Tyr Ala Pro Pro
385                 390                 395                 400

Ile Ala Gly Asn Ile Thr Cys Thr Ser Asn Ile Thr Gly Leu Leu Leu
                405                 410                 415

Thr Arg Asp Gly Gly Asn Asn Ser Thr Glu Thr Glu Thr Phe Arg Pro
            420                 425                 430

Gly Gly Gly Asp Met Arg Asp Asn Trp Arg Ser Glu Leu Tyr Lys Tyr
            435                 440                 445

Lys Val Val Glu Ile Lys Pro Leu Gly Ile Ala Pro Thr Gly Ala Lys
    450                 455                 460

Arg Arg Val Val Glu Arg Glu Lys Arg Ala Val Gly Ile Gly Ala Val
465                 470                 475                 480

Phe Leu Gly Phe Leu Gly Ala Ala Gly Ser Thr Met Gly Ala Ala Ser
                485                 490                 495

Ile Thr Leu Thr Val Gln Ala Arg Gln Leu Leu Ser Gly Ile Val Gln
            500                 505                 510

Gln Gln Ser Asn Leu Leu Lys Ala Ile Glu Ala Gln Gln His Leu Leu
            515                 520                 525
```

```
Gln Leu Thr Val Trp Gly Ile Lys Gln Leu Gln Thr Arg Val Leu Ala
            530                 535                 540

Ile Glu Arg Tyr Leu Lys Asp Gln Gln Leu Leu Gly Leu Trp Gly Cys
545                 550                 555                 560

Ser Ala Lys Leu Ile Cys Thr Thr Ala Val Pro Trp Asn Ser Ser Trp
                565                 570                 575

Ser Asn Lys Ser Glu Thr Glu Ile Trp Asn Asn Met Thr Trp Met Gln
                580                 585                 590

Trp Asp Arg Glu Ile Asn Asn Tyr Thr Asn Thr Ile Tyr Arg Leu Leu
            595                 600                 605

Glu Glu Ser Gln Asn Gln Gln Glu Lys Asn Glu Asn Asp Leu Leu Ala
            610                 615                 620

Leu Asp Lys Trp Asn Ser Leu Trp Asp Trp Phe Gly Ile Ser Asn Trp
625                 630                 635                 640

Leu Trp Tyr Ile Arg
                645

<210> SEQ ID NO 4
<211> LENGTH: 645
<212> TYPE: PRT
<213> ORGANISM: Artificial Sequence
<220> FEATURE:
<223> OTHER INFORMATION: Synthetic construct

<400> SEQUENCE: 4

Val Gly Asn Leu Trp Val Thr Val Tyr Tyr Gly Val Pro Val Trp Arg
1               5                   10                  15

Glu Ala Lys Thr Thr Leu Phe Cys Ala Ser Asp Ala Lys Ala Tyr Asp
                20                  25                  30

Arg Glu Val His Asn Val Trp Ala Thr His Ala Cys Val Pro Thr Asp
            35                  40                  45

Pro Asn Pro Gln Glu Ile Val Leu Glu Asn Val Thr Glu Asn Phe Asn
        50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Ala Phe Asn Ser Ser Ser His Thr Asn Ser
                100                 105                 110

Ser Ile Ala Met Gln Glu Met Lys Asn Cys Ser Phe Asn Ala Thr Thr
            115                 120                 125

Glu Ile Arg Asp Arg Lys Lys Glu Met Tyr Ala Leu Phe Tyr Lys Leu
        130                 135                 140

Asp Ile Val Pro Ile Asn Lys Asn Gly Arg Gln Tyr Arg Leu Ile Asn
145                 150                 155                 160

Cys Asn Thr Ser Thr Leu Thr Gln Ala Cys Pro Lys Val Ser Phe Asp
                165                 170                 175

Pro Ile Pro Ile His Tyr Cys Thr Pro Ala Gly Phe Ala Ile Leu Lys
                180                 185                 190

Cys Asn Asn Lys Thr Phe Asn Gly Thr Gly Pro Cys Thr Asn Val Ser
            195                 200                 205

Thr Val Gln Cys Thr His Gly Ile Lys Pro Val Val Ser Thr Gln Leu
        210                 215                 220

Leu Leu Asn Gly Ser Leu Ala Glu Glu Asp Ile Ile Ile Arg Ser Glu
225                 230                 235                 240
```

```
Asn Leu Ser Asn Asn Ala Lys Thr Ile Ile Val His Leu Asn Glu Ser
                245                 250                 255
Val Glu Ile Thr Cys Ile Arg Pro Ser Asn Asn Thr Arg Lys Ser Val
            260                 265                 270
Arg Ile Gly Pro Gly Gln Thr Phe Tyr Ala Asn Asn Asp Ile Ile Gly
        275                 280                 285
Asn Ile Arg Lys Ala Tyr Cys Glu Ile Asn Glu Thr Lys Trp Asn Asn
    290                 295                 300
Thr Leu His Asn Val Ser Lys Lys Leu Val Glu His Phe Pro Asn Lys
305                 310                 315                 320
Thr Thr Ile Arg Phe Asp Arg His Ser Gly Gly Asp Leu Glu Ile Thr
                325                 330                 335
Thr His Ser Phe Asn Cys Gly Gly Glu Phe Phe Tyr Cys Asn Thr Ser
            340                 345                 350
Gly Leu Phe Asn Ile Ser Tyr Asn Ser Asn Tyr Thr Tyr Asn Asp Thr
        355                 360                 365
Lys His Asn Gly Thr Lys Val Ile Thr Leu Pro Cys Arg Ile Lys Gln
    370                 375                 380
Ile Ile Asn Met Trp Gln Glu Val Gly Arg Ala Met Tyr Ala Pro Pro
385                 390                 395                 400
Ile Ala Gly Asn Ile Thr Cys Thr Ser Asn Ile Thr Gly Leu Leu Leu
                405                 410                 415
Thr Arg Asp Gly Gly Asn Asn Ser Thr Glu Thr Glu Thr Phe Arg Pro
            420                 425                 430
Gly Gly Gly Asp Met Arg Asp Asn Trp Arg Ser Glu Leu Tyr Lys Tyr
        435                 440                 445
Lys Val Val Glu Ile Lys Pro Leu Gly Ile Ala Pro Thr Gly Ala Lys
    450                 455                 460
Arg Arg Val Val Glu Arg Glu Lys Arg Ala Val Gly Ile Gly Ala Val
465                 470                 475                 480
Phe Leu Gly Phe Leu Gly Ala Ala Gly Ser Thr Met Gly Ala Ala Ser
                485                 490                 495
Ile Thr Leu Thr Val Gln Ala Arg Gln Leu Leu Ser Gly Ile Val Gln
            500                 505                 510
Gln Gln Ser Asn Leu Leu Lys Ala Ile Glu Ala Gln Gln His Leu Leu
        515                 520                 525
Gln Leu Thr Val Trp Gly Ile Lys Gln Leu Gln Thr Arg Val Leu Ala
    530                 535                 540
Ile Glu Arg Tyr Leu Lys Asp Gln Gln Leu Leu Gly Leu Trp Gly Cys
545                 550                 555                 560
Ser Ala Lys Leu Ile Cys Thr Thr Ala Val Pro Trp Asn Ser Ser Trp
                565                 570                 575
Ser Asn Lys Ser Glu Thr Glu Ile Trp Asn Asn Met Thr Trp Met Gln
            580                 585                 590
Trp Asp Arg Glu Ile Asn Asn Tyr Thr Asn Thr Ile Tyr Arg Leu Leu
        595                 600                 605
Glu Glu Ser Gln Asn Gln Gln Glu Lys Asn Glu Asn Asp Leu Leu Ala
    610                 615                 620
Leu Asp Lys Trp Asn Ser Leu Trp Asp Trp Phe Gly Ile Ser Asn Trp
625                 630                 635                 640
Leu Trp Tyr Ile Arg
                645
```

```
<210> SEQ ID NO 5
<211> LENGTH: 37
<212> TYPE: PRT
<213> ORGANISM: Artificial Sequence
<220> FEATURE:
<223> OTHER INFORMATION: Synthetic construct

<400> SEQUENCE: 5

Ser Arg Ile Glu Gly Arg Gly Ser Gly Gly Tyr Ile Pro Glu Ala Pro
1               5                   10                  15

Arg Asp Gly Gln Ala Tyr Val Arg Lys Asp Gly Glu Trp Val Leu Leu
            20                  25                  30

Ser Thr Phe Leu Gly
        35

<210> SEQ ID NO 6
<211> LENGTH: 111
<212> TYPE: DNA
<213> ORGANISM: Artificial Sequence
<220> FEATURE:
<223> OTHER INFORMATION: Synthetic construct

<400> SEQUENCE: 6
tcccggatcg agggcagagg cagcggaggc tatattcccg aggcccccag agatggccag      60
gcctacgtgc ggaaagatgg cgagtgggtg ctgctgagta ccttcctggg c              111

<210> SEQ ID NO 7
<211> LENGTH: 1935
<212> TYPE: DNA
<213> ORGANISM: Artificial Sequence
<220> FEATURE:
<223> OTHER INFORMATION: Synthetic construct

<400> SEQUENCE: 7
gtgggcaacc tgtgggtcac cgtgtactat ggcgtgcccg tgtggcggga agccaagacc      60
acactgttct gtgccagcga cgccaaggcc tacgaccgcg aggtgcacaa tgtgtgggcc     120
acccatgcct gcgtgcccac cgatcccaac ccccaggaaa tcgtgctgga aaacgtgacc     180
gagaacttca acatgtggaa gaacgacatg gtggaccaga tgcacgagga catcatcagc     240
ctgtgggacc agagcctgaa gccctgcgtg aagctgaccc ctctgtgcgt gaccctggaa     300
tgcaccgcct tcaacagcag cagccacacc aacagctcta tcgccatgca ggaaatgaag     360
aactgcagct tcaatatgac caccgagctg cgggacaaga aaagaaggt gtccgccctg      420 ttctacaagc tggacatcgt gcccctgaac aagaacggcc ggcagtaccg gctgatcaac     480
tgcaacacca gcaccctgac ccaggcctgc cccaaggtgt ccttcgaccc catccccatc     540
cactactgta cccctgccgg ctacgccatc ctgaagtgca acaacaagac cttcaacggc     600
accggcccct gcaacaacgt gtccaccgtg cagtgtaccc acggcatcaa gcccgtggtg     660
tccacccagc tgctgctgaa tggcagcctg gccgaggaag atatcatcat cagaagcgag     720
aacctgacca caacgccaa gacaatcatt gtgcatctga cgagagcgt ggaaattgtg       780 tgcatccggc caacaacaa caccagaaag agcatccgga tcggccctgg ccagaccttc     840
tacgccaaca cgacatcat cggcgacatc cggcaggccc actgcaatat cagcaaagag     900
aagtggaaca ataccctgca ccgcgtgtgg aaaaagctgg tggaacactt ccctaacaag     960
accaccatca gattcgaccg gcactctggc ggcgacctgg aaatcaccac ccacagcttc    1020
aactgtggcg gcgagttctt ctactgcaat acctccggcc tgttcaacat cacctacaac    1080
agcaactaca cctacaatga caccaagcac aacgggacca agtgatcac cctgccctgc    1140
```

```
agaatcaagc agatcattaa catgtggcag gaagtgggca gggctatgta cgcccctcct   1200
atcgccggca acatcacatg caccagcaat atcaccggcc tgctgctgac cagggacggc   1260
ggcaacaata gcaccgagac agagacattc agacccggcg gaggcgacat gagagacaac   1320
tggcggagcg agctgtacaa gtacaaggtg gtggaaatca agcccctggg aatcgcccct   1380
accggcgcca agagaagagt ggtggaacgc gagaagcggg ccgtgggaat cggagccgtg   1440
ttcctgggat ttctgggagc cgccggaagc acaatgggcg ctgccagcat cacccctgaca  1500 gtgcaggcta gacagctgct gagcggcatc gtgcagcagc agagcaacct gctgaaggcc   1560
atcgaggccc agcagcatct gctgcagctg accgtgtggg ggatcaagca gctgcagacc   1620
agagtgctgg ccattgagag atacctgaag gaccagcagc tgctgggcct gtggggctgt   1680
tctgccaagc tgatctgtac caccgccgtg ccttggaaca gctcctggtc caacaagagc   1740
gaaaccgaga tctggaacaa catgacctgg atgcagtggg acagagagat cagcaattac   1800
accaacacca tctaccggct gctggaagag agccagaacc agcaggaaaa gaacgagaac   1860
gacctgctgg ccctggacaa gtggaactcc ctgtgggatt ggttcggcat cagcaactgg   1920
ctgtggtaca tccgg                                                    1935

<210> SEQ ID NO 8
<211> LENGTH: 1935
<212> TYPE: DNA
<213> ORGANISM: Artificial Sequence
<220> FEATURE:
<223> OTHER INFORMATION: Synthetic construct

<400> SEQUENCE: 8
gtgggcaacc tgtgggtcac cgtgtactat ggcgtgcccg tgtggcggga agccgagaca     60
acactgttct gtgccagcga cgccaaggcc tacgaccgcg aggtgcacaa tgtgtgggcc    120
acccatgcct gcgtgcccac cgatcccaac ccccaggaaa tcgtgctgga aaacgtgacc    180
gagaacttca acatgtggaa gaacgacatg gtggaccaga tgcacgagga catcatcagc    240
ctgtgggacc agagcctgaa gccctgcgtg aagctgaccc ctctgtgcgt gaccctggac    300
tgcaaggcct tcaacagcag cagccacacc aacagctcta tcgccatgca ggaaatgaag    360
aactgcacct tcaacatcac caccagcgtg aagggcaagc ggcagcagga cacgccctg     420 ttctacaagc tggacatcgt gccctgaac aagaacggcc ggcagtaccg gctgatcaac    480
tgcaacacca gcaccctgac ccaggcctgc cccaaggtgt ccttcgaccc catccccatc    540
cactactgta cccctgccgg ctacgccatc ctgaagtgca caacaagac cttcaacggc    600 accggcccct gcaacaacgt gtccaccgtg cagtgtaccc acggcatcaa gcccgtggtg    660
tccacccagc tgctgctgaa tggcagcctg gccgaggaag atatcatcat cagaagcgag    720
aacctgacca caacgccaa gaccatcatt gtgcatctga cgagagcgt ggaaattgtg     780 tgcgtgcggc caacaacaa caccagaaag agcatccgga tcggccctgg ccagaccttc    840
tacgccaaca acgagatcat cggcgacatc cggcaggccc actgcaatat cagcaaagag    900
aagtggaaca tacccctgca ccgcgtgtgg aaaaagctgg tggaacactt ccctaacaag    960
accaccatca gattcgaccg gcactctggc ggcgacctgg aaatcaccac ccacagcttc   1020
aactgtggcg gcgagttctt ctactgcaat acctccggcc tgttcaatat cacctacaac   1080
agcaactaca cctacaatga caccaagcac aacgggacca agtgatcac cctgccctgc   1140 agaatcaagc agatcattaa catgtggcag gaagtgggca gggctatgta cgcccctcct   1200
```

| | |
|---|---|
| atcgccggca acatcacatg caccagcaac attaccggcc tgctgctgac cagggacggc | 1260 |
| ggcaacaata gcaccgagac agagacattc agacccggcg gaggcgacat gagagacaac | 1320 |
| tggcggagcg agctgtacaa gtacaaggtg gtggaaatca agccctggg aatcgcccct | 1380 |
| accggcgcca agagaagagt ggtggaacgc gagaagcggg ccgtgggaat cggagccgtg | 1440 |
| tttctgggct ttctgggagc cgccggaagc acaatgggcg ctgccagcat caccctgaca | 1500 |
| gtgcaggcta gacagctgct gagcggcatc gtgcagcagc agagcaacct gctgaaggcc | 1560 |
| atcgaggccc agcagcatct gctgcagctg accgtgtggg ggatcaagca gctgcagacc | 1620 |
| agagtgctgg ccattgagag atacctgaag gaccagcagc tgctgggcct gtggggctgt | 1680 |
| tctgccaagc tgatctgtac caccgccgtg ccttggaaca gctcctggtc caacaagagc | 1740 |
| gaaaccgaga tctggaacaa catgacctgg atgcagtggg acagagagat cagcaattac | 1800 |
| accaacacca tctacaggct gctggaagag agccagaacc agcaggaaaa gaacgagaac | 1860 |
| gacctgctgg ccctggacaa gtggaactcc ctgtgggatt ggttcggcat cagcaactgg | 1920 |
| ctgtggtaca tccgg | 1935 |

<210> SEQ ID NO 9
<211> LENGTH: 1935
<212> TYPE: DNA
<213> ORGANISM: Artificial Sequence
<220> FEATURE:
<223> OTHER INFORMATION: Synthetic construct

<400> SEQUENCE: 9

| | |
|---|---|
| gtgggcaacc tgtgggtcac cgtgtactat ggcgtgcccg tgtggcggga agccaagacc | 60 |
| acactgttct gtgccagcga cgccaaggcc tacgaccgcg aggtgcacaa tgtgtgggcc | 120 |
| acccatgcct gcgtgcccac cgatcccaac ccccaggaaa tcgtgctgga aaacgtgacc | 180 |
| gagaacttca acatgtggaa gaacgacatg gtggaccaga tgcacgagga catcatcagc | 240 |
| ctgtgggacc agagcctgaa gccctgcgtg aagctgaccc ctctgtgcgt gaccctgaac | 300 |
| tgcaccgcct tcaacagcag cagccacacc aacagctcta tcgccatgca ggaaatgaag | 360 |
| aactgcagct tcaaggccac caccgagatc cgggaccgga gaaagagat gtacgccctg | 420 |
| ttctacaagc tggacatcgt gcccatcaac aagaacggcc ggcagtaccg gctgatcaac | 480 |
| tgcaacacca gcaccctgac ccaggcctgc cccaaggtgt ccttcgaccc catccccatc | 540 |
| cactactgta cccctgccgg cttcgccatc ctgaagtgca acaacaagac cttcaacggc | 600 |
| accggcccct gcaccaacgt gtccaccgtg cagtgtaccc acggcatcaa gcccgtggtg | 660 |
| tccacccagc tgctgctgaa tggcagcctg gccgaggaag atatcatcat cagaagcgag | 720 |
| aacctgacca caacgccaa gacaatcatc gtgcacctga cgagagcgt ggaaatcaat | 780 |
| tgcaccagac ccggcaacaa caccagaaag agcatccgga tcggccctgg ccagaccttc | 840 |
| tacgccaaca cgacatcat cggcgacatc cggcaggccc actgcaacat ctctgaggcc | 900 |
| aagtggaaca acacactgca ccaggtggcc aagaaactgg tggaacactt ccctaacaag | 960 |
| accaccatca gattcgaccg gcactctggc ggcgacctgg aaatcaccac ccacagcttc | 1020 |
| aactgtggcg gcgagttctt ctactgcaat acctccggcc tgttcaacat cacctacaac | 1080 |
| agcaactaca cctacaatga caccaagcac aacgggacca agtgatcac cctgccctgc | 1140 |
| agaatcaagc agatcattaa catgtggcag gaagtgggca gggctatgta tgcccctcct | 1200 |
| atcgccggca acattacctg caccagcaat atcaccggcc tgctgctgac cagggacggc | 1260 |
| ggcaacaata gcaccgagac agagacattc cggcctggcg gcggagacat gagagacaat | 1320 |

```
tggcggagcg agctgtacaa gtacaaggtg gtggaaatca agcccctggg aatcgcccct      1380
accggcgcca agagaagagt ggtggaacgc gagaagcggg ccgtgggaat cggagccgtg      1440
ttcctgggat ttctgggagc cgccggaagc acaatgggcg ctgccagcat caccctgaca      1500
gtgcaggcta gacagctgct gagcggcatc gtgcagcagc agagcaacct gctgaaggcc      1560
atcgaggccc agcagcatct gctgcagctg accgtgtggg ggatcaagca gctgcagacc      1620
agagtgctgg ccattgagag ataccctgaag gaccagcagc tgctgggcct gtggggctgt     1680
tctgccaagc tgatctgtac caccgccgtg ccttggaaca gctcctggtc caacaagagc      1740
gaaaccgaga tctggaacaa tatgacatgg atgcagtggg accgcgagat caacaattac      1800
accaacacca tctaccggct gctggaagag agccagaacc agcaggaaaa gaacgagaac      1860
gacctgctgg ccctggacaa gtggaactcc ctgtgggatt ggttcggcat cagcaactgg      1920
ctgtggtaca tccgc                                                      1935

<210> SEQ ID NO 10
<211> LENGTH: 1935
<212> TYPE: DNA
<213> ORGANISM: Artificial Sequence
<220> FEATURE:
<223> OTHER INFORMATION: Synthetic construct

<400> SEQUENCE: 10
gtgggcaacc tgtgggtcac cgtgtactat ggcgtgcccg tgtggcggga agccaagacc        60
acactgttct gtgccagcga cgccaaggcc tacgaccgcg aggtgcacaa tgtgtgggcc       120
acccatgcct gcgtgcccac cgatcccaac ccccaggaaa tcgtgctgga aaacgtgacc       180
gagaacttca acatgtggaa gaacgacatg gtggaccaga tgcacgagga catcatcagc       240
ctgtgggacc agagcctgaa gccctgcgtg aagctgaccc ctctgtgcgt gaccctgaac       300
tgcaccgcct tcaacagcag cagccacacc aacagctcta cgccatgca ggaaatgaag        360 aactgcagct tcaacgccac caccgagatc cgggaccgga agaaagagat gtacgccctg       420
ttctacaagc tggacatcgt gcccatcaac aagaacggcc ggcagtaccg gctgatcaac       480
tgcaacacca gcaccctgac ccaggcctgc cccaaggtgt ccttcgaccc catccccatc       540
cactactgta cccctgccgg cttcgccatc ctgaagtgca acaacaagac cttcaacggc       600
accggcccct gcaccaacgt gtccaccgtg cagtgtaccc acggcatcaa gcccgtggtg       660
tccacccagc tgctgctgaa tggcagcctg gccgaggaag atatcatcat cagaagcgag       720
aacctgagca caacgccaa gacaatcatc gtgcacctga cgagagcgt ggaaatcacc         780 tgtatccggc ccagcaacaa caccagaaag agcgtgcgga tcggccctgg ccagaccttc       840
tacgccaaca cgacatcat cggcaacatc cggaaggcct actgcgagat caacgagaca        900
aagtggaaca cacactgca taatgtgtcc aagaaactgg tggaacactt ccctaacaag        960
accaccatca gattcgaccg gcactctggc ggcgacctgg aaattaccac ccacagcttc      1020
aattgtggcg gcgagttctt ctactgcaat acctccggcc tgttcaacat cagctacaac      1080
agcaactaca cctacaacga caccaagcac acgggaccaa agtgatcac cctgccctgc       1140 cggatcaagc agatcattaa catgtggcag gaagtgggca gggctatgta tgcccctcct      1200
atcgccggca acattacctg cacctccaac atcaccggcc tgctgctgac cagagatggc      1260
ggcaacaact ccaccgagac agagacattc agacccggcg aggcgacat gagagacaac      1320 tggcggagcg agctgtacaa gtacaaggtg gtggaaatca agcccctggg aatcgcccct     1380
```

-continued

```
accggcgcca agagaagagt ggtggaacgc gagaagcggg ccgtgggaat cggagccgtg    1440
ttcctgggat ttctgggagc cgccggaagc acaatgggcg ctgccagcat caccctgaca    1500
gtgcaggcta gacagctgct gagcggcatc gtgcagcagc agagcaacct gctgaaggcc    1560
atcgaggccc agcagcatct gctgcagctg accgtgtggg gaatcaagca gctgcagaca    1620
cgggtgctgg ccattgagag atacctgaag gaccagcagc tgctgggcct gtggggctgt    1680
tctgccaagc tgatctgtac caccgccgtg ccctggaaca gctcctggtc aacaagagc     1740 gaaaccgaga tctggaacaa tatgacctgg atgcagtggg accgggaaat caacaattac    1800
accaacacca tctaccggct gctggaagag agccagaacc agcaggaaaa gaacgagaac    1860
gacctgctgg ccctggacaa gtggaactcc ctgtgggatt ggttcggcat cagcaactgg    1920
ctgtggtaca tccgc                                                     1935
```

<210> SEQ ID NO 11
<211> LENGTH: 688
<212> TYPE: PRT
<213> ORGANISM: Artificial Sequence
<220> FEATURE:
<223> OTHER INFORMATION: Synthetic construct

<400> SEQUENCE: 11

```
Val Gly Asn Leu Trp Val Thr Val Tyr Tyr Gly Val Pro Val Trp Arg
1               5                   10                  15

Glu Ala Lys Thr Thr Leu Phe Cys Ala Ser Asp Ala Lys Ala Tyr Asp
            20                  25                  30

Arg Glu Val His Asn Val Trp Ala Thr His Ala Cys Val Pro Thr Asp
        35                  40                  45

Pro Asn Pro Gln Glu Ile Val Leu Glu Asn Val Thr Glu Asn Phe Asn
    50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Glu Cys Thr Ala Phe Asn Ser Ser Ser His Thr Asn Ser
            100                 105                 110

Ser Ile Ala Met Gln Glu Met Lys Asn Cys Ser Phe Asn Met Thr Thr
        115                 120                 125

Glu Leu Arg Asp Lys Lys Lys Val Ser Ala Leu Phe Tyr Lys Leu
    130                 135                 140

Asp Ile Val Pro Leu Asn Lys Asn Gly Arg Gln Tyr Arg Leu Ile Asn
145                 150                 155                 160

Cys Asn Thr Ser Thr Leu Thr Gln Ala Cys Pro Lys Val Ser Phe Asp
                165                 170                 175

Pro Ile Pro Ile His Tyr Cys Thr Pro Ala Gly Tyr Ala Ile Leu Lys
            180                 185                 190

Cys Asn Asn Lys Thr Phe Asn Gly Thr Gly Pro Cys Asn Asn Val Ser
        195                 200                 205

Thr Val Gln Cys Thr His Gly Ile Lys Pro Val Val Ser Thr Gln Leu
    210                 215                 220

Leu Leu Asn Gly Ser Leu Ala Glu Glu Asp Ile Ile Arg Ser Glu
225                 230                 235                 240

Asn Leu Thr Asn Asn Ala Lys Thr Ile Ile Val His Leu Asn Glu Ser
                245                 250                 255

Val Glu Ile Val Cys Ile Arg Pro Asn Asn Asn Thr Arg Lys Ser Ile
```

```
                260                 265                 270
Arg Ile Gly Pro Gly Gln Thr Phe Tyr Ala Asn Asn Asp Ile Ile Gly
            275                 280                 285
Asp Ile Arg Gln Ala His Cys Asn Ile Ser Lys Glu Lys Trp Asn Asn
290                 295                 300
Thr Leu His Arg Val Trp Lys Lys Leu Val Glu His Phe Pro Asn Lys
305                 310                 315                 320
Thr Thr Ile Arg Phe Asp Arg His Ser Gly Gly Asp Leu Glu Ile Thr
                325                 330                 335
Thr His Ser Phe Asn Cys Gly Gly Glu Phe Phe Tyr Cys Asn Thr Ser
                340                 345                 350
Gly Leu Phe Asn Ile Thr Tyr Asn Ser Asn Tyr Thr Tyr Asn Asp Thr
                355                 360                 365
Lys His Asn Gly Thr Lys Val Ile Thr Leu Pro Cys Arg Ile Lys Gln
            370                 375                 380
Ile Ile Asn Met Trp Gln Glu Val Gly Arg Ala Met Tyr Ala Pro Pro
385                 390                 395                 400
Ile Ala Gly Asn Ile Thr Cys Thr Ser Asn Ile Thr Gly Leu Leu Leu
                405                 410                 415
Thr Arg Asp Gly Gly Asn Asn Ser Thr Glu Thr Glu Thr Phe Arg Pro
                420                 425                 430
Gly Gly Gly Asp Met Arg Asp Asn Trp Arg Ser Glu Leu Tyr Lys Tyr
                435                 440                 445
Lys Val Val Glu Ile Lys Pro Leu Gly Ile Ala Pro Thr Gly Ala Lys
            450                 455                 460
Arg Arg Val Val Glu Arg Glu Lys Arg Ala Val Gly Ile Gly Ala Val
465                 470                 475                 480
Phe Leu Gly Phe Leu Gly Ala Ala Gly Ser Thr Met Gly Ala Ala Ser
                485                 490                 495
Ile Thr Leu Thr Val Gln Ala Arg Gln Leu Leu Ser Gly Ile Val Gln
                500                 505                 510
Gln Gln Ser Asn Leu Leu Lys Ala Ile Glu Ala Gln Gln His Leu Leu
            515                 520                 525
Gln Leu Thr Val Trp Gly Ile Lys Gln Leu Gln Thr Arg Val Leu Ala
            530                 535                 540
Ile Glu Arg Tyr Leu Lys Asp Gln Gln Leu Leu Gly Leu Trp Gly Cys
545                 550                 555                 560
Ser Ala Lys Leu Ile Cys Thr Thr Ala Val Pro Trp Asn Ser Ser Trp
                565                 570                 575
Ser Asn Lys Ser Glu Thr Glu Ile Trp Asn Asn Met Thr Trp Met Gln
                580                 585                 590
Trp Asp Arg Glu Ile Ser Asn Tyr Thr Asn Thr Ile Tyr Arg Leu Leu
                595                 600                 605
Glu Glu Ser Gln Asn Gln Gln Glu Lys Asn Glu Asn Asp Leu Leu Ala
            610                 615                 620
Leu Asp Lys Trp Asn Ser Leu Trp Asp Trp Phe Gly Ile Ser Asn Trp
625                 630                 635                 640
Leu Trp Tyr Ile Arg Ser Arg Ile Glu Gly Arg Gly Ser Gly Gly Tyr
                645                 650                 655
Ile Pro Glu Ala Pro Arg Asp Gly Gln Ala Tyr Val Arg Lys Asp Gly
                660                 665                 670
Glu Trp Val Leu Leu Ser Thr Phe Leu Gly His His His His His His
            675                 680                 685
```

```
<210> SEQ ID NO 12
<211> LENGTH: 688
<212> TYPE: PRT
<213> ORGANISM: Artificial Sequence
<220> FEATURE:
<223> OTHER INFORMATION: Synthetic construct

<400> SEQUENCE: 12

Val Gly Asn Leu Trp Val Thr Val Tyr Gly Val Pro Val Trp Arg
1               5                   10                  15

Glu Ala Glu Thr Thr Leu Phe Cys Ala Ser Asp Ala Lys Ala Tyr Asp
                20                  25                  30

Arg Glu Val His Asn Val Trp Ala Thr His Ala Cys Val Pro Thr Asp
            35                  40                  45

Pro Asn Pro Gln Glu Ile Val Leu Glu Asn Val Thr Glu Asn Phe Asn
        50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asp Cys Lys Ala Phe Asn Ser Ser Ser His Thr Asn Ser
                100                 105                 110

Ser Ile Ala Met Gln Glu Met Lys Asn Cys Thr Phe Asn Ile Thr Thr
            115                 120                 125

Ser Val Lys Gly Lys Arg Gln Gln Glu His Ala Leu Phe Tyr Lys Leu
        130                 135                 140

Asp Ile Val Pro Leu Asn Lys Asn Gly Arg Gln Tyr Arg Leu Ile Asn
145                 150                 155                 160

Cys Asn Thr Ser Thr Leu Thr Gln Ala Cys Pro Lys Val Ser Phe Asp
                165                 170                 175

Pro Ile Pro Ile His Tyr Cys Thr Pro Ala Gly Tyr Ala Ile Leu Lys
                180                 185                 190

Cys Asn Asn Lys Thr Phe Asn Gly Thr Gly Pro Cys Asn Asn Val Ser
            195                 200                 205

Thr Val Gln Cys Thr His Gly Ile Lys Pro Val Val Ser Thr Gln Leu
        210                 215                 220

Leu Leu Asn Gly Ser Leu Ala Glu Glu Asp Ile Ile Arg Ser Glu
225                 230                 235                 240

Asn Leu Thr Asn Asn Ala Lys Thr Ile Ile Val His Leu Asn Glu Ser
                245                 250                 255

Val Glu Ile Val Cys Val Arg Pro Asn Asn Asn Thr Arg Lys Ser Ile
                260                 265                 270

Arg Ile Gly Pro Gly Gln Thr Phe Tyr Ala Asn Asn Glu Ile Ile Gly
            275                 280                 285

Asp Ile Arg Gln Ala His Cys Asn Ile Ser Lys Glu Lys Trp Asn Asn
        290                 295                 300

Thr Leu His Arg Val Trp Lys Lys Leu Val Glu His Phe Pro Asn Lys
305                 310                 315                 320

Thr Thr Ile Arg Phe Asp Arg His Ser Gly Gly Asp Leu Glu Ile Thr
                325                 330                 335

Thr His Ser Phe Asn Cys Gly Gly Glu Phe Phe Tyr Cys Asn Thr Ser
                340                 345                 350

Gly Leu Phe Asn Ile Thr Tyr Asn Ser Asn Tyr Thr Tyr Asn Asp Thr
            355                 360                 365
```

```
Lys His Asn Gly Thr Lys Val Ile Thr Leu Pro Cys Arg Ile Lys Gln
            370                 375                 380

Ile Ile Asn Met Trp Gln Glu Val Gly Arg Ala Met Tyr Ala Pro Pro
385                 390                 395                 400

Ile Ala Gly Asn Ile Thr Cys Thr Ser Asn Ile Thr Gly Leu Leu Leu
                405                 410                 415

Thr Arg Asp Gly Gly Asn Asn Ser Thr Glu Thr Glu Thr Phe Arg Pro
            420                 425                 430

Gly Gly Gly Asp Met Arg Asp Asn Trp Arg Ser Glu Leu Tyr Lys Tyr
            435                 440                 445

Lys Val Val Glu Ile Lys Pro Leu Gly Ile Ala Pro Thr Gly Ala Lys
450                 455                 460

Arg Arg Val Val Glu Arg Glu Lys Arg Ala Val Gly Ile Gly Ala Val
465                 470                 475                 480

Phe Leu Gly Phe Leu Gly Ala Ala Gly Ser Thr Met Gly Ala Ala Ser
                485                 490                 495

Ile Thr Leu Thr Val Gln Ala Arg Gln Leu Leu Ser Gly Ile Val Gln
                500                 505                 510

Gln Gln Ser Asn Leu Leu Lys Ala Ile Glu Ala Gln Gln His Leu Leu
            515                 520                 525

Gln Leu Thr Val Trp Gly Ile Lys Gln Leu Gln Thr Arg Val Leu Ala
530                 535                 540

Ile Glu Arg Tyr Leu Lys Asp Gln Gln Leu Leu Gly Leu Trp Gly Cys
545                 550                 555                 560

Ser Ala Lys Leu Ile Cys Thr Thr Ala Val Pro Trp Asn Ser Ser Trp
                565                 570                 575

Ser Asn Lys Ser Glu Thr Glu Ile Trp Asn Asn Met Thr Trp Met Gln
            580                 585                 590

Trp Asp Arg Glu Ile Ser Asn Tyr Thr Asn Thr Ile Tyr Arg Leu Leu
            595                 600                 605

Glu Glu Ser Gln Asn Gln Gln Glu Lys Asn Glu Asn Asp Leu Leu Ala
            610                 615                 620

Leu Asp Lys Trp Asn Ser Leu Trp Asp Trp Phe Gly Ile Ser Asn Trp
625                 630                 635                 640

Leu Trp Tyr Ile Arg Ser Arg Ile Glu Gly Arg Gly Ser Gly Gly Tyr
                645                 650                 655

Ile Pro Glu Ala Pro Arg Asp Gly Gln Ala Tyr Val Arg Lys Asp Gly
            660                 665                 670

Glu Trp Val Leu Leu Ser Thr Phe Leu Gly His His His His His His
            675                 680                 685

<210> SEQ ID NO 13
<211> LENGTH: 688
<212> TYPE: PRT
<213> ORGANISM: Artificial Sequence
<220> FEATURE:
<223> OTHER INFORMATION: Synthetic construct

<400> SEQUENCE: 13

Val Gly Asn Leu Trp Val Thr Val Tyr Tyr Gly Val Pro Val Trp Arg
1               5                   10                  15

Glu Ala Lys Thr Thr Leu Phe Cys Ala Ser Asp Ala Lys Ala Tyr Asp
            20                  25                  30

Arg Glu Val His Asn Val Trp Ala Thr His Ala Cys Val Pro Thr Asp
            35                  40                  45
```

-continued

Pro Asn Pro Gln Glu Ile Val Leu Glu Asn Val Thr Glu Asn Phe Asn
    50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Ala Phe Asn Ser Ser His Thr Asn Ser
            100                 105                 110

Ser Ile Ala Met Gln Glu Met Lys Asn Cys Ser Phe Lys Ala Thr Thr
        115                 120                 125

Glu Ile Arg Asp Arg Lys Lys Glu Met Tyr Ala Leu Phe Tyr Lys Leu
    130                 135                 140

Asp Ile Val Pro Ile Asn Lys Asn Gly Arg Gln Tyr Arg Leu Ile Asn
145                 150                 155                 160

Cys Asn Thr Ser Thr Leu Thr Gln Ala Cys Pro Lys Val Ser Phe Asp
                165                 170                 175

Pro Ile Pro Ile His Tyr Cys Thr Pro Ala Gly Phe Ala Ile Leu Lys
            180                 185                 190

Cys Asn Asn Lys Thr Phe Asn Gly Thr Gly Pro Cys Thr Asn Val Ser
        195                 200                 205

Thr Val Gln Cys Thr His Gly Ile Lys Pro Val Val Ser Thr Gln Leu
    210                 215                 220

Leu Leu Asn Gly Ser Leu Ala Glu Glu Asp Ile Ile Arg Ser Glu
225                 230                 235                 240

Asn Leu Thr Asn Asn Ala Lys Thr Ile Ile Val His Leu Asn Glu Ser
                245                 250                 255

Val Glu Ile Asn Cys Thr Arg Pro Gly Asn Asn Thr Arg Lys Ser Ile
            260                 265                 270

Arg Ile Gly Pro Gly Gln Thr Phe Tyr Ala Asn Asn Asp Ile Ile Gly
        275                 280                 285

Asp Ile Arg Gln Ala His Cys Asn Ile Ser Glu Ala Lys Trp Asn Asn
    290                 295                 300

Thr Leu His Gln Val Ala Lys Lys Leu Val Glu His Phe Pro Asn Lys
305                 310                 315                 320

Thr Thr Ile Arg Phe Asp Arg His Ser Gly Gly Asp Leu Glu Ile Thr
                325                 330                 335

Thr His Ser Phe Asn Cys Gly Gly Glu Phe Phe Tyr Cys Asn Thr Ser
            340                 345                 350

Gly Leu Phe Asn Ile Thr Tyr Asn Ser Asn Tyr Thr Tyr Asn Asp Thr
        355                 360                 365

Lys His Asn Gly Thr Lys Val Ile Thr Leu Pro Cys Arg Ile Lys Gln
    370                 375                 380

Ile Ile Asn Met Trp Gln Glu Val Gly Arg Ala Met Tyr Ala Pro Pro
385                 390                 395                 400

Ile Ala Gly Asn Ile Thr Cys Thr Ser Asn Ile Thr Gly Leu Leu Leu
                405                 410                 415

Thr Arg Asp Gly Gly Asn Asn Ser Thr Glu Thr Glu Thr Phe Arg Pro
            420                 425                 430

Gly Gly Gly Asp Met Arg Asp Asn Trp Arg Ser Glu Leu Tyr Lys Tyr
        435                 440                 445

Lys Val Val Glu Ile Lys Pro Leu Gly Ile Ala Pro Thr Gly Ala Lys
    450                 455                 460

Arg Arg Val Val Glu Arg Glu Lys Arg Ala Val Gly Ile Gly Ala Val
465                 470                 475                 480

Phe Leu Gly Phe Leu Gly Ala Ala Gly Ser Thr Met Gly Ala Ala Ser
            485                 490                 495

Ile Thr Leu Thr Val Gln Ala Arg Gln Leu Leu Ser Gly Ile Val Gln
            500                 505                 510

Gln Gln Ser Asn Leu Leu Lys Ala Ile Glu Ala Gln Gln His Leu Leu
            515                 520                 525

Gln Leu Thr Val Trp Gly Ile Lys Gln Leu Gln Thr Arg Val Leu Ala
            530                 535                 540

Ile Glu Arg Tyr Leu Lys Asp Gln Gln Leu Leu Gly Leu Trp Gly Cys
545                 550                 555                 560

Ser Ala Lys Leu Ile Cys Thr Thr Ala Val Pro Trp Asn Ser Ser Trp
                565                 570                 575

Ser Asn Lys Ser Glu Thr Glu Ile Trp Asn Asn Met Thr Trp Met Gln
                580                 585                 590

Trp Asp Arg Glu Ile Asn Asn Tyr Thr Asn Thr Ile Tyr Arg Leu Leu
            595                 600                 605

Glu Glu Ser Gln Asn Gln Gln Glu Lys Asn Glu Asn Asp Leu Leu Ala
            610                 615                 620

Leu Asp Lys Trp Asn Ser Leu Trp Asp Trp Phe Gly Ile Ser Asn Trp
625                 630                 635                 640

Leu Trp Tyr Ile Arg Ser Arg Ile Glu Gly Arg Gly Ser Gly Gly Tyr
                645                 650                 655

Ile Pro Glu Ala Pro Arg Asp Gly Gln Ala Tyr Val Arg Lys Asp Gly
            660                 665                 670

Glu Trp Val Leu Leu Ser Thr Phe Leu Gly His His His His His His
            675                 680                 685

<210> SEQ ID NO 14
<211> LENGTH: 688
<212> TYPE: PRT
<213> ORGANISM: Artificial Sequence
<220> FEATURE:
<223> OTHER INFORMATION: Synthetic construct

<400> SEQUENCE: 14

Val Gly Asn Leu Trp Val Thr Val Tyr Tyr Gly Val Pro Val Trp Arg
1               5                   10                  15

Glu Ala Lys Thr Thr Leu Phe Cys Ala Ser Asp Ala Lys Ala Tyr Asp
            20                  25                  30

Arg Glu Val His Asn Val Trp Ala Thr His Ala Cys Val Pro Thr Asp
        35                  40                  45

Pro Asn Pro Gln Glu Ile Val Leu Glu Asn Val Thr Glu Asn Phe Asn
    50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Ala Phe Asn Ser Ser Ser His Thr Asn Ser
            100                 105                 110

Ser Ile Ala Met Gln Glu Met Lys Asn Cys Ser Phe Asn Ala Thr Thr
        115                 120                 125

Glu Ile Arg Asp Arg Lys Lys Glu Met Tyr Ala Leu Phe Tyr Lys Leu
    130                 135                 140

-continued

Asp Ile Val Pro Ile Asn Lys Asn Gly Arg Gln Tyr Arg Leu Ile Asn
145                 150                 155                 160

Cys Asn Thr Ser Thr Leu Thr Gln Ala Cys Pro Lys Val Ser Phe Asp
            165                 170                 175

Pro Ile Pro Ile His Tyr Cys Thr Pro Ala Gly Phe Ala Ile Leu Lys
            180                 185                 190

Cys Asn Asn Lys Thr Phe Asn Gly Thr Gly Pro Cys Thr Asn Val Ser
            195                 200                 205

Thr Val Gln Cys Thr His Gly Ile Lys Pro Val Val Ser Thr Gln Leu
    210                 215                 220

Leu Leu Asn Gly Ser Leu Ala Glu Glu Asp Ile Ile Arg Ser Glu
225                 230                 235                 240

Asn Leu Ser Asn Asn Ala Lys Thr Ile Ile Val His Leu Asn Glu Ser
            245                 250                 255

Val Glu Ile Thr Cys Ile Arg Pro Ser Asn Asn Thr Arg Lys Ser Val
            260                 265                 270

Arg Ile Gly Pro Gly Gln Thr Phe Tyr Ala Asn Asn Asp Ile Ile Gly
    275                 280                 285

Asn Ile Arg Lys Ala Tyr Cys Glu Ile Asn Glu Thr Lys Trp Asn Asn
    290                 295                 300

Thr Leu His Asn Val Ser Lys Lys Leu Val Glu His Phe Pro Asn Lys
305                 310                 315                 320

Thr Thr Ile Arg Phe Asp Arg His Ser Gly Gly Asp Leu Glu Ile Thr
            325                 330                 335

Thr His Ser Phe Asn Cys Gly Gly Glu Phe Phe Tyr Cys Asn Thr Ser
            340                 345                 350

Gly Leu Phe Asn Ile Ser Tyr Asn Ser Asn Tyr Thr Tyr Asn Asp Thr
            355                 360                 365

Lys His Asn Gly Thr Lys Val Ile Thr Leu Pro Cys Arg Ile Lys Gln
            370                 375                 380

Ile Ile Asn Met Trp Gln Glu Val Gly Arg Ala Met Tyr Ala Pro Pro
385                 390                 395                 400

Ile Ala Gly Asn Ile Thr Cys Thr Ser Asn Ile Thr Gly Leu Leu Leu
            405                 410                 415

Thr Arg Asp Gly Gly Asn Asn Ser Thr Glu Thr Glu Thr Phe Arg Pro
            420                 425                 430

Gly Gly Gly Asp Met Arg Asp Asn Trp Arg Ser Glu Leu Tyr Lys Tyr
            435                 440                 445

Lys Val Val Glu Ile Lys Pro Leu Gly Ile Ala Pro Thr Gly Ala Lys
    450                 455                 460

Arg Arg Val Val Glu Arg Glu Lys Arg Ala Val Gly Ile Gly Ala Val
465                 470                 475                 480

Phe Leu Gly Phe Leu Gly Ala Ala Gly Ser Thr Met Gly Ala Ala Ser
            485                 490                 495

Ile Thr Leu Thr Val Gln Ala Arg Gln Leu Leu Ser Gly Ile Val Gln
            500                 505                 510

Gln Gln Ser Asn Leu Leu Lys Ala Ile Glu Ala Gln Gln His Leu Leu
            515                 520                 525

Gln Leu Thr Val Trp Gly Ile Lys Gln Leu Gln Thr Arg Val Leu Ala
            530                 535                 540

Ile Glu Arg Tyr Leu Lys Asp Gln Gln Leu Leu Gly Leu Trp Gly Cys
545                 550                 555                 560

Ser Ala Lys Leu Ile Cys Thr Thr Ala Val Pro Trp Asn Ser Ser Trp

```
                565                 570                 575
Ser Asn Lys Ser Glu Thr Glu Ile Trp Asn Asn Met Thr Trp Met Gln
            580                 585                 590

Trp Asp Arg Glu Ile Asn Asn Tyr Thr Asn Thr Ile Tyr Arg Leu Leu
            595                 600                 605

Glu Glu Ser Gln Asn Gln Gln Glu Lys Asn Glu Asn Asp Leu Leu Ala
    610                 615                 620

Leu Asp Lys Trp Asn Ser Leu Trp Asp Trp Phe Gly Ile Ser Asn Trp
625                 630                 635                 640

Leu Trp Tyr Ile Arg Ser Arg Ile Glu Gly Arg Gly Ser Gly Gly Tyr
                645                 650                 655

Ile Pro Glu Ala Pro Arg Asp Gly Gln Ala Tyr Val Arg Lys Asp Gly
            660                 665                 670

Glu Trp Val Leu Leu Ser Thr Phe Leu Gly His His His His His His
            675                 680                 685

<210> SEQ ID NO 15
<211> LENGTH: 1989
<212> TYPE: DNA
<213> ORGANISM: Human immunodeficiency virus type 1

<400> SEQUENCE: 15
gtgggcaacc tgtgggtgac agtgtactac ggcgtgcccg tgtggcgcga ggccaagacc      60
accctgttct gcgccagcga cgccaaggcc tacgaccgcg aggtgcacaa cgtgtgggcc     120
acccacgcct gcgtgccaac agaccccaac ccccaggaaa tcgtcctgga aaacgtgacc     180
gagaacttca acatgtggaa gaacgacatg gtggaccaga tgcacgagga catcatcagc     240
ctgtgggacc agagcctgaa gccctgcgtg aagctgaccc tctgtgcgt gaccctgaac      300 tgcaccaacg tgaccagcag cgccgccaat gtgacctcta cgtgaccaa cgacgccaac     360 aacgcctcca cgccaacgg ccggaacgtg atcaacgagg acatgcagaa ctgcagcttc     420
aacgccacca ccgagatccg ggaccggaag aaagagatgt acgccctgtt ctacaagctg     480
gacatcgtgc ccctggacgg cgagaagtcc gacaaccggt acagactgat caactgcaac     540
accagcaccc tgacccaggc ctgccccaag gtgtccttcg accccatccc catccactac     600
tgcacccctg ccggcttcgc catcctgaag tgcaacaaca agaccttcaa cggcaccggc     660
ccctgcaaca acgtgtccac cgtgcagtgc acccacggca tcaagcccgt ggtgtccacc     720
cagctgctgc tgaacggcag cctggccgag gaagatatca tcatcagaag cgagaacctg     780
accaacaatg ccaagaccat catcgtgcac ctgaacgaga gcgtggaaat cgtgtgcacc     840
cggcccaaca acaacaccag aaagagcatc cggatcggcc ctggccagac cttctacgcc     900
aacaatgaca tcatcggcga catccggcag gcccactgca acatcagcga ggaaaagtgg    960
aacaacaccc tgcaccgcgt gtggaagaaa ctggtggaac acttccccaa caagaccacc   1020
atcagattcg accggcactc tggcggcgac ctggaaatca ccacccacag cttcaactgt   1080
ggcggcgagt tcttctactg caataccagc ggcctgttca acatcaccta acaacagcaac  1140 tacacctaca cgacaccaa gcacaacggc accaaagtga tcaccctgcc ctgccggatc     1200
aagcagatca tcaatatgtg gcaagaagtg gcagagcta tgtacgcccc tcctatcgcc    1260
ggcaacatca catgcaccag caacatcacc ggcctgctgc tgacccggga cggcggcaac    1320
aacagcaccg agacagagac attcagaccc ggcggaggcg acatgcggga caattggcgg    1380
agcgagctgt acaagtacaa ggtggtggaa atcaagcccc tgggaatcgc ccccaccggc    1440
```

```
gccaagagaa gagtggtgga acgcgagaag cgggccgtgg gcatcggcgc cgtgtttctg    1500
ggctttctgg gagccgccgg aagcacaatg ggcgctgcct ccatcaccct gaccgtgcag    1560
gccagacagc tgctgagcgg catcgtgcag cagcagagca acctgctcaa ggccatcgag    1620
gcccagcagc atctgctgca gctgaccgtg tggggcatca gcagctgca gacccggggtg    1680 ctggccatcg agagatacct gaaggaccag cagctcctgg gcctgtgggg ctgcagcgcc    1740
aagctgatct gcaccaccgc cgtgccctgg aacagcagct ggtccaacaa gagcgaaacc    1800
gagatctgga acaacatgac ctggatgcag tgggaccgcg agatcaacaa ctacaccaac    1860
accatctacc ggctgctgga agagagccaa aaccagcagg aaaagaacga gaacgacctg    1920
ctggccctgg acaagtggaa ctccctgtgg gattggttcg gcatcagcaa ctggctgtgg    1980
tacatcaga                                                            1989
```

<210> SEQ ID NO 16
<211> LENGTH: 663
<212> TYPE: PRT
<213> ORGANISM: Human immunodeficiency virus type 1

<400> SEQUENCE: 16

```
Val Gly Asn Leu Trp Val Thr Val Tyr Tyr Gly Val Pro Val Trp Arg
1               5                   10                  15

Glu Ala Lys Thr Thr Leu Phe Cys Ala Ser Asp Ala Lys Ala Tyr Asp
            20                  25                  30

Arg Glu Val His Asn Val Trp Ala Thr His Ala Cys Val Pro Thr Asp
        35                  40                  45

Pro Asn Pro Gln Glu Ile Val Leu Glu Asn Val Thr Glu Asn Phe Asn
    50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Asn Val Thr Ser Ala Ala Asn Val Thr
            100                 105                 110

Ser Asn Val Thr Asn Asp Ala Asn Asn Ala Ser Asn Ala Asn Gly Arg
        115                 120                 125

Asn Val Ile Asn Glu Asp Met Gln Asn Cys Ser Phe Asn Ala Thr Thr
    130                 135                 140

Glu Ile Arg Asp Arg Lys Lys Glu Met Tyr Ala Leu Phe Tyr Lys Leu
145                 150                 155                 160

Asp Ile Val Pro Leu Asp Gly Glu Lys Ser Asp Asn Arg Tyr Arg Leu
                165                 170                 175

Ile Asn Cys Asn Thr Ser Thr Leu Thr Gln Ala Cys Pro Lys Val Ser
            180                 185                 190

Phe Asp Pro Ile Pro Ile His Tyr Cys Thr Pro Ala Gly Phe Ala Ile
        195                 200                 205

Leu Lys Cys Asn Asn Lys Thr Phe Asn Gly Thr Gly Pro Cys Asn Asn
    210                 215                 220

Val Ser Thr Val Gln Cys Thr His Gly Ile Lys Pro Val Val Ser Thr
225                 230                 235                 240

Gln Leu Leu Leu Asn Gly Ser Leu Ala Glu Glu Asp Ile Ile Ile Arg
                245                 250                 255

Ser Glu Asn Leu Thr Asn Asn Ala Lys Thr Ile Ile Val His Leu Asn
            260                 265                 270
```

Glu Ser Val Glu Ile Val Cys Thr Arg Pro Asn Asn Thr Arg Lys
              275                 280                 285

Ser Ile Arg Ile Gly Pro Gly Gln Thr Phe Tyr Ala Asn Asn Asp Ile
        290                 295                 300

Ile Gly Asp Ile Arg Gln Ala His Cys Asn Ile Ser Glu Glu Lys Trp
305                 310                 315                 320

Asn Asn Thr Leu His Arg Val Trp Lys Lys Leu Val Glu His Phe Pro
                325                 330                 335

Asn Lys Thr Thr Ile Arg Phe Asp His Ser Gly Gly Asp Leu Glu
            340                 345                 350

Ile Thr Thr His Ser Phe Asn Cys Gly Gly Glu Phe Phe Tyr Cys Asn
355                 360                 365

Thr Ser Gly Leu Phe Asn Ile Thr Tyr Asn Ser Asn Tyr Thr Tyr Asn
    370                 375                 380

Asp Thr Lys His Asn Gly Thr Lys Val Ile Thr Leu Pro Cys Arg Ile
385                 390                 395                 400

Lys Gln Ile Ile Asn Met Trp Gln Glu Val Gly Arg Ala Met Tyr Ala
                405                 410                 415

Pro Pro Ile Ala Gly Asn Ile Thr Cys Thr Ser Asn Ile Thr Gly Leu
            420                 425                 430

Leu Leu Thr Arg Asp Gly Gly Asn Asn Ser Thr Glu Thr Glu Thr Phe
        435                 440                 445

Arg Pro Gly Gly Gly Asp Met Arg Asp Asn Trp Arg Ser Glu Leu Tyr
    450                 455                 460

Lys Tyr Lys Val Val Glu Ile Lys Pro Leu Gly Ile Ala Pro Thr Gly
465                 470                 475                 480

Ala Lys Ser Ser Val Val Glu Arg Ala Lys Ser Ala Val Gly Ile Gly
                485                 490                 495

Ala Val Phe Leu Gly Phe Leu Gly Ala Ala Gly Ser Thr Met Gly Ala
            500                 505                 510

Ala Ser Ile Thr Leu Thr Val Gln Ala Arg Gln Leu Leu Ser Gly Ile
        515                 520                 525

Val Gln Gln Gln Ser Asn Leu Leu Lys Ala Ile Glu Ala Gln Gln His
    530                 535                 540

Leu Leu Gln Leu Thr Val Trp Gly Ile Lys Gln Leu Gln Thr Arg Val
545                 550                 555                 560

Leu Ala Ile Glu Arg Tyr Leu Lys Asp Gln Gln Leu Leu Gly Leu Trp
                565                 570                 575

Gly Cys Ser Ala Lys Leu Ile Cys Thr Thr Ala Val Pro Trp Asn Ser
            580                 585                 590

Ser Trp Ser Asn Lys Ser Glu Thr Glu Ile Trp Asn Asn Met Thr Trp
        595                 600                 605

Met Gln Trp Asp Arg Glu Ile Asn Asn Tyr Thr Asn Thr Ile Tyr Arg
    610                 615                 620

Leu Leu Glu Glu Ser Gln Asn Gln Gln Glu Lys Asn Glu Asn Asp Leu
625                 630                 635                 640

Leu Ala Leu Asp Lys Trp Asn Ser Leu Trp Asp Trp Phe Gly Ile Ser
                645                 650                 655

Asn Trp Leu Trp Tyr Ile Arg
            660

<210> SEQ ID NO 17
<211> LENGTH: 29
<212> TYPE: PRT

<213> ORGANISM: Artificial Sequence
<220> FEATURE:
<223> OTHER INFORMATION: Synthetic construct

<400> SEQUENCE: 17

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala
            20                  25

<210> SEQ ID NO 18
<211> LENGTH: 87
<212> TYPE: DNA
<213> ORGANISM: Artificial Sequence
<220> FEATURE:
<223> OTHER INFORMATION: Synthetic construct

<400> SEQUENCE: 18
atgagagtgc ggggcatcca gcggaattgc agcacctgt ggcgctgggg cacactgatc      60
ctgggcatgc tgatgatctg cagcgcc                                        87

<210> SEQ ID NO 19
<211> LENGTH: 717
<212> TYPE: PRT
<213> ORGANISM: Artificial Sequence
<220> FEATURE:
<223> OTHER INFORMATION: Synthetic construct

<400> SEQUENCE: 19

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Val Gly Asn
            20                  25                  30

Leu Trp Val Thr Val Tyr Tyr Gly Val Pro Val Trp Arg Glu Ala Lys
        35                  40                  45

Thr Thr Leu Phe Cys Ala Ser Asp Ala Lys Ala Tyr Asp Arg Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Glu Cys Thr Ala Phe Asn Ser Ser Ser His Thr Asn Ser Ser Ile Ala
    130                 135                 140

Met Gln Glu Met Lys Asn Cys Ser Phe Asn Met Thr Thr Glu Leu Arg
145                 150                 155                 160

Asp Lys Lys Lys Lys Val Ser Ala Leu Phe Tyr Lys Leu Asp Ile Val
                165                 170                 175

Pro Leu Asn Lys Asn Gly Arg Gln Tyr Arg Leu Ile Asn Cys Asn Thr
            180                 185                 190

Ser Thr Leu Thr Gln Ala Cys Pro Lys Val Ser Phe Asp Pro Ile Pro
        195                 200                 205

Ile His Tyr Cys Thr Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln

```
            225                 230                 235                 240
Cys Thr His Gly Ile Lys Pro Val Val Ser Thr Gln Leu Leu Leu Asn
                245                 250                 255
Gly Ser Leu Ala Glu Glu Asp Ile Ile Ile Arg Ser Glu Asn Leu Thr
                260                 265                 270
Asn Asn Ala Lys Thr Ile Ile Val His Leu Asn Glu Ser Val Glu Ile
                275                 280                 285
Val Cys Ile Arg Pro Asn Asn Thr Arg Lys Ser Ile Arg Ile Gly
    290                 295                 300
Pro Gly Gln Thr Phe Tyr Ala Asn Asn Asp Ile Ile Gly Asp Ile Arg
305                 310                 315                 320
Gln Ala His Cys Asn Ile Ser Lys Glu Lys Trp Asn Asn Thr Leu His
                325                 330                 335
Arg Val Trp Lys Lys Leu Val Glu His Phe Pro Asn Lys Thr Thr Ile
                340                 345                 350
Arg Phe Asp Arg His Ser Gly Gly Asp Leu Glu Ile Thr Thr His Ser
                355                 360                 365
Phe Asn Cys Gly Gly Glu Phe Phe Tyr Cys Asn Thr Ser Gly Leu Phe
                370                 375                 380
Asn Ile Thr Tyr Asn Ser Asn Tyr Thr Tyr Asn Asp Thr Lys His Asn
385                 390                 395                 400
Gly Thr Lys Val Ile Thr Leu Pro Cys Arg Ile Lys Gln Ile Ile Asn
                405                 410                 415
Met Trp Gln Glu Val Gly Arg Ala Met Tyr Ala Pro Pro Ile Ala Gly
                420                 425                 430
Asn Ile Thr Cys Thr Ser Asn Ile Thr Gly Leu Leu Leu Thr Arg Asp
                435                 440                 445
Gly Gly Asn Asn Ser Thr Glu Thr Glu Thr Phe Arg Pro Gly Gly Gly
                450                 455                 460
Asp Met Arg Asp Asn Trp Arg Ser Glu Leu Tyr Lys Tyr Lys Val Val
465                 470                 475                 480
Glu Ile Lys Pro Leu Gly Ile Ala Pro Thr Gly Ala Lys Arg Arg Val
                485                 490                 495
Val Glu Arg Glu Lys Arg Ala Val Gly Ile Gly Ala Val Phe Leu Gly
                500                 505                 510
Phe Leu Gly Ala Ala Gly Ser Thr Met Gly Ala Ala Ser Ile Thr Leu
                515                 520                 525
Thr Val Gln Ala Arg Gln Leu Leu Ser Gly Ile Val Gln Gln Gln Ser
                530                 535                 540
Asn Leu Leu Lys Ala Ile Glu Ala Gln Gln His Leu Leu Gln Leu Thr
545                 550                 555                 560
Val Trp Gly Ile Lys Gln Leu Gln Thr Arg Val Leu Ala Ile Glu Arg
                565                 570                 575
Tyr Leu Lys Asp Gln Gln Leu Leu Gly Leu Trp Gly Cys Ser Ala Lys
                580                 585                 590
Leu Ile Cys Thr Thr Ala Val Pro Trp Asn Ser Ser Trp Ser Asn Lys
                595                 600                 605
Ser Glu Thr Glu Ile Trp Asn Asn Met Thr Trp Met Gln Trp Asp Arg
                610                 615                 620
Glu Ile Ser Asn Tyr Thr Asn Thr Ile Tyr Arg Leu Leu Glu Glu Ser
625                 630                 635                 640
Gln Asn Gln Gln Glu Lys Asn Glu Asn Asp Leu Leu Ala Leu Asp Lys
                645                 650                 655
```

```
Trp Asn Ser Leu Trp Asp Trp Phe Gly Ile Ser Asn Trp Leu Trp Tyr
            660             665                 670

Ile Arg Ser Arg Ile Glu Gly Arg Gly Ser Gly Gly Tyr Ile Pro Glu
            675             680                 685

Ala Pro Arg Asp Gly Gln Ala Tyr Val Arg Lys Asp Gly Glu Trp Val
            690             695                 700

Leu Leu Ser Thr Phe Leu Gly His His His His His His
705                 710             715

<210> SEQ ID NO 20
<211> LENGTH: 717
<212> TYPE: PRT
<213> ORGANISM: Artificial Sequence
<220> FEATURE:
<223> OTHER INFORMATION: Synthetic construct

<400> SEQUENCE: 20

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Val Gly Asn
            20                  25                  30

Leu Trp Val Thr Val Tyr Tyr Gly Val Pro Val Trp Arg Glu Ala Glu
            35                  40                  45

Thr Thr Leu Phe Cys Ala Ser Asp Ala Lys Ala Tyr Asp Arg Glu Val
        50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asp Cys Lys Ala Phe Asn Ser Ser His Thr Asn Ser Ser Ile Ala
    130                 135                 140

Met Gln Glu Met Lys Asn Cys Thr Phe Asn Ile Thr Thr Ser Val Lys
145                 150                 155                 160

Gly Lys Arg Gln Gln Glu His Ala Leu Phe Tyr Lys Leu Asp Ile Val
                165                 170                 175

Pro Leu Asn Lys Asn Gly Arg Gln Tyr Arg Leu Ile Asn Cys Asn Thr
            180                 185                 190

Ser Thr Leu Thr Gln Ala Cys Pro Lys Val Ser Phe Asp Pro Ile Pro
        195                 200                 205

Ile His Tyr Cys Thr Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Asp Ile Ile Ile Arg Ser Glu Asn Leu Thr
            260                 265                 270

Asn Asn Ala Lys Thr Ile Ile Val His Leu Asn Glu Ser Val Glu Ile
        275                 280                 285

Val Cys Val Arg Pro Asn Asn Asn Thr Arg Lys Ser Ile Arg Ile Gly
    290                 295                 300
```

```
Pro Gly Gln Thr Phe Tyr Ala Asn Asn Glu Ile Ile Gly Asp Ile Arg
305                 310                 315                 320

Gln Ala His Cys Asn Ile Ser Lys Glu Lys Trp Asn Asn Thr Leu His
            325                 330                 335

Arg Val Trp Lys Lys Leu Val Glu His Phe Pro Asn Lys Thr Thr Ile
            340                 345                 350

Arg Phe Asp Arg His Ser Gly Gly Asp Leu Glu Ile Thr Thr His Ser
            355                 360                 365

Phe Asn Cys Gly Gly Glu Phe Phe Tyr Cys Asn Thr Ser Gly Leu Phe
        370                 375                 380

Asn Ile Thr Tyr Asn Ser Asn Tyr Thr Tyr Asn Asp Thr Lys His Asn
385                 390                 395                 400

Gly Thr Lys Val Ile Thr Leu Pro Cys Arg Ile Lys Gln Ile Ile Asn
                405                 410                 415

Met Trp Gln Glu Val Gly Arg Ala Met Tyr Ala Pro Pro Ile Ala Gly
            420                 425                 430

Asn Ile Thr Cys Thr Ser Asn Ile Thr Gly Leu Leu Leu Thr Arg Asp
            435                 440                 445

Gly Gly Asn Ser Thr Glu Thr Glu Thr Phe Arg Pro Gly Gly Gly
        450                 455                 460

Asp Met Arg Asp Asn Trp Arg Ser Glu Leu Tyr Lys Tyr Lys Val Val
465                 470                 475                 480

Glu Ile Lys Pro Leu Gly Ile Ala Pro Thr Gly Ala Lys Arg Arg Val
                485                 490                 495

Val Glu Arg Glu Lys Arg Ala Val Gly Ile Gly Ala Val Phe Leu Gly
            500                 505                 510

Phe Leu Gly Ala Ala Gly Ser Thr Met Gly Ala Ala Ser Ile Thr Leu
        515                 520                 525

Thr Val Gln Ala Arg Gln Leu Leu Ser Gly Ile Val Gln Gln Gln Ser
    530                 535                 540

Asn Leu Leu Lys Ala Ile Glu Ala Gln Gln His Leu Leu Gln Leu Thr
545                 550                 555                 560

Val Trp Gly Ile Lys Gln Leu Gln Thr Arg Val Leu Ala Ile Glu Arg
                565                 570                 575

Tyr Leu Lys Asp Gln Gln Leu Leu Gly Leu Trp Gly Cys Ser Ala Lys
            580                 585                 590

Leu Ile Cys Thr Thr Ala Val Pro Trp Asn Ser Ser Trp Ser Asn Lys
        595                 600                 605

Ser Glu Thr Glu Ile Trp Asn Asn Met Thr Trp Met Gln Trp Asp Arg
    610                 615                 620

Glu Ile Ser Asn Tyr Thr Asn Thr Ile Tyr Arg Leu Leu Glu Glu Ser
625                 630                 635                 640

Gln Asn Gln Gln Glu Lys Asn Glu Asn Asp Leu Leu Ala Leu Asp Lys
                645                 650                 655

Trp Asn Ser Leu Trp Asp Trp Phe Gly Ile Ser Asn Trp Leu Trp Tyr
            660                 665                 670

Ile Arg Ser Arg Ile Glu Gly Arg Gly Ser Gly Gly Tyr Ile Pro Glu
        675                 680                 685

Ala Pro Arg Asp Gly Gln Ala Tyr Val Arg Lys Asp Gly Glu Trp Val
    690                 695                 700

Leu Leu Ser Thr Phe Leu Gly His His His His His
705                 710                 715
```

```
<210> SEQ ID NO 21
<211> LENGTH: 717
<212> TYPE: PRT
<213> ORGANISM: Artificial Sequence
<220> FEATURE:
<223> OTHER INFORMATION: Synthetic construct

<400> SEQUENCE: 21
```

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Val Gly Asn
            20                  25                  30

Leu Trp Val Thr Val Tyr Tyr Gly Val Pro Val Trp Arg Glu Ala Lys
        35                  40                  45

Thr Thr Leu Phe Cys Ala Ser Asp Ala Lys Ala Tyr Asp Arg Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Ala Phe Asn Ser Ser His Thr Asn Ser Ser Ile Ala
    130                 135                 140

Met Gln Glu Met Lys Asn Cys Ser Phe Lys Ala Thr Thr Glu Ile Arg
145                 150                 155                 160

Asp Arg Lys Lys Glu Met Tyr Ala Leu Phe Tyr Lys Leu Asp Ile Val
                165                 170                 175

Pro Ile Asn Lys Asn Gly Arg Gln Tyr Arg Leu Ile Asn Cys Asn Thr
            180                 185                 190

Ser Thr Leu Thr Gln Ala Cys Pro Lys Val Ser Phe Asp Pro Ile Pro
        195                 200                 205

Ile His Tyr Cys Thr Pro Ala Gly Phe Ala Ile Leu Lys Cys Asn Asn
    210                 215                 220

Lys Thr Phe Asn Gly Thr Gly Pro Cys Thr Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Asp Ile Ile Ile Arg Ser Glu Asn Leu Thr
            260                 265                 270

Asn Asn Ala Lys Thr Ile Ile Val His Leu Asn Glu Ser Val Glu Ile
        275                 280                 285

Asn Cys Thr Arg Pro Gly Asn Asn Thr Arg Lys Ser Ile Arg Ile Gly
    290                 295                 300

Pro Gly Gln Thr Phe Tyr Ala Asn Asn Asp Ile Gly Asp Ile Arg
305                 310                 315                 320

Gln Ala His Cys Asn Ile Ser Glu Ala Lys Trp Asn Asn Thr Leu His
                325                 330                 335

Gln Val Ala Lys Lys Leu Val Glu His Phe Pro Asn Lys Thr Thr Ile
            340                 345                 350

Arg Phe Asp Arg His Ser Gly Gly Asp Leu Glu Ile Thr Thr His Ser
        355                 360                 365

Phe Asn Cys Gly Gly Glu Phe Phe Tyr Cys Asn Thr Ser Gly Leu Phe
            370                 375                 380

Asn Ile Thr Tyr Asn Ser Asn Tyr Thr Tyr Asn Asp Thr Lys His Asn
385                 390                 395                 400

Gly Thr Lys Val Ile Thr Leu Pro Cys Arg Ile Lys Gln Ile Ile Asn
                405                 410                 415

Met Trp Gln Glu Val Gly Arg Ala Met Tyr Ala Pro Pro Ile Ala Gly
            420                 425                 430

Asn Ile Thr Cys Thr Ser Asn Ile Thr Gly Leu Leu Leu Thr Arg Asp
            435                 440                 445

Gly Gly Asn Asn Ser Thr Glu Thr Glu Thr Phe Arg Pro Gly Gly Gly
450                 455                 460

Asp Met Arg Asp Asn Trp Arg Ser Glu Leu Tyr Lys Tyr Lys Val Val
465                 470                 475                 480

Glu Ile Lys Pro Leu Gly Ile Ala Pro Thr Gly Ala Lys Arg Arg Val
                485                 490                 495

Val Glu Arg Glu Lys Arg Ala Val Gly Ile Gly Ala Val Phe Leu Gly
            500                 505                 510

Phe Leu Gly Ala Ala Gly Ser Thr Met Gly Ala Ala Ser Ile Thr Leu
            515                 520                 525

Thr Val Gln Ala Arg Gln Leu Leu Ser Gly Ile Val Gln Gln Gln Ser
            530                 535                 540

Asn Leu Leu Lys Ala Ile Glu Ala Gln Gln His Leu Leu Gln Leu Thr
545                 550                 555                 560

Val Trp Gly Ile Lys Gln Leu Gln Thr Arg Val Leu Ala Ile Glu Arg
                565                 570                 575

Tyr Leu Lys Asp Gln Gln Leu Leu Gly Leu Trp Gly Cys Ser Ala Lys
            580                 585                 590

Leu Ile Cys Thr Thr Ala Val Pro Trp Asn Ser Ser Trp Ser Asn Lys
            595                 600                 605

Ser Glu Thr Glu Ile Trp Asn Asn Met Thr Trp Met Gln Trp Asp Arg
            610                 615                 620

Glu Ile Asn Asn Tyr Thr Asn Thr Ile Tyr Arg Leu Leu Glu Glu Ser
625                 630                 635                 640

Gln Asn Gln Gln Glu Lys Asn Glu Asn Asp Leu Leu Ala Leu Asp Lys
                645                 650                 655

Trp Asn Ser Leu Trp Asp Trp Phe Gly Ile Ser Asn Trp Leu Trp Tyr
            660                 665                 670

Ile Arg Ser Arg Ile Glu Gly Arg Gly Ser Gly Gly Tyr Ile Pro Glu
            675                 680                 685

Ala Pro Arg Asp Gly Gln Ala Tyr Val Arg Lys Asp Gly Glu Trp Val
690                 695                 700

Leu Leu Ser Thr Phe Leu Gly His His His His His
705                 710                 715

<210> SEQ ID NO 22
<211> LENGTH: 717
<212> TYPE: PRT
<213> ORGANISM: Artificial Sequence
<220> FEATURE:
<223> OTHER INFORMATION: Synthetic construct

<400> SEQUENCE: 22

Met Arg Val Arg Gly Ile Gln Arg Asn Cys Gln His Leu Trp Arg Trp
1               5                   10                  15

-continued

Gly Thr Leu Ile Leu Gly Met Leu Met Ile Cys Ser Ala Val Gly Asn
                20                  25                  30

Leu Trp Val Thr Val Tyr Tyr Gly Val Pro Val Trp Arg Glu Ala Lys
        35                  40                  45

Thr Thr Leu Phe Cys Ala Ser Asp Ala Lys Ala Tyr Asp Arg Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Ala Phe Asn Ser Ser His Thr Asn Ser Ser Ile Ala
    130                 135                 140

Met Gln Glu Met Lys Asn Cys Ser Phe Asn Ala Thr Glu Ile Arg
145                 150                 155                 160

Asp Arg Lys Lys Glu Met Tyr Ala Leu Phe Tyr Lys Leu Asp Ile Val
                165                 170                 175

Pro Ile Asn Lys Asn Gly Arg Gln Tyr Arg Leu Ile Asn Cys Asn Thr
            180                 185                 190

Ser Thr Leu Thr Gln Ala Cys Pro Lys Val Ser Phe Asp Pro Ile Pro
        195                 200                 205

Ile His Tyr Cys Thr Pro Ala Gly Phe Ala Ile Leu Lys Cys Asn Asn
210                 215                 220

Lys Thr Phe Asn Gly Thr Gly Pro Cys Thr Asn Val Ser Thr Val Gln
225                 230                 235                 240

Cys Thr His Gly Ile Lys Pro Val Val Ser Thr Gln Leu Leu Leu Asn
            245                 250                 255

Gly Ser Leu Ala Glu Glu Asp Ile Ile Ile Arg Ser Glu Asn Leu Ser
        260                 265                 270

Asn Asn Ala Lys Thr Ile Ile Val His Leu Asn Glu Ser Val Glu Ile
    275                 280                 285

Thr Cys Ile Arg Pro Ser Asn Asn Thr Arg Lys Ser Val Arg Ile Gly
290                 295                 300

Pro Gly Gln Thr Phe Tyr Ala Asn Asn Asp Ile Ile Gly Asn Ile Arg
305                 310                 315                 320

Lys Ala Tyr Cys Glu Ile Asn Glu Thr Lys Trp Asn Asn Thr Leu His
            325                 330                 335

Asn Val Ser Lys Lys Leu Val Glu His Phe Pro Asn Lys Thr Ile
        340                 345                 350

Arg Phe Asp Arg His Ser Gly Gly Asp Leu Glu Ile Thr Thr His Ser
    355                 360                 365

Phe Asn Cys Gly Gly Glu Phe Phe Tyr Cys Asn Thr Ser Gly Leu Phe
    370                 375                 380

Asn Ile Ser Tyr Asn Ser Asn Tyr Thr Tyr Asn Asp Thr Lys His Asn
385                 390                 395                 400

Gly Thr Lys Val Ile Thr Leu Pro Cys Arg Ile Lys Gln Ile Ile Asn
            405                 410                 415

Met Trp Gln Glu Val Gly Arg Ala Met Tyr Ala Pro Pro Ile Ala Gly
        420                 425                 430

Asn Ile Thr Cys Thr Ser Asn Ile Thr Gly Leu Leu Leu Thr Arg Asp

```
                        435                 440                 445
Gly Gly Asn Asn Ser Thr Glu Thr Glu Thr Phe Arg Pro Gly Gly Gly
        450                 455                 460

Asp Met Arg Asp Asn Trp Arg Ser Glu Leu Tyr Lys Tyr Lys Val Val
465                 470                 475                 480

Glu Ile Lys Pro Leu Gly Ile Ala Pro Thr Gly Ala Lys Arg Arg Val
                485                 490                 495

Val Glu Arg Glu Lys Arg Ala Val Gly Ile Gly Ala Val Phe Leu Gly
            500                 505                 510

Phe Leu Gly Ala Ala Gly Ser Thr Met Gly Ala Ala Ser Ile Thr Leu
        515                 520                 525

Thr Val Gln Ala Arg Gln Leu Leu Ser Gly Ile Val Gln Gln Gln Ser
530                 535                 540

Asn Leu Leu Lys Ala Ile Glu Ala Gln Gln His Leu Leu Gln Leu Thr
545                 550                 555                 560

Val Trp Gly Ile Lys Gln Leu Gln Thr Arg Val Leu Ala Ile Glu Arg
                565                 570                 575

Tyr Leu Lys Asp Gln Gln Leu Leu Gly Leu Trp Gly Cys Ser Ala Lys
            580                 585                 590

Leu Ile Cys Thr Thr Ala Val Pro Trp Asn Ser Ser Trp Ser Asn Lys
        595                 600                 605

Ser Glu Thr Glu Ile Trp Asn Asn Met Thr Trp Met Gln Trp Asp Arg
610                 615                 620

Glu Ile Asn Asn Tyr Thr Asn Thr Ile Tyr Arg Leu Leu Glu Glu Ser
625                 630                 635                 640

Gln Asn Gln Gln Glu Lys Asn Glu Asn Asp Leu Leu Ala Leu Asp Lys
                645                 650                 655

Trp Asn Ser Leu Trp Asp Trp Phe Gly Ile Ser Asn Trp Leu Trp Tyr
            660                 665                 670

Ile Arg Ser Arg Ile Glu Gly Arg Gly Ser Gly Gly Tyr Ile Pro Glu
        675                 680                 685

Ala Pro Arg Asp Gly Gln Ala Tyr Val Arg Lys Asp Gly Glu Trp Val
690                 695                 700

Leu Leu Ser Thr Phe Leu Gly His His His His His
705                 710                 715

<210> SEQ ID NO 23
<211> LENGTH: 731
<212> TYPE: PRT
<213> ORGANISM: Human immunodeficiency virus type 1

<400> SEQUENCE: 23

Met Asp Ala Met Lys Arg Gly Leu Cys Cys Val Leu Leu Leu Cys Gly
1               5                   10                  15

Ala Val Phe Val Ser Pro Ser Ala Ser Val Gly Asn Leu Trp Val Thr
            20                  25                  30

Val Tyr Tyr Gly Val Pro Val Trp Arg Glu Ala Lys Thr Thr Leu Phe
        35                  40                  45

Cys Ala Ser Asp Ala Lys Ala Tyr Asp Arg Glu Val His Asn Val Trp
    50                  55                  60

Ala Thr His Ala Cys Val Pro Thr Asp Pro Asn Pro Gln Glu Ile Val
65                  70                  75                  80

Leu Glu Asn Val Thr Glu Asn Phe Asn Met Trp Lys Asn Asp Met Val
                85                  90                  95
```

```
Asp Gln Met His Glu Asp Ile Ile Ser Leu Trp Asp Gln Ser Leu Lys
            100                 105                 110

Pro Cys Val Lys Leu Thr Pro Leu Cys Val Thr Leu Asn Cys Thr Asn
        115                 120                 125

Val Thr Ser Ser Ala Ala Asn Val Thr Ser Asn Val Thr Asn Asp Ala
130                 135                 140

Asn Asn Ala Ser Asn Ala Asn Gly Arg Asn Val Ile Asn Glu Asp Met
145                 150                 155                 160

Gln Asn Cys Ser Phe Asn Ala Thr Thr Glu Ile Arg Asp Arg Lys Lys
                165                 170                 175

Glu Met Tyr Ala Leu Phe Tyr Lys Leu Asp Ile Val Pro Leu Asp Gly
            180                 185                 190

Glu Lys Ser Asp Asn Arg Tyr Arg Leu Ile Asn Cys Asn Thr Ser Thr
        195                 200                 205

Leu Thr Gln Ala Cys Pro Lys Val Ser Phe Asp Pro Ile Pro Ile His
210                 215                 220

Tyr Cys Thr Pro Ala Gly Phe Ala Ile Leu Lys Cys Asn Asn Lys Thr
225                 230                 235                 240

Phe Asn Gly Thr Gly Pro Cys Asn Asn Val Ser Thr Val Gln Cys Thr
                245                 250                 255

His Gly Ile Lys Pro Val Val Ser Thr Gln Leu Leu Leu Asn Gly Ser
            260                 265                 270

Leu Ala Glu Glu Asp Ile Ile Ile Arg Ser Glu Asn Leu Thr Asn Asn
        275                 280                 285

Ala Lys Thr Ile Ile Val His Leu Asn Glu Ser Val Glu Ile Val Cys
290                 295                 300

Thr Arg Pro Asn Asn Asn Thr Arg Lys Ser Ile Arg Ile Gly Pro Gly
305                 310                 315                 320

Gln Thr Phe Tyr Ala Asn Asn Asp Ile Ile Gly Asp Ile Arg Gln Ala
                325                 330                 335

His Cys Asn Ile Ser Glu Glu Lys Trp Asn Thr Leu His Arg Val
            340                 345                 350

Trp Lys Lys Leu Val Glu His Phe Pro Asn Lys Thr Thr Ile Arg Phe
        355                 360                 365

Asp Arg His Ser Gly Gly Asp Leu Glu Ile Thr Thr His Ser Phe Asn
370                 375                 380

Cys Gly Gly Glu Phe Phe Tyr Cys Asn Thr Ser Gly Leu Phe Asn Ile
385                 390                 395                 400

Thr Tyr Asn Ser Asn Tyr Thr Tyr Asn Asp Thr Lys His Asn Gly Thr
                405                 410                 415

Lys Val Ile Thr Leu Pro Cys Arg Ile Lys Gln Ile Ile Asn Met Trp
            420                 425                 430

Gln Glu Val Gly Arg Ala Met Tyr Ala Pro Pro Ile Ala Gly Asn Ile
        435                 440                 445

Thr Cys Thr Ser Asn Ile Thr Gly Leu Leu Leu Thr Arg Asp Gly Gly
450                 455                 460

Asn Asn Ser Thr Glu Thr Glu Thr Phe Arg Pro Gly Gly Gly Asp Met
465                 470                 475                 480

Arg Asp Asn Trp Arg Ser Glu Leu Tyr Lys Tyr Lys Val Val Glu Ile
                485                 490                 495

Lys Pro Leu Gly Ile Ala Pro Thr Gly Ala Lys Ser Ser Val Val Glu
            500                 505                 510

Arg Ala Lys Ser Ala Val Gly Ile Gly Ala Val Phe Leu Gly Phe Leu
```

```
                515                 520                 525
Gly Ala Ala Gly Ser Thr Met Gly Ala Ala Ser Ile Thr Leu Thr Val
            530                 535                 540

Gln Ala Arg Gln Leu Leu Ser Gly Ile Val Gln Gln Ser Asn Leu
545                 550                 555                 560

Leu Lys Ala Ile Glu Ala Gln Gln His Leu Leu Gln Leu Thr Val Trp
                565                 570                 575

Gly Ile Lys Gln Leu Gln Thr Arg Val Leu Ala Ile Glu Arg Tyr Leu
            580                 585                 590

Lys Asp Gln Gln Leu Leu Gly Leu Trp Gly Cys Ser Ala Lys Leu Ile
                595                 600                 605

Cys Thr Thr Ala Val Pro Trp Asn Ser Ser Trp Ser Asn Lys Ser Glu
            610                 615                 620

Thr Glu Ile Trp Asn Asn Met Thr Trp Met Gln Trp Asp Arg Glu Ile
625                 630                 635                 640

Asn Asn Tyr Thr Asn Thr Ile Tyr Arg Leu Leu Glu Glu Ser Gln Asn
                645                 650                 655

Gln Gln Glu Lys Asn Glu Asn Asp Leu Leu Ala Leu Asp Lys Trp Asn
            660                 665                 670

Ser Leu Trp Asp Trp Phe Gly Ile Ser Asn Trp Leu Trp Tyr Ile Arg
            675                 680                 685

Ser Arg Ile Glu Gly Arg Gly Ser Gly Gly Tyr Ile Pro Glu Ala Pro
            690                 695                 700

Arg Asp Gly Gln Ala Tyr Val Arg Lys Asp Gly Glu Trp Val Leu Leu
705                 710                 715                 720

Ser Thr Phe Leu Gly His His His His His His
                725                 730

<210> SEQ ID NO 24
<211> LENGTH: 2205
<212> TYPE: DNA
<213> ORGANISM: Human immunodeficiency virus type 1

<400> SEQUENCE: 24
atgagagtgc ggggcatcca gcggaactgc cagcatctgt ggcgctgggg caccctgatc    60
ctgggcatgc tgatgatctg cagcgccgtg ggcaacctgt gggtgacagt gtactacggc   120
gtgcccgtgt ggcgcgaggc caagaccacc ctgttctgcg ccagcgacgc caaggcctac   180
gaccgcgagg tgcacaacgt gtgggccacc cacgcctgcg tgccaacaga ccccaacccc   240
caggaaatcg tcctggaaaa cgtgaccgag aacttcaaca tgtggaagaa cgacatggtg   300
gaccagatgc acgaggacat catcagcctg tgggaccaga gcctgaagcc ctgcgtgaag   360
ctgacccctc tgtgcgtgac cctgaactgc accaacgtga ccagcagcgc cgccaatgtg   420
acctctaacg tgaccaacga cgccaacaac gcctccaacg ccaacggccg gaacgtgatc   480
aacgaggaca tgcagaactg cagcttcaac gccaccaccg agatccggga ccggaagaaa   540
gagatgtacg ccctgttcta caagctggac atcgtgcccc tggacggcga agtccgac    600 aaccggtaca gactgatcaa ctgcaacacc agcaccctga cccaggcctg ccccaaggtg   660
tccttcgacc ccatccccat ccactactgc accccctgcc gcttcgccat cctgaagtgc   720
aacaacaaga ccttcaacgg caccggcccc tgcaacaacg tgtccaccgt gcagtgcacc   780
cacggcatca gcccgtggt gtccacccag ctgctgctga cggcagcct ggccgaggaa   840 gatatcatca tcagaagcga gaacctgacc aacaatgcca gaccatcat cgtgcacctg   900
```

| | |
|---|---|
| aacgagagcg tggaaatcgt gtgcacccgg cccaacaaca acaccagaaa gagcatccgg | 960 |
| atcggccctg gccagacctt ctacgccaac aatgacatca tcggcgacat ccggcaggcc | 1020 |
| cactgcaaca tcagcgagga aaagtggaac aacaccctgc accgcgtgtg gaagaaactg | 1080 |
| gtggaacact tccccaacaa gaccaccatc agattcgacc ggcactctgg cggcgacctg | 1140 |
| gaaatcacca cccacagctt caactgtggc ggcgagttct tctactgcaa taccagcggc | 1200 |
| ctgttcaaca tcacctacaa cagcaactac acctacaacg acaccaagca caacggcacc | 1260 |
| aaagtgatca ccctgccctg ccggatcaag cagatcatca atatgtggca agaagtgggc | 1320 |
| agagctatgt acgcccctcc tatcgccggc aacatcacat gcaccagcaa catcaccggc | 1380 |
| ctgctgctga cccgggacgg cggcaacaac agcaccgaga cagagacatt cagacccggc | 1440 |
| ggaggcgaca tgcgggacaa ttggcggagc gagctgtaca agtacaaggt ggtgaaaatc | 1500 |
| aagcccctgg gaatcgcccc caccggcgcc aagagaagag tggtggaacg cgagaagcgg | 1560 |
| gccgtgggca tcggcgccgt gtttctgggc tttctgggag ccgccggaag cacaatgggc | 1620 |
| gctgcctcca tcaccctgac cgtgcaggcc agacagctgc tgagcggcat cgtgcagcag | 1680 |
| cagagcaacc tgctcaaggc catcgaggcc cagcagcatc tgctgcagct gaccgtgtgg | 1740 |
| ggcatcaagc agctgcagac ccgggtgctg gccatcgaga gataccctga aggaccagca | 1800 |
| ctcctgggcc tgtggggctg cagcgccaag ctgatctgca ccaccgccgt gccctggaac | 1860 |
| agcagctggt ccaacaagag cgaaaccgag atctggaaca acatgacctg gatgcagtgg | 1920 |
| gaccgcgaga tcaacaacta caccaacacc atctaccggc tgctggaaga gagccagaac | 1980 |
| cagcaggaaa agaacgagaa cgacctgctg gccctggaca gtggaactc cctgtgggat | 2040 |
| tggttcggca tcagcaactg gctgtggtac atcagaagcc ggatcgaggg cagaggcagc | 2100 |
| ggcggctata tccccgaggc ccctagagat ggccaggcct acgtgcggaa ggacggcgag | 2160 |
| tgggtgctgc tgagcacctt cctgggccac caccaccatc accac | 2205 |

<210> SEQ ID NO 25
<211> LENGTH: 2151
<212> TYPE: DNA
<213> ORGANISM: Artificial Sequence
<220> FEATURE:
<223> OTHER INFORMATION: Synthetic construct

<400> SEQUENCE: 25

| | |
|---|---|
| atgagagtgc ggggcatcca gcggaattgc cagcacctgt ggcgctgggg cacactgatc | 60 |
| ctgggcatgc tgatgatctg cagcgccgtg gcaacctgt gggtcaccgt gtactatggc | 120 |
| gtgcccgtgt ggcgggaagc caagaccaca ctgttctgtg ccagcgacgc caaggcctac | 180 |
| gaccgcgagg tgcacaatgt gtgggccacc catgcctgcg tgcccaccga tcccaacccc | 240 |
| caggaaatcg tgctggaaaa cgtgaccgag aacttcaaca tgtggaagaa cgacatggtg | 300 |
| gaccagatgc acgaggacat catcagcctg tgggaccaga gcctgaagcc ctgcgtgaag | 360 |
| ctgacccctc tgtgcgtgac cctggaatgc accgccttca cagcagcag ccacaccaac | 420 |
| agctctatcg ccatgcagga aatgaagaac tgcagcttca atatgaccac cgagctgcgg | 480 |
| gacaagaaaa agaaggtgtc cgccctgttc tacaagctgg acatcgtgcc cctgaacaag | 540 |
| aacggccggc agtaccggct gatcaactgc aacaccagca ccctgaccca ggcctgcccc | 600 |
| aaggtgtcct tcgaccccat ccccatccac tactgtaccc ctgccggcta cgccatcctg | 660 |
| aagtgcaaca caagacctt caacggcacc ggccctgca caacgtgtc caccgtgcag | 720 |
| tgtacccacg gcatcaagcc cgtggtgtcc acccagctgc tgctgaatgg cagcctggcc | 780 |

```
gaggaagata tcatcatcag aagcgagaac ctgaccaaca acgccaagac aatcattgtg    840
catctgaacg agagcgtgga aattgtgtgc atccggccca acaacaacac cagaaagagc    900
atccggatcg ccctggcca gaccttctac gccaacaacg acatcatcgg cgacatccgg    960
caggcccact gcaatatcag caaagagaag tggaacaata ccctgcaccg cgtgtggaaa   1020
aagctggtgg aacacttccc taacaagacc accatcagat cgaccggca ctctggcggc   1080 gacctggaaa tcaccaccca cagcttcaac tgtggcggcg agttcttcta ctgcaatacc   1140
tccggcctgt tcaacatcac ctacaacagc aactacacct acaatgacac caagcacaac   1200
gggaccaaag tgatcaccct gccctgcaga atcaagcaga tcattaacat gtggcaggaa   1260
gtgggcaggg ctatgtacgc ccctcctatc gccggcaaca tcacatgcac cagcaatatc   1320
accggcctgc tgctgaccag ggacggcggc aacaatagca ccgagacaga gacattcaga   1380
cccggcggag gcgacatgag agacaactgg cggagcgagc tgtacaagta caaggtggtg   1440
gaaatcaagc ccctgggaat cgcccctacc ggcgccaaga agagtggt ggaacgcgag    1500 aagcgggccg tgggaatcgg agccgtgttc ctgggatttc tgggagccgc cggaagcaca   1560
atgggcgctg ccagcatcac cctgacagtg caggctagac agctgctgag cggcatcgtg   1620
cagcagcaga gcaacctgct gaaggccatc gaggcccagc agcatctgct gcagctgacc   1680
gtgtggggga tcaagcagct gcagaccaga gtgctggcca ttgagagata cctgaaggac   1740
cagcagctgc tgggcctgtg gggctgttct gccaagctga tctgtaccac cgccgtgcct   1800
tggaacagct cctggtccaa caagagcgaa accgagatct ggaacaacat gacctggatg   1860
cagtgggaca gagagatcag caattacacc aacaccatct accggctgct ggaagagagc   1920
cagaaccagc aggaaaagaa cgagaacgac ctgctggccc tggacaagtg gaactccctg   1980
tgggattggt tcggcatcag caactggctg tggtacatcc ggtcccggat cgagggcaga   2040
ggcagcggag gctatattcc cgaggccccc agagatggcc aggcctacgt gcggaaagat   2100
ggcgagtggg tgctgctgag taccttcctg ggccaccatc accaccacca c           2151
```

<210> SEQ ID NO 26  
<211> LENGTH: 2151  
<212> TYPE: DNA  
<213> ORGANISM: Artificial Sequence  
<220> FEATURE:  
<223> OTHER INFORMATION: Synthetic construct

<400> SEQUENCE: 26

```
atgagagtgc ggggcatcca gcggaattgc cagcacctgt ggcgctgggg cacactgatc     60
ctgggcatgc tgatgatctg cagcgccgtg gcaacctgt gggtcaccgt gtactatggc    120
gtgcccgtgt ggcgggaagc cgagacaaca ctgttctgtg ccagcgacgc caaggcctac    180
gaccgcgagg tgcacaatgt gtgggccacc catgcctgcg tgcccaccga tcccaacccc    240
caggaaatcg tgctggaaaa cgtgaccgag aacttcaaca tgtggaagaa cgacatggtg    300
gaccagatgc acgaggacat catcagcctg tgggaccaga gcctgaagcc ctgcgtgaag    360
ctgacccctc tgtgcgtgac cctggactgc aaggccttca cagcagcag ccacaccaac    420 agctctatcg ccatgcagga aatgaagaac tgcaccttca acatcaccac cagcgtgaag    480
ggcaagcggc agcaggaaca cgccctgttc tacaagctgg acatcgtgcc cctgaacaag    540
aacgccggag agtaccggct gatcaactgc aacaccagca ccctgaccca ggcctgcccc    600
aaggtgtcct tcgaccccat ccccatccac tactgtaccc ctgccggcta cgccatcctg    660
```

| | |
|---|---|
| aagtgcaaca caagaccttt caacggcacc ggccctgca caacgtgtc caccgtgcag | 720 |
| tgtacccacg gcatcaagcc cgtggtgtcc acccagctgc tgctgaatgg cagcctggcc | 780 |
| gaggaagata tcatcatcag aagcgagaac ctgaccaaca cgccaagac catcattgtg | 840 |
| catctgaacg agagcgtgga aattgtgtgc gtgcggccca caacaacac cagaaagagc | 900 |
| atccggatcg gccctggcca gaccttctac gccaacaacg agatcatcgg cgacatccgg | 960 |
| caggcccact gcaatatcag caaagagaag tggaacaata ccctgcaccg cgtgtggaaa | 1020 |
| aagctggtgg aacacttccc taacaagacc accatcagat cgaccggca ctctggcggc | 1080 |
| gacctggaaa tcaccaccca cagcttcaac tgtggcggcg agttcttcta ctgcaatacc | 1140 |
| tccggcctgt tcaatatcac ctacaacagc aactacacct acaatgacac caagcacaac | 1200 |
| gggaccaaag tgatcaccct gccctgcaga atcaagcaga tcattaacat gtggcaggaa | 1260 |
| gtgggcaggg ctatgtacgc ccctcctatc gccggcaaca tcacatgcac cagcaacatt | 1320 |
| accggcctgc tgctgaccag ggacggcggc aacaatagca ccgagacaga gacattcaga | 1380 |
| cccgcggag gcgacatgag agacaactgg cgagcgagc tgtacaagta caaggtggtg | 1440 |
| gaaatcaagc ccctgggaat cgccctacc ggcgccaaga aagagtggt ggaacgcgag | 1500 |
| aagcgggccg tggaatcgg agccgtgttt ctgggctttc tggagccgc cggaagcaca | 1560 |
| atgggcgctg ccagcatcac cctgacagtg caggctagac agctgctgag cggcatcgtg | 1620 |
| cagcagcaga gcaacctgct gaaggccatc gaggcccagc agcatctgct gcagctgacc | 1680 |
| gtgtggggga tcaagcagct gcagaccaga gtgctggcca ttgagagata cctgaaggac | 1740 |
| cagcagctgc tgggcctgtg gggctgttct gccaagctga tctgtaccac cgccgtgcct | 1800 |
| tggaacagct cctggtccaa caagagcgaa accgagatct ggaacaacat gacctggatg | 1860 |
| cagtgggaca gagagatcag caattacacc aacaccatct acaggctgct ggaagagagc | 1920 |
| cagaaccagc aggaaaagaa cgagaacgac ctgctggccc tggacaagtg gaactccctg | 1980 |
| tgggattggt tcggcatcag caactggctg tggtacatcc ggtcccggat cgagggcaga | 2040 |
| ggcagcggag gctatattcc cgaggccccc agagatggcc aggcctacgt gcggaaagat | 2100 |
| ggcgagtggg tgctgctgag taccttcctg ggccaccatc accatcatca c | 2151 |

<210> SEQ ID NO 27
<211> LENGTH: 2151
<212> TYPE: DNA
<213> ORGANISM: Artificial Sequence
<220> FEATURE:
<223> OTHER INFORMATION: Synthetic construct

<400> SEQUENCE: 27

| | |
|---|---|
| atgagagtgc ggggcatcca gcggaattgc cagcacctgt ggcgctgggg cacactgatc | 60 |
| ctgggcatgc tgatgatctg cagcgccgtg ggcaacctgt gggtcaccgt gtactatggc | 120 |
| gtgcccgtgt ggcgggaagc caagaccaca ctgttctgtg ccagcgacgc caaggcctac | 180 |
| gaccgcgagg tgcacaatgt gtgggccacc catgcctgcg tgcccaccga tcccaacccc | 240 |
| caggaaatcg tgctggaaaa cgtgaccgag aacttcaaca tgtggaagaa cgacatggtg | 300 |
| gaccagatgc acgaggacat catcagcctg tgggaccaga gcctgaagcc ctgcgtgaag | 360 |
| ctgaccccctc tgtgcgtgac cctgaactgc accgccttca cagcagcag ccacaccaac | 420 |
| agctctatcg ccatgcagga aatgaagaac tgcagcttca aggccaccac cgagatccgg | 480 |
| gaccggaaga aagagatgta cgccctgttc tacaagctgg acatcgtgcc catcaacaag | 540 |
| aacggccggc agtaccggct gatcaactgc aacaccagca ccctgaccca ggcctgcccc | 600 |

-continued

| | |
|---|---|
| aaggtgtcct tcgaccccat ccccatccac tactgtaccc ctgccggctt cgccatcctg | 660 |
| aagtgcaaca acaagacctt caacggcacc ggcccctgca ccaacgtgtc caccgtgcag | 720 |
| tgtacccacg gcatcaagcc cgtggtgtcc acccagctgc tgctgaatgg cagcctggcc | 780 |
| gaggaagata tcatcatcag aagcgagaac ctgaccaaca acgccaagac aatcatcgtg | 840 |
| cacctgaacg agagcgtgga aatcaattgc accagacccg gcaacaacac cagaaagagc | 900 |
| atccggatcg ccctggcca gaccttctac gccaacaacg catcatcgg cgacatccgg | 960 |
| caggcccact gcaacatctc tgaggccaag tggaacaaca cactgcacca ggtggccaag | 1020 |
| aaactggtgg aacacttccc taacaagacc accatcagat cgaccggca ctctggcggc | 1080 |
| gacctggaaa tcaccaccca cagcttcaac tgtggcggcg agttcttcta ctgcaatacc | 1140 |
| tccggcctgt tcaacatcac ctacaacagc aactacacct acaatgacac caagcacaac | 1200 |
| gggaccaaag tgatcaccct gccctgcaga atcaagcaga tcattaacat gtggcaggaa | 1260 |
| gtgggcaggc tatgtatgc ccctcctatc gccggcaaca ttacctgcac cagcaatatc | 1320 |
| accggcctgc tgctgaccag ggacggcggc aacaatagca ccgagacaga gacattccgg | 1380 |
| cctggcggcg agacatgag agacaattgg cggagcgagc tgtacaagta caaggtggtg | 1440 |
| gaaatcaagc ccctgggaat cgcccctacc ggcgccaaga aagagtggt ggaacgcgag | 1500 |
| aagcgggccg tgggaatcgg agccgtgttc ctgggatttc tgggagccgc cggaagcaca | 1560 |
| atgggcgctg ccagcatcac cctgacagtg caggctagac agctgctgag cggcatcgtg | 1620 |
| cagcagcaga gcaacctgct gaaggccatc gaggcccagc agcatctgct gcagctgacc | 1680 |
| gtgtggggga tcaagcagct gcagaccaga gtgctggcca ttgagagata cctgaaggac | 1740 |
| cagcagctgc tgggcctgtg gggctgttct gccaagctga tctgtaccac cgccgtgcct | 1800 |
| tggaacagct cctggtccaa caagagcgaa accgagatct ggaacaatat gacatggatg | 1860 |
| cagtgggacc gcgagatcaa caattacacc aacaccatct accggctgct ggaagagagc | 1920 |
| cagaaccagc aggaaaagaa cgagaacgac ctgctggccc tggacaagtg gaactccctg | 1980 |
| tgggattggt tcggcatcag caactggctg tggtacatcc gcagccggat cgagggcaga | 2040 |
| ggcagcggag gctatattcc cgaggccccc agagatggcc aggcctacgt gcggaaagat | 2100 |
| ggcgagtggg tgctgctgag taccttcctg ggccaccatc accaccacca c | 2151 |

<210> SEQ ID NO 28
<211> LENGTH: 2151
<212> TYPE: DNA
<213> ORGANISM: Artificial Sequence
<220> FEATURE:
<223> OTHER INFORMATION: Synthetic construct

<400> SEQUENCE: 28

| | |
|---|---|
| atgagagtgc ggggcatcca gcggaattgc cagcacctgt ggcgctgggg cacactgatc | 60 |
| ctgggcatgc tgatgatctg cagcgccgtg gcaacctgt gggtcaccgt gtactatggc | 120 |
| gtgcccgtgt ggcgggaagc caagaccaca ctgttctgtg ccagcgacgc caaggcctac | 180 |
| gaccgcgagg tgcacaatgt gtgggccacc catgcctgcg tgcccaccga tcccaacccc | 240 |
| caggaaatcg tgctggaaaa cgtgaccgag aacttcaaca tgtggaagaa cgacatggtg | 300 |
| gaccagatgc acgaggacat catcagcctg tgggaccaga gcctgaagcc ctgcgtgaag | 360 |
| ctgacccctc tgtgcgtgac cctgaactgc accgccttca acagcagcag ccacaccaac | 420 |
| agctctatcg ccatgcagga aatgaagaac tgcagcttca acgccaccac cgagatccgg | 480 |

```
gaccggaaga aagagatgta cgccctgttc tacaagctgg acatcgtgcc catcaacaag      540
aacggccggc agtaccggct gatcaactgc aacaccagca ccctgaccca ggcctgcccc      600
aaggtgtcct tcgaccccat ccccatccac tactgtaccc ctgccggctt cgccatcctg      660
aagtgcaaca acaagacctt caacggcacc ggccccctgca ccaacgtgtc caccgtgcag      720
tgtacccacg gcatcaagcc cgtggtgtcc acccagctgc tgctgaatgg cagcctggcc      780
gaggaagata tcatcatcag aagcgagaac ctgagcaaca cgccaagac aatcatcgtg       840 cacctgaacg agagcgtgga atcacctgt atccggccca gcaacaacac cagaaagagc       900
gtgcggatcg ccctggcca gaccttctac gccaacaacg acatcatcgg caacatccgg       960
aaggcctact gcgagatcaa cgagacaaag tggaacaaca cactgcataa tgtgtccaag     1020
aaactggtgg aacacttccc taacaagacc accatcagat cgaccggca ctctggcggc      1080 gacctggaaa ttaccaccca cagcttcaat tgtggcggcg agttcttcta ctgcaatacc     1140
tccggcctgt tcaacatcag ctacaacagc aactacacct acaacgacac caagcacaac     1200
gggaccaaag tgatcaccct gccctgccgg atcaagcaga tcattaacat gtggcaggaa     1260
gtgggcaggg ctatgtatgc ccctcctatc gccggcaaca ttacctgcac ctccaacatc     1320
accgccctgc tgctgaccag agatggcggc aacaactcca ccgagacaga gacattcaga     1380
cccggcggag cgacatgag agacaactgg cggagcgagc tgtacaagta caaggtggtg      1440
gaaatcaagc ccctgggaat cgcccctacc ggcgccaaga agagtggt ggaacgcgag       1500 aagcgggccg tgggaatcgg agccgtgttc ctgggatttc tgggagccgc cggaagcaca     1560
atgggcgctg ccagcatcac cctgacagtg caggctagac agctgctgag cggcatcgtg     1620
cagcagcaga gcaacctgct gaaggccatc gaggcccagc agcatctgct gcagctgacc     1680
gtgtggggaa tcaagcagct gcagacacgg gtgctggcca ttgagagata cctgaaggac     1740
cagcagctgc tgggcctgtg gggctgttct gccaagctga tctgtaccac cgccgtgccc     1800
tggaacagct cctggtccaa caagagcgaa accgagatct ggaacaatat gacctggatg     1860
cagtgggacc gggaaatcaa caattacacc aacaccatct accggctgct ggaagagagc     1920
cagaaccagc aggaaaagaa cgagaacgac ctgctggccc tggacaagtg gaactccctg     1980
tgggattggt tcggcatcag caactggctg tggtacatcc gcagccggat cgagggcaga     2040
ggcagcggag gctatattcc cgaggcccct agagatggcc aggcctacgt gcggaaagac     2100
ggcgaatggg tgctgctgtc caccttcctg ggccaccatc accaccacca c              2151
```

<210> SEQ ID NO 29  
<211> LENGTH: 6  
<212> TYPE: PRT  
<213> ORGANISM: Artificial Sequence  
<220> FEATURE:  
<223> OTHER INFORMATION: Synthetic construct

<400> SEQUENCE: 29

His His His His His His  
1               5

<210> SEQ ID NO 30  
<211> LENGTH: 711  
<212> TYPE: PRT  
<213> ORGANISM: Artificial Sequence  
<220> FEATURE:  
<223> OTHER INFORMATION: Synthetic construct

<400> SEQUENCE: 30

```
Met Arg Val Arg Gly Ile Gln Arg Asn Cys Gln His Leu Trp Arg Trp
1               5                   10                  15
Gly Thr Leu Ile Leu Gly Met Leu Met Ile Cys Ser Ala Val Gly Asn
            20                  25                  30
Leu Trp Val Thr Val Tyr Tyr Gly Val Pro Val Trp Arg Glu Ala Lys
        35                  40                  45
Thr Thr Leu Phe Cys Ala Ser Asp Ala Lys Ala Tyr Asp Arg Glu Val
50                  55                  60
His Asn Val Trp Ala Thr His Ala Cys Val Pro Thr Asp Pro Asn Pro
65                  70                  75                  80
Gln Glu Ile Val Leu Glu Asn Val Thr Glu Asn Phe Asn Met Trp Lys
                85                  90                  95
Asn Asp Met Val Asp Gln Met His Glu Asp Ile Ile Ser Leu Trp Asp
            100                 105                 110
Gln Ser Leu Lys Pro Cys Val Lys Leu Thr Pro Leu Cys Val Thr Leu
        115                 120                 125
Glu Cys Thr Ala Phe Asn Ser Ser His Thr Asn Ser Ser Ile Ala
    130                 135                 140
Met Gln Glu Met Lys Asn Cys Ser Phe Asn Met Thr Thr Glu Leu Arg
145                 150                 155                 160
Asp Lys Lys Lys Val Ser Ala Leu Phe Tyr Lys Leu Asp Ile Val
                165                 170                 175
Pro Leu Asn Lys Asn Gly Arg Gln Tyr Arg Leu Ile Asn Cys Asn Thr
            180                 185                 190
Ser Thr Leu Thr Gln Ala Cys Pro Lys Val Ser Phe Asp Pro Ile Pro
        195                 200                 205
Ile His Tyr Cys Thr Pro Ala Gly Tyr Ala Ile Leu Lys Cys Asn Asn
    210                 215                 220
Lys Thr Phe Asn Gly Thr Gly Pro Cys Asn Asn Val Ser Thr Val Gln
225                 230                 235                 240
Cys Thr His Gly Ile Lys Pro Val Val Ser Thr Gln Leu Leu Leu Asn
                245                 250                 255
Gly Ser Leu Ala Glu Glu Asp Ile Ile Ile Arg Ser Glu Asn Leu Thr
            260                 265                 270
Asn Asn Ala Lys Thr Ile Ile Val His Leu Asn Glu Ser Val Glu Ile
        275                 280                 285
Val Cys Ile Arg Pro Asn Asn Asn Thr Arg Lys Ser Ile Arg Ile Gly
    290                 295                 300
Pro Gly Gln Thr Phe Tyr Ala Asn Asn Asp Ile Ile Gly Asp Ile Arg
305                 310                 315                 320
Gln Ala His Cys Asn Ile Ser Lys Glu Lys Trp Asn Asn Thr Leu His
                325                 330                 335
Arg Val Trp Lys Lys Leu Val Glu His Phe Pro Asn Lys Thr Thr Ile
            340                 345                 350
Arg Phe Asp Arg His Ser Gly Gly Asp Leu Glu Ile Thr Thr His Ser
        355                 360                 365
Phe Asn Cys Gly Gly Glu Phe Phe Tyr Cys Asn Thr Ser Gly Leu Phe
    370                 375                 380
Asn Ile Thr Tyr Asn Ser Asn Tyr Thr Tyr Asn Asp Thr Lys His Asn
385                 390                 395                 400
Gly Thr Lys Val Ile Thr Leu Pro Cys Arg Ile Lys Gln Ile Ile Asn
                405                 410                 415
Met Trp Gln Glu Val Gly Arg Ala Met Tyr Ala Pro Pro Ile Ala Gly
```

```
                420             425             430
Asn Ile Thr Cys Thr Ser Asn Ile Thr Gly Leu Leu Leu Thr Arg Asp
            435                 440                 445

Gly Gly Asn Asn Ser Thr Glu Thr Glu Thr Phe Arg Pro Gly Gly Gly
        450                 455                 460

Asp Met Arg Asp Asn Trp Arg Ser Glu Leu Tyr Lys Tyr Lys Val Val
465                 470                 475                 480

Glu Ile Lys Pro Leu Gly Ile Ala Pro Thr Gly Ala Lys Arg Arg Val
            485                 490                 495

Val Glu Arg Glu Lys Arg Ala Val Gly Ile Gly Ala Val Phe Leu Gly
        500                 505                 510

Phe Leu Gly Ala Ala Gly Ser Thr Met Gly Ala Ala Ser Ile Thr Leu
            515                 520                 525

Thr Val Gln Ala Arg Gln Leu Leu Ser Gly Ile Val Gln Gln Gln Ser
        530                 535                 540

Asn Leu Leu Lys Ala Ile Glu Ala Gln Gln His Leu Leu Gln Leu Thr
545                 550                 555                 560

Val Trp Gly Ile Lys Gln Leu Gln Thr Arg Val Leu Ala Ile Glu Arg
            565                 570                 575

Tyr Leu Lys Asp Gln Gln Leu Leu Gly Leu Trp Gly Cys Ser Ala Lys
        580                 585                 590

Leu Ile Cys Thr Thr Ala Val Pro Trp Asn Ser Ser Trp Ser Asn Lys
            595                 600                 605

Ser Glu Thr Glu Ile Trp Asn Asn Met Thr Trp Met Gln Trp Asp Arg
        610                 615                 620

Glu Ile Ser Asn Tyr Thr Asn Thr Ile Tyr Arg Leu Leu Glu Glu Ser
625                 630                 635                 640

Gln Asn Gln Gln Glu Lys Asn Glu Asn Asp Leu Leu Ala Leu Asp Lys
            645                 650                 655

Trp Asn Ser Leu Trp Asp Trp Phe Gly Ile Ser Asn Trp Leu Trp Tyr
        660                 665                 670

Ile Arg Ser Arg Ile Glu Gly Arg Gly Ser Gly Gly Tyr Ile Pro Glu
            675                 680                 685

Ala Pro Arg Asp Gly Gln Ala Tyr Val Arg Lys Asp Gly Glu Trp Val
        690                 695                 700

Leu Leu Ser Thr Phe Leu Gly
705                 710

<210> SEQ ID NO 31
<211> LENGTH: 711
<212> TYPE: PRT
<213> ORGANISM: Artificial Sequence
<220> FEATURE:
<223> OTHER INFORMATION: Synthetic construct

<400> SEQUENCE: 31

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Val Gly Asn
            20                  25                  30

Leu Trp Val Thr Val Tyr Tyr Gly Val Pro Val Trp Arg Glu Ala Glu
        35                  40                  45

Thr Thr Leu Phe Cys Ala Ser Asp Ala Lys Ala Tyr Asp Arg Glu Val
    50                  55                  60

His Asn Val Trp Ala Thr His Ala Cys Val Pro Thr Asp Pro Asn Pro
```

```
                65                  70                  75                  80
        Gln Glu Ile Val Leu Glu Asn Val Thr Glu Asn Phe Asn Met Trp Lys
                            85                  90                  95
        Asn Asp Met Val Asp Gln Met His Glu Asp Ile Ile Ser Leu Trp Asp
                            100                 105                 110
        Gln Ser Leu Lys Pro Cys Val Lys Leu Thr Pro Leu Cys Val Thr Leu
                            115                 120                 125
        Asp Cys Lys Ala Phe Asn Ser Ser Ser His Thr Asn Ser Ser Ile Ala
                            130                 135                 140
        Met Gln Glu Met Lys Asn Cys Thr Phe Asn Ile Thr Thr Ser Val Lys
        145                 150                 155                 160
        Gly Lys Arg Gln Gln Glu His Ala Leu Phe Tyr Lys Leu Asp Ile Val
                            165                 170                 175
        Pro Leu Asn Lys Asn Gly Arg Gln Tyr Arg Leu Ile Asn Cys Asn Thr
                            180                 185                 190
        Ser Thr Leu Thr Gln Ala Cys Pro Lys Val Ser Phe Asp Pro Ile Pro
                            195                 200                 205
        Ile His Tyr Cys Thr Pro Ala Gly Tyr Ala Ile Leu Lys Cys Asn Asn
                            210                 215                 220
        Lys Thr Phe Asn Gly Thr Gly Pro Cys Asn Asn Val Ser Thr Val Gln
        225                 230                 235                 240
        Cys Thr His Gly Ile Lys Pro Val Val Ser Thr Gln Leu Leu Leu Asn
                            245                 250                 255
        Gly Ser Leu Ala Glu Glu Asp Ile Ile Ile Arg Ser Glu Asn Leu Thr
                            260                 265                 270
        Asn Asn Ala Lys Thr Ile Ile Val His Leu Asn Glu Ser Val Glu Ile
                            275                 280                 285
        Val Cys Val Arg Pro Asn Asn Thr Arg Lys Ser Ile Arg Ile Gly
                            290                 295                 300
        Pro Gly Gln Thr Phe Tyr Ala Asn Asn Glu Ile Ile Gly Asp Ile Arg
        305                 310                 315                 320
        Gln Ala His Cys Asn Ile Ser Lys Glu Lys Trp Asn Asn Thr Leu His
                            325                 330                 335
        Arg Val Trp Lys Lys Leu Val Glu His Phe Pro Asn Lys Thr Thr Ile
                            340                 345                 350
        Arg Phe Asp Arg His Ser Gly Gly Asp Leu Glu Ile Thr Thr His Ser
                            355                 360                 365
        Phe Asn Cys Gly Gly Glu Phe Phe Tyr Cys Asn Thr Ser Gly Leu Phe
                            370                 375                 380
        Asn Ile Thr Tyr Asn Ser Asn Tyr Thr Tyr Asn Asp Thr Lys His Asn
        385                 390                 395                 400
        Gly Thr Lys Val Ile Thr Leu Pro Cys Arg Ile Lys Gln Ile Ile Asn
                            405                 410                 415
        Met Trp Gln Glu Val Gly Arg Ala Met Tyr Ala Pro Pro Ile Ala Gly
                            420                 425                 430
        Asn Ile Thr Cys Thr Ser Asn Ile Thr Gly Leu Leu Leu Thr Arg Asp
                            435                 440                 445
        Gly Gly Asn Asn Ser Thr Glu Thr Glu Thr Phe Arg Pro Gly Gly Gly
                            450                 455                 460
        Asp Met Arg Asp Asn Trp Arg Ser Glu Leu Tyr Lys Tyr Lys Val Val
        465                 470                 475                 480
        Glu Ile Lys Pro Leu Gly Ile Ala Pro Thr Gly Ala Lys Arg Arg Val
                            485                 490                 495
```

```
Val Glu Arg Glu Lys Arg Ala Val Gly Ile Gly Ala Val Phe Leu Gly
            500                 505                 510

Phe Leu Gly Ala Ala Gly Ser Thr Met Gly Ala Ala Ser Ile Thr Leu
            515                 520                 525

Thr Val Gln Ala Arg Gln Leu Leu Ser Gly Ile Val Gln Gln Gln Ser
530                 535                 540

Asn Leu Leu Lys Ala Ile Glu Ala Gln Gln His Leu Leu Gln Leu Thr
545                 550                 555                 560

Val Trp Gly Ile Lys Gln Leu Gln Thr Arg Val Leu Ala Ile Glu Arg
                565                 570                 575

Tyr Leu Lys Asp Gln Gln Leu Leu Gly Leu Trp Gly Cys Ser Ala Lys
            580                 585                 590

Leu Ile Cys Thr Thr Ala Val Pro Trp Asn Ser Ser Trp Ser Asn Lys
            595                 600                 605

Ser Glu Thr Glu Ile Trp Asn Asn Met Thr Trp Met Gln Trp Asp Arg
            610                 615                 620

Glu Ile Ser Asn Tyr Thr Asn Thr Ile Tyr Arg Leu Leu Glu Glu Ser
625                 630                 635                 640

Gln Asn Gln Gln Glu Lys Asn Glu Asn Asp Leu Leu Ala Leu Asp Lys
                645                 650                 655

Trp Asn Ser Leu Trp Asp Trp Phe Gly Ile Ser Asn Trp Leu Trp Tyr
            660                 665                 670

Ile Arg Ser Arg Ile Glu Gly Arg Gly Ser Gly Gly Tyr Ile Pro Glu
            675                 680                 685

Ala Pro Arg Asp Gly Gln Ala Tyr Val Arg Lys Asp Gly Glu Trp Val
            690                 695                 700

Leu Leu Ser Thr Phe Leu Gly
705                 710

<210> SEQ ID NO 32
<211> LENGTH: 725
<212> TYPE: PRT
<213> ORGANISM: Artificial Sequence
<220> FEATURE:
<223> OTHER INFORMATION: Synthetic construct

<400> SEQUENCE: 32

Met Asp Ala Met Lys Arg Gly Leu Cys Cys Val Leu Leu Leu Cys Gly
1               5                   10                  15

Ala Val Phe Val Ser Pro Ser Ala Ser Val Gly Asn Leu Trp Val Thr
            20                  25                  30

Val Tyr Tyr Gly Val Pro Val Trp Arg Glu Ala Lys Thr Thr Leu Phe
        35                  40                  45

Cys Ala Ser Asp Ala Lys Ala Tyr Asp Arg Glu Val His Asn Val Trp
    50                  55                  60

Ala Thr His Ala Cys Val Pro Thr Asp Pro Asn Pro Gln Glu Ile Val
65                  70                  75                  80

Leu Glu Asn Val Thr Glu Asn Phe Asn Met Trp Lys Asn Asp Met Val
                85                  90                  95

Asp Gln Met His Glu Asp Ile Ile Ser Leu Trp Asp Gln Ser Leu Lys
            100                 105                 110

Pro Cys Val Lys Leu Thr Pro Leu Cys Val Thr Leu Asn Cys Thr Asn
        115                 120                 125

Val Thr Ser Ser Ala Ala Asn Val Thr Ser Asn Val Thr Asn Asp Ala
    130                 135                 140
```

```
Asn Asn Ala Ser Asn Ala Asn Gly Arg Asn Val Ile Asn Glu Asp Met
145                 150                 155                 160

Gln Asn Cys Ser Phe Asn Ala Thr Thr Glu Ile Arg Asp Arg Lys Lys
                165                 170                 175

Glu Met Tyr Ala Leu Phe Tyr Lys Leu Asp Ile Val Pro Leu Asp Gly
            180                 185                 190

Glu Lys Ser Asp Asn Arg Tyr Arg Leu Ile Asn Cys Asn Thr Ser Thr
        195                 200                 205

Leu Thr Gln Ala Cys Pro Lys Val Ser Phe Asp Pro Ile Pro Ile His
    210                 215                 220

Tyr Cys Thr Pro Ala Gly Phe Ala Ile Leu Lys Cys Asn Asn Lys Thr
225                 230                 235                 240

Phe Asn Gly Thr Gly Pro Cys Asn Asn Val Ser Thr Val Gln Cys Thr
                245                 250                 255

His Gly Ile Lys Pro Val Val Ser Thr Gln Leu Leu Leu Asn Gly Ser
            260                 265                 270

Leu Ala Glu Glu Asp Ile Ile Ile Arg Ser Glu Asn Leu Thr Asn Asn
        275                 280                 285

Ala Lys Thr Ile Ile Val His Leu Asn Glu Ser Val Glu Ile Val Cys
    290                 295                 300

Thr Arg Pro Asn Asn Asn Thr Arg Lys Ser Ile Arg Ile Gly Pro Gly
305                 310                 315                 320

Gln Thr Phe Tyr Ala Asn Asn Asp Ile Ile Gly Asp Ile Arg Gln Ala
                325                 330                 335

His Cys Asn Ile Ser Glu Glu Lys Trp Asn Asn Thr Leu His Arg Val
            340                 345                 350

Trp Lys Lys Leu Val Glu His Phe Pro Asn Lys Thr Thr Ile Arg Phe
        355                 360                 365

Asp Arg His Ser Gly Gly Asp Leu Glu Ile Thr Thr His Ser Phe Asn
    370                 375                 380

Cys Gly Gly Glu Phe Phe Tyr Cys Asn Thr Ser Gly Leu Phe Asn Ile
385                 390                 395                 400

Thr Tyr Asn Ser Asn Tyr Thr Tyr Asn Asp Thr Lys His Asn Gly Thr
                405                 410                 415

Lys Val Ile Thr Leu Pro Cys Arg Ile Lys Gln Ile Ile Asn Met Trp
            420                 425                 430

Gln Glu Val Gly Arg Ala Met Tyr Ala Pro Pro Ile Ala Gly Asn Ile
        435                 440                 445

Thr Cys Thr Ser Asn Ile Thr Gly Leu Leu Leu Thr Arg Asp Gly Gly
    450                 455                 460

Asn Asn Ser Thr Glu Thr Glu Thr Phe Arg Pro Gly Gly Gly Asp Met
465                 470                 475                 480

Arg Asp Asn Trp Arg Ser Glu Leu Tyr Lys Tyr Lys Val Val Glu Ile
                485                 490                 495

Lys Pro Leu Gly Ile Ala Pro Thr Gly Ala Lys Ser Ser Val Val Glu
            500                 505                 510

Arg Ala Lys Ser Ala Val Gly Ile Gly Ala Val Phe Leu Gly Phe Leu
        515                 520                 525

Gly Ala Ala Gly Ser Thr Met Gly Ala Ala Ser Ile Thr Leu Thr Val
    530                 535                 540

Gln Ala Arg Gln Leu Leu Ser Gly Ile Val Gln Gln Ser Asn Leu
545                 550                 555                 560
```

```
Leu Lys Ala Ile Glu Ala Gln Gln His Leu Leu Gln Leu Thr Val Trp
                565                 570                 575

Gly Ile Lys Gln Leu Gln Thr Arg Val Leu Ala Ile Glu Arg Tyr Leu
            580                 585                 590

Lys Asp Gln Gln Leu Leu Gly Leu Trp Gly Cys Ser Ala Lys Leu Ile
        595                 600                 605

Cys Thr Thr Ala Val Pro Trp Asn Ser Ser Trp Ser Asn Lys Ser Glu
    610                 615                 620

Thr Glu Ile Trp Asn Asn Met Thr Trp Met Gln Trp Asp Arg Glu Ile
625                 630                 635                 640

Asn Asn Tyr Thr Asn Thr Ile Tyr Arg Leu Leu Glu Glu Ser Gln Asn
                645                 650                 655

Gln Gln Glu Lys Asn Glu Asn Asp Leu Leu Ala Leu Asp Lys Trp Asn
            660                 665                 670

Ser Leu Trp Asp Trp Phe Gly Ile Ser Asn Trp Leu Trp Tyr Ile Arg
        675                 680                 685

Ser Arg Ile Glu Gly Arg Gly Ser Gly Gly Tyr Ile Pro Glu Ala Pro
    690                 695                 700

Arg Asp Gly Gln Ala Tyr Val Arg Lys Asp Gly Glu Trp Val Leu Leu
705                 710                 715                 720

Ser Thr Phe Leu Gly
                725

<210> SEQ ID NO 33
<211> LENGTH: 40
<212> TYPE: PRT
<213> ORGANISM: Artificial Sequence
<220> FEATURE:
<223> OTHER INFORMATION: Synthetic construct

<400> SEQUENCE: 33

Cys Ser Phe Asn Met Thr Thr Glu Leu Arg Asp Lys Lys Lys Lys Val
1               5                   10                  15

Ser Ala Leu Phe Tyr Lys Leu Asp Ile Val Pro Leu Asn Lys Asn Gly
            20                  25                  30

Arg Gln Tyr Arg Leu Ile Asn Cys
        35                  40

<210> SEQ ID NO 34
<211> LENGTH: 40
<212> TYPE: PRT
<213> ORGANISM: Artificial Sequence
<220> FEATURE:
<223> OTHER INFORMATION: Synthetic construct

<400> SEQUENCE: 34

Cys Thr Phe Asn Ile Thr Thr Ser Val Lys Gly Lys Arg Gln Gln Glu
1               5                   10                  15

His Ala Leu Phe Tyr Lys Leu Asp Ile Val Pro Leu Asn Lys Asn Gly
            20                  25                  30

Arg Gln Tyr Arg Leu Ile Asn Cys
        35                  40

<210> SEQ ID NO 35
<211> LENGTH: 35
<212> TYPE: PRT
<213> ORGANISM: Artificial Sequence
<220> FEATURE:
<223> OTHER INFORMATION: Synthetic construct
```

<400> SEQUENCE: 35

Cys Thr Arg Pro Gly Asn Asn Thr Arg Lys Ser Ile Arg Ile Gly Pro
1               5                   10                  15

Gly Gln Thr Phe Tyr Ala Asn Asn Asp Ile Ile Gly Asp Ile Arg Gln
            20                  25                  30

Ala His Cys
        35

<210> SEQ ID NO 36
<211> LENGTH: 35
<212> TYPE: PRT
<213> ORGANISM: Artificial Sequence
<220> FEATURE:
<223> OTHER INFORMATION: Synthetic construct

<400> SEQUENCE: 36

Cys Ile Arg Pro Ser Asn Asn Thr Arg Lys Ser Val Arg Ile Gly Pro
1               5                   10                  15

Gly Gln Thr Phe Tyr Ala Asn Asn Asp Ile Ile Gly Asn Ile Arg Lys
            20                  25                  30

Ala Tyr Cys
        35

<210> SEQ ID NO 37
<211> LENGTH: 118
<212> TYPE: DNA
<213> ORGANISM: Artificial Sequence
<220> FEATURE:
<223> OTHER INFORMATION: Synthetic construct

<400> SEQUENCE: 37
cgagctgcgg gacaagaaaa agaaggtgtc cgccctgttc tacaagctgg acatcgtgcc    60
cctgaacaag aacggccggc agtaccggct gatcaactgc aacaccagca ccctgacc    118

<210> SEQ ID NO 38
<211> LENGTH: 118
<212> TYPE: DNA
<213> ORGANISM: Artificial Sequence
<220> FEATURE:
<223> OTHER INFORMATION: Synthetic construct

<400> SEQUENCE: 38
cagcgtgaag ggcaagcggc agcaggaaca cgccctgttc tacaagctgg acatcgtgcc    60
cctgaacaag aacggccggc agtaccggct gatcaactgc aacaccagca ccctgacc    118

<210> SEQ ID NO 39
<211> LENGTH: 106
<212> TYPE: DNA
<213> ORGANISM: Artificial Sequence
<220> FEATURE:
<223> OTHER INFORMATION: Synthetic construct

<400> SEQUENCE: 39
caccagaaag agcatccgga tcggccctgg ccagaccttc tacgccaaca acgacatcat    60
cggcgacatc cggcaggccc actgcaacat ctctgaggcc aagtgg                  106

<210> SEQ ID NO 40
<211> LENGTH: 106
<212> TYPE: DNA
<213> ORGANISM: Human immunodeficiency virus type 1

<400> SEQUENCE: 40

```
caccagaaag agcgtgcgga tcggccctgg ccagaccttc tacgccaaca acgacatcat    60
cggcaacatc cggaaggcct actgcgagat caacgagaca aagtgg                  106
```

<210> SEQ ID NO 41
<211> LENGTH: 714
<212> TYPE: PRT
<213> ORGANISM: Artificial Sequence
<220> FEATURE:
<223> OTHER INFORMATION: Synthetic construct (C97ZA012 gp140Fd)

<400> SEQUENCE: 41

```
Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
                20                  25                  30

Leu Trp Val Gly Asn Met Trp Val Thr Val Tyr Tyr Gly Val Pro Val
            35                  40                  45

Trp Thr Asp Ala Lys Thr Thr Leu Phe Cys Ala Ser Asp Thr Lys Ala
        50                  55                  60

Tyr Asp Arg Glu Val His Asn Val Trp Ala Thr His Ala Cys Val Pro
65                  70                  75                  80

Thr Asp Pro Asn Pro Gln Glu Ile Val Leu Glu Asn Val Thr Glu Asn
                85                  90                  95

Phe Asn Met Trp Lys Asn Asp Met Val Asp Gln Met His Glu Asp Ile
                100                 105                 110

Ile Ser Leu Trp Asp Gln Ser Leu Lys Pro Cys Val Lys Leu Thr Pro
            115                 120                 125

Leu Cys Val Thr Leu His Cys Thr Asn Ala Thr Phe Lys Asn Asn Val
        130                 135                 140

Thr Asn Asp Met Asn Lys Glu Ile Arg Asn Cys Ser Phe Asn Thr Thr
145                 150                 155                 160

Thr Glu Ile Arg Asp Lys Lys Gln Gln Gly Tyr Ala Leu Phe Tyr Arg
                165                 170                 175

Pro Asp Ile Val Leu Leu Lys Glu Asn Arg Asn Asn Ser Asn Asn Ser
            180                 185                 190

Glu Tyr Ile Leu Ile Asn Cys Asn Ala Ser Thr Ile Thr Gln Ala Cys
        195                 200                 205

Pro Lys Val Asn Phe Asp Pro Ile Pro Ile His Tyr Cys Ala Pro Ala
    210                 215                 220

Gly Tyr Ala Ile Leu Lys Asn Asn Lys Thr Phe Ser Gly Lys Gly Pro
225                 230                 235                 240

Cys Asn Asn Val Ser Thr Val Gln Cys Thr His Gly Ile Lys Pro Val
                245                 250                 255

Val Ser Thr Gln Leu Leu Leu Asn Gly Ser Leu Ala Glu Lys Glu Ile
            260                 265                 270

Ile Ile Arg Ser Glu Asn Leu Thr Asp Asn Val Lys Thr Ile Ile Val
        275                 280                 285

His Leu Asn Lys Ser Val Glu Ile Val Cys Thr Arg Pro Asn Asn Asn
    290                 295                 300

Thr Arg Lys Ser Met Arg Ile Gly Pro Gly Gln Thr Phe Tyr Ala Thr
305                 310                 315                 320

Gly Asp Ile Ile Gly Asp Ile Arg Gln Ala Tyr Cys Asn Ile Ser Gly
                325                 330                 335

Ser Lys Trp Asn Glu Thr Leu Lys Arg Val Lys Glu Lys Leu Gln Glu
```

```
                340             345             350
Asn Tyr Asn Asn Asn Lys Thr Ile Lys Phe Ala Pro Ser Ser Gly Gly
            355                 360                 365

Asp Leu Glu Ile Thr Thr His Ser Phe Asn Cys Arg Gly Glu Phe Phe
        370                 375                 380

Tyr Cys Asn Thr Thr Arg Leu Phe Asn Asn Asn Ala Thr Glu Asp Glu
385                 390                 395                 400

Thr Ile Thr Leu Pro Cys Arg Ile Lys Gln Ile Ile Asn Met Trp Gln
                405                 410                 415

Gly Val Gly Arg Ala Met Tyr Ala Pro Pro Ile Ala Gly Asn Ile Thr
            420                 425                 430

Cys Lys Ser Asn Ile Thr Gly Leu Leu Leu Val Arg Asp Gly Gly Glu
            435                 440                 445

Asp Asn Lys Thr Glu Glu Ile Phe Arg Pro Gly Gly Gly Asn Met Lys
        450                 455                 460

Asp Asn Trp Arg Ser Glu Leu Tyr Lys Tyr Lys Val Ile Glu Leu Lys
465                 470                 475                 480

Pro Leu Gly Ile Ala Pro Thr Gly Ala Lys Arg Arg Val Val Glu Arg
                485                 490                 495

Glu Lys Arg Ala Val Gly Ile Gly Ala Val Phe Leu Gly Phe Leu Gly
            500                 505                 510

Ala Ala Gly Ser Thr Met Gly Ala Ala Ser Leu Thr Leu Thr Val Gln
            515                 520                 525

Ala Arg Gln Leu Leu Ser Ser Ile Val Gln Gln Gln Ser Asn Leu Leu
        530                 535                 540

Arg Ala Ile Glu Ala Gln Gln His Met Leu Gln Leu Thr Val Trp Gly
545                 550                 555                 560

Ile Lys Gln Leu Gln Thr Arg Val Leu Ala Ile Glu Arg Tyr Leu Lys
                565                 570                 575

Asp Gln Gln Leu Leu Gly Ile Trp Gly Cys Ser Gly Lys Leu Ile Cys
            580                 585                 590

Thr Thr Asn Val Pro Trp Asn Ser Trp Ser Asn Lys Ser Gln Thr
            595                 600                 605

Asp Ile Trp Asn Asn Met Thr Trp Met Glu Trp Asp Arg Glu Ile Ser
        610                 615                 620

Asn Tyr Thr Asp Thr Ile Tyr Arg Leu Leu Glu Asp Ser Gln Thr Gln
625                 630                 635                 640

Gln Glu Lys Asn Glu Lys Asp Leu Leu Ala Leu Asp Ser Trp Lys Asn
                645                 650                 655

Leu Trp Ser Trp Phe Asp Ile Ser Asn Trp Leu Trp Tyr Ile Lys Ser
            660                 665                 670

Arg Ile Glu Gly Arg Gly Ser Gly Gly Tyr Ile Pro Glu Ala Pro Arg
            675                 680                 685

Asp Gly Gln Ala Tyr Val Arg Lys Asp Gly Glu Trp Val Leu Leu Ser
        690                 695                 700

Thr Phe Leu Gly His His His His His
705                 710

<210> SEQ ID NO 42
<211> LENGTH: 723
<212> TYPE: PRT
<213> ORGANISM: Artificial Sequence
<220> FEATURE:
<223> OTHER INFORMATION: Synthetic construct (92UG037.8 gp140Fd)
```

<400> SEQUENCE: 42

```
Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Ile Tyr Met Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Gln Leu Thr Pro Leu Cys Val Thr Leu
        115                 120                 125

Asp Cys Ser Tyr Asn Ile Thr Asn Asn Ile Thr Asn Ser Ile Thr Asn
    130                 135                 140

Ser Ser Val Asn Met Arg Glu Glu Ile Lys Asn Cys Ser Phe Asn Met
145                 150                 155                 160

Thr Thr Glu Leu Arg Asp Lys Asn Arg Lys Val Tyr Ser Leu Phe Tyr
                165                 170                 175

Lys Leu Asp Val Val Gln Ile Asn Asn Gly Asn Asn Ser Ser Asn Leu
            180                 185                 190

Tyr Arg Leu Ile Asn Cys Asn Thr Ser Ala Leu Thr Gln Ala Cys Pro
        195                 200                 205

Lys Val Thr Phe Glu Pro Ile Pro Ile Arg Tyr Cys Ala Pro Ala Gly
    210                 215                 220

Tyr Ala Ile Leu Lys Cys Asn Asp Lys Glu Phe Asn Gly Thr Gly Leu
225                 230                 235                 240

Cys Lys Asn Val Ser Thr Val Gln Cys Thr His Gly Ile Arg Pro Val
                245                 250                 255

Val Ser Thr Gln Leu Leu Leu Asn Gly Ser Leu Ala Glu Gly Lys Val
            260                 265                 270

Met Ile Arg Ser Glu Asn Ile Thr Asn Asn Val Lys Asn Ile Ile Val
        275                 280                 285

Gln Leu Asn Glu Thr Val Thr Ile Asn Cys Thr Arg Pro Asn Asn Asn
    290                 295                 300

Thr Arg Lys Ser Val Arg Ile Gly Pro Gly Gln Thr Phe Tyr Ala Thr
305                 310                 315                 320

Gly Asp Ile Ile Gly Asp Ile Arg Gln Ala His Cys Asn Val Ser Gly
                325                 330                 335

Ser Gln Trp Asn Arg Ala Leu His Gln Val Val Gly Gln Leu Arg Glu
            340                 345                 350

Tyr Trp Asn Thr Thr Ile Ile Phe Lys Asn Ser Ser Gly Gly Asp Leu
        355                 360                 365

Glu Ile Thr Thr His Ser Phe Asn Cys Gly Gly Glu Phe Phe Tyr Cys
    370                 375                 380

Asn Thr Ser Gly Leu Phe Asn Ser Asn Trp Thr His Asn Asp Thr Ala
385                 390                 395                 400

Ser Met Lys Pro Asn Asp Thr Ile Thr Leu Pro Cys Arg Ile Lys Gln
                405                 410                 415
```

-continued

```
Ile Ile Asn Met Trp Gln Arg Val Gly Gln Ala Ile Tyr Ala Pro Pro
            420                 425                 430

Ile Gln Gly Val Ile Arg Cys Glu Ser Asn Ile Thr Gly Leu Ile Leu
            435                 440                 445

Thr Arg Asp Gly Gly Asn Ile Asn Glu Ser Gln Ile Phe Arg Pro
450                 455                 460

Gly Gly Gly Asp Met Arg Asp Asn Trp Arg Ser Glu Leu Tyr Lys Tyr
465                 470                 475                 480

Lys Val Val Arg Ile Glu Pro Leu Gly Val Ala Pro Thr Lys Ala Lys
                485                 490                 495

Arg Arg Val Val Glu Arg Glu Lys Arg Ala Val Val Glu Leu Gly Ala
                500                 505                 510

Val Phe Ile Gly Phe Leu Gly Thr Ala Gly Ser Thr Met Gly Ala Ala
            515                 520                 525

Ser Ile Thr Leu Thr Val Gln Val Arg Lys Leu Leu Ser Gly Ile Val
            530                 535                 540

Gln Gln Gln Ser Asn Leu Leu Arg Ala Ile Glu Ala Gln Gln His Leu
545                 550                 555                 560

Leu Lys Leu Thr Val Trp Gly Ile Lys Gln Leu Gln Ala Arg Val Leu
                565                 570                 575

Ala Val Glu Arg Tyr Leu Arg Asp Gln Gln Leu Leu Gly Ile Trp Gly
            580                 585                 590

Cys Ser Gly Lys Leu Ile Cys Thr Thr Asn Val Pro Trp Asn Ser Ser
            595                 600                 605

Trp Ser Asn Lys Ser Glu Arg Glu Ile Trp Glu Asn Met Thr Trp Leu
            610                 615                 620

Gln Trp Asp Lys Glu Ile Ser Asn Tyr Thr His Ile Ile Tyr Glu Leu
625                 630                 635                 640

Ile Glu Glu Ser Gln Lys Gln Glu Lys Asn Glu Gln Glu Leu Leu
                645                 650                 655

Glu Leu Asp Lys Trp Ala Asn Leu Trp Asn Trp Phe Asp Ile Ser Asn
            660                 665                 670

Trp Leu Trp Tyr Ile Lys Glu Phe Ser Arg Ile Glu Gly Arg Gly Ser
            675                 680                 685

Gly Gly Tyr Ile Pro Glu Ala Pro Arg Asp Gly Gln Ala Tyr Val Arg
690                 695                 700

Lys Asp Gly Glu Trp Val Leu Leu Ser Thr Phe Leu Gly His His
705                 710                 715                 720

His His His
```

<210> SEQ ID NO 43
<211> LENGTH: 719
<212> TYPE: PRT
<213> ORGANISM: Artificial Sequence
<220> FEATURE:
<223> OTHER INFORMATION: Synthetic construct (Mosaic 3.1 gp140Fd)

<400> SEQUENCE: 43

```
Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala Ala Gly Lys
                20                  25                  30

Leu Trp Val Thr Val Tyr Tyr Gly Val Pro Val Trp Lys Glu Ala Thr
            35                  40                  45
```

```
Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
 65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Asp Val Arg Asn Val Thr Asn Ala Thr Asn Thr
    130                 135                 140

Asn Ser Ser Trp Gly Glu Pro Met Glu Lys Gly Glu Ile Lys Asn Cys
145                 150                 155                 160

Ser Phe Asn Ile Thr Thr Ser Ile Arg Asn Lys Val Gln Lys Gln Tyr
                165                 170                 175

Ala Leu Phe Tyr Lys Leu Asp Val Val Pro Ile Asp Asn Asp Ser Asn
            180                 185                 190

Asn Thr Asn Tyr Arg Leu Ile Ser Cys Asn Thr Ser Val Ile Thr Gln
        195                 200                 205

Ala Cys Pro Lys Val Ser Phe Glu Pro Ile Pro Ile His Tyr Cys Ala
    210                 215                 220

Pro Ala Gly Phe Ala Ile Leu Lys Cys Asn Asp Lys Lys Phe Asn Gly
225                 230                 235                 240

Thr Gly Pro Cys Thr Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Glu Asn Phe Thr Asn Asn Ala Lys Thr
        275                 280                 285

Ile Met Val Gln Leu Asn Val Ser Val Glu Ile Asn Cys Thr Arg Pro
    290                 295                 300

Asn Asn Asn Thr Arg Lys Ser Ile His Ile Gly Pro Gly Arg Ala Phe
305                 310                 315                 320

Tyr Thr Ala Gly Asp Ile Ile Gly Asp Ile Arg Gln Ala His Cys Asn
                325                 330                 335

Ile Ser Arg Ala Asn Trp Asn Asn Thr Leu Arg Gln Ile Val Glu Lys
            340                 345                 350

Leu Gly Lys Gln Phe Gly Asn Asn Lys Thr Ile Val Phe Asn His Ser
        355                 360                 365

Ser Gly Gly Asp Pro Glu Ile Val Met His Ser Phe Asn Cys Gly Gly
    370                 375                 380

Glu Phe Phe Tyr Cys Asn Ser Thr Lys Leu Phe Asn Ser Thr Trp Thr
385                 390                 395                 400

Trp Asn Asn Ser Thr Trp Asn Thr Lys Arg Ser Asn Asp Thr Glu
                405                 410                 415

Glu His Ile Thr Leu Pro Cys Arg Ile Lys Gln Ile Ile Asn Met Trp
            420                 425                 430

Gln Glu Val Gly Lys Ala Met Tyr Ala Pro Pro Ile Arg Gly Gln Ile
        435                 440                 445

Arg Cys Ser Ser Asn Ile Thr Gly Leu Leu Leu Thr Arg Asp Gly Gly
    450                 455                 460

Asn Asp Thr Ser Gly Thr Glu Ile Phe Arg Pro Gly Gly Gly Asp Met
```

```
            465                 470                 475                 480
Arg Asp Asn Trp Arg Ser Glu Leu Tyr Lys Tyr Lys Val Val Lys Ile
                    485                 490                 495

Glu Pro Leu Gly Val Ala Pro Thr Lys Ala Lys Arg Val Val Gln
                500                 505                 510

Ser Glu Lys Ser Ala Val Gly Ile Gly Ala Val Phe Leu Gly Phe Leu
            515                 520                 525

Gly Ala Ala Gly Ser Thr Met Gly Ala Ala Ser Met Thr Leu Thr Val
530                 535                 540

Gln Ala Arg Leu Leu Leu Ser Gly Ile Val Gln Gln Gln Asn Asn Leu
545                 550                 555                 560

Leu Arg Ala Ile Glu Ala Gln Gln His Leu Leu Gln Leu Thr Val Trp
                565                 570                 575

Gly Ile Lys Gln Leu Gln Ala Arg Val Leu Ala Val Glu Arg Tyr Leu
                580                 585                 590

Lys Asp Gln Gln Leu Leu Gly Ile Trp Gly Cys Ser Gly Lys Leu Ile
            595                 600                 605

Cys Thr Thr Thr Val Pro Trp Asn Ala Ser Trp Ser Asn Lys Ser Leu
610                 615                 620

Asp Lys Ile Trp Asn Asn Met Thr Trp Met Glu Trp Glu Arg Glu Ile
625                 630                 635                 640

Asn Asn Tyr Thr Ser Leu Ile Tyr Thr Leu Ile Glu Glu Ser Gln Asn
                645                 650                 655

Gln Gln Glu Lys Asn Glu Gln Glu Leu Leu Glu Leu Asp Lys Trp Ala
                660                 665                 670

Ser Leu Trp Asn Trp Phe Asp Ile Ser Asn Trp Leu Trp Gly Tyr Ile
            675                 680                 685

Pro Glu Ala Pro Arg Asp Gly Gln Ala Tyr Val Arg Lys Asp Gly Glu
            690                 695                 700

Trp Val Leu Leu Ser Thr Phe Leu Gly His His His His His His
705                 710                 715

<210> SEQ ID NO 44
<211> LENGTH: 714
<212> TYPE: PRT
<213> ORGANISM: Artificial Sequence
<220> FEATURE:
<223> OTHER INFORMATION: Synthetic construct (405C gp140Fd)

<400> SEQUENCE: 44

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Val Gly Asn
                20                  25                  30

Met Trp Val Thr Val Tyr Tyr Gly Val Pro Val Trp Thr Glu Ala Lys
            35                  40                  45

Ala Thr Leu Phe Cys Ala Ser Asp Ala Lys Ala Tyr Glu Lys Glu Val
        50                  55                  60

His Asn Val Trp Ala Thr His Ala Cys Val Pro Thr Asp Pro Asn Pro
65                  70                  75                  80

Gln Glu Ile Ile Leu Glu Asn Val Thr Glu Asn Phe Asn Met Trp Lys
                85                  90                  95

Asn Asp Met Val Asp Gln Met His Glu Asp Ile Ile Ser Ile Trp Asp
            100                 105                 110

Gln Ser Leu Lys Pro Cys Val Lys Leu Thr Pro Leu Cys Val Thr Leu
```

```
            115                 120                 125
Thr Cys Lys Asn Ile Thr Asn Val Thr Asn Ile Phe Asn Ser Ser
    130                 135                 140
Glu Gly Ile Asn Met Lys Glu Ile Lys Asn Cys Ser Phe Asn Thr
145                 150                 155                 160
Thr Thr Glu Ile Arg Asp Lys Lys Lys Glu Tyr Ala Leu Phe Tyr
                165                 170                 175
Lys Pro Asp Ile Val Gln Leu Gly Arg Asn Ser Ser Arg Tyr Ile
                180                 185                 190
Leu Ile Asn Cys Asn Ser Ser Thr Ile Thr Gln Ala Cys Pro Lys Val
            195                 200                 205
Thr Phe Asp Pro Ile Pro Ile His Tyr Cys Ala Pro Ala Gly Tyr Ala
    210                 215                 220
Ile Leu Lys Cys Asn Asn Lys Thr Phe Asn Gly Thr Pro Cys Ser
225                 230                 235                 240
Asn Ile Ser Thr Val Gln Cys Thr His Gly Ile Lys Pro Val Val Ser
                245                 250                 255
Thr Gln Leu Leu Leu Asn Gly Ser Leu Ser Glu Gly Glu Ile Met Ile
                260                 265                 270
Arg Ser Glu Asn Leu Thr Asp Asn Thr Lys Thr Ile Ile Val His Leu
            275                 280                 285
Asn Glu Ser Val Glu Ile Val Cys Ile Arg Pro Gly Asn Asn Thr Arg
    290                 295                 300
Lys Gly Ile Arg Ile Gly Pro Gly Gln Val Phe Tyr Ala Thr Gly Asp
305                 310                 315                 320
Ile Ile Gly Asp Ile Arg Gln Ala Tyr Cys Asn Ile Ser Gly Lys Trp
                325                 330                 335
Asn Thr Thr Leu Glu Lys Val Lys Lys Leu Lys Glu His Phe Pro
                340                 345                 350
Asn Lys Thr Ile Asn Phe Asn Ser Ser Gly Gly Asp Leu Glu Ile
            355                 360                 365
Thr Thr His Ser Phe Asn Cys Arg Gly Glu Phe Phe Tyr Cys Asn Thr
    370                 375                 380
Thr Lys Leu Phe Thr Asn Thr Thr Asn Thr Thr Ile Leu Ile Pro
385                 390                 395                 400
Cys Arg Ile Lys Gln Phe Val Asn Met Trp Gln Glu Val Gly Arg Ala
                405                 410                 415
Met Tyr Ala Pro Pro Ile Ala Gly Asn Ile Thr Cys Asn Ser Ser Ile
                420                 425                 430
Thr Gly Leu Leu Leu Val Arg Asp Gly Gly Ile Ser Asn Asp Thr Asn
            435                 440                 445
Asn Thr Thr Glu Thr Phe Arg Pro Gly Gly Gly Asn Met Lys Asp Asn
    450                 455                 460
Trp Arg Ser Glu Leu Tyr Ser Tyr Lys Val Val Glu Leu Lys Pro Leu
465                 470                 475                 480
Gly Val Ala Pro Thr Gly Ala Lys Arg Arg Val Val Glu Met Glu Arg
                485                 490                 495
Ser Lys Arg Ala Val Gly Ile Gly Ala Ala Leu Leu Gly Phe Leu Gly
                500                 505                 510
Ala Ala Gly Ser Thr Met Gly Ala Ala Ser Met Ala Leu Thr Val Gln
            515                 520                 525
Ala Arg Gln Leu Leu Ser Gly Ile Val Gln Gln Gln Ser Asn Leu Leu
    530                 535                 540
```

Arg Ala Ile Glu Ala Gln Gln His Met Leu Gln Leu Thr Val Trp Gly
545                 550                 555                 560

Ile Lys Gln Leu Gln Thr Arg Val Leu Ala Ile Glu Arg Tyr Leu Lys
                565                 570                 575

Asp Gln Gln Leu Leu Gly Leu Trp Gly Cys Ser Gly Lys Ile Ile Cys
            580                 585                 590

Thr Thr Asn Val Pro Trp Asn Ser Ser Trp Ser Asn Lys Ser Lys Glu
        595                 600                 605

Asp Ile Trp Asp Asn Met Thr Trp Met Gln Trp Asp Arg Glu Val Ser
610                 615                 620

Asn Tyr Thr Glu Thr Ile Tyr Arg Leu Leu Glu Ser Gln Thr Gln
625                 630                 635                 640

Gln Glu Lys Asn Glu Lys Glu Leu Leu Glu Leu Ser Lys Trp Asp Ser
                645                 650                 655

Leu Trp Ser Trp Phe Asn Ile Thr Asn Trp Leu Trp Tyr Thr Lys Ser
            660                 665                 670

Arg Ile Glu Gly Arg Gly Ser Gly Gly Tyr Ile Pro Glu Ala Pro Arg
        675                 680                 685

Asp Gly Gln Ala Tyr Val Arg Lys Asp Gly Glu Trp Val Leu Leu Ser
690                 695                 700

Thr Phe Leu Gly His His His His His His
705                 710

<210> SEQ ID NO 45
<211> LENGTH: 701
<212> TYPE: PRT
<213> ORGANISM: Artificial Sequence
<220> FEATURE:
<223> OTHER INFORMATION: Synthetic construct (PVO.4 gp140Fd)

<400> SEQUENCE: 45

Met Arg Val Thr Gly Ile Arg Lys Asn Tyr Gln His Ser Trp Arg Trp
1               5                   10                  15

Gly Met Met Leu Leu Gly Met Leu Met Ile Cys Ser Ala Glu Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asn Thr Glu Val
    50                  55                  60

His Asn Val Trp Ala Thr His Ala Cys Val Pro Thr Asp Pro Asn Pro
65                  70                  75                  80

Gln Glu Val Gly Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Ser Asp Leu Arg Asn Ala Thr Asn Thr Asn Pro Thr Val
    130                 135                 140

Ser Ser Arg Val Ile Lys Lys Glu Met Met Gly Glu Val Lys Asn Cys
145                 150                 155                 160

Ser Phe Asn Val Thr Thr Asp Ile Arg Asp Arg Met Gln Lys Val Tyr
                165                 170                 175

Ala Leu Phe Tyr Arg Pro Asp Val Val Pro Ile Gln Asp His Thr Ile
            180                 185                 190

```
Glu Asn Asn Asn Thr Ile Glu Asn Asn Thr Thr Tyr Arg Leu Ile Ser
            195                 200                 205

Cys Asn Thr Ser Val Ile Thr Gln Ala Cys Pro Lys Ile Ser Phe Glu
    210                 215                 220

Pro Ile Pro Ile His Tyr Cys Thr Pro Ala Gly Phe Ala Ile Leu Lys
225                 230                 235                 240

Cys Asn Asp Lys Lys Phe Asn Gly Ser Gly Pro Cys Thr Asn Val Ser
                245                 250                 255

Thr Val Gln Cys Thr His Gly Ile Arg Pro Val Val Ser Thr Gln Leu
                260                 265                 270

Leu Leu Asn Gly Ser Arg Ala Glu Glu Val Ile Ile Arg Ser Glu
            275                 280                 285

Asn Phe Thr Asn Asn Ala Lys Thr Ile Ile Val Gln Leu Asn Lys Thr
    290                 295                 300

Val Glu Ile Asn Cys Thr Arg Pro Asn Asn Thr Arg Lys Ser Ile
305                 310                 315                 320

Ser Ile Gly Pro Gly Arg Ala Phe Tyr Ala Thr Gly Asp Ile Ile Gly
                325                 330                 335

Asp Ile Arg Gln Ala His Cys Asn Leu Ser Arg Ala Glu Trp Asn Thr
            340                 345                 350

Leu Lys Tyr Ile Ser Thr Lys Leu Arg Glu Gln Phe Gly Asn Lys Thr
            355                 360                 365

Ile Ile Phe Asn Gly Ser Ser Gly Gly Asp Pro Glu Ile Val Thr His
            370                 375                 380

Ser Phe Asn Cys Gly Gly Glu Phe Phe Tyr Cys Asn Thr Thr Lys Leu
385                 390                 395                 400

Phe Asn Ser Thr Trp Asp Ala Asn Gly Asn Cys Thr Gly Cys Asp Glu
                405                 410                 415

Ser Asp Gly Asn Asn Thr Ile Thr Leu Pro Cys Arg Ile Lys Gln Ile
                420                 425                 430

Val Asn Met Trp Gln Glu Val Gly Lys Ala Met Tyr Ala Pro Pro Ile
            435                 440                 445

Lys Gly Leu Ile Lys Cys Thr Ser Asn Ile Thr Gly Leu Leu Leu Thr
            450                 455                 460

Arg Asp Gly Gly Ala Asn Asn Thr Asn Glu Thr Phe Arg Pro Gly Gly
465                 470                 475                 480

Gly Asp Met Arg Asp Asn Trp Arg Ser Glu Leu Tyr Lys Tyr Lys Val
                485                 490                 495

Val Gln Ile Glu Pro Leu Gly Ile Ala Pro Thr Arg Ala Arg Arg
            500                 505                 510

Val Val Gln Arg Glu Lys Arg Ala Val Gly Thr Leu Gly Ala Met Phe
            515                 520                 525

Leu Gly Phe Leu Gly Ala Ala Gly Ser Thr Met Gly Ala Ala Ser Val
    530                 535                 540

Thr Leu Thr Val Gln Ala Arg Gln Leu Leu Ser Gly Ile Val Gln Gln
545                 550                 555                 560

Gln Asn Asn Leu Leu Lys Ala Ile Glu Ala Gln Gln His Met Leu Gln
                565                 570                 575

Leu Thr Val Trp Gly Ile Lys Gln Leu Gln Ala Arg Val Leu Ala Ile
            580                 585                 590

Glu Arg Tyr Leu Lys Asp Gln Gln Leu Leu Gly Ile Trp Gly Cys Ser
            595                 600                 605
```

```
Gly Lys Leu Ile Cys Thr Thr Ala Val Pro Trp Asn Thr Ser Trp Ser
    610                 615                 620
Asn Lys Ser Phe Asn Lys Ile Trp Asp Asn Met Thr Trp Met Glu Trp
625                 630                 635                 640
Glu Arg Glu Ile Asp Asn Tyr Thr Gly Leu Ile Tyr Asn Leu Leu Glu
                645                 650                 655
Glu Ser Gln Asn Gln Gln Lys Asn Glu Gln Asp Leu Leu Ala Leu
            660                 665                 670
Asp Lys Trp Glu Ser Leu Trp Asn Trp Phe Ser Ile Thr Lys Trp Leu
        675                 680                 685
Trp Tyr Ile Lys Gly Ser Gly His His His His His His
690                 695                 700
```

<210> SEQ ID NO 46
<211> LENGTH: 856
<212> TYPE: PRT
<213> ORGANISM: Artificial Sequence
<220> FEATURE:
<223> OTHER INFORMATION: Synthetic construct (HXB2)

<400> SEQUENCE: 46

```
Met Arg Val Lys Glu Lys Tyr Gln His Leu Trp Arg Trp Gly Trp Arg
1               5                   10                  15
Trp Gly Thr Met Leu Leu Gly Met Leu Met Ile Cys Ser Ala Thr Glu
                20                  25                  30
Lys Leu Trp Val Thr Val Tyr Tyr Gly Val Pro Val Trp Lys Glu Ala
            35                  40                  45
Thr Thr Thr Leu Phe Cys Ala Ser Asp Ala Lys Ala Tyr Asp Thr Glu
        50                  55                  60
Val His Asn Val Trp Ala Thr His Ala Cys Val Pro Thr Asp Pro Asn
65                  70                  75                  80
Pro Gln Glu Val Val Leu Val Asn Val Thr Glu Asn Phe Asn Met Trp
                85                  90                  95
Lys Asn Asp Met Val Glu Gln Met His Glu Asp Ile Ile Ser Leu Trp
                100                 105                 110
Asp Gln Ser Leu Lys Pro Cys Val Lys Leu Thr Pro Leu Cys Val Ser
            115                 120                 125
Leu Lys Cys Thr Asp Leu Lys Asn Asp Thr Asn Thr Asn Ser Ser Ser
        130                 135                 140
Gly Arg Met Ile Met Glu Lys Gly Glu Ile Lys Asn Cys Ser Phe Asn
145                 150                 155                 160
Ile Ser Thr Ser Ile Arg Gly Lys Val Gln Lys Glu Tyr Ala Phe Phe
                165                 170                 175
Tyr Lys Leu Asp Ile Ile Pro Ile Asp Asn Asp Thr Thr Ser Tyr Lys
            180                 185                 190
Leu Thr Ser Cys Asn Thr Ser Val Ile Thr Gln Ala Cys Pro Lys Val
        195                 200                 205
Ser Phe Glu Pro Ile Pro Ile His Tyr Cys Ala Pro Ala Gly Phe Ala
    210                 215                 220
Ile Leu Lys Cys Asn Asn Lys Thr Phe Asn Gly Thr Gly Pro Cys Thr
225                 230                 235                 240
Asn Val Ser Thr Val Gln Cys Thr His Gly Ile Arg Pro Val Val Ser
                245                 250                 255
Thr Gln Leu Leu Leu Asn Gly Ser Leu Ala Glu Glu Glu Val Val Ile
            260                 265                 270
```

```
Arg Ser Val Asn Phe Thr Asp Asn Ala Lys Thr Ile Ile Val Gln Leu
            275                 280                 285

Asn Thr Ser Val Glu Ile Asn Cys Thr Arg Pro Asn Asn Asn Thr Arg
        290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
    530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
```

```
                690                 695                 700
Val Asn Arg Val Arg Gln Gly Tyr Ser Pro Leu Ser Phe Gln Thr His
705                     710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
        770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
            805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
            835                 840                 845

Gln Gly Leu Glu Arg Ile Leu Leu
    850                 855
```